United States Patent [19]
Kojima et al.

[11] Patent Number: 5,965,591
[45] Date of Patent: Oct. 12, 1999

[54] ISOXAZOLE DERIVATIVES

[75] Inventors: Koichi Kojima, Yokohama; Junichi Sakai, Koshigaya; Yuichi Aizawa, Yokohama; Naozumi Samata; Masao Kozuka, both of Tokyo; Kenji Yoshimi, Yokohama; Isao Kaneko, Tokyo; Kazuo Koyama, Kawaguchi, all of Japan

[73] Assignee: Sankyo Company, Limited, Tokyo, Japan

[21] Appl. No.: 08/806,854

[22] Filed: Feb. 26, 1997

Related U.S. Application Data

[63] Continuation of application No. PCT/JP95/01714, Aug. 29, 1995, abandoned.

[30] Foreign Application Priority Data

Aug. 30, 1994 [JP] Japan .................................. 6-205363
Jun. 16, 1995 [JP] Japan .................................. 7-150571

[51] Int. Cl.⁶ .......................... C07D 261/20; A61K 31/42
[52] U.S. Cl. .......................... 514/379; 548/241; 548/242; 548/110; 544/127; 544/133; 546/116; 546/198
[58] Field of Search .................... 546/241, 242; 514/380, 379

[56] References Cited

U.S. PATENT DOCUMENTS

| | | |
|---|---|---|
| 3,812,187 | 5/1974 | Karady et al. . |
| 5,578,627 | 11/1996 | Takeda et al. ............ 548/241 |
| 5,750,542 | 5/1998 | Villalubos et al. ........ 548/241 |
| 5,856,503 | 1/1999 | Aebi et al. ............... 548/241 |

FOREIGN PATENT DOCUMENTS

| | | |
|---|---|---|
| 48-8630 | 3/1973 | Japan . |
| 1265824 | 3/1972 | United Kingdom . |
| WO 94/07490 | 4/1994 | WIPO . |
| 96-06837 | 7/1996 | WIPO . |

OTHER PUBLICATIONS

T. Vitali, F. Mossini, G. Bertaccini and M. Impicciatore, "Proprietá Biologiche Di Composti 1,2–Benzisotiazolici", (1968), 1081–1096, *Farmaco., Ed. Sci.*, 23 and English–language abstract thereof (CA, 70:37702).

T. Vitali, E. Gaetani, P. Mantovani and A. Agosti, "Proprietá Biologiche Di Composti 1,2–Benzistiazolici", (1969), 440–448, *Farmaco., Ed. Sci.*, 24 and English–language abstract thereof (CA 71:49831).

*Primary Examiner*—Donald G. Daus
*Attorney, Agent, or Firm*—Frishauf, Holtz, Goodman, Langer & Chick, P.C.

[57] ABSTRACT

An isoxazole compound having the following formula:

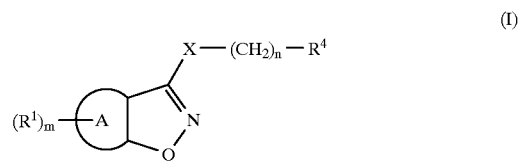

wherein $R^1$ represents hydrogen, halogen, alkyl, alkoxy, hydroxyl, alkylthio, amino, alkanoyl, alkanoylamino, alkanoyloxy, alkoxycarbonyl, carboxy, (alkylthio) thiocarbonyl, carbamoyl, nitro or cyano; $R^2$ represents an amino; m is 1; n is 1 to 6; ring A represents a phenyl ring or a naphthyl ring; and X represents oxygen or sulfur. The isoxazole compound has an excellent monoamine oxidase inhibitory activity, and is useful for treating Parkinson's disease, depression and Alzheimer's disease.

32 Claims, No Drawings

ISOXAZOLE DERIVATIVES

This application is a continuation application of International Application PCT/JP95/01714 filed Aug. 29, 1995 (now abandoned), the entire contents of which are incorporated herein by reference.

FIELD OF THE INVENTION

This invention concerns isoxazole derivatives exhibiting excellent type B and type A monoamine oxidase inhibitory activities (type B monoamine oxidase inhibition is particularly excellent) and theraeputic effects or preventive effects on neuropathies including Parkinson's disease, and depression (particularly Parkinson's disease); and a therapeutic effect for Alzheimer's disease. It also concerns monoamine oxidase inhibitors containing isoxazole derivatives as active component.

BACKGROUND OF THE INVENTION

Parkinson's disease is a chronic progressive disease which causes akinesia, muscular rigidity and tremor as a result of degeneration of dopaminergic neurons in the substantia nigra. It has been known that Parkinson's disease is caused by a decrease in the cerebral concentration of dopamine, a neurotransmitter, particularly in the caudate nucleus and putamen due to degenerative, vascular and inflammatory changes of the basal nucleus. Administration of levodopa is the most effective therapeutics and widely applied in order to supplement the decreased dopamine in the brain, particularly in the striatum. However, the single therapy with levodopa is problematic since it is associated with serious adverse reactions. Recently, trials to treat Parkinson's disease by inhibiting type-B monoamine oxidase, which is a dopamine decomposing enzyme, and preventing decomposition of dopamine are being conducted actively and deprenyl has been launched as a type-B monoamine oxidase inhibitor.

Now, in the Japanese Patent No. Sho 47-6302, it is mentioned that benzisoxazole derivatives, such as Compound A and B, are utilizable as local anaesthetics, antihistaminic agents, anti-inflammatory agents, tonics and antispasmodics with general effects on the nervous system as well as having cardiovascular effects.

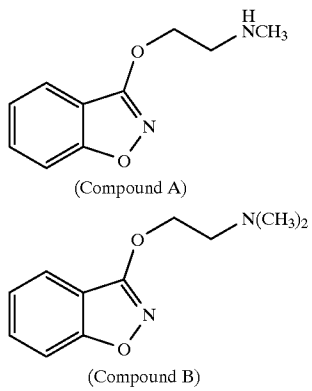

(Compound A)

(Compound B)

Moreover, in *Farmaco Ed. Sci.*, 23, 1081 (1968)., ibid., 24, 440 (1969)., it is mentioned that Compound B possesses anti-inflammatory effects and local (infiltration) anaesthetic effect. However, it is fully unknown that Compounds A and B have monoamine oxidase inhibitory activity.

THE INVENTION

Summary of the Invention have eagerly studied synthesis and pharmacological actions of isoxazoles aiming at development of excellent therapeutics for Parkinson's disease for a long time and found that isoxazole derivatives having particular structures possess potent inhibitory effects on type-B and type-A monoamine oxidases (inhibition of type-B monoamine oxidase is particularly potent) and therapuetic or preventive effects on neuropathies including Parkinson's disease, and depression (particularly Parkinson's disease); and a therapeutic effect for Alzheimer's disease leading to completion of the invention.

This invention offers isoxazole derivatives showing excellent type-B monoamine oxidase inhibitory activity and type-A monoamine oxidase inhibitory activity, the synthetic method for them and monoamine oxidase inhibitors having isoxazole derivatives as the active component.

Isoxazole derivatives of this invention have a general formula (I),

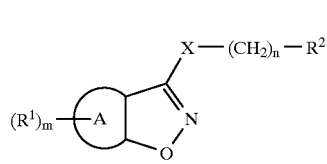

(I)

wherein $R^1$ represents a hydrogen atom; halogen atom; $C_1$–$C_6$ alkyl; halogen- or $C_1$–$C_4$ alkoxy-substituted $C_1$–$C_4$ alkyl; $C_1$–$C_6$ alkoxy; halogeno $C_1$–$C_6$ alkoxy; hydroxy; $C_1$–$C_6$ alkylthio; amino; mono $C_1$–$C_6$ alkylamino; di $C_1$–$C_6$ alkylamino; $C_1$–$C_6$ alkanoyl; $C_1$–$C_6$ alkanoylamino; $C_1$–$C_6$ alkanoyloxy; $C_1$–$C_6$ alkoxycarbonyl; carboxy; ($C_1$–$C_6$ alkylthio) thiocarbonyl; carbamoyl; mono $C_1$–$C_6$ alkylcarbamoyl; di $C_1$–$C_6$ alkylcarbamoyl; nitro or cyano radical, $R^2$ represents an amino radical, m represents an integer from 1 to 3, n represents an integer from 1 to 6, ring A represents a phenyl ring fused with the isoxazole ring, a naphthyl ring fused with the isoxazole ring or an aromatic heterocyclic ring of 5 or 6 members, containing 1 or 2 heterogenous atoms selected from the group consisting of oxygen, nitrogen and sulphur, fused with the isoxazole ring, and X represents an oxygen or a sulphur atom.

Provided that, when m is an integer of 2 or 3, the substituents $R^1$ are the same or different.

Also, active components of a monoamine oxidase inhibitor of this invention are an isoxazole derivative having the general formula (II),

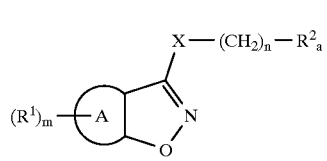

(II)

wherein $R^1$, m, n, Ring A and X are the same as those mentioned above and $R^2_a$ represents an amino; mono $C_1$–$C_4$ alkylamino; di $C_1$–$C_4$ alkylamino; or a heterocyclic ring of 5 or 6 members containing 1 nitrogen atom and optionally another nitrogen atom or oxygen atom (provided that the radical concerned binds via the nitrogen atom).

The "halogen atom" in the above definition of $R^1$ in the general formula (I) and (II) may be fluorine, chlorine, bromine or iodine atom, preferably fluorine, chlorine or bromine atom, and more preferably, fluorine or chlorine atom.

The "$C_1$–$C_6$ alkyl radical" in the above definition of $R^1$ is a straight or branched alkyl radical of 1 to 6 carbon atoms. It may be, for example, methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl radical, preferably $C_1$–$C_4$ alkyl radical, and more preferably, methyl or ethyl radical. Methyl radical is particularly favorable.

The "halogen- or $C_1$–$C_4$ alkoxy-substituted $C_1$–$C_4$ alkyl radical" in the above definition of $R^1$ is the radical in which the halogen mentioned above or the $C_1$–$C_4$ alkoxy radical mentioned below is substituted on the $C_1$–$C_4$ alkyl radical mentioned above; the halogen-substituted alkyl radical may be, for example, fluoromethyl, difluoromethyl, trifluoromethyl, 2-fluoroethyl, 2-chloroethyl, 2,2,2-trifluoroethyl, 3-fluoropropyl, 3-chloropropyl, 3-bromopropyl, 4-fluorobutyl or 4-chlorobutyl radical while the alkoxy-substituted alkyl radical may be methoxymethyl, ethoxymethyl, propoxymethyl, butoxymethyl, methoxyethyl, ethoxyethyl, propoxyethyl, butoxyethyl, propoxypropyl or butoxybutyl radical, preferably fluoromethyl, difluoromethyl, trifluoromethyl, 2-fluoroethyl, 2-chloroethyl, 2,2,2-trifluoroethyl, methoxymethyl or methoxyethyl radical, and more preferably, fluoromethyl, difluoromethyl, trifluoromethyl, 2-fluoroethyl, 2,2,2-trifluoroethyl, methoxymethyl or methoxyethyl radical, and further more preferably trifluoromethyl, 2,2,2-trifluoroethyl or methoxymethyl radical. Trifluoromethyl radical is particularly favorable.

The "$C_1$–$C_6$ alkoxy radical" in the above definition of $R^1$ is the radical in which the "$C_1$–$C_6$ alkyl radical" mentioned above is bound to an oxygen atom and it may be methoxy, ethoxy, propoxy, isopropoxy, butoxy, isobutoxy, s-butoxy, t-butoxy, pentoxy, isopentoxy, 2-methylbutoxy, neopentoxy, 1-ethylpropoxy, hexyloxy, 4-methylpentoxy, 3-methylpentoxy, 2-methylpentoxy, 1-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy or 2-ethylbutoxy radical, preferably $C_1$–$C_4$ alkoxy radical, and more preferably methoxy or ethoxy radical. Methoxy radical is particularly favorable.

The "halogeno-$C_1$–$C_6$-alkoxy radical" in the above definition of $R^1$ is the radical in which the halogen atom mentioned above binds to the $C_1$–$C_6$ alkoxy radical mentioned above and it may be fluoromethoxy, chloromethoxy, bromomethoxy, iodomethoxy, difluoromethoxy, dichloromethoxy, dibromomethoxy, trifluoromethoxy, trichloromethoxy, 1-fluoroethoxy, 2-fluoroethoxy, 2-chloroethyoxy, 2,2,2-trifluoroethoxy, 2,2,2-trichloroethoxy, 3-fluoropropoxy, 3-bromopropoxy, 4-fluorobutoxy, 5-fluoropentoxy or 6-iodohexyloxy radical, preferably fluoromethoxy, chloromethoxy, difluoromethoxy, dichloromethoxy, trifluoromethoxy, trichloromethoxy, 1-fluoroethoxy, 2-fluoroethoxy, 2-chloroethoxy or 2,2,2-trifluoroethoxy radical, and more preferably fluoromethoxy, difluoromethoxy, trifluoromethoxy or 2,2,2-trifluoromethoxy radical. Difluoromethoxy radical is particularly favorable.

The "$C_1$–$C_6$ alkylthio radical" in the above definition of $R^1$ is the radical in which the "$C_1$–$C_6$ alkyl radical" mentioned above binds to a sulphur atom and it may be methylthio, ethylthio, propylthio, isopropylthio, butylthio, isobutylthio, s-buthylthio, t-buthylthio, pentylthio, isopentylthio, 2-methylbutylthio, neopentylthio, 1-ethylpropylthio, hexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio or 2-ethylbutylthio radical, prepferably $C_1$–$C_4$ alkylthio radical, and more preferably methylthio or ethylthio radical. Methylthio radical is particularly favorable.

The "mono $C_1$–$C_6$ alkylamino radical" in the above definition of $R^1$ is the radical in which "$C_1$–$C_6$ alkyl radical" mentioned above binds to an amino radical. It may be methylamino, ethylamino, propylamino, isopropylamino, butylamino, isobutylamino, s-butylamino, t-butylamino, pentylamino or hexylamino radical, preferably mono $C_1$–$C_4$ alkylamino radical, and more preferably, methylamino or ethylamino radical. Methylamino radical is particularly favorable.

The "di $C_1$–$C_6$ alkylamino radical" in the above definition of $R^1$ may be, for example, dimethylamino, ethylmethylamino, methylpropylamino, isopropylmethylamino, butylmethylamino, isobutylmethylamino, s-butylmethylamino, t-butylmethylamino, diethylamino, ethylpropylamino, ethylisobutylamino, dipropylamino, dibutylamino, dipentylamino or dihexylamino radical, preferably di $C_1$–$C_4$ alkylamino radical, and more preferably, dimethylamino or diethylamino radical. Dimethylamino radical is particularly favorable.

The "$C_1$–$C_6$ alkanoyl radical" in the above definition of $R^1$ is a straight or branched alkanoyl radical of 1 to 6 carbon atoms and it may be formyl, acetyl, propionyl, butyryl, isobutyryl, pentanoyl, pivaloyl, valeryl or isovaleryl radical, preferably $C_1$–$C_4$ alkanoyl radical, and more preferably formyl or acetyl radical.

The "$C_1$–$C_6$ alkanoylamino radical" in the above definition of $R^1$ is a straight or branched alkanoylamino radical of 1 to 6 carbon atoms and it may be formylamino, acetylamino, propionylamino, butyrylamino, isobutyrylamino, pentanoylamino, pivaloylamino, valerylamino or isovalerylamino radicals, preferably $C_1$–$C_4$ aklanoylamino radical, and more preferably formylamino or acetylamino radical.

The "$C_1$–$C_6$ alkanoyloxy radical" in the above definition of $R^1$ is a straight or branched alkanoyloxy radical of 1 to 6 carbon atoms and it may be formyloxy, acetyloxy, propionyloxy, butyryloxy, isobutyryloxy, pentanoyloxy, pivaloyloxy, valeryloxy or isovaleryloxy radical, preferably $C_1$–$C_4$ alkanoyloxy radical, and more preferably formyoxy or acetyloxy radical.

The "$C_1$–$C_6$ alkoxycarbonyl radical" in the above definition of $R^1$ may be methoxycarbonyl, ethoxycarbonyl, propoxycarbonyl, isoopropoxycarbonyl, butoxycarbonyl, isobutoxycarbonyl, s-butoxycarbonyl, t-butoxycarbonyl, pentoxycarbonyl or hexyloxycarbonyl radical, preferably $C_1$–$C_4$ alkoxycarbonyl radical, and more preferably methoxycarbonyl or ethoxycarbonyl radical. Methoxycarbonyl radical is the most favorable.

The "($C_1$–$C_6$ alkylthio)thiocarbonyl radical" in the above definition of $R^1$ is a thiocarbonyl radical to which a straight or branched alkylthio radical of 1 to 6 carbon atoms are bound and it may be (methylthio)thiocarbonyl, (ethylthio)thiocarbonyl, (propylthio)thiocarbonyl, (isopropylthio)thiocarbonyl, (butylthio)thiocarbonyl, (isobutylthio)thiocarbonyl, (s-buthylthio)thiocarbonyl, (t-butylthio)thiocarbonyl, (pentylthio)thiocarbonyl or (hexylthio)thiocarbonyl radical, preferably ($C_1$–$C_4$ alkylthio)

thiocarbonyl radical, and more preferably (methylthio) thiocarbonyl or (ethylthio)thiocarbonyl radical. (Methylthio) thiocarbonyl radical is the most favorable.

The "mono $C_1$–$C_6$ alkylcarbamoyl" radical in the above definition of $R^1$ may be methylcarbamoyl, ethylcarbamoyl, propylcarbamoyl, isopropylcaraomoyl, butylcarbamoyl, isobutylcarbamoyl, s-butylcarbamoyl, t-butylcarbamoyl, pentylcarbamoyl or hexylcarbamoyl radical, preferably mono $C_1$–$C_4$ alkylcarbamoyl radical and, more preferably methylcarbamoyl or ethylcarbamoyl radical.

The "di $C_1$–$C_6$ alkylcarbamoyl radical" in the above definition of $R^1$ may be dimethylcarbamoyl, ethylmethylcarbamoyl, diethylcarbamoyl, dipropylcarbamoyl, diisopropylcarbamoyl, dibutylcarbamoyl, diisobutylcarbamoyl, di-s-butylcarbamoyl, di-t-butylcarbamoyl, dipentylcarbamoyl or dihexylcarbamoyl radical, preferably di $C_1$–$C_4$ alkylcarbamoyl and, more preferably dimethylcarbamoyl or diethylcarbamoyl radicals. Dimethylcarbamoyl radical is particularly favorable.

The "aromatic heterocyclic ring of 5 or 6 members, containing 1 or 2 heterogenous atoms chosen from the group consisting of oxygen, nitrogen and sulphur, fused with an isoxazole" in the above definition of the ring A may be, for example, furyl, thienyl, pyrrolyl, imidazolyl, pyrazolyl, thiazolyl, isothiazolyl, oxazolyl, isoxazolyl, pyridyl, pyrazinyl, pyrimidinyl or pyridazinyl rings, preferably furyl, thienyl or pyridyl rings, and more preferably pyridyl rings.

Moreover, the above isoxazole compound fused with a furyl, thienyl or pyridyl ring is a compound having the structure shown by the formulae (III) to (XII) below. It is preferably those having the structures shown by the formulae (III), (IV), (IX), (X), (XI) or (XII) and, more preferably, the formulae (IX), (X), (XI), or (XII), and further more preferably, (IX) or (XII). A compound having the structure shown by the formula (XII) is particularly favorable.

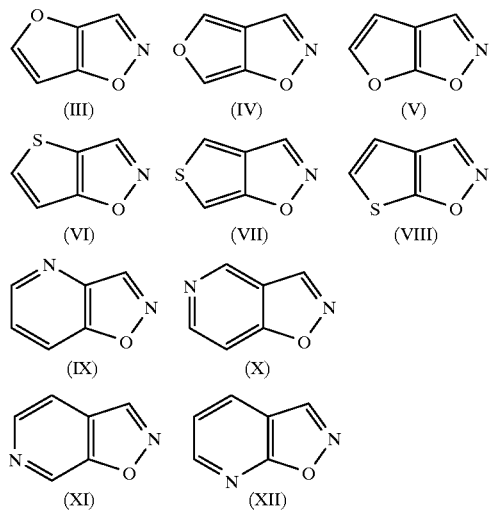

The "mono $C_1$–$C_4$ alkylamino radical" in the above definition of $R^2a$ is the same as that of $R^1$ mentioned above and methylamino radical is particularly favorable.

The "di $C_1$–$C_4$ alkylamino radical" in the above definition of $R^2a$ is the same as that of $R^1$ mentioned above and dimethylamino radical is particularly favorable.

The "heterocyclic ring of 5 or 6 members containing 1 nitrogen atom and optionally another nitrogen atom or oxygen atom (provided that the radical concerned binds on the nitrogen atom)" in the above definition of $R^2a$ may be, for example, pyrrolyl, imidazolyl, pyrazolyl, pyrrolidinyl, pyrrolinyl, imidazolidinyl, imidazolinyl, pyrazolidinyl, pyrazolinyl, piperidinyl, piperazinyl or morpholinyl radical, preferably piperidinyl or morpholinyl radical.

If $R^1$ is a basic radical such as an amino or alkylamino radical in the compounds (I) and (II) of this invention, it can be converted into a corresponding pharmaceutically acceptable salt by the acid treatment according to a usual method. For instance, a salt can be obtained by treating the compound (1) or (II) with a corresponding acid for 5 to 30 minutes in a solvent (e.g., ethers, dioxane in particular) at the room temperature and either filtering the precipitated crystals or removing the solvent by evaporation under reduced pressure. Such a salt may be a mineral acid salt such as a hydrochloride, hydrobromide, hydroiodide, nitrate, perchlorate, sulphate or phosphate, a sulfonate such as methanesulfonate, trifluoromethanesulfonate, ethanesulfonate, benzenesulfonate or p-toluenesulfonate, a carboxylate such as fumarate, succinate, citrate, tartarate, oxalate or maleate, or an amino acid salt such as glutaminate or aspartate.

If $R^1$ in the compounds (I) and (II) of this invention is an acidic radical such as a hydroxyl or carboxyl group, it can be converted to a corresponding pharmaceutically acceptable salt by the alkaline treatment according to a usual method. For instance, a salt of the compound (I) or (II) can be obtained by treating compound (I) or (II) with a corresponding base for 5 to 30 minutes in a solvent (e.g., ethers, ether or tetrahydrofuran in particular) at the room temperature and either filtering the precipitated crystals or removing the solvent by evaporation under reduced pressure. Such a salt may be an alkali metal salt such as a sodium or a potassium salt, an alkali earth metal salt such as a calcium or a magnesium salt, or an organic amine salt such as guanidine, triethylamine or dicyclohexylamine.

The compound (I) or (II) of this invention or their salts may absorb moisture, adsorb water or become a hydrate by leaving them in the air or by recrystallization and these salts containing water-molecules are also included in this invention.

The compound (I) or (II) of this invention or their salts may contain asymmetric carbons in their molecules and, thus, stereoisomers of R- and S-configuration may exist. These respective compounds as well as their mixture in an arbitrary ratio are also included in the invention.

The following compounds are preferred as the compound (I) in this invention;

(1) these compounds with $R^1$ being hydrogen, halogen, $C_1$–$C_4$ alkyl, fluoromethyl, difluoromethyl, trifluoromethyl, 2-fluoroethyl, 2-chloroethyl, 2,2,2-trifluoroethyl, methoxymethyl, methoxyethyl, $C_1$–$C_4$ alkoxy, fluoromethoxy, chloromethoxy, difluoromethoxy, dichloromethoxy, trifluoromethoxy, trichloromethoxy, 1-fluoroethoxy, 2-fluoroethoxy, 2-chloroethoxy, 2,2,2-trifluoroethoxy, hydroxy, $C_1$–$C_4$ alkylthio, amino, mono $C_1$–$C_4$ alkylamino, di $C_1$–$C_4$ alkylamino, formyl, acetyl, formylamino, acetylamino, $C_1$–$C_4$ alkanoyloxy, $C_1$–$C_4$ alkoxycarbonyl, carboxy, (methylthio)thiocarbonyl, (ethylthio)thiocarbonyl, carbamoyl, methylcarbamoyl, ethylcarbamoyl, dimethylcarbamoyl, diethylcarbamoyl, nitro or cyano radical.

(2) these compounds with $R^1$ being hydrogen, halogen, $C_1$–$C_4$ alkyl, fluoromethyl, difluoromethyl, trifluoromethyl, 2-fluoroethyl, 2,2,2-trifluoroethyl, methoxymethyl, methoxyethyl, $C_1$–$C_4$ alkoxy, difluoromethoxy, hydroxy, $C_1$–$C_4$ alkylthio, amino, methylamino, ethylamino, dimethylamino, diethylamino, (3) these compounds with $R^1$ being hydrogen, fluorine, chlorine, bromine, methyl, ethyl, trifluoromethyl, methoxy, ethoxy, difluoromethoxy, hydroxy, methylthio, ethylthio, amino, methylamino, ethylamino, dimethylamino, formyloxy, acetyloxy, methoxycarbonyl, ethoxycarbonyl, carboxy, carbamoyl, nitro or cyano radical.
(4) these compounds with $R^1$ being hydrogen, fluorine, chlorine, bromine, methyl, methoxy, methylthio, difluoromethoxy, methoxycarbonyl, nitro or cyano radical.
(5) these compounds with m being 2.
(6) these compounds with m being 1.
(7) these compounds with n being 2 to 4.
(8) these compounds with n being 2.
(9) these compounds with the ring A being phenyl, naphthyl, furyl, thienyl, pyrrolyl, imidazolyl, pyrazolyl, thiazolyl, isothiazolyl, oxazolyl, isoxazolyl, pyridyl, pyrazinyl, pyrimidinyl or pyridazinyl ring.
(10) these compounds with the ring A being phenyl, naphthyl or pyridyl ring.
(11) these compounds with the ring A being phenyl or pyridyl ring.
(12) these compounds with the ring A being phenyl ring.
(13) these compounds with X being an oxygen.
(14) 3-(2-aminoethoxy)benzisoxazole,
  3-(2-aminoethylthio)benzisoxazole,
  3-(2-aminoethoxy)-fluorobenzisoxazole,
  3-(2-aminoethylthio)-fluorobenzisoxazole,
  3-(2-aminoethoxy)-fluoro-methylbenzisoxazole,
  3-(2-aminoethylthio)-fluoro-methylbenzisoxazole,
  3-(2-aminoethoxy)-fluoro-methylthiobenzisoxazole,
  3-(2-aminoethoxy)-fluoro-methoxycarbonylbenzisoxazole,
  3-(2-aminoethoxy)-fluoro-carbamoylbenzisoxazole,
  3-(2-aminoethoxy)-fluoro-cyanobenzisoxazole,
  3-(2-aminoethylthio)-fluoro-cyanobenzisoxazole,
  3-(2-aminoethoxy)-chlorobenzisoxazole,
  3-(2-aminoethylthio)chlorobenzisoxazole,
  3-(2-aminoethoxy)-dichlrobenzisoxazole,
  3-(2-aminoethylthio)-dichlorobenzisoxazole,
  3-(2-aminoethoxy)-chloro-methylbenzisoxazole,
  3-(2-aminoethylthio)-chloro-methylbenzisoxazole,
  3-(2-aminoethoxy)-chloro-carbamoylbenzisoxazole,
  3-(2-aminoethoxy)-chloro-cyanobenzisoxazole,
  3-(2-aminoethylthio)-chloro-cyanobenzisoxazole,
  3-(2-aminoethoxy)-dichloro-methylbenzisoxazole,
  3-(2-aminoethoxy)-bromobenzisoxazole,
  3-(2-aminoethoxy)-bromo-methylbenzisoxazole,
  3-(2-aminoethoxy)-methylbenzisoxazole,
  3-(2-aminoethylthio)-methylbenzisoxazole,
  3-(2-aminoethoxy)-dimethylbenzisoxazole,
  3-(2-aminoethoxy)-methyl-methoxybenzisoxazole,
  3-(2-aminoethoxy)-methyl-methylthiobenzisoxazole,
  3-(2-aminoethoxy)-methyl-methoxycarbonylbenzisoxazole,
  3-(2-aminoethoxy)-methyl-carbamoylbenzisoxazole,
  3-(2-aminoethoxy)-methyl-cyanobenzisoxazole,
  3-(2-aminoethoxy)-trifluoromethylbenzisoxazole,
  3-(2-aminoethoxy)-methoxybenzisoxazole,
  3-(2-aminoethylthio)-methoxybenzisoxazole,
  3-(2-aminoethoxy)-difluoromethoxybenzisoxazole,
  3-(2-aminoethoxy)-hydroxybenzisoxazole,
  3-(2-aminoethoxy)-aminobenzisoxazole,
  3-(2-aminoethylthio)-aminobenzisoxazole,
  3-(2-aminoethoxy)-methylaminobenzisoxazole,
  3-(2-aminoethoxy)-dimethylaminobenzisoxazole,
  3-(2-aminoethoxy)-acetyloxybenzisoxazole,
  3-(2-aminoethoxy)-carboxybenzisoxazole,
  3-(2-aminoethoxy)-methoxycarbonylbenzisoxazole,
  3-(2-aminoethoxy)-carbamoylbenzisoxazole,
  3-(2-aminoethoxy)-nitrobenzisoxazole,
  3-(2-aminoethylthio)-nitrobenzisoxazole,
  3-(2-aminoethoxy)-cyanobenzisoxazole,
  3-(2-aminoethoxy)-naphthoisoxazole,
  3-(2-aminoethoxy)-pyridoisoxazole,
  3-(2-aminoethoxy)-chloropyridoisoxazole,
  3-(2-aminoethylthio)-chloropyridoisoxazole,
  3-(2-aminoethoxy)-methylpyridoisoxazole, or
  3-(2-aminoethoxy)-trifluoromethylpyridoisoxazole can be given.

Those of any combination of 1 to 5 selected from the groups (1)–(4), (5)–(6), (7)–(8), (9)–(12) and (13) are also favorable and the following combinations are given as examples.
(15) (1) and (7),
(16) (2), (7) and (9),
(17) (2), (8) and (10),
(18) (3), (8) and (10),
(19) (3), (5), (8) and (11),
(20) (4), (8) and (10),
(21) (4), (5), (8) and (11),
(22) (4), (5), (8) and (12).

The following compounds are preferred as the compound (II), an active component of a monoamineoxidase inhibitor in this invention;
(1) these compounds with $R^1$ being hydrogen, halogen, $C_1$–$C_4$ alkyl, fluoromethyl, difluoromethyl, trifluoromethyl, 2-fluoroethyl, 2-chloroethyl, 2,2,2-trifluoroethyl, methoxymethyl, methoxyethyl, $C_1$–$C_4$ alkoxy, fluoromethoxy, chloromethoxy, difluoromethoxy, dichloromethoxy, trifluoromethoxy, trichloromethoxy, 1-fluoroethoxy, 2-fluoroethoxy, 2-chloroethoxy, 2,2,2-trifluoroethoxy, hydroxy, $C_1$–$C_4$ alkylthio, amino, mono $C_1$–$C_4$ alkylamino, di $C_1$–$C_4$ alkylamino, formyl, acetyl, formylamino, acetylamino, $C_1$–$C_4$ alkanoyloxy, $C_1$–$C_4$ alkoxycarbonyl, carboxy, (methylthio)thiocarbonyl, (ethylthio)thiocarbonyl, carbamoyl, methylcarbamoyl, ethylcarbamoyl, dimethylcarbamoyl, diethylcarbamoyl, nitro or cyano radical.
(2) these compounds with $R^1$ being hydrogen, halogen, $C_1$–$C_4$ alkyl, fluoromethyl, difluoromethyl, trifluoromethyl, 2-fluoroethyl, 2,2,2-trifluoroethyl, methoxymethyl, methoxyethyl, $C_1$–$C_4$ alkoxy, difluoromethoxy, hydroxy, $C_1$–$C_4$ alkylthio, amino, methylamino, ethylamino, dimethylamino, diethylamino, formyl, acetyl, formylamino, acetylamino, $C_1$–$C_4$ alkoxycarbonyl, carboxy, carbamoyl, methylcarbamoyl, ethylcarbamoyl, dimethylcarbamoyl, diethylcarbamoyl, nitro or cyano radical.
(3) these compounds with $R^1$ being hydrogen, fluorine, chlorine, bromine, methyl, ethyl, trifluoromethyl, methoxy, ethoxy, difluoromethoxy, hydroxy, methylthio, ethylthio, amino, methylamino, ethylamino, dimethylamino, formyloxy, acetyloxy, methoxycarbonyl, ethoxycarbonyl, carboxy, carbamoyl, nitro or cyano radical.

(4) these compounds with $R^1$ being hydrogen, fluorine, chlorine, bromine, methyl, methoxy, methylthio, difluoromethoxy, methoxycarbonyl, nitro or cyano radical.

(5) these compounds with $R^2a$ being amino, methylamino, dimethylamino, piperidinyl, or morpholinyl radical.

(6) these compounds with $R^2a$ being amino, piperidinyl or morpholinyl radical.

(7) these compounds with $R^2a$ being amino radical.

(8) these compounds with m being 2.

(9) these compounds with m being 1.

(10) these compounds with n being 2 to 4.

(11) these compounds with n being 2.

(12) these compounds with the ring A being phenyl, naphthyl, furyl, thienyl, pyrrolyl, imidazolyl, pyrazolyl, thiazolyl, isothiazolyl, oxazolyl, isoxazolyl, pyridyl, pyrazinyl, pyrimidinyl or pyridazinyl ring.

(13) these compounds with the ring A being phenyl, naphthyl or pyridyl ring.

(14) these compounds with the ring A being phenyl or pyridyl ring.

(15) these compounds with the ring A being phenyl ring.

(16) these compounds with X being an oxygen.

(17) 3-(2-aminoethoxy)benzisoxazole, 3-(2-aminoethylthio)benzisoxazole, 3-(2-aminoethoxy)-fluorobenzisoxazole, 3-(2-aminoethylthio)-fluorobenzisoxazole, 3-(2-aminoethoxy)-fluoro-methylbenzisoxazole, 3-(2-aminoethylthio)-fluoro-methylbenzisoxazole, 3-(2-aminoethoxy)-fluoro-methylthiobenzisoxazole, 3-(2-aminoethoxy)-fluoro-methoxycarbonylbenzisoxazole, 3-(2-aminoethoxy)-fluoro-carbamoylbenzisoxazole, 3-(2-aminoethoxy)-fluoro-cyanobenzisoxazole, 3-(2-aminoethylthio)-fluoro-cyanobenzisoxazole, 3-(2-aminoethoxy)-chlorobenzisoxazole, 3-(2-aminoethylthio)chlorobenzisoxazole, 3-(2-aminoethoxy)-dichlrobenzisoxazole, 3-(2-aminoethylthio)-dichlorobenzisoxazole, 3-(2-aminoethoxy)-chloro-methylbenzisoxazole, 3-(2-aminoethylthio)-chloro-methylbenzisoxazole, 3-(2-aminoethoxy)-chloro-carbamoylbenzisoxazole, 3-(2-aminoethoxy)-chloro-cyanobenzisoxazole, 3-(2-aminoethylthio)-chloro-cyanobenzisoxazole, 3-(2-aminoethoxy)-dichloro-methylbenzisoxazole, 3-(2-aminoethoxy)-bromobenzisoxazole, 3-(2-aminoethoxy)-bromo-methylbenzisoxazole, 3-(2-aminoethoxy)-methylbenzisoxazole, 3-(2-aminoethylthio)-methylbenzisoxazole, 3-(2-aminoethoxy)-dimethylbenzisoxazole, 3-(2-aminoethoxy)-methyl-methoxybenzisoxazole, 3-(2-aminoethoxy)-methyl-methylthiobenzisoxazole, 3-(2-aminoethoxy)-methyl-methoxycarbonylbenzisoxazole, 3-(2-aminoethoxy)-methyl-carbamoylbenzisoxazole, 3-(2-aminoethoxy)-methyl-cyanobenzisoxazole, 3-(2-aminoethoxy)-trifluoromethylbenzisoxazole, 3-(2-aminoethoxy)-methoxybenzisoxazole, 3-(2-aminoethylthio)-methoxybenzisoxazole, 3-(2-aminoethoxy)-difluoromethoxybenzisoxazole, 3-(2-aminoethoxy)-hydroxybenzisoxazole, 3-(2-aminoethoxy)-aminobenzisoxazole, 3-(2-aminoethylthio)-aminobenzisoxazole, 3-(2-aminoethoxy)-methylaminobenzisoxazole, 3-(2-aminoethoxy)-dimethylaminobenzisoxazole, 3-(2-aminoethoxy)-acetyloxybenzisoxazole, 3-(2-aminoethoxy)-carboxybenzisoxazole, 3-(2-aminoethoxy)-methoxycarbonylbenzisoxazole, 3-(2-aminoethoxy)-carbamoylbenzisoxazole, 3-(2-aminoethoxy)-nitrobenzisoxazole, 3-(2-aminoethylthio)-nitrobenzisoxazole, 3-(2-aminoethoxy)-cyanobenzisoxazole, 3-(2-aminoethoxy)-naphthoisoxazole, 3-(2-aminoethoxy)-pyridoisoxazole, 3-(2-aminoethoxy)-chloropyridoisoxazole, 3-(2-aminoethylthio)-chloropyridoisoxazole, 3-(2-aminoethoxy)-methylpyridoisoxazole, or 3-(2-aminoethoxy)-trifluoromethylpyridoisoxazole can be given.

Those of any combination of 1 to 6 selected from the groups (1)–(4), (5)–(7), (8)–(9), (10)–(11), (12)–(15) and (16) are also favorable and the following combinations are given as examples.

(17) (1), (5) and (10),

(18) (2), (7), (10) and (12),

(19) (2), (7), (11) and (13),

(20) (3), (7), (11) and (13),

(21) (3), (7), (8), (11) and (14),

(22) (4), (7), (11) and (13),

(23) (4), (7), (8), (11) and (14),

(24) (4), (7), (8), (11) and (15).

The compounds in the following tables can be given as typical compounds of this invention but it is not restricted to these compounds.

Abbreviations in the table are as follows.

Ac: acetyl

Et: ethyl

Me: methyl

Ph: phenyl

Pip: piperidino $Pr^i$: isopropyl

Mor: morpholino provided that $(R^1)_m$ shows 1, 2 or 3 substituted radicals on the ring A in all.

TABLE 1

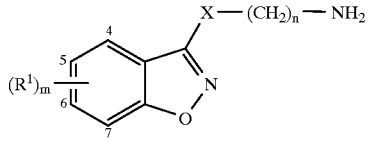

(Ia)

| Compound No. | $(R^1)_m$ | n | X |
|---|---|---|---|
| 1-1 | H | 1 | O |
| 1-2 | H | 1 | S |
| 1-3 | H | 2 | O |
| 1-4 | H | 2 | S |
| 1-5 | H | 3 | O |
| 1-6 | H | 3 | S |
| 1-7 | H | 4 | O |
| 1-8 | H | 4 | S |
| 1-9 | H | 5 | O |
| 1-10 | H | 5 | S |
| 1-11 | H | 6 | O |
| 1-12 | H | 6 | S |
| 1-13 | 4-F | 2 | O |
| 1-14 | 4-F | 2 | S |
| 1-15 | 5-F | 2 | O |
| 1-16 | 5-F 4-F | 2 | O |
| 1-17 | 5-F 6-F | 2 | O |
| 1-18 | 5-F 7-F | 2 | O |
| 1-19 | 5-F 4-Cl | 2 | O |
| 1-20 | 5-F 6-Cl | 2 | O |
| 1-21 | 5-F 7-Cl | 2 | O |
| 1-22 | 5-F 4-Me | 2 | O |
| 1-23 | 5-F 6-Me | 2 | O |
| 1-24 | 5-F 7-Me | 2 | O |
| 1-25 | 5-F 4-OMe | 2 | O |
| 1-26 | 5-F 6-OMe | 2 | O |
| 1-27 | 5-F 7-OMe | 2 | O |
| 1-28 | 5-F 4-CN | 2 | O |
| 1-29 | 5-F 6-CN | 2 | O |
| 1-30 | 5-F 7-CN | 2 | O |
| 1-31 | 5-F | 2 | S |
| 1-32 | 5-F 4-F | 2 | S |
| 1-33 | 5-F 6-F | 2 | S |
| 1-34 | 5-F 7-F | 2 | S |
| 1-35 | 5-F 4-Cl | 2 | S |
| 1-36 | 5-F 6-Cl | 2 | S |
| 1-37 | 5-F 7-Cl | 2 | S |
| 1-38 | 5-F 4-Me | 2 | S |
| 1-39 | 5-F 6-Me | 2 | S |
| 1-40 | 5-F 7-Me | 2 | S |
| 1-41 | 5-F 4-OMe | 2 | S |
| 1-42 | 5-F 6-OMe | 2 | S |
| 1-43 | 5-F 7-OMe | 2 | S |
| 1-44 | 5-F 4-CN | 2 | S |
| 1-45 | 5-F 6-CN | 2 | S |
| 1-46 | 5-F 7-CN | 2 | S |
| 1-47 | 6-F | 2 | O |
| 1-48 | 6-F | 2 | S |
| 1-49 | 7-F | 2 | O |
| 1-50 | 7-F | 2 | S |
| 1-51 | 4-Cl | 2 | O |
| 1-52 | 4-Cl | 2 | S |
| 1-53 | 5-Cl | 2 | O |
| 1-54 | 5-Cl 4-F | 2 | O |
| 1-55 | 5-Cl 6-F | 2 | O |
| 1-56 | 5-Cl 7-F | 2 | O |
| 1-57 | 5-Cl 4-Cl | 2 | O |
| 1-58 | 5-Cl 6-Cl | 2 | O |
| 1-59 | 5-Cl 7-Cl | 2 | O |
| 1-60 | 5-Cl 4-Me | 2 | O |
| 1-61 | 5-Cl 6-Me | 2 | O |
| 1-62 | 5-Cl 7-Me | 2 | O |
| 1-63 | 5-Cl 4-OMe | 2 | O |
| 1-64 | 5-Cl 6-OMe | 2 | O |
| 1-65 | 5-Cl 7-OMe | 2 | O |
| 1-66 | 5-Cl 4-CN | 2 | O |
| 1-67 | 5-Cl 6-CN | 2 | O |

TABLE 1-continued

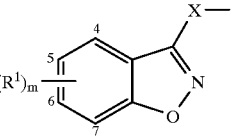

(Ia)

| Compound No. | $(R^1)_m$ | n | X |
|---|---|---|---|
| 1-68 | 5-Cl 7-CN | 2 | O |
| 1-69 | 5-Cl | 2 | S |
| 1-70 | 5-Cl 4-F | 2 | S |
| 1-71 | 5-Cl 6-F | 2 | S |
| 1-72 | 5-Cl 7-F | 2 | S |
| 1-73 | 5-Cl 4-Cl | 2 | S |
| 1-74 | 5-Cl 6-Cl | 2 | S |
| 1-75 | 5-Cl 7-Cl | 2 | S |
| 1-76 | 5-Cl 4-Me | 2 | S |
| 1-77 | 5-Cl 6-Me | 2 | S |
| 1-78 | 5-Cl 7-Me | 2 | S |
| 1-79 | 5-Cl 4-OMe | 2 | S |
| 1-80 | 5-Cl 6-OMe | 2 | S |
| 1-81 | 5-Cl 7-OMe | 2 | S |
| 1-82 | 5-Cl 4-CN | 2 | S |
| 1-83 | 5-Cl 6-CN | 2 | S |
| 1-84 | 5-Cl 7-CN | 2 | S |
| 1-85 | 6-Cl | 2 | O |
| 1-86 | 6-Cl 7-Cl | 2 | O |
| 1-87 | 6-Cl 4-Me | 2 | O |
| 1-88 | 6-Cl 5-Me | 2 | O |
| 1-89 | 6-Cl 7-Me | 2 | O |
| 1-90 | 6-Cl 4-OMe | 2 | O |
| 1-91 | 6-Cl 5-OMe | 2 | O |
| 1-92 | 6-Cl 7-OMe | 2 | O |
| 1-93 | 6-Cl 4-CN | 2 | O |
| 1-94 | 6-Cl 5-CN | 2 | O |
| 1-95 | 6-Cl 7-CN | 2 | O |
| 1-96 | 6-Cl | 2 | S |
| 1-97 | 7-Cl | 2 | O |
| 1-98 | 7-Cl 4-Me | 2 | O |
| 1-99 | 7-Cl 5-Me | 2 | O |
| 1-100 | 7-Cl 6-Me | 2 | O |
| 1-101 | 7-Cl 4-OMe | 2 | O |
| 1-102 | 7-Cl 5-OMe | 2 | O |
| 1-103 | 7-Cl 6-OMe | 2 | O |
| 1-104 | 7-Cl 4-CN | 2 | O |
| 1-105 | 7-Cl 5-CN | 2 | O |
| 1-106 | 7-Cl 6-CN | 2 | O |
| 1-107 | 7-Cl | 2 | S |
| 1-108 | 7-Cl 4-Me | 2 | S |
| 1-109 | 7-Cl 5-Me | 2 | S |
| 1-110 | 7-Cl 6-Me | 2 | S |
| 1-111 | 7-Cl 4-OMe | 2 | S |
| 1-112 | 7-Cl 5-OMe | 2 | S |
| 1-113 | 7-Cl 6-OMe | 2 | S |
| 1-114 | 7-Cl 4-CN | 2 | S |
| 1-115 | 7-Cl 5-CN | 2 | S |
| 1-116 | 7-Cl 6-CN | 2 | S |
| 1-117 | 4-Br | 2 | O |
| 1-118 | 4-Br | 2 | S |
| 1-119 | 5-Br | 2 | O |
| 1-120 | 5-Br 4-F | 2 | O |
| 1-121 | 5-Br 6-F | 2 | O |
| 1-122 | 5-Br 7-F | 2 | O |
| 1-123 | 5-Br 4-Cl | 2 | O |
| 1-124 | 5-Br 6-Cl | 2 | O |
| 1-125 | 5-Br 7-Cl | 2 | O |
| 1-126 | 5-Br 4-Me | 2 | O |
| 1-127 | 5-Br 6-Me | 2 | O |
| 1-128 | 5-Br 7-Me | 2 | O |
| 1-129 | 5-Br 4-OMe | 2 | O |
| 1-130 | 5-Br 6-OMe | 2 | O |
| 1-131 | 5-Br 7-OMe | 2 | O |
| 1-132 | 5-Br 4-CN | 2 | O |
| 1-133 | 5-Br 6-CN | 2 | O |
| 1-134 | 5-Br 7-CN | 2 | O |

TABLE 1-continued

Structure (Ia): benzisoxazole with X—(CH₂)ₙ—NH₂ at position 3, (R¹)ₘ on benzene ring positions 4,5,6,7.

| Compound No. | (R¹)ₘ | n | X |
|---|---|---|---|
| 1-135 | 5-Br | 2 | S |
| 1-136 | 6-Br | 2 | O |
| 1-137 | 6-Br | 2 | S |
| 1-138 | 7-Br | 2 | O |
| 1-139 | 7-Br | 2 | S |
| 1-140 | 4-Me | 2 | O |
| 1-141 | 4-Me | 2 | S |
| 1-142 | 5-Me | 2 | O |
| 1-143 | 5-Me 6-Me | 2 | O |
| 1-144 | 5-Me 7-Me | 2 | O |
| 1-145 | 5-Me 4-OMe | 2 | O |
| 1-146 | 5-Me 6-OMe | 2 | O |
| 1-147 | 5-Me 7-OMe | 2 | O |
| 1-148 | 5-Me 4-CN | 2 | O |
| 1-149 | 5-Me 6-CN | 2 | O |
| 1-150 | 5-Me 7-CN | 2 | O |
| 1-151 | 5-Me | 2 | S |
| 1-152 | 5-Me 6-Me | 2 | S |
| 1-153 | 5-Me 7-Me | 2 | S |
| 1-154 | 5-Me 4-OMe | 2 | S |
| 1-155 | 5-Me 6-OMe | 2 | S |
| 1-156 | 5-Me 7-OMe | 2 | S |
| 1-157 | 5-Me 4-CN | 2 | S |
| 1-158 | 5-Me 6-CN | 2 | S |
| 1-159 | 5-Me 7-CN | 2 | S |
| 1-160 | 6-Me | 2 | O |
| 1-161 | 6-Me 7-Me | 2 | O |
| 1-162 | 6-Me 4-OMe | 2 | O |
| 1-163 | 6-Me 5-OMe | 2 | O |
| 1-164 | 6-Me 7-OMe | 2 | O |
| 1-165 | 6-Me 4-CN | 2 | O |
| 1-166 | 6-Me 5-CN | 2 | O |
| 1-167 | 6-Me 7-CN | 2 | O |
| 1-168 | 6-Me | 2 | S |
| 1-169 | 7-Me | 2 | O |
| 1-170 | 7-Me 4-OMe | 2 | O |
| 1-171 | 7-Me 5-OMe | 2 | O |
| 1-172 | 7-Me 6-OMe | 2 | O |
| 1-173 | 7-Me 4-CN | 2 | O |
| 1-174 | 7-Me 5-CN | 2 | O |
| 1-175 | 7-Me 6-CN | 2 | O |
| 1-176 | 7-Me | 2 | S |
| 1-177 | 7-Me 4-OMe | 2 | S |
| 1-178 | 7-Me 5-OMe | 2 | S |
| 1-179 | 7-Me 6-OMe | 2 | S |
| 1-180 | 7-Me 4-CN | 2 | S |
| 1-181 | 7-Me 5-CN | 2 | S |
| 1-182 | 7-Me 6-CN | 2 | S |
| 1-183 | 4-Et | 2 | O |
| 1-184 | 4-Et | 2 | S |
| 1-185 | 5-Et | 2 | O |
| 1-186 | 5-Et | 2 | S |
| 1-187 | 6-Et | 2 | O |
| 1-188 | 6-Et | 2 | S |
| 1-189 | 7-Et | 2 | O |
| 1-190 | 7-Et | 2 | S |
| 1-191 | 4-OMe | 2 | O |
| 1-192 | 4-OMe | 2 | S |
| 1-193 | 5-OMe | 2 | O |
| 1-194 | 5-OMe 4-CN | 2 | O |
| 1-195 | 5-OMe 6-CN | 2 | O |
| 1-196 | 5-OMe 7-CN | 2 | O |
| 1-197 | 5-OMe | 2 | S |
| 1-198 | 6-OMe | 2 | O |
| 1-199 | 6-OMe | 2 | S |
| 1-200 | 7-OMe | 2 | O |
| 1-201 | 7-OMe 4-Me | 2 | O |
| 1-202 | 7-OMe 5-OMe | 2 | O |
| 1-203 | 7-OMe 6-OMe | 2 | O |
| 1-204 | 7-OMe 4-CN | 2 | O |
| 1-205 | 7-OMe 5-CN | 2 | O |
| 1-206 | 7-OMe 6-CN | 2 | O |
| 1-207 | 7-OMe | 2 | S |
| 1-208 | 7-OMe 4-Me | 2 | S |
| 1-209 | 7-OMe 5-OMe | 2 | S |
| 1-210 | 7-OMe 6-Me | 2 | S |
| 1-211 | 7-OMe 4-CN | 2 | S |
| 1-212 | 7-OMe 5-CN | 2 | S |
| 1-213 | 7-OMe 6-CN | 2 | S |
| 1-214 | 4-OEt | 2 | O |
| 1-215 | 4-OEt | 2 | S |
| 1-216 | 5-OEt | 2 | O |
| 1-217 | 5-OEt | 2 | S |
| 1-218 | 6-OEt | 2 | O |
| 1-219 | 6-OEt | 2 | S |
| 1-220 | 7-OEt | 2 | O |
| 1-221 | 7-OEt | 2 | S |
| 1-222 | 4-OCHF$_2$ | 2 | O |
| 1-223 | 4-OCHF$_2$ | 2 | S |
| 1-224 | 5-OCHF$_2$ | 2 | O |
| 1-225 | 5-OCHF$_2$ 4-F | 2 | O |
| 1-226 | 5-OCHF$_2$ 6-F | 2 | O |
| 1-227 | 5-OCHF$_2$ 7-F | 2 | O |
| 1-228 | 5-OCHF$_2$ 4-Cl | 2 | O |
| 1-229 | 5-OCHF$_2$ 6-Cl | 2 | O |
| 1-230 | 5-OCHF$_2$ 7-Cl | 2 | O |
| 1-231 | 5-OCHF$_2$ 4-Me | 2 | O |
| 1-232 | 5-OCHF$_2$ 6-Me | 2 | O |
| 1-233 | 5-OCHF$_2$ 7-Me | 2 | O |
| 1-234 | 5-OCHF$_2$ 4-OMe | 2 | O |
| 1-235 | 5-OCHF$_2$ 6-OMe | 2 | O |
| 1-236 | 5-OCHF$_2$ 7-OMe | 2 | O |
| 1-237 | 5-OCHF$_2$ 4-CN | 2 | O |
| 1-238 | 5-OCHF$_2$ 6-CN | 2 | O |
| 1-239 | 5-OCHF$_2$ 7-CN | 2 | O |
| 1-240 | 5-OCHF$_2$ | 2 | S |
| 1-241 | 6-OCHF$_2$ | 2 | O |
| 1-242 | 6-OCHF$_2$ | 2 | S |
| 1-243 | 7-OCHF$_2$ | 2 | O |
| 1-244 | 7-OCHF$_2$ | 2 | S |
| 1-245 | 4-OH | 2 | O |
| 1-246 | 4-OH | 2 | S |
| 1-247 | 5-OH | 2 | O |
| 1-248 | 5-OH 4-F | 2 | O |
| 1-249 | 5-OH 6-F | 2 | O |
| 1-250 | 5-OH 7-F | 2 | O |
| 1-251 | 5-OH 4-Cl | 2 | O |
| 1-252 | 5-OH 6-Cl | 2 | O |
| 1-253 | 5-OH 7-Cl | 2 | O |
| 1-254 | 5-OH 4-Me | 2 | O |
| 1-255 | 5-OH 6-Me | 2 | O |
| 1-256 | 5-OH 7-Me | 2 | O |
| 1-257 | 5-OH 4-OMe | 2 | O |
| 1-258 | 5-OH 6-OMe | 2 | O |
| 1-259 | 5-OH 7-OMe | 2 | O |
| 1-260 | 5-OH 4-CN | 2 | O |
| 1-261 | 5-OH 6-CN | 2 | O |
| 1-262 | 5-OH 7-CN | 2 | O |
| 1-263 | 5-OH | 2 | S |
| 1-264 | 6-OH | 2 | O |
| 1-265 | 6-OH | 2 | S |
| 1-266 | 7-OH | 2 | O |
| 1-267 | 7-OH | 2 | S |
| 1-268 | 4-SMe | 2 | O |

TABLE 1-continued $$\text{(R}^1\text{)}_m \underset{6}{\overset{5}{\underset{7}{\bigg|}}} \overset{4}{\underset{\text{N}}{\bigg|}} \overset{X-(CH_2)_n-NH_2}{\underset{\text{O}}{\bigg|}}$$

(Ia)

| Compound No. | (R¹)ₘ | n | X |
|---|---|---|---|
| 1-269 | 4-SMe 5-F | 2 | O |
| 1-270 | 4-SMe 6-F | 2 | O |
| 1-271 | 4-SMe 7-F | 2 | O |
| 1-272 | 4-SMe 5-Cl | 2 | O |
| 1-273 | 4-SMe 6-Cl | 2 | O |
| 1-274 | 4-SMe 7-Cl | 2 | O |
| 1-275 | 4-SMe 5-Me | 2 | O |
| 1-276 | 4-SMe 6-Me | 2 | O |
| 1-277 | 4-SMe 7-Me | 2 | O |
| 1-278 | 4-SMe 5-OMe | 2 | O |
| 1-279 | 4-SMe 6-OMe | 2 | O |
| 1-280 | 4-SMe 7-OMe | 2 | O |
| 1-281 | 4-SMe 5-CN | 2 | O |
| 1-282 | 4-SMe 6-CN | 2 | O |
| 1-283 | 4-SMe 7-CN | 2 | O |
| 1-284 | 4-SMe | 2 | S |
| 1-285 | 5-SMe | 2 | O |
| 1-286 | 5-SMe | 2 | S |
| 1-287 | 6-SMe | 2 | O |
| 1-288 | 6-SMe | 2 | S |
| 1-289 | 7-SMe | 2 | O |
| 1-290 | 7-SMe | 2 | S |
| 1-291 | 4-NH₂ | 2 | O |
| 1-292 | 4-NH₂ | 2 | S |
| 1-293 | 5-NH₂ | 2 | O |
| 1-294 | 5-NH₂ | 2 | S |
| 1-295 | 5-NH₂ 4-F | 2 | S |
| 1-296 | 5-NH₂ 6-F | 2 | S |
| 1-297 | 5-NH₂ 7-F | 2 | S |
| 1-298 | 5-NH₂ 4-Cl | 2 | S |
| 1-299 | 5-NH₂ 6-Cl | 2 | S |
| 1-300 | 5-NH₂ 7-Cl | 2 | S |
| 1-301 | 5-NH₂ 4-Me | 2 | S |
| 1-302 | 5-NH₂ 6-Me | 2 | S |
| 1-303 | 5-NH₂ 7-Me | 2 | S |
| 1-304 | 5-NH₂ 4-OMe | 2 | S |
| 1-305 | 5-NH₂ 6-OMe | 2 | S |
| 1-306 | 5-NH₂ 7-OMe | 2 | S |
| 1-307 | 5-NH₂ 4-CN | 2 | S |
| 1-308 | 5-NH₂ 6-CN | 2 | S |
| 1-309 | 5-NH₂ 7-CN | 2 | S |
| 1-310 | 6-NH₂ | 2 | O |
| 1-311 | 6-NH₂ | 2 | S |
| 1-312 | 7-NH₂ | 2 | O |
| 1-313 | 7-NH₂ 4-F | 2 | O |
| 1-314 | 7-NH₂ 5-F | 2 | O |
| 1-315 | 7-NH₂ 6-F | 2 | O |
| 1-316 | 7-NH₂ 4-Cl | 2 | O |
| 1-317 | 7-NH₂ 5-Cl | 2 | O |
| 1-318 | 7-NH₂ 6-Cl | 2 | O |
| 1-319 | 7-NH₂ 4-Me | 2 | O |
| 1-320 | 7-NH₂ 5-Me | 2 | O |
| 1-321 | 7-NH₂ 6-Me | 2 | O |
| 1-322 | 7-NH₂ 4-OMe | 2 | O |
| 1-323 | 7-NH₂ 5-OMe | 2 | O |
| 1-324 | 7-NH₂ 6-OMe | 2 | O |
| 1-325 | 7-NH₂ 4-CN | 2 | O |
| 1-326 | 7-NH₂ 5-CN | 2 | O |
| 1-327 | 7-NH₂ 6-CN | 2 | O |
| 1-328 | 7-NH₂ | 2 | S |
| 1-329 | 7-NH₂ 4-F | 2 | S |
| 1-330 | 7-NH₂ 5-F | 2 | S |
| 1-331 | 7-NH₂ 6-F | 2 | S |
| 1-332 | 7-NH₂ 4-Cl | 2 | S |
| 1-333 | 7-NH₂ 5-Cl | 2 | S |
| 1-334 | 7-NH₂ 6-Cl | 2 | S |
| 1-335 | 7-NH₂ 4-Me | 2 | S |
| 1-336 | 7-NH₂ 5-Me | 2 | S |
| 1-337 | 7-NH₂ 6-Me | 2 | S |
| 1-338 | 7-NH₂ 4-OMe | 2 | S |
| 1-339 | 7-NH₂ 5-OMe | 2 | S |
| 1-340 | 7-NH₂ 6-OMe | 2 | S |
| 1-341 | 7-NH₂ 4-CN | 2 | S |
| 1-342 | 7-NH₂ 5-CN | 2 | S |
| 1-343 | 7-NH₂ 6-CN | 2 | S |
| 1-344 | 4-NHMe | 2 | O |
| 1-345 | 4-NHMe | 2 | S |
| 1-346 | 5-NHMe | 2 | O |
| 1-347 | 5-NHMe 4-F | 2 | O |
| 1-348 | 5-NHMe 6-F | 2 | O |
| 1-349 | 5-NHMe 7-F | 2 | O |
| 1-350 | 5-NHMe 4-Cl | 2 | O |
| 1-351 | 5-NHMe 6-Cl | 2 | O |
| 1-352 | 5-NHMe 7-Cl | 2 | O |
| 1-353 | 5-NHMe 4-Me | 2 | O |
| 1-354 | 5-NHMe 6-Me | 2 | O |
| 1-355 | 5-NHMe 7-Me | 2 | O |
| 1-356 | 5-NHMe 4-OMe | 2 | O |
| 1-357 | 5-NHMe 6-OMe | 2 | O |
| 1-358 | 5-NHMe 7-OMe | 2 | O |
| 1-359 | 5-NHMe 4-CN | 2 | O |
| 1-360 | 5-NHMe 6-CN | 2 | O |
| 1-361 | 5-NHMe 7-CN | 2 | O |
| 1-362 | 5-NHMe | 2 | S |
| 1-363 | 6-NHMe | 2 | O |
| 1-364 | 6-NHMe | 2 | S |
| 1-365 | 7-NHMe | 2 | O |
| 1-366 | 7-NHMe 4-F | 2 | O |
| 1-367 | 7-NHMe 5-F | 2 | O |
| 1-368 | 7-NHMe 6-F | 2 | O |
| 1-369 | 7-NHMe 4-Cl | 2 | O |
| 1-370 | 7-NHMe 5-Cl | 2 | O |
| 1-371 | 7-NHMe 6-Cl | 2 | O |
| 1-372 | 7-NHMe 4-Me | 2 | O |
| 1-373 | 7-NHMe 5-Me | 2 | O |
| 1-374 | 7-NHMe 6-Me | 2 | O |
| 1-375 | 7-NHMe 4-OMe | 2 | O |
| 1-376 | 7-NHMe 5-OMe | 2 | O |
| 1-377 | 7-NHMe 6-OMe | 2 | O |
| 1-378 | 7-NHMe 4-CN | 2 | O |
| 1-379 | 7-NHMe 5-CN | 2 | O |
| 1-380 | 7-NHMe 6-CN | 2 | O |
| 1-381 | 7-NHMe | 2 | S |
| 1-382 | 4-OAc | 2 | O |
| 1-383 | 4-OAc | 2 | S |
| 1-384 | 5-OAc | 2 | O |
| 1-385 | 5-OAc 4-F | 2 | O |
| 1-386 | 5-OAc 6-F | 2 | O |
| 1-387 | 5-OAc 7-F | 2 | O |
| 1-388 | 5-OAc 4-Cl | 2 | O |
| 1-389 | 5-OAc 6-Cl | 2 | O |
| 1-390 | 5-OAc 7-Cl | 2 | O |
| 1-391 | 5-OAc 4-Me | 2 | O |
| 1-392 | 5-OAc 6-Me | 2 | O |
| 1-393 | 5-OAc 7-Me | 2 | O |
| 1-394 | 5-OAc 4-OMe | 2 | O |
| 1-395 | 5-OAc 6-OMe | 2 | O |
| 1-396 | 5-OAc 7-OMe | 2 | O |
| 1-397 | 5-OAc 4-CN | 2 | O |
| 1-398 | 5-OAc 6-CN | 2 | O |
| 1-399 | 5-OAc 7-CN | 2 | O |
| 1-400 | 5-OAc | 2 | S |
| 1-401 | 6-OAc | 2 | O |
| 1 402 | 6-OAc | 2 | S |

TABLE 1-continued $$\text{(Ia)}$$

Structure: benzisoxazole with $(R^1)_m$ substituents at positions 4,5,6,7 and $X-(CH_2)_n-NH_2$ at position 3.

| Compound No. | $(R^1)_m$ | n | X |
|---|---|---|---|
| 1-403 | 7-OAc | 2 | O |
| 1-404 | 7-OAc | 2 | S |
| 1-405 | 4-COOMe | 2 | O |
| 1-406 | 4-COOMe 5-F | 2 | O |
| 1-407 | 4-COOMe 6-F | 2 | O |
| 1-408 | 4-COOMe 7-F | 2 | O |
| 1-409 | 4-COOMe 5-Cl | 2 | O |
| 1-410 | 4-COOMe 6-Cl | 2 | O |
| 1-411 | 4-COOMe 7-Cl | 2 | O |
| 1-412 | 4-COOMe 5-Me | 2 | O |
| 1-413 | 4-COOMe 6-Me | 2 | O |
| 1-414 | 4-COOMe 7-Me | 2 | O |
| 1-415 | 4-COOMe 5-OMe | 2 | O |
| 1-416 | 4-COOMe 6-OMe | 2 | O |
| 1-417 | 4-COOMe 7-OMe | 2 | O |
| 1-418 | 4-COOMe 5-CN | 2 | O |
| 1-419 | 4-COOMe 6-CN | 2 | O |
| 1-420 | 4-COOMe 7-CN | 2 | O |
| 1-421 | 4-COOMe | 2 | S |
| 1-422 | 5-COOMe | 2 | O |
| 1-423 | 5-COOMe 4-F | 2 | O |
| 1-424 | 5-COOMe 6-F | 2 | O |
| 1-425 | 5-COOMe 7-F | 2 | O |
| 1-426 | 5-COOMe 4-Cl | 2 | O |
| 1-427 | 5-COOMe 6-Cl | 2 | O |
| 1-428 | 5-COOMe 7-Cl | 2 | O |
| 1-429 | 5-COOMe 4-Me | 2 | O |
| 1-430 | 5-COOMe 6-Me | 2 | O |
| 1-431 | 5-COOMe 7-Me | 2 | O |
| 1-432 | 5-COOMe 4-OMe | 2 | O |
| 1-433 | 5-COOMe 6-OMe | 2 | O |
| 1-434 | 5-COOMe 7-OMe | 2 | O |
| 1-435 | 5-COOMe 4-CN | 2 | O |
| 1-436 | 5-COOMe 6-CN | 2 | O |
| 1-437 | 5-COOMe 7-CN | 2 | O |
| 1-438 | 5-COOMe | 2 | S |
| 1-439 | 6-COOMe | 2 | O |
| 1-440 | 6-COOMe | 2 | S |
| 1-441 | 7-COOMe | 2 | O |
| 1-442 | 7-COOMe 4-F | 2 | O |
| 1-443 | 7-COOMe 5-F | 2 | O |
| 1-444 | 7-COOMe 6-F | 2 | O |
| 1-445 | 7-COOMe 4-Cl | 2 | O |
| 1-446 | 7-COOMe 5-Cl | 2 | O |
| 1-447 | 7-COOMe 5-Br | 2 | O |
| 1-448 | 7-COOMe 4-Me | 2 | O |
| 1-449 | 7-COOMe 5-Me | 2 | O |
| 1-450 | 7-COOMe 6-Me | 2 | O |
| 1-451 | 7-COOMe 4-OMe | 2 | O |
| 1-452 | 7-COOMe 5-OMe | 2 | O |
| 1-453 | 7-COOMe 6-OMe | 2 | O |
| 1-454 | 7-COOMe 4-CN | 2 | O |
| 1-455 | 7-COOMe 5-CN | 2 | O |
| 1-456 | 7-COOMe 6-CN | 2 | O |
| 1-457 | 7-COOMe | 2 | S |
| 1-458 | 4-COOH | 2 | O |
| 1-459 | 4-COOH | 2 | S |
| 1-460 | 5-COOH | 2 | O |
| 1-461 | 5-COOH | 2 | S |
| 1-462 | 6-COOH | 2 | O |
| 1-463 | 6-COOH | 2 | S |
| 1-464 | 7-COOH | 2 | O |
| 1-465 | 5-CF$_3$ 4-Me | 2 | O |
| 1-466 | 5-CF$_3$ 7-Me | 2 | O |
| 1-467 | 5-CF$_3$ 4-CN | 2 | O |
| 1-468 | 5-CF$_3$ 7-CN | 2 | O |
| 1-469 | 5-CF$_3$ 4-CF$_3$ | 2 | O |
| 1-470 | 5-CF$_3$ 7-CF$_3$ | 2 | O |
| 1-471 | 4-CF$_3$ | 2 | O |
| 1-472 | 4-CF$_3$ 5-Me | 2 | O |
| 1-473 | 4-CF$_3$ 5-F | 2 | O |
| 1-474 | 4-CF$_3$ 5-OMe | 2 | O |
| 1-475 | 4-CF$_3$ 5-SMe | 2 | O |
| 1-476 | 4-CF$_3$ 5-CN | 2 | O |
| 1-477 | 4-CF$_3$ 5-N(Me)$_2$ | 2 | O |
| 1-478 | 4-CF$_3$ 5-NO$_2$ | 2 | O |
| 1-479 | 4-CF$_3$ 5-Cl | 2 | O |
| 1-480 | 7-CF$_3$ | 2 | O |
| 1-481 | 4-CONH$_2$ | 2 | O |
| 1-482 | 4-CONH$_2$ 5-F | 2 | O |
| 1-483 | 4-CONH$_2$ 6-F | 2 | O |
| 1-484 | 4-CONH$_2$ 7-F | 2 | O |
| 1-485 | 4-CONH$_2$ 5-Cl | 2 | O |
| 1-486 | 4-CONH$_2$ 6-Cl | 2 | O |
| 1-487 | 4-CONH$_2$ 7-Cl | 2 | O |
| 1-488 | 4-CONH$_2$ 5-Me | 2 | O |
| 1-489 | 4-CONH$_2$ 6-Me | 2 | O |
| 1-490 | 4-CONH$_2$ 7-Me | 2 | O |
| 1-491 | 4-CONH$_2$ 5-OMe | 2 | O |
| 1-492 | 4-CONH$_2$ 6-OMe | 2 | O |
| 1-493 | 4-CONH$_2$ 7-OMe | 2 | O |
| 1-494 | 4-CONH$_2$ 5-CN | 2 | O |
| 1-495 | 4-CONH$_2$ 6-CN | 2 | O |
| 1-496 | 4-CONH$_2$ 7-CN | 2 | O |
| 1-497 | 4-CONH$_2$ | 2 | S |
| 1-498 | 5-CONH$_2$ | 2 | O |
| 1-499 | 5-CONH$_2$ | 2 | S |
| 1-500 | 6-CONH$_2$ | 2 | O |
| 1-501 | 6-CONH$_2$ | 2 | S |
| 1-502 | 7-CONH$_2$ | 2 | O |
| 1-503 | 5-SMe 4-Me | 2 | O |
| 1-504 | 5-SMe 5-CN | 2 | O |
| 1-505 | 5-SMe 7-Me | 2 | O |
| 1-506 | 5-SMe 7-CN | 2 | O |
| 1-507 | 5-CN 4-Me | 2 | O |
| 1-508 | 5-CN 4-CN | 2 | O |
| 1-509 | 7-CONH$_2$ 4-Me | 2 | O |
| 1-510 | 5-CN 7-CN | 2 | O |
| 1-511 | 7-CONH$_2$ 6-Me | 2 | O |
| 1-512 | 7-SMe 5-Cl | 2 | O |
| 1-513 | 7-SMe 5-Br | 2 | O |
| 1-514 | 7-SMe 5-NO$_2$ | 2 | O |
| 1-515 | 7-SMe 5-OMe | 2 | O |
| 1-516 | 7-SMe 5-CN | 2 | O |
| 1-517 | 7-SMe 4-CN | 2 | O |
| 1-518 | 7-CONH$_2$ | 2 | S |
| 1-519 | 4-NO$_2$ | 2 | O |
| 1-520 | 4-NO$_2$ | 2 | S |
| 1-521 | 5-NO$_2$ | 2 | O |
| 1-522 | 5-NO$_2$ 4-F | 2 | O |
| 1-523 | 5-NO$_2$ 6-F | 2 | O |
| 1-524 | 5-NO$_2$ 7-F | 2 | O |
| 1-525 | 5-NO$_2$ 4-Cl | 2 | O |
| 1-526 | 5-NO$_2$ 6-Cl | 2 | O |
| 1-527 | 5-NO$_2$ 7-Cl | 2 | O |
| 1-528 | 5-NO$_2$ 4-Me | 2 | O |
| 1-529 | 5-NO$_2$ 6-Me | 2 | O |
| 1-530 | 5-NO$_2$ 7-Me | 2 | O |
| 1-531 | 5-NO$_2$ 4-OMe | 2 | O |
| 1-532 | 5-NO$_2$ 6-OMe | 2 | O |
| 1-533 | 5-NO$_2$ 7-OMe | 2 | O |
| 1-534 | 5-NO$_2$ 4-CN | 2 | O |
| 1-535 | 5-NO$_2$ 6-CN | 2 | O |
| 1-536 | 5-NO$_2$ 7-CN | 2 | O |

TABLE 1-continued structure (Ia): benzisoxazole with X-(CH$_2$)$_n$-NH$_2$ at position 3, (R$^1$)$_m$ substituents on benzene ring (positions 4,5,6,7)

| Compound No. | (R$^1$)$_m$ | n | X |
|---|---|---|---|
| 1-537 | 5-NO$_2$ | 2 | S |
| 1-538 | 5-NO$_2$ 4-F | 2 | S |
| 1-539 | 5-NO$_2$ 6-F | 2 | S |
| 1-540 | 5-NO$_2$ 7-F | 2 | S |
| 1-541 | 5-NO$_2$ 4-Cl | 2 | S |
| 1-542 | 5-NO$_2$ 6-Cl | 2 | S |
| 1-543 | 5-NO$_2$ 7-Cl | 2 | S |
| 1-544 | 5-NO$_2$ 4-Me | 2 | S |
| 1-545 | 5-NO$_2$ 6-Me | 2 | S |
| 1-546 | 5-NO$_2$ 7-Me | 2 | S |
| 1-547 | 5-NO$_2$ 4-OMe | 2 | S |
| 1-548 | 5-NO$_2$ 6-OMe | 2 | S |
| 1-549 | 5-NO$_2$ 7-OMe | 2 | S |
| 1-550 | 5-NO$_2$ 4-CN | 2 | S |
| 1-551 | 5-NO$_2$ 6-CN | 2 | S |
| 1-552 | 5-NO$_2$ 7-CN | 2 | S |
| 1-553 | 6-NO$_2$ | 2 | O |
| 1-554 | 6-NO$_2$ | 2 | S |
| 1-555 | 7-NO$_2$ | 2 | O |
| 1-556 | 7-NO$_2$ | 2 | S |
| 1-557 | 7-NO$_2$ 4-F | 2 | S |
| 1-558 | 7-NO$_2$ 5-F | 2 | S |
| 1-559 | 7-NO$_2$ 6-F | 2 | S |
| 1-560 | 7-NO$_2$ 4-Cl | 2 | S |
| 1-561 | 7-NO$_2$ 5-Cl | 2 | S |
| 1-562 | 7-NO$_2$ 6-Cl | 2 | S |
| 1-563 | 7-NO$_2$ 4-Me | 2 | S |
| 1-564 | 7-NO$_2$ 5-Me | 2 | S |
| 1-565 | 7-NO$_2$ 6-Me | 2 | S |
| 1-566 | 7-NO$_2$ 4-OMe | 2 | S |
| 1-567 | 7-NO$_2$ 5-OMe | 2 | S |
| 1-568 | 7-NO$_2$ 6-OMe | 2 | S |
| 1-569 | 7-NO$_2$ 4-CN | 2 | S |
| 1-570 | 7-NO$_2$ 5-CN | 2 | S |
| 1-571 | 7-NO$_2$ 6-CN | 2 | S |
| 1-572 | 4-CN | 2 | O |
| 1-573 | 4-CN | 2 | S |
| 1-574 | 5-CN | 2 | O |
| 1-575 | 5-CN | 2 | S |
| 1-576 | 6-CN | 2 | O |
| 1-577 | 6-CN | 2 | S |
| 1-578 | 7-CN | 2 | O |
| 1-579 | 7-CN | 2 | S |
| 1-580 | 5-OMe 4-Me | 2 | O |
| 1-581 | 7-Me 4-Me | 2 | O |
| 1-582 | 6-Me 4-Me | 2 | O |
| 1-583 | 5-Me 4-Me | 2 | O |
| 1-584 | 4-N(Me)$_2$ | 2 | O |
| 1-585 | 4-N(Me)$_2$ | 2 | S |
| 1-586 | 5-N(Me)$_2$ | 2 | O |
| 1-587 | 5-N(Me)$_2$ | 2 | S |
| 1-588 | 6-N(Me)$_2$ | 2 | O |
| 1-589 | 6-N(Me)$_2$ | 2 | S |
| 1-590 | 7-N(Me)$_2$ | 2 | O |
| 1-591 | 7-N(Me)$_2$ | 2 | S |
| 1-592 | 4-Cl 6-Me | 2 | O |
| 1-593 | 4-Cl 6-Me | 2 | S |
| 1-594 | 4-F 5-Me | 2 | O |
| 1-595 | 4-F 5-Me | 2 | S |
| 1-596 | 4-F 7-Me | 2 | O |
| 1-597 | 4-F 7-Me | 2 | S |
| 1-598 | 5-Cl 7-CONH$_2$ | 2 | O |
| 1-599 | 5-Cl 7-CONH$_2$ | 2 | S |
| 1-600 | 5-F 4-CS$_2$Me | 2 | O |
| 1-601 | 5-F 4-CS$_2$Me | 2 | S |
| 1-602 | 5-F 4-CF$_3$ | 2 | S |
| 1-603 | 7-CF$_3$ | 2 | S |
| 1-604 | 4-F 7-Cl | 2 | O |
| 1-605 | 4-F 7-Cl | 2 | S |
| 1-606 | 4-F 7-CN | 2 | O |
| 1-607 | 4-F 7-CN | 2 | S |
| 1-608 | 7-F 4-Cl | 2 | O |
| 1-609 | 7-F 4-Cl | 2 | S |
| 1-610 | 7-F 4-Me | 2 | O |
| 1-611 | 7-F 4-Me | 2 | S |
| 1-612 | 7-F 4-CN | 2 | O |
| 1-613 | 7-F 4-CN | 2 | S |
| 1-614 | 4-Me 7-CN | 2 | O |
| 1-615 | 4-Me 7-CN | 2 | S |
| 1-616 | 5-F 7-F 4-Me | 2 | O |
| 1-617 | 5-F 7-F 4-Me | 2 | S |
| 1-618 | 5-Cl 7-Cl 4-Me | 2 | O |
| 1-619 | 5-Cl 7-Cl 4-Me | 2 | S |
| 1-620 | 5-Cl 7-Cl 4-COOH | 2 | O |
| 1-621 | 5-Cl 7-Cl 4-COOH | 2 | S |
| 1-622 | 5-Cl 7-Cl 4-COOMe | 2 | O |
| 1-623 | 5-Cl 7-Cl 4-COOMe | 2 | S |
| 1-624 | 5-Cl 7-Cl 4-CONH$_2$ | 2 | O |
| 1-625 | 5-Cl 7-Cl 4-CONH$_2$ | 2 | S |
| 1-626 | 5-Cl 7-Cl 4-CN | 2 | O |
| 1-627 | 5-Cl 7-Cl 4-CN | 2 | S |

TABLE 2 structure (Ib): naphtho-isoxazole with X-(CH$_2$)$_n$-NH$_2$ at position 3, (R$^1$)$_m$ substituents on positions 4–9

| Compound No. | (R$^1$)$_m$ | n | X |
|---|---|---|---|
| 2-1 | H | 1 | O |
| 2-2 | H | 1 | S |
| 2-3 | H | 2 | O |
| 2-4 | 4-F | 2 | O |
| 2-5 | 5-F | 2 | O |
| 2-6 | 6-F | 2 | O |
| 2-7 | 7-F | 2 | O |
| 2-8 | 8-F | 2 | O |
| 2-9 | 9-F | 2 | O |
| 2-10 | 4-Cl | 2 | O |
| 2-11 | 5-Cl | 2 | O |
| 2-12 | 6-Cl | 2 | O |
| 2-13 | 7-Cl | 2 | O |
| 2-14 | 8-Cl | 2 | O |
| 2-15 | 9-Cl | 2 | O |
| 2-16 | 5-NHMe | 2 | O |
| 2-17 | 6-NHMe | 2 | O |
| 2-18 | 7-NHMe | 2 | O |
| 2-19 | 4-Me | 2 | O |
| 2-20 | 5-Me | 2 | O |
| 2-21 | 6-Me | 2 | O |
| 2-22 | 7-Me | 2 | O |
| 2-23 | 8-Me | 2 | O |
| 2-24 | 9-Me | 2 | O |
| 2-25 | 5-N(Me)$_2$ | 2 | O |
| 2-26 | 6-N(Me)$_2$ | 2 | O |

TABLE 2-continued

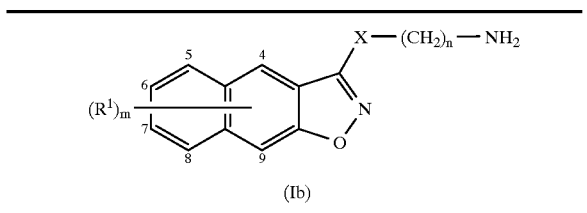

(Ib)

| Compound No. | (R¹)ₘ | n | X |
|---|---|---|---|
| 2-27 | 7-N(Me)₂ | 2 | O |
| 2-28 | 8-N(Me)₂ | 2 | O |
| 2-29 | 4-OMe | 2 | O |
| 2-30 | 5-OMe | 2 | O |
| 2-31 | 6-OMe | 2 | O |
| 2-32 | 7-OMe | 2 | O |
| 2-33 | 8-OMe | 2 | O |
| 2-34 | 9-OMe | 2 | O |
| 2-35 | 5-OEt | 2 | O |
| 2-36 | 6-OEt | 2 | O |
| 2-37 | 7-OEt | 2 | O |
| 2-38 | 8-OEt | 2 | O |
| 2-39 | 5-OCHF₂ | 2 | O |
| 2-40 | 6-OCHF₂ | 2 | O |
| 2-41 | 7-OCHF₂ | 2 | O |
| 2-42 | 8-OCHF₂ | 2 | O |
| 2-43 | 5-NO₂ | 2 | O |
| 2-44 | 6-NO₂ | 2 | O |
| 2-45 | 7-NO₂ | 2 | O |
| 2-46 | 8-NO₂ | 2 | O |
| 2-47 | 4-CN | 2 | O |
| 2-48 | 5-CN | 2 | O |
| 2-49 | 6-CN | 2 | O |
| 2-50 | 7-CN | 2 | O |
| 2-51 | 8-CN | 2 | O |
| 2-52 | 9-CN | 2 | O |
| 2-53 | H | 2 | S |
| 2-54 | 4-F | 2 | S |
| 2-55 | 5-F | 2 | S |
| 2-56 | 6-F | 2 | S |
| 2-57 | 7-F | 2 | S |
| 2-58 | 8-F | 2 | S |
| 2-59 | 9-F | 2 | S |
| 2-60 | 4-Cl | 2 | S |
| 2-61 | 5-Cl | 2 | S |
| 2-62 | 6-Cl | 2 | S |
| 2-63 | 7-Cl | 2 | S |
| 2-64 | 8-Cl | 2 | S |
| 2-65 | 9-Cl | 2 | S |
| 2-66 | 5-NHMe | 2 | S |
| 2-67 | 6-NHMe | 2 | S |
| 2-68 | 7-NHMe | 2 | S |
| 2-69 | 4-Me | 2 | S |
| 2-70 | 5-Me | 2 | S |
| 2-71 | 6-Me | 2 | S |
| 2-72 | 7-Me | 2 | S |
| 2-73 | 8-Me | 2 | S |
| 2-74 | 9-Me | 2 | S |
| 2-75 | 5-N(Me)₂ | 2 | S |
| 2-76 | 6-N(Me)₂ | 2 | S |
| 2-77 | 7-N(Me)₂ | 2 | S |
| 2-78 | 8-N(Me)₂ | 2 | S |
| 2-79 | 4-OMe | 2 | S |
| 2-80 | 5-OMe | 2 | S |
| 2-81 | 6-OMe | 2 | S |
| 2-82 | 7-OMe | 2 | S |
| 2-83 | 8-OMe | 2 | S |
| 2-84 | 9-OMe | 2 | S |
| 2-85 | 5-OEt | 2 | S |
| 2-86 | 6-OEt | 2 | S |
| 2-87 | 7-OEt | 2 | S |
| 2-88 | 8-OEt | 2 | S |
| 2-89 | 5-OCHF₂ | 2 | S |
| 2-90 | 6-OCHF₂ | 2 | S |
| 2-91 | 7-OCHF₂ | 2 | S |
| 2-92 | 8-OCHF₂ | 2 | S |
| 2-93 | 5-NO₂ | 2 | S |

TABLE 2-continued

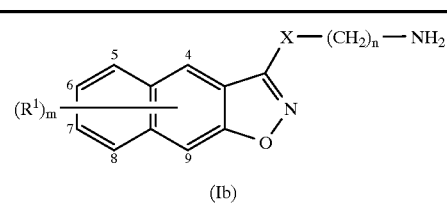

(Ib)

| Compound No. | (R¹)ₘ | n | X |
|---|---|---|---|
| 2-94 | 6-NO₂ | 2 | S |
| 2-95 | 7-NO₂ | 2 | S |
| 2-96 | 8-NO₂ | 2 | S |
| 2-97 | 4-CN | 2 | S |
| 2-98 | 5-CN | 2 | S |
| 2-99 | 6-CN | 2 | S |
| 2-100 | 7-CN | 2 | S |
| 2-101 | 8-CN | 2 | S |
| 2-102 | 9-CN | 2 | S |
| 2-103 | H | 3 | O |
| 2-104 | H | 3 | S |
| 2-105 | H | 4 | O |
| 2-106 | H | 4 | S |
| 2-107 | H | 5 | O |
| 2-108 | H | 5 | S |
| 2-109 | H | 6 | O |
| 2-110 | H | 6 | S |

TABLE 3

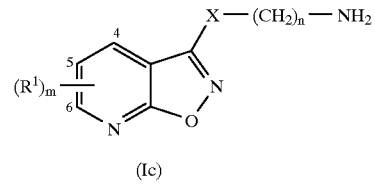

(Ic)

| Compound No. | (R¹)ₘ | n | X |
|---|---|---|---|
| 3-1 | H | 1 | O |
| 3-2 | H | 2 | O |
| 3-3 | H | 2 | S |
| 3-4 | H | 3 | O |
| 3-5 | 4-F | 2 | O |
| 3-6 | 4-F | 2 | S |
| 3-7 | 4-F | 3 | O |
| 3-8 | 4-F | 4 | O |
| 3-9 | 5-F | 2 | O |
| 3-10 | 5-F | 2 | S |
| 3-11 | 5-F | 3 | O |
| 3-12 | 6-F | 2 | O |
| 3-13 | 6-F | 2 | S |
| 3-14 | 6-F | 3 | O |
| 3-15 | 4-Cl | 2 | O |
| 3-16 | 4-Cl | 2 | S |
| 3-17 | 4-Cl | 3 | O |
| 3-18 | 5-Cl | 2 | O |
| 3-19 | 5-Cl | 2 | S |
| 3-20 | 5-Cl | 3 | O |
| 3-21 | 6-Cl | 2 | O |
| 3-22 | 6-Cl | 2 | S |
| 3-23 | 6-Cl | 3 | O |
| 3-24 | 4-Cl 6-Cl | 2 | O |
| 3-25 | 4-Cl 6-Cl | 2 | S |
| 3-26 | 4-Br | 2 | O |
| 3-27 | 4-Br | 2 | S |
| 3-28 | 5-Br | 2 | O |
| 3-29 | 5-Br | 2 | S |
| 3-30 | 5-Br | 3 | O |
| 3-31 | 6-Br | 2 | O |
| 3-32 | 6-Br | 2 | S |

TABLE 3-continued

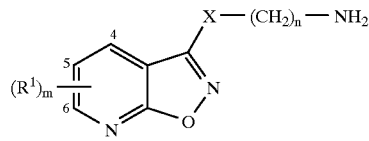

(Ic)

| Compound No. | (R¹)ₘ | n | X |
|---|---|---|---|
| 3-33 | 6-Br | 3 | O |
| 3-34 | 4-Br 6-Cl | 2 | O |
| 3-35 | 4-Br 6-Cl | 2 | S |
| 3-36 | 4-Me | 2 | O |
| 3-37 | 4-Me | 2 | S |
| 3-38 | 5-Me | 2 | O |
| 3-39 | 5-Me | 2 | S |
| 3-40 | 5-Me | 3 | O |
| 3-41 | 6-Me | 2 | O |
| 3-42 | 6-Me | 2 | S |
| 3-43 | 6-Me | 3 | O |
| 3-44 | 6-Me 4-Cl | 2 | O |
| 3-45 | 6-Me 4-Cl | 2 | S |
| 3-46 | 4-CN | 2 | O |
| 3-47 | 4-CN | 2 | S |
| 3-48 | 5-CN | 2 | O |
| 3-49 | 5-CN | 2 | S |
| 3-50 | 5-CN | 3 | O |
| 3-51 | 6-CN | 2 | O |
| 3-52 | 6-CN | 2 | S |
| 3-53 | 6-CN | 3 | O |
| 3-54 | 6-CN 4-Cl | 2 | O |
| 3-55 | 6-Et 4-Cl | 2 | S |
| 3-56 | 4-OMe | 2 | O |
| 3-57 | 4-OMe | 2 | S |
| 3-58 | 5-OMe | 2 | O |
| 3-59 | 5-OMe | 2 | S |
| 3-60 | 5-OMe | 3 | O |
| 3-61 | 6-OMe | 2 | O |
| 3-62 | 6-OMe | 2 | S |
| 3-63 | 6-OMe | 3 | O |
| 3-64 | 4-OEt | 2 | O |
| 3-65 | 4-OEt | 2 | S |
| 3-66 | 5-OEt | 2 | O |
| 3-67 | 5-OEt | 2 | S |
| 3-68 | 5-OEt | 3 | O |
| 3-69 | 6-OEt | 2 | O |
| 3-70 | 6-OEt | 2 | S |
| 3-71 | 6-OEt | 3 | O |
| 3-72 | 4-NO₂ | 2 | O |
| 3-73 | 4-NO₂ | 2 | S |
| 3-74 | 4-NO₂ | 3 | O |
| 3-75 | 5-NO₂ | 2 | O |
| 3-76 | 5-NO₂ | 2 | S |
| 3-77 | 5-NO₂ | 3 | O |
| 3-78 | 6-NO₂ | 2 | O |
| 3-79 | 6-NO₂ | 2 | S |
| 3-80 | 6-NO₂ | 3 | O |
| 3-81 | 4-NO₂ 6-Cl | 2 | O |
| 3-82 | 4-NO₂ 6-Cl | 2 | S |
| 3-83 | 4-CF₃ | 2 | O |
| 3-84 | 4-CF₃ | 2 | S |
| 3-85 | 5-CF₃ | 2 | O |
| 3-86 | 5-CF₃ | 2 | S |
| 3-87 | 5-CF₃ | 3 | O |
| 3-88 | 6-CF₃ | 2 | O |
| 3-89 | 6-CF₃ | 2 | S |
| 3-90 | 6-CF₃ | 3 | O |

TABLE 4

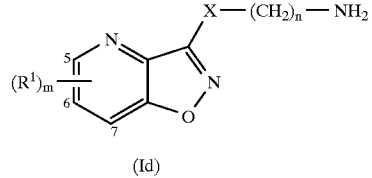

(Id)

| Compound No. | (R¹)ₘ | n | X |
|---|---|---|---|
| 4-1 | H | 1 | O |
| 4-2 | H | 2 | O |
| 4-3 | H | 2 | S |
| 4-4 | H | 3 | O |
| 4-5 | 5-F | 2 | O |
| 4-6 | 5-F | 2 | S |
| 4-7 | 5-F | 3 | O |
| 4-8 | 6-F | 2 | O |
| 4-9 | 6-F | 2 | S |
| 4-10 | 6-F | 3 | O |
| 4-11 | 7-Cl | 2 | O |
| 4-12 | 7-Cl | 2 | S |
| 4-13 | 7-Cl | 3 | O |
| 4-14 | 5-Cl | 2 | O |
| 4-15 | 5-Cl | 2 | S |
| 4-16 | 5-Cl | 3 | O |
| 4-17 | 6-Cl | 2 | O |
| 4-18 | 6-Cl | 2 | S |
| 4-19 | 6-Cl | 3 | O |
| 4-20 | 7-Br | 2 | O |
| 4-21 | 7-Br | 2 | S |
| 4-22 | 5-Br | 2 | O |
| 4-23 | 5-Br | 2 | S |
| 4-24 | 5-Br | 3 | O |
| 4-25 | 6-Br | 2 | O |
| 4-26 | 6-Br | 2 | S |
| 4-27 | 6-Br | 3 | O |
| 4-28 | 7-Br 6-Cl | 2 | O |
| 4-29 | 7-Br 6-Cl | 2 | S |
| 4-30 | 7-Me | 2 | O |
| 4-31 | 7-Me | 2 | S |
| 4-32 | 5-Me | 2 | O |
| 4-33 | 5-Me | 2 | S |
| 4-34 | 5-Me | 3 | O |
| 4-35 | 6-Me | 2 | O |
| 4-36 | 6-Me | 2 | S |
| 4-37 | 6-Me | 3 | O |
| 4-38 | 6-Me 7-Cl | 2 | O |
| 4-39 | 6-Me 7-Cl | 2 | S |
| 4-40 | 7-CN | 2 | O |
| 4-41 | 7-CN | 2 | S |
| 4-42 | 5-CN | 2 | O |
| 4-43 | 5-CN | 2 | S |
| 4-44 | 5-CN | 3 | O |
| 4-45 | 6-CN | 2 | O |
| 4-46 | 6-CN | 2 | S |
| 4-47 | 6-CN | 3 | O |
| 4-48 | 6-CN 7-Cl | 2 | O |
| 4-49 | 6-Et 7-Cl | 2 | S |
| 4-50 | 7-OMe | 2 | O |
| 4-51 | 7-OMe | 2 | S |
| 4-52 | 5-OMe | 2 | O |
| 4-53 | 5-OMe | 2 | S |
| 4-54 | 5-OMe | 3 | O |
| 4-55 | 6-OMe | 2 | O |
| 4-56 | 6-OMe | 2 | S |
| 4-57 | 6-OMe | 3 | O |
| 4-58 | 7-OEt | 2 | O |
| 4-59 | 7-OEt | 2 | S |
| 4-60 | 5-OEt | 2 | O |
| 4-61 | 5-OEt | 2 | S |
| 4-62 | 5-OEt | 3 | O |
| 4-63 | 6-OEt | 2 | O |
| 4-64 | 6-OEt | 2 | S |
| 4-65 | 6-OEt | 3 | O |
| 4-66 | 7-NO₂ | 2 | O |
| 4-67 | 7-NO₂ | 2 | S |

TABLE 4-continued (Id)

| Compound No. | (R¹)ₘ | n | X |
|---|---|---|---|
| 4-68 | 7-NO₂ | 3 | O |
| 4-69 | 5-NO₂ | 2 | O |
| 4-70 | 5-NO₂ | 2 | S |
| 4-71 | 5-NO₂ | 3 | O |
| 4-72 | 6-NO₂ | 2 | O |
| 4-73 | 6-NO₂ | 2 | S |
| 4-74 | 6-NO₂ | 3 | O |
| 4-75 | 7-NO₂ 6-Cl | 2 | O |
| 4-76 | 7-NO₂ 6-Cl | 2 | S |

TABLE 5

(Ie)

| Compound No. | (R¹)ₘ | n | X |
|---|---|---|---|
| 5-1 | H | 1 | O |
| 5-2 | H | 2 | O |
| 5-3 | H | 2 | S |
| 5-4 | H | 3 | O |
| 5-5 | 4-F | 2 | O |
| 5-6 | 4-F | 2 | S |
| 5-7 | 4-F | 3 | O |
| 5-8 | 6-F | 2 | O |
| 5-9 | 6-F | 2 | S |
| 5-10 | 6-F | 3 | O |
| 5-11 | 7-Cl | 2 | O |
| 5-12 | 7-Cl | 2 | S |
| 5-13 | 7-Cl | 3 | O |
| 5-14 | 4-Cl | 2 | O |
| 5-15 | 4-Cl | 2 | S |
| 5-16 | 4-Cl | 3 | O |
| 5-17 | 6-Cl | 2 | O |
| 5-18 | 6-Cl | 2 | S |
| 5-19 | 6-Cl | 3 | O |
| 5-20 | 7-Br | 2 | O |
| 5-21 | 7-Br | 2 | S |
| 5-22 | 4-Br | 2 | O |
| 5-23 | 4-Br | 2 | S |
| 5-24 | 4-Br | 3 | O |
| 5-25 | 6-Br | 2 | O |
| 5-26 | 6-Br | 2 | S |
| 5-27 | 6-Br | 3 | O |
| 5-28 | 7-Br 6-Cl | 2 | O |
| 5-29 | 7-Br 6-Cl | 2 | S |
| 5-30 | 7-Me | 2 | O |
| 5-31 | 7-Me | 2 | S |
| 5-32 | 4-Me | 2 | O |
| 5-33 | 4-Me | 2 | S |
| 5-34 | 4-Me | 3 | O |
| 5-35 | 6-Me | 2 | O |
| 5-36 | 6-Me | 2 | S |
| 5-37 | 6-Me | 3 | O |
| 5-38 | 6-Me 7-Cl | 2 | O |
| 5-39 | 6-Me 7-Cl | 2 | S |
| 5-40 | 7-CN | 2 | O |
| 5-41 | 7-CN | 2 | S |

TABLE 5-continued (Ie)

| Compound No. | (R¹)ₘ | n | X |
|---|---|---|---|
| 5-42 | 4-CN | 2 | O |
| 5-43 | 4-CN | 2 | S |
| 5-44 | 4-CN | 3 | O |
| 5-45 | 6-CN | 2 | O |
| 5-46 | 6-CN | 2 | S |
| 5-47 | 6-CN | 3 | O |
| 5-48 | 6-CN 7-Cl | 2 | O |
| 5-49 | 6-Et 7-Cl | 2 | S |
| 5-50 | 7-OMe | 2 | O |
| 5-51 | 7-OMe | 2 | S |
| 5-52 | 4-OMe | 2 | O |
| 5-53 | 4-OMe | 2 | S |
| 5-54 | 4-OMe | 3 | O |
| 5-55 | 6-OMe | 2 | O |
| 5-56 | 6-OMe | 2 | S |
| 5-57 | 6-OMe | 3 | O |
| 5-58 | 7-OEt | 2 | O |
| 5-59 | 7-OEt | 2 | S |
| 5-60 | 4-OEt | 2 | O |
| 5-61 | 4-OEt | 2 | S |
| 5-62 | 4-OEt | 3 | O |
| 5-63 | 6-OEt | 2 | O |
| 5-64 | 6-OEt | 2 | S |
| 5-65 | 6-OEt | 3 | O |
| 5-66 | 7-NO₂ | 2 | O |
| 5-67 | 7-NO₂ | 2 | S |
| 5-68 | 7-NO₂ | 3 | O |
| 5-69 | 4-NO₂ | 2 | O |
| 5-70 | 4-NO₂ | 2 | S |
| 5-71 | 4-NO₂ | 3 | O |
| 5-72 | 6-NO₂ | 2 | O |
| 5-73 | 6-NO₂ | 2 | S |
| 5-74 | 6-NO₂ | 3 | O |
| 5-75 | 7-NO₂ 6-Cl | 2 | O |
| 5-76 | 7-NO₂ 6-Cl | 2 | S |

TABLE 6

(If)

| Compound No. | (R¹)ₘ | n | X |
|---|---|---|---|
| 6-1 | H | 1 | O |
| 6-2 | H | 2 | O |
| 6-3 | H | 2 | S |
| 6-4 | H | 3 | O |
| 6-5 | 4-F | 2 | O |
| 6-6 | 4-F | 2 | S |
| 6-7 | 4-F | 3 | O |
| 6-8 | 5-F | 2 | O |
| 6-9 | 5-F | 2 | S |
| 6-10 | 5-F | 3 | O |
| 6-11 | 7-Cl | 2 | O |
| 6-12 | 7-Cl | 2 | S |
| 6-13 | 7-Cl | 3 | O |
| 6-14 | 4-Cl | 2 | O |
| 6-15 | 4-Cl | 2 | S |

TABLE 6-continued (If)

$(R^1)_m$ — [isoxazolopyridine ring, positions 4,5,7] — X—(CH$_2$)$_n$—NH$_2$

| Compound No. | $(R^1)_m$ | n | X |
|---|---|---|---|
| 6-16 | 4-Cl | 3 | O |
| 6-17 | 5-Cl | 2 | O |
| 6-18 | 5-Cl | 2 | S |
| 6-19 | 5-Cl | 3 | O |
| 6-20 | 7-Br | 2 | O |
| 6-21 | 7-Br | 2 | S |
| 6-22 | 4-Br | 2 | O |
| 6-23 | 4-Br | 2 | S |
| 6-24 | 4-Br | 3 | O |
| 6-25 | 5-Br | 2 | O |
| 6-26 | 5-Br | 2 | S |
| 6-27 | 5-Br | 3 | O |
| 6-28 | 7-Br 5-Cl | 2 | O |
| 6-29 | 7-Br 5-Cl | 2 | S |
| 6-30 | 7-Me | 2 | O |
| 6-31 | 7-Me | 2 | S |
| 6-32 | 4-Me | 2 | O |
| 6-33 | 4-Me | 2 | S |
| 6-34 | 4-Me | 3 | O |
| 6-35 | 5-Me | 2 | O |
| 6-36 | 5-Me | 2 | S |
| 6-37 | 5-Me | 3 | O |
| 6-38 | 5-Me 7-Cl | 2 | O |
| 6-39 | 5-Me 7-Cl | 2 | S |
| 6-40 | 7-CN | 2 | O |
| 6-41 | 7-CN | 2 | S |
| 6-42 | 4-CN | 2 | O |
| 6-43 | 4-CN | 2 | S |
| 6-44 | 4-CN | 3 | O |
| 6-45 | 5-CN | 2 | O |
| 6-46 | 5-CN | 2 | S |
| 6-47 | 5-CN | 3 | O |
| 6-48 | 5-CN 7-Cl | 2 | O |
| 6-49 | 5-Et 7-Cl | 2 | S |
| 6-50 | 7-OMe | 2 | O |
| 6-51 | 7-OMe | 2 | S |
| 6-52 | 4-OMe | 2 | O |
| 6-53 | 4-OMe | 2 | S |
| 6-54 | 4-OMe | 3 | O |
| 6-55 | 5-OMe | 2 | O |
| 6-56 | 5-OMe | 2 | S |
| 6-57 | 5-OMe | 3 | O |
| 6-58 | 7-OEt | 2 | O |
| 6-59 | 7-OEt | 2 | S |
| 6-60 | 4-OEt | 2 | O |
| 6-61 | 4-OEt | 2 | S |
| 6-62 | 4-OEt | 3 | O |
| 6-63 | 5-OEt | 2 | O |
| 6-64 | 5-OEt | 2 | S |
| 6-65 | 5-OEt | 3 | O |
| 6-66 | 7-NO$_2$ | 2 | O |
| 6-67 | 7-NO$_2$ | 2 | S |
| 6-68 | 7-NO$_2$ | 3 | O |
| 6-69 | 4-NO$_2$ | 2 | O |
| 6-70 | 4-NO$_2$ | 2 | S |
| 6-71 | 4-NO$_2$ | 3 | O |
| 6-72 | 5-NO$_2$ | 2 | O |
| 6-73 | 5-NO$_2$ | 2 | S |
| 6-74 | 5-NO$_2$ | 3 | O |
| 6-75 | 7-NO$_2$ 5-Cl | 2 | O |
| 6-76 | 7-NO$_2$ 5-Cl | 2 | S |

TABLE 7

(Ig)

$(R^1)_m$ — [thieno-isoxazoline ring, positions 5,6] — X—(CH$_2$)$_n$—NH$_2$

| Compound No. | $(R^1)_m$ | n | X |
|---|---|---|---|
| 7-1 | H | 2 | O |
| 7-2 | H | 2 | S |
| 7-3 | 5-F | 2 | O |
| 7-4 | 5-F | 2 | S |
| 7-5 | 6-F | 2 | O |
| 7-6 | 6-F | 2 | S |
| 7-7 | 5-Cl | 2 | O |
| 7-8 | 5-Cl | 2 | S |
| 7-9 | 6-Cl | 2 | O |
| 7-10 | 6-Cl | 2 | S |
| 7-11 | 6-Cl | 3 | O |
| 7-12 | 5-Br | 2 | O |
| 7-13 | 5-Br | 2 | S |
| 7-14 | 6-Br | 2 | O |
| 7-15 | 6-Br | 2 | S |
| 7-16 | 5-Me | 2 | O |
| 7-17 | 5-Me | 2 | S |
| 7-18 | 6-Me | 2 | O |
| 7-19 | 6-Me | 2 | S |
| 7-20 | 5-Et | 2 | O |
| 7-21 | 5-Et | 2 | S |
| 7-22 | 6-Et | 2 | O |
| 7-23 | 6-Et | 2 | S |
| 7-24 | 5-OMe | 2 | O |
| 7-25 | 5-OMe | 2 | S |
| 7-26 | 6-OMe | 2 | O |
| 7-27 | 6-OMe | 2 | S |
| 7-28 | 5-OEt | 2 | O |
| 7-29 | 5-OEt | 2 | S |
| 7-30 | 6-OEt | 2 | O |
| 7-31 | 6-OEt | 2 | S |
| 7-32 | 5-NO$_2$ | 2 | O |
| 7-33 | 5-NO$_2$ | 2 | S |
| 7-34 | 6-NO$_2$ | 2 | O |
| 7-35 | 6-NO$_2$ | 2 | S |

TABLE 8

(Ih)

$(R^1)_m$ — [isothiazolo-isoxazoline ring, positions 4,5] — X—(CH$_2$)$_n$—NH$_2$

| Compound No. | $(R^1)_m$ | n | X |
|---|---|---|---|
| 8-1 | H | 2 | O |
| 8-2 | H | 2 | S |
| 8-3 | 4-F | 2 | O |
| 8-4 | 4-F | 2 | O |
| 8-5 | 5-F | 2 | O |
| 8-6 | 5-F | 2 | S |
| 8-7 | 4-Cl | 2 | O |
| 8-8 | 5-Cl | 2 | O |
| 8-9 | 4-Br | 2 | O |
| 8-10 | 4-Br | 2 | S |
| 8-11 | 5-Br | 2 | O |
| 8-12 | 5-Br | 2 | S |
| 8-13 | 4-Me | 2 | O |
| 8-14 | 4-Me | 2 | S |
| 8-15 | 5-Me | 2 | O |
| 8-16 | 5-Me | 2 | S |
| 8-17 | 4-Et | 2 | O |

TABLE 8-continued

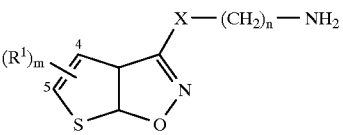

(Ih)

| Compound No. | $(R^1)_m$ | n | X |
|---|---|---|---|
| 8-18 | 4-Et | 2 | S |
| 8-19 | 5-Et | 2 | O |
| 8-20 | 5-Et | 2 | S |
| 8-21 | 4-OMe | 2 | O |
| 8-22 | 4-OMe | 2 | S |
| 8-23 | 5-OMe | 2 | O |
| 8-24 | 5-OMe | 2 | S |
| 8-25 | 4-OEt | 2 | O |
| 8-26 | 4-OEt | 2 | S |
| 8-27 | 5-OEt | 2 | O |
| 8-28 | 5-OEt | 2 | S |
| 8-29 | 4-NO$_2$ | 2 | O |
| 8-30 | 4-NO$_2$ | 2 | S |
| 8-31 | 5-NO$_2$ | 2 | O |
| 8-32 | 5-NO$_2$ | 2 | S |

TABLE 9

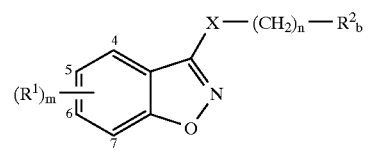

(IIa)

| Compound No. | $(R^1)_m$ | n | $R_b^2$ | X |
|---|---|---|---|---|
| 9-1 | H | 2 | NHMe | O |
| 9-2 | H | 2 | NMe$_2$ | O |
| 9-3 | H | 2 | Pip | O |
| 9-4 | H | 2 | Mor | O |
| 9-5 | H | 2 | NHMe | S |
| 9-6 | H | 2 | NMe$_2$ | S |
| 9-7 | H | 2 | Pip | S |
| 9-8 | H | 2 | Mor | S |
| 9-9 | 4-F | 2 | Pip | O |
| 9-10 | 4-F | 2 | Mor | O |
| 9-11 | 4-F | 2 | Pip | S |
| 9-12 | 4-F | 2 | Mor | S |
| 9-13 | 5-F | 2 | NHMe | O |
| 9-14 | 5-F | 2 | NMe$_2$ | O |
| 9-15 | 5-F | 2 | Pip | O |
| 9-16 | 5-F | 2 | Mor | O |
| 9-17 | 5-F | 2 | NHMe | S |
| 9-18 | 5-F | 2 | NMe$_2$ | S |
| 9-19 | 6-F | 2 | NHMe | O |
| 9-20 | 6-F | 2 | NMe$_2$ | O |
| 9-22 | 6-F | 2 | Mor | O |
| 9-23 | 6-F | 2 | NHMe | S |
| 9-24 | 6-F | 2 | NMe$_2$ | S |
| 9-25 | 7-F | 2 | NHMe | O |
| 9-26 | 7-F | 2 | NMe$_2$ | O |
| 9-27 | 7-F | 2 | Pip | O |
| 9-28 | 7-F | 2 | Mor | O |
| 9-29 | 5-F 7-Cl | 2 | NHMe | O |
| 9-30 | 5-F 7-Cl | 2 | NMe$_2$ | O |
| 9-31 | 5-F 7-Cl | 2 | Pip | O |
| 9-32 | 5-F 7-Cl | 2 | Mor | O |
| 9-33 | 5-F 7-Cl | 2 | NHMe | S |
| 9-34 | 5-F 7-Cl | 2 | NMe$_2$ | S |
| 9-35 | 7-F 5-Cl | 2 | Pip | O |
| 9-36 | 7-F 5-Cl | 2 | Mor | O |
| 9-37 | 4-Cl | 2 | NHMe | O |
| 9-38 | 4-Cl | 2 | NMe$_2$ | O |

TABLE 9-continued (IIa)

| Compound No. | $(R^1)_m$ | n | $R_b^2$ | X |
|---|---|---|---|---|
| 9-39 | 4-Cl | 2 | Pip | O |
| 9-40 | 4-Cl | 2 | Mor | O |
| 9-41 | 4-Cl | 2 | NHMe | S |
| 9-42 | 4-Cl | 2 | NMe$_2$ | S |
| 9-43 | 5-Cl | 2 | NHMe | O |
| 9-44 | 5-Cl | 2 | NMe$_2$ | O |
| 9-45 | 5-Cl | 2 | Pip | O |
| 9-46 | 5-Cl | 2 | Mor | O |
| 9-47 | 5-Cl | 2 | NHMe | S |
| 9-48 | 5-Cl | 2 | NMe$_2$ | S |
| 9-49 | 6-Cl | 2 | NHMe | O |
| 9-50 | 6-Cl | 2 | NMe$_2$ | O |
| 9-51 | 6-Cl | 2 | Pip | O |
| 9-52 | 6-Cl | 2 | Mor | O |
| 9-53 | 7-Cl | 2 | NHMe | O |
| 9-54 | 7-Cl | 2 | NMe$_2$ | O |
| 9-55 | 7-Cl | 2 | Pip | O |
| 9-56 | 7-Cl | 2 | Mor | O |
| 9-57 | 4-Cl 6-Cl | 2 | NHMe | O |
| 9-58 | 4-Cl 6-Cl | 2 | NMe$_2$ | O |
| 9-59 | 4-Cl 6-Cl | 2 | Pip | O |
| 9-60 | 4-Cl 6-Cl | 2 | Mor | O |
| 9-61 | 5-Cl 7-Cl | 2 | NHMe | O |
| 9-62 | 5-Cl 7-Cl | 2 | NMe$_2$ | O |
| 9-63 | 5-Cl 7-Cl | 2 | Pip | O |
| 9-64 | 5-Cl 7-Cl | 2 | Mor | O |
| 9-65 | 5-Cl 7-Cl | 2 | NHMe | S |
| 9-66 | 5-Cl 7-Cl | 2 | NMe$_2$ | S |
| 9-67 | 5-Cl 7-Cl | 2 | Pip | S |
| 9-68 | 5-Cl 7-Cl | 2 | Mor | S |
| 9-69 | 4-Br | 2 | Pip | O |
| 9-70 | 5-Br | 2 | NHMe | O |
| 9-71 | 5-Br | 2 | NMe$_2$ | O |
| 9-72 | 5-Br | 2 | Pip | O |
| 9-73 | 5-Br | 2 | Mor | O |
| 9-74 | 6-Br | 2 | NHMe | O |
| 9-75 | 6-Br | 2 | NMe$_2$ | O |
| 9-76 | 6-Br | 2 | Pip | O |
| 9-77 | 6-Br | 2 | Mor | O |
| 9-78 | 7-Br | 2 | NHMe | O |
| 9-79 | 7-Br | 2 | NMe$_2$ | O |
| 9-80 | 7-Br | 2 | Pip | O |
| 9-81 | 7-Br | 2 | Mor | O |
| 9-82 | 4-Br 6-Cl | 2 | Pip | O |
| 9-83 | 5-Br 7-Cl | 2 | Pip | O |
| 9-84 | 4-Me | 2 | NHMe | O |
| 9-85 | 4-Me | 2 | NMe$_2$ | O |
| 9-86 | 4-Me | 2 | Pip | O |
| 9-87 | 4-Me | 2 | Mor | O |
| 9-88 | 5-Me | 2 | NHMe | O |
| 9-89 | 5-Me | 2 | NMe$_2$ | O |
| 9-90 | 5-Me | 2 | Pip | O |
| 9-91 | 5-Me | 2 | Mor | O |
| 9-92 | 5-Me | 2 | NHMe | S |
| 9-93 | 5-Me | 2 | NMe$_2$ | S |
| 9-94 | 5-Me | 2 | Pip | S |
| 9-95 | 5-Me | 2 | Mor | S |
| 9-96 | 6-Me | 2 | NHMe | O |
| 9-97 | 6-Me | 2 | NMe$_2$ | O |
| 9-98 | 6-Me | 2 | Pip | O |
| 9-99 | 6-Me | 2 | Mor | O |
| 9-100 | 7-Me | 2 | NHMe | O |
| 9-101 | 7-Me | 2 | NMe$_2$ | O |
| 9-102 | 7-Me | 2 | Pip | O |
| 9-103 | 7-Me | 2 | Mor | O |
| 9-104 | 5-Me 7-Cl | 2 | Pip | O |
| 9-105 | 5-Me 7-Cl | 2 | Pip | S |

TABLE 9-continued (IIa)

| Compound No. | $(R^1)_m$ | n | $R_b^2$ | X |
|---|---|---|---|---|
| 9-106 | 6-Me 4-Cl | 2 | Pip | O |
| 9-107 | 7-Me 5-Cl | 2 | Pip | O |
| 9-108 | 7-Me 5-Cl | 2 | Pip | S |
| 9-109 | 4-Et | 2 | Pip | O |
| 9-110 | 4-Et | 2 | Mor | O |
| 9-111 | 5-Et | 2 | Pip | O |
| 9-112 | 5-Et | 2 | Mor | O |
| 9-113 | 6-Et | 2 | Pip | O |
| 9-114 | 6-Et | 2 | Mor | O |
| 9-115 | 7-Et | 2 | Pip | O |
| 9-116 | 7-Et | 2 | Mor | O |
| 9-117 | 5-Et 7-Cl | 2 | Mor | O |
| 9-118 | 6-Et 4-Cl | 2 | Mor | O |
| 9-119 | 7-Et 5-Cl | 2 | Mor | O |
| 9-120 | 4-OMe | 2 | NHMe | O |
| 9-121 | 4-OMe | 2 | $NMe_2$ | O |
| 9-122 | 4-OMe | 2 | Pip | O |
| 9-123 | 4-OMe | 2 | Mor | O |
| 9-124 | 4-OMe | 2 | NHMe | S |
| 9-125 | 4-OMe | 2 | $NMe_2$ | S |
| 9-126 | 4-OMe | 2 | Pip | S |
| 9-127 | 4-OMe | 2 | Mor | S |
| 9-128 | 5-OMe | 2 | NHMe | O |
| 9-129 | 5-OMe | 2 | $NMe_2$ | O |
| 9-130 | 5-OMe | 2 | Pip | O |
| 9-131 | 5-OMe | 2 | Mor | O |
| 9-132 | 5-OMe | 2 | NHMe | S |
| 9-133 | 5-OMe | 2 | $NMe_2$ | S |
| 9-134 | 5-OMe | 2 | Pip | S |
| 9-135 | 5-OMe | 2 | Mor | S |
| 9-136 | 6-OMe | 2 | NHMe | O |
| 9-137 | 6-OMe | 2 | $NMe_2$ | O |
| 9-138 | 6-OMe | 2 | Pip | O |
| 9-139 | 6-OMe | 2 | Mor | O |
| 9-140 | 7-OMe | 2 | NHMe | O |
| 9-141 | 7-OMe | 2 | $NMe_2$ | O |
| 9-142 | 7-OMe | 2 | Pip | O |
| 9-143 | 7-OMe | 2 | Mor | O |
| 9-144 | 5-OMe 7-Cl | 2 | Pip | O |
| 9-145 | 7-OMe 5-Cl | 2 | Pip | O |
| 9-146 | 4-OEt | 2 | Pip | O |
| 9-147 | 4-OEt | 2 | Mor | O |
| 9-148 | 5-OEt | 2 | Pip | O |
| 9-149 | 5-OEt | 2 | Mor | O |
| 9-150 | 6-OEt | 2 | Pip | O |
| 9-151 | 6-OEt | 2 | Mor | O |
| 9-152 | 7-OEt | 2 | Pip | O |
| 9-153 | 7-OEt | 2 | Mor | O |
| 9-154 | 5-OEt 7-Cl | 2 | Mor | O |
| 9-155 | 7-OEt 5-Cl | 2 | Mor | O |
| 9-156 | $4-NO_2$ | 2 | NHMe | O |
| 9-157 | $4-NO_2$ | 2 | $NMe_2$ | O |
| 9-158 | $4-NO_2$ | 2 | Pip | O |
| 9-159 | $4-NO_2$ | 2 | Mor | O |
| 9-160 | $4-NO_2$ | 2 | NHMe | S |
| 9-161 | $4-NO_2$ | 2 | $NMe_2$ | S |
| 9-162 | $4-NO_2$ | 2 | Pip | S |
| 9-163 | $4-NO_2$ | 2 | Mor | S |
| 9-164 | $5-NO_2$ | 2 | NHMe | O |
| 9-165 | $5-NO_2$ | 2 | $NMe_2$ | O |
| 9-166 | $5-NO_2$ | 2 | Pip | O |
| 9-167 | $5-NO_2$ | 2 | Mor | O |
| 9-168 | $5-NO_2$ | 2 | NHMe | S |
| 9-169 | $5-NO_2$ | 2 | $NMe_2$ | S |
| 9-170 | $5-NO_2$ | 2 | Pip | S |
| 9-171 | $5-NO_2$ | 2 | Mor | S |
| 9-172 | $6-NO_2$ | 2 | NHMe | O |
| 9-173 | $6-NO_2$ | 2 | $NMe_2$ | O |
| 9-174 | $6-NO_2$ | 2 | Pip | O |
| 9-175 | $6-NO_2$ | 2 | Mor | O |
| 9-176 | $7-NO_2$ | 2 | NHMe | O |
| 9-177 | $7-NO_2$ | 2 | $NMe_2$ | O |
| 9-178 | $7-NO_2$ | 2 | Pip | O |
| 9-179 | $7-NO_2$ | 2 | Mor | O |
| 9-180 | $4-NO_2$ 6-Cl | 2 | Pip | O |
| 9-181 | $5-NO_2$ 7-Cl | 2 | Pip | O |
| 9-182 | $5-NO_2$ 7-Cl | 2 | Pip | S |

TABLE 10

(IIb)

| Compound No. | $(R^1)_m$ | n | $R_b^2$ | X |
|---|---|---|---|---|
| 10-1 | H | 2 | NHMe | O |
| 10-2 | H | 2 | $NMe_2$ | O |
| 10-3 | H | 2 | Pip | O |
| 10-4 | H | 2 | Mor | O |
| 10-5 | H | 2 | NHMe | S |
| 10-6 | H | 2 | $NMe_2$ | S |
| 10-7 | H | 2 | Pip | S |
| 10-8 | H | 2 | Mor | S |
| 10-9 | 4-F | 2 | NHMe | O |
| 10-10 | 5-F | 2 | $NMe_2$ | O |
| 10-11 | 6-F | 2 | Pip | O |
| 10-12 | 7-F | 2 | Mor | O |
| 10-13 | 8-F | 2 | Pip | O |
| 10-14 | 9-F | 2 | Mor | O |
| 10-15 | 5-F | 2 | $NMe_2$ | S |
| 10-16 | 6-F | 2 | Pip | S |
| 10-17 | 7-F | 2 | Mor | S |
| 10-18 | 8-F | 2 | Pip | S |
| 10-19 | 5-Cl | 2 | $NMe_2$ | O |
| 10-20 | 6-Cl | 2 | Pip | O |
| 10-21 | 7-Cl | 2 | Mor | O |
| 10-22 | 8-Cl | 2 | Pip | O |
| 10-23 | 5-Cl | 2 | $NMe_2$ | S |
| 10-24 | 6-Cl | 2 | Pip | S |
| 10-25 | 7-Cl | 2 | Mor | S |
| 10-26 | 8-Cl | 2 | Pip | S |
| 10-27 | 8-Br | 2 | Pip | O |
| 10-28 | 5-Br | 2 | $NMe_2$ | S |
| 10-29 | 5-Me | 2 | $NMe_2$ | O |
| 10-30 | 6-Me | 2 | Pip | O |
| 10-31 | 7-Me | 2 | Mor | O |
| 10-32 | 8-Me | 2 | Pip | O |
| 10-33 | 5-Me | 2 | $NMe_2$ | S |
| 10-34 | 6-Me | 2 | Pip | S |
| 10-35 | 7-Me | 2 | Mor | S |
| 10-36 | 8-Me | 2 | Pip | S |
| 10-37 | 8-Et | 2 | Pip | O |
| 10-38 | 5-Et | 2 | $NMe_2$ | S |
| 10-39 | 5-OMe | 2 | $NMe_2$ | O |
| 10-40 | 6-OMe | 2 | Pip | O |
| 10-41 | 7-OMe | 2 | Mor | O |

TABLE 10-continued (IIb)

$$\text{structure with } X-(CH_2)_n-R^2_b$$

| Compound No. | $(R^1)_m$ | n | $R^2_b$ | X |
|---|---|---|---|---|
| 10-42 | 8-OMe | 2 | Pip | O |
| 10-43 | 5-OMe | 2 | $NMe_2$ | S |
| 10-44 | 6-OMe | 2 | Pip | S |
| 10-45 | 7-OMe | 2 | Mor | S |
| 10-46 | 8-OMe | 2 | Pip | S |
| 10-47 | 8-OEt | 2 | Pip | O |
| 10-48 | 5-OEt | 2 | $NMe_2$ | S |
| 10-49 | $8\text{-OCHF}_2$ | 2 | Pip | O |
| 10-50 | $5\text{-OCHF}_2$ | 2 | $NMe_2$ | S |
| 10-51 | $5\text{-NO}_2$ | 2 | $NMe_2$ | O |
| 10-52 | $6\text{-NO}_2$ | 2 | Pip | O |
| 10-53 | $7\text{-NO}_2$ | 2 | Mor | O |
| 10-54 | $8\text{-NO}_2$ | 2 | Pip | O |
| 10-55 | $5\text{-NO}_2$ | 2 | $NMe_2$ | S |
| 10-56 | $6\text{-NO}_2$ | 2 | Pip | S |
| 10-57 | $7\text{-NO}_2$ | 2 | Mor | S |
| 10-58 | $8\text{-NO}_2$ | 2 | Pip | S |
| 10-59 | 5-CN | 2 | $NMe_2$ | O |
| 10-60 | 6-CN | 2 | Pip | O |
| 10-61 | 7-CN | 2 | Mor | O |
| 10-62 | 8-CN | 2 | Pip | O |
| 10-63 | 5-CN | 2 | $NMe_2$ | S |
| 10-64 | 6-CN | 2 | Pip | S |
| 10-65 | 7-CN | 2 | Mor | S |
| 10-66 | 8-CN | 2 | Pip | S |

TABLE 11

(IIc)

$$\text{structure with } X-(CH_2)_n-R^2_b$$

| Compound No. | $(R^1)_m$ | n | $R^2_b$ | X |
|---|---|---|---|---|
| 11-1 | H | 2 | NHMe | O |
| 11-2 | H | 2 | $NMe_2$ | O |
| 11-3 | H | 2 | Pip | O |
| 11-4 | H | 2 | Mor | O |
| 11-5 | H | 2 | NHMe | S |
| 11-6 | H | 2 | $NMe_2$ | S |
| 11-7 | H | 2 | Pip | S |
| 11-8 | H | 2 | Mor | S |
| 11-9 | 4-F | 2 | Pip | O |
| 11-10 | 4-F | 2 | Mor | O |
| 11-11 | 4-F | 2 | Pip | S |
| 11-12 | 4-F | 2 | Mor | S |
| 11-13 | 5-F | 2 | NHMe | O |
| 11-14 | 5-F | 2 | $NMe_2$ | O |
| 11-15 | 5-F | 2 | Pip | O |
| 11-16 | 5-F | 2 | Mor | O |
| 11-17 | 5-F | 2 | NHMe | S |
| 11-18 | 5-F | 2 | $NMe_2$ | S |
| 11-19 | 6-F | 2 | NHMe | O |
| 11-20 | 6-F | 2 | $NMe_2$ | O |
| 11-21 | 6-F | 2 | Pip | O |
| 11-22 | 6-F | 2 | Mor | O |
| 11-23 | 4-Cl | 2 | NHMe | O |
| 11-24 | 4-Cl | 2 | $NMe_2$ | O |
| 11-25 | 4-Cl | 2 | Pip | O |
| 11-26 | 4-Cl | 2 | Mor | O |

TABLE 11-continued (IIc)

$$\text{structure with } X-(CH_2)_n-R^2_b$$

| Compound No. | $(R^1)_m$ | n | $R^2_b$ | X |
|---|---|---|---|---|
| 11-27 | 4-Cl | 2 | NHMe | S |
| 11-28 | 4-Cl | 2 | $NMe_2$ | S |
| 11-29 | 5-Cl | 2 | NHMe | O |
| 11-30 | 5-Cl | 2 | $NMe_2$ | O |
| 11-31 | 5-Cl | 2 | Pip | O |
| 11-32 | 5-Cl | 2 | Mor | O |
| 11-33 | 5-Cl | 2 | NHMe | S |
| 11-34 | 5-Cl | 2 | $NMe_2$ | S |
| 11-35 | 5-Cl | 2 | Pip | S |
| 11-36 | 5-Cl | 2 | Mor | S |
| 11-37 | 6-Cl | 2 | NHMe | O |
| 11-38 | 6-Cl | 2 | $NMe_2$ | O |
| 11-39 | 6-Cl | 2 | Pip | O |
| 11-40 | 6-Cl | 2 | Mor | O |
| 11-41 | 4-Cl 6-Cl | 2 | NHMe | O |
| 11-42 | 4-Cl 6-Cl | 2 | $NMe_2$ | O |
| 11-43 | 4-Cl 6-Cl | 2 | Pip | O |
| 11-44 | 4-Br | 2 | Mor | O |
| 11-45 | 5-Br | 2 | NHMe | O |
| 11-46 | 5-Br | 2 | $NMe_2$ | O |
| 11-47 | 5-Br | 2 | Pip | O |
| 11-48 | 5-Br | 2 | Mor | O |
| 11-49 | 5-Br | 2 | NHMe | S |
| 11-50 | 5-Br | 2 | $NMe_2$ | S |
| 11-51 | 6-Br | 2 | NHMe | O |
| 11-52 | 6-Br | 2 | $NMe_2$ | O |
| 11-53 | 6-Br | 2 | Pip | O |
| 11-54 | 6-Br | 2 | Mor | O |
| 11-55 | 4-Br 6-Cl | 2 | Pip | O |
| 11-56 | 4-Me | 2 | NHMe | O |
| 11-57 | 4-Me | 2 | $NMe_2$ | O |
| 11-58 | 4-Me | 2 | Pip | O |
| 11-59 | 4-Me | 2 | Mor | O |
| 11-60 | 4-Me | 2 | NHMe | S |
| 11-61 | 4-Me | 2 | $NMe_2$ | S |
| 11-62 | 4-Me | 2 | Pip | S |
| 11-63 | 4-Me | 2 | Mor | S |
| 11-64 | 5-Me | 2 | NHMe | O |
| 11-65 | 5-Me | 2 | $NMe_2$ | O |
| 11-66 | 5-Me | 2 | Pip | O |
| 11-67 | 5-Me | 2 | Mor | O |
| 11-68 | 5-Me | 2 | NHMe | S |
| 11-69 | 5-Me | 2 | $NMe_2$ | S |
| 11-70 | 6-Me | 2 | NHMe | O |
| 11-71 | 6-Me | 2 | $NMe_2$ | O |
| 11-72 | 6-Me | 2 | Pip | O |
| 11-73 | 6-Me | 2 | Mor | O |
| 11-74 | 6-Me 4-Cl | 2 | Pip | O |
| 11-75 | 4-Et | 2 | Pip | O |
| 11-76 | 4-Et | 2 | Mor | O |
| 11-77 | 5-Et | 2 | Pip | O |
| 11-78 | 5-Et | 2 | Mor | O |
| 11-79 | 5-Et | 2 | Pip | S |
| 11-80 | 5-Et | 2 | Mor | S |
| 11-81 | 6-Et | 2 | Pip | O |
| 11-82 | 6-Et | 2 | Mor | O |
| 11-83 | 6-Et 4-Cl | 2 | Mor | O |
| 11-84 | 4-OMe | 2 | NHMe | O |
| 11-85 | 4-OMe | 2 | $NMe_2$ | O |
| 11-86 | 4-OMe | 2 | Pip | O |
| 11-87 | 4-OMe | 2 | Mor | O |
| 11-88 | 4-OMe | 2 | NHMe | S |
| 11-89 | 4-OMe | 2 | $NMe_2$ | S |
| 11-90 | 4-OMe | 2 | Pip | S |
| 11-91 | 4-OMe | 2 | Mor | S |
| 11-92 | 5-OMe | 2 | NHMe | O |
| 11-93 | 5-OMe | 2 | $NMe_2$ | O |

TABLE 11-continued (IIc)

$(R^1)_m$ — isoxazolo-pyridine — $X-(CH_2)_n-R^2_b$

| Compound No. | $(R^1)_m$ | n | $R^2_b$ | X |
|---|---|---|---|---|
| 11-94 | 5-OMe | 2 | Pip | O |
| 11-95 | 5-OMe | 2 | Mor | O |
| 11-96 | 5-OMe | 2 | NHMe | S |
| 11-97 | 5-OMe | 2 | NMe₂ | S |
| 11-98 | 5-OMe | 2 | Pip | S |
| 11-99 | 5-OMe | 2 | Mor | S |
| 11-100 | 6-OMe | 2 | NHMe | O |
| 11-101 | 6-OMe | 2 | NMe₂ | O |
| 11-102 | 6-OMe | 2 | Pip | O |
| 11-103 | 6-OMe | 2 | Mor | O |
| 11-104 | 4-OEt | 2 | Pip | O |
| 11-105 | 4-OEt | 2 | Mor | O |
| 11-106 | 4-OEt | 2 | Pip | S |
| 11-107 | 4-OEt | 2 | Mor | S |
| 11-108 | 5-OEt | 2 | Pip | O |
| 11-109 | 5-OEt | 2 | Mor | O |
| 11-110 | 5-OEt | 2 | Pip | S |
| 11-111 | 5-OEt | 2 | Mor | S |
| 11-112 | 6-OEt | 2 | Pip | O |
| 11-113 | 6-OEt | 2 | Mor | O |
| 11-114 | 4-NO₂ | 2 | NHMe | O |
| 11-115 | 4-NO₂ | 2 | NMe₂ | O |
| 11-116 | 4-NO₂ | 2 | Pip | O |
| 11-117 | 4-NO₂ | 2 | Mor | O |
| 11-118 | 4-NO₂ | 2 | NHMe | S |
| 11-119 | 4-NO₂ | 2 | NMe₂ | S |
| 11-120 | 4-NO₂ | 2 | Pip | S |
| 11-121 | 4-NO₂ | 2 | Mor | S |
| 11-122 | 5-NO₂ | 2 | NHMe | O |
| 11-123 | 5-NO₂ | 2 | NMe₂ | O |
| 11-124 | 5-NO₂ | 2 | Pip | O |
| 11-125 | 5-NO₂ | 2 | Mor | O |
| 11-126 | 5-NO₂ | 2 | NHMe | S |
| 11-127 | 5-NO₂ | 2 | NMe₂ | S |
| 11-128 | 5-NO₂ | 2 | Pip | S |
| 11-129 | 5-NO₂ | 2 | Mor | S |
| 11-130 | 6-NO₂ | 2 | NHMe | O |
| 11-131 | 6-NO₂ | 2 | NMe₂ | O |
| 11-132 | 6-NO₂ | 2 | Pip | O |
| 11-133 | 6-NO₂ | 2 | Mor | O |
| 11-134 | 4-NO₂ 6-Cl | 2 | Pip | O |

TABLE 12

(IId)

$(R^1)_m$ — isoxazolo-pyridine — $X-(CH_2)_n-R^2_b$

| Compound No. | $(R^1)_m$ | n | $R^2_b$ | X |
|---|---|---|---|---|
| 12-1 | H | 2 | NHMe | O |
| 12-2 | H | 2 | NMe₂ | O |
| 12-3 | H | 2 | Pip | O |
| 12-4 | H | 2 | Mor | O |
| 12-5 | H | 2 | NHMe | S |
| 12-6 | H | 2 | NMe₂ | S |
| 12-7 | H | 2 | Pip | S |
| 12-8 | H | 2 | Mor | S |
| 12-9 | 7-F | 2 | Pip | O |
| 12-10 | 7-F | 2 | Mor | O |
| 12-11 | 7-F | 2 | Pip | S |
| 12-12 | 7-F | 2 | Mor | S |
| 12-13 | 5-F | 2 | NHMe | O |
| 12-14 | 5-F | 2 | NMe₂ | O |
| 12-15 | 5-F | 2 | Pip | O |
| 12-16 | 5-F | 2 | Mor | O |
| 12-17 | 5-F | 2 | NHMe | S |
| 12-18 | 5-F | 2 | NM₂ | S |
| 12-19 | 6-F | 2 | NHMe | O |
| 12-20 | 6-F | 2 | NMe₂ | O |
| 12-21 | 6-F | 2 | Pip | O |
| 12-22 | 6-F | 2 | Mor | O |
| 12-23 | 7-Cl | 2 | NHMe | O |
| 12-24 | 7-Cl | 2 | NMe₂ | O |
| 12-25 | 7-Cl | 2 | Pip | O |
| 12-26 | 7-Cl | 2 | Mor | O |
| 12-27 | 7-Cl | 2 | NHMe | S |
| 12-28 | 7-Cl | 2 | NMe₂ | S |
| 12-29 | 5-Cl | 2 | NHMe | O |
| 12-30 | 5-Cl | 2 | NMe₂ | O |
| 12-31 | 5-Cl | 2 | Pip | O |
| 12-32 | 5-Cl | 2 | Mor | O |
| 12-33 | 5-Cl | 2 | NHMe | S |
| 12-34 | 5-Cl | 2 | NMe₂ | S |
| 12-35 | 5-Cl | 2 | Pip | S |
| 12-36 | 5-Cl | 2 | Mor | S |
| 12-37 | 6-Cl | 2 | NHMe | O |
| 12-38 | 6-Cl | 2 | NMe₂ | O |
| 12-39 | 6-Cl | 2 | Pip | O |
| 12-40 | 6-Cl | 2 | Mor | O |
| 12-41 | 7-Cl 6-Cl | 2 | NHMe | O |
| 12-42 | 7-Cl 6-Cl | 2 | NMe₂ | O |
| 12-43 | 7-Cl 6-Cl | 2 | Pip | O |
| 12-44 | 7-Br | 2 | Mor | O |
| 12-45 | 5-Br | 2 | NHMe | O |
| 12-46 | 5-Br | 2 | NMe₂ | O |
| 12-47 | 5-Br | 2 | Pip | O |
| 12-48 | 5-Br | 2 | Mor | O |
| 12-49 | 5-Br | 2 | NHMe | S |
| 12-50 | 5-Br | 2 | NM₂ | S |
| 12-51 | 6-Br | 2 | NHMe | O |
| 12-52 | 6-Br | 2 | NMe₂ | O |
| 12-53 | 6-Br | 2 | Pip | O |
| 12-54 | 6-Br | 2 | Mor | O |
| 12-55 | 7-Br 6-Cl | 2 | Pip | O |
| 12-56 | 7-Me | 2 | NHMe | O |
| 12-57 | 7-Me | 2 | NMe₂ | O |
| 12-58 | 7-Me | 2 | Pip | O |
| 12-59 | 7-Me | 2 | Mor | O |
| 12-60 | 7-Me | 2 | NHMe | S |
| 12-61 | 7-Me | 2 | NMe₂ | S |
| 12-62 | 7-Me | 2 | Pip | S |
| 12-63 | 7-Me | 2 | Mor | S |
| 12-64 | 5-Me | 2 | NHMe | O |
| 12-65 | 5-Me | 2 | NMe₂ | O |
| 12-66 | 5-Me | 2 | Pip | O |
| 12-67 | 5-Me | 2 | Mor | O |
| 12-68 | 5-Me | 2 | NHMe | S |
| 12-69 | 5-Me | 2 | NMe₂ | S |
| 12-70 | 6-Me | 2 | NHMe | O |
| 12-71 | 6-Me | 2 | NMe₂ | O |
| 12-72 | 6-Me | 2 | Pip | O |
| 12-73 | 6-Me | 2 | Mor | O |
| 12-74 | 6-Me 7-Cl | 2 | Pip | O |
| 12-75 | 7-Et | 2 | Pip | O |
| 12-76 | 7-Et | 2 | Mor | O |
| 12-77 | 5-Et | 2 | Pip | O |

TABLE 12-continued (IId)

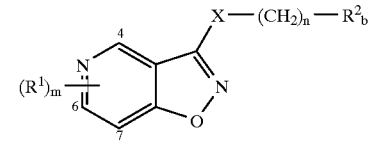

| Compound No. | $(R^1)_m$ | n | $R^2_b$ | X |
|---|---|---|---|---|
| 12-78 | 5-Et | 2 | Mor | O |
| 12-79 | 5-Et | 2 | Pip | S |
| 12-80 | 5-Et | 2 | Mor | S |
| 12-81 | 6-Et | 2 | Pip | O |
| 12-82 | 6-Et | 2 | Mor | O |
| 12-83 | 6-Et 7-Cl | 2 | Mor | O |
| 12-84 | 7-OMe | 2 | NHMe | O |
| 12-85 | 7-OMe | 2 | NMe$_2$ | O |
| 12-86 | 7-OMe | 2 | Pip | O |
| 12-87 | 7-OMe | 2 | Mor | O |
| 12-88 | 7-OMe | 2 | NHMe | S |
| 12-89 | 7-OMe | 2 | NMe$_2$ | S |
| 12-90 | 7-OMe | 2 | Pip | S |
| 12-91 | 7-OMe | 2 | Mor | S |
| 12-92 | 5-OMe | 2 | NHMe | O |
| 12-93 | 5-OMe | 2 | NMe$_2$ | O |
| 12-94 | 5-OMe | 2 | Pip | O |
| 12-95 | 5-OMe | 2 | Mor | O |
| 12-96 | 5-OMe | 2 | NHMe | S |
| 12-97 | 5-OMe | 2 | NMe$_2$ | S |
| 12-98 | 5-OMe | 2 | Pip | S |
| 12-99 | 5-OMe | 2 | Mor | S |
| 12-100 | 6-OMe | 2 | NHMe | O |
| 12-101 | 6-OMe | 2 | NMe$_2$ | O |
| 12-102 | 6-OMe | 2 | Pip | O |
| 12-103 | 6-OMe | 2 | Mor | O |
| 12-104 | 7-OEt | 2 | Pip | O |
| 12-105 | 7-OEt | 2 | Mor | O |
| 12-106 | 7-OEt | 2 | Pip | S |
| 12-107 | 7-OEt | 2 | Mor | S |
| 12-108 | 5-OEt | 2 | Pip | O |
| 12-109 | 5-OEt | 2 | Mor | O |
| 12-110 | 5-OEt | 2 | Pip | S |
| 12-111 | 5-OEt | 2 | Mor | S |
| 12-112 | 6-OEt | 2 | Pip | O |
| 12-113 | 6-OEt | 2 | Mor | O |
| 12-114 | 7-NO$_2$ | 2 | NHMe | O |
| 12-115 | 7-NO$_2$ | 2 | NMe$_2$ | O |
| 12-116 | 7-NO$_2$ | 2 | Pip | O |
| 12-117 | 7-NO$_2$ | 2 | Mor | O |
| 12-118 | 7-NO$_2$ | 2 | NHMe | S |
| 12-119 | 7-NO$_2$ | 2 | NMe$_2$ | S |
| 12-120 | 7-NO$_2$ | 2 | Pip | S |
| 12-121 | 7-NO$_2$ | 2 | Mor | S |
| 12-122 | 5-NO$_2$ | 2 | NHMe | O |
| 12-123 | 5-NO$_2$ | 2 | NMe$_2$ | O |
| 12-124 | 5-NO$_2$ | 2 | Pip | O |
| 12-125 | 5-NO$_2$ | 2 | Mor | O |
| 12-126 | 5-NO$_2$ | 2 | NHMe | S |
| 12-127 | 5-NO$_2$ | 2 | NMe$_2$ | S |
| 12-128 | 5-NO$_2$ | 2 | Pip | S |
| 12-129 | 5-NO$_2$ | 2 | Mor | S |
| 12-130 | 6-NO$_2$ | 2 | NHMe | O |
| 12-131 | 6-NO$_2$ | 2 | NMe$_2$ | O |
| 12-132 | 6-NO$_2$ | 2 | Pip | O |
| 12-133 | 6-NO$_2$ | 2 | Mor | O |
| 12-134 | 7-NO$_2$ 6-Cl | 2 | Pip | O |

TABLE 13

(IIe)

| Compound No. | $(R^1)_m$ | n | $R^2_b$ | X |
|---|---|---|---|---|
| 13-1 | H | 2 | NHMe | O |
| 13-2 | H | 2 | NMe$_2$ | O |
| 13-3 | H | 2 | Pip | O |
| 13-4 | H | 2 | Mor | O |
| 13-5 | H | 2 | NHMe | S |
| 13-6 | H | 2 | NMe$_2$ | S |
| 13-7 | H | 2 | Pip | S |
| 13-8 | H | 2 | Mor | S |
| 13-9 | 7-F | 2 | Pip | O |
| 13-10 | 7-F | 2 | Mor | O |
| 13-11 | 7-F | 2 | Pip | S |
| 13-12 | 7-F | 2 | Mor | S |
| 13-13 | 4-F | 2 | NHMe | O |
| 13-14 | 4-F | 2 | NMe$_2$ | O |
| 13-15 | 4-F | 2 | Pip | O |
| 13-16 | 4-F | 2 | Mor | O |
| 13-17 | 4-F | 2 | NHMe | S |
| 13-18 | 4-F | 2 | NMe$_2$ | S |
| 13-19 | 6-F | 2 | NHMe | O |
| 13-20 | 6-F | 2 | NMe$_2$ | O |
| 13-21 | 6-F | 2 | Pip | O |
| 13-22 | 6-F | 2 | Mor | O |
| 13-23 | 7-Cl | 2 | NHMe | O |
| 13-24 | 7-Cl | 2 | NMe$_2$ | O |
| 13-25 | 7-Cl | 2 | Pip | O |
| 13-26 | 7-Cl | 2 | Mor | O |
| 13-27 | 7-Cl | 2 | NHMe | S |
| 13-28 | 7-Cl | 2 | NMe$_2$ | S |
| 13-29 | 4-Cl | 2 | NHMe | O |
| 13-30 | 4-Cl | 2 | NMe$_2$ | O |
| 13-31 | 4-Cl | 2 | Pip | O |
| 13-32 | 4-Cl | 2 | Mor | O |
| 13-33 | 4-Cl | 2 | NHMe | S |
| 13-34 | 4-Cl | 2 | NMe$_2$ | S |
| 13-35 | 4-Cl | 2 | Pip | S |
| 13-36 | 4-Cl | 2 | Mor | S |
| 13-37 | 6-Cl | 2 | NHMe | O |
| 13-38 | 6-Cl | 2 | NMe$_2$ | O |
| 13-39 | 6-Cl | 2 | Pip | O |
| 13-40 | 6-Cl | 2 | Mor | O |
| 13-41 | 7-Cl 6-Cl | 2 | NHMe | O |
| 13-42 | 7-Cl 6-Cl | 2 | NMe$_2$ | O |
| 13-43 | 7-Cl 6-Cl | 2 | Pip | O |
| 13-44 | 7-Br | 2 | Mor | O |
| 13-45 | 4-Br | 2 | NHMe | O |
| 13-46 | 4-Br | 2 | NMe$_2$ | O |
| 13-47 | 4-Br | 2 | Pip | O |
| 13-48 | 4-Br | 2 | Mor | O |
| 13-49 | 4-Br | 2 | NHMe | S |
| 13-50 | 4-Br | 2 | NMe$_2$ | S |
| 13-51 | 6-Br | 2 | NHMe | O |
| 13-52 | 6-Br | 2 | NMe$_2$ | O |
| 13-53 | 6-Br | 2 | Pip | O |
| 13-54 | 6-Br | 2 | Mor | O |
| 13-55 | 7-Br 6-Cl | 2 | Pip | O |
| 13-56 | 7-Me | 2 | NHMe | O |
| 13-57 | 7-Me | 2 | NMe$_2$ | O |
| 13-58 | 7-Me | 2 | Pip | O |
| 13-59 | 7-Me | 2 | Mor | O |
| 13-60 | 7-Me | 2 | NHMe | S |
| 13-61 | 7-Me | 2 | NMe$_2$ | S |
| 13-62 | 7-Me | 2 | Pip | S |
| 13-63 | 7-Me | 2 | Mor | S |
| 13-64 | 4-Me | 2 | NHMe | O |
| 13-65 | 4-Me | 2 | NMe$_2$ | O |
| 13-66 | 4-Me | 2 | Pip | O |
| 13-67 | 4-Me | 2 | Mor | O |

TABLE 13-continued (IIe) structure: (R¹)ₘ-substituted pyrido-isoxazole with X—(CH₂)ₙ—R²ᵦ at position 3

| Compound No. | (R¹)ₘ | n | R²ᵦ | X |
|---|---|---|---|---|
| 13-68 | 4-Me | 2 | NHMe | S |
| 13-69 | 4-Me | 2 | NMe₂ | S |
| 13-70 | 6-Me | 2 | NHMe | O |
| 13-71 | 6-Me | 2 | NMe₂ | O |
| 13-72 | 6-Me | 2 | Pip | O |
| 13-73 | 6-Me | 2 | Mor | O |
| 13-74 | 6-Me 7-Cl | 2 | Pip | O |
| 13-75 | 7-Et | 2 | Pip | O |
| 13-76 | 7-Et | 2 | Mor | O |
| 13-77 | 4-Et | 2 | Pip | O |
| 13-78 | 4-Et | 2 | Mor | O |
| 13-79 | 4-Et | 2 | Pip | S |
| 13-80 | 4-Et | 2 | Mor | S |
| 13-81 | 6-Et | 2 | Pip | O |
| 13-82 | 6-Et | 2 | Mor | O |
| 13-83 | 6-Et 7-Cl | 2 | Mor | O |
| 13-84 | 7-OMe | 2 | NHMe | O |
| 13-85 | 7-OMe | 2 | NMe₂ | O |
| 13-86 | 7-OMe | 2 | Pip | O |
| 13-87 | 7-OMe | 2 | Mor | O |
| 13-88 | 7-OMe | 2 | NHMe | S |
| 13-89 | 7-OMe | 2 | NMe₂ | S |
| 13-90 | 7-OMe | 2 | Pip | S |
| 13-91 | 7-OMe | 2 | Mor | S |
| 13-92 | 4-OMe | 2 | NHMe | O |
| 13-93 | 4-OMe | 2 | NMe₂ | O |
| 13-94 | 4-OMe | 2 | Pip | O |
| 13-95 | 4-OMe | 2 | Mor | O |
| 13-96 | 4-OMe | 2 | NHMe | S |
| 13-97 | 4-OMe | 2 | NMe₂ | S |
| 13-98 | 4-OMe | 2 | Pip | S |
| 13-99 | 4-OMe | 2 | Mor | S |
| 13-100 | 6-OMe | 2 | NHMe | O |
| 13-101 | 6-OMe | 2 | NMe₂ | O |
| 13-102 | 6-OMe | 2 | Pip | O |
| 13-103 | 6-OMe | 2 | Mor | O |
| 13-104 | 7-OEt | 2 | Pip | O |
| 13-105 | 7-OEt | 2 | Mor | O |
| 13-106 | 7-OEt | 2 | Pip | S |
| 13-107 | 7-OEt | 2 | Mor | S |
| 13-108 | 4-OEt | 2 | Pip | O |
| 13-109 | 4-OEt | 2 | Mor | O |
| 13-110 | 4-OEt | 2 | Pip | S |
| 13-111 | 4-OEt | 2 | Mor | S |
| 13-112 | 6-OEt | 2 | Pip | O |
| 13-113 | 6-OEt | 2 | Mor | O |
| 13-114 | 7-NO₂ | 2 | NHMe | O |
| 13-115 | 7-NO₂ | 2 | NMe₂ | O |
| 13-116 | 7-NO₂ | 2 | Pip | O |
| 13-117 | 7-NO₂ | 2 | Mor | O |
| 13-118 | 7-NO₂ | 2 | NHMe | S |
| 13-119 | 7-NO₂ | 2 | NMe₂ | S |
| 13-120 | 7-NO₂ | 2 | Pip | S |
| 13-121 | 7-NO₂ | 2 | Mor | S |
| 13-122 | 4-NO₂ | 2 | NHMe | O |
| 13-123 | 4-NO₂ | 2 | NMe₂ | O |
| 13-124 | 4-NO₂ | 2 | Pip | O |
| 13-125 | 4-NO₂ | 2 | Mor | O |
| 13-126 | 4-NO₂ | 2 | NHMe | S |
| 13-127 | 4-NO₂ | 2 | NMe₂ | S |
| 13-128 | 4-NO₂ | 2 | Pip | S |
| 13-129 | 4-NO₂ | 2 | Mor | S |
| 13-130 | 6-NO₂ | 2 | NHMe | O |
| 13-131 | 6-NO₂ | 2 | NMe₂ | O |
| 13-132 | 6-NO₂ | 2 | Pip | O |
| 13-133 | 6-NO₂ | 2 | Mor | O |
| 13-134 | 7-NO₂ 6-Cl | 2 | Pip | O |

TABLE 14

(IIf) structure: (R¹)ₘ-substituted pyrido-isoxazole with X—(CH₂)ₙ—R²ᵦ at position 3

| Compound No. | (R¹)ₘ | n | R²ᵦ | X |
|---|---|---|---|---|
| 14-1 | H | 2 | NHMe | O |
| 14-2 | H | 2 | NMe₂ | O |
| 14-3 | H | 2 | Pip | O |
| 14-4 | H | 2 | Mor | O |
| 14-5 | H | 2 | NHMe | S |
| 14-6 | H | 2 | NMe₂ | S |
| 14-7 | H | 2 | Pip | S |
| 14-8 | H | 2 | Mor | S |
| 14-9 | 7-F | 2 | Pip | O |
| 14-10 | 7-F | 2 | Mor | O |
| 14-11 | 7-F | 2 | Pip | S |
| 14-12 | 7-F | 2 | Mor | S |
| 14-13 | 4-F | 2 | NHMe | O |
| 14-14 | 4-F | 2 | NMe₂ | O |
| 14-15 | 4-F | 2 | Pip | O |
| 14-16 | 4-F | 2 | Mor | O |
| 14-17 | 4-F | 2 | NHMe | S |
| 14-18 | 4-F | 2 | NMe₂ | S |
| 14-19 | 5-F | 2 | NHMe | O |
| 14-20 | 5-F | 2 | NMe₂ | O |
| 14-21 | 5-F | 2 | Pip | O |
| 14-22 | 5-F | 2 | Mor | O |
| 14-23 | 7-Cl | 2 | NHMe | O |
| 14-24 | 7-Cl | 2 | NMe₂ | O |
| 14-25 | 7-Cl | 2 | Pip | O |
| 14-26 | 7-Cl | 2 | Mor | O |
| 14-27 | 7-Cl | 2 | NHMe | S |
| 14-28 | 7-Cl | 2 | NMe₂ | S |
| 14-29 | 4-Cl | 2 | NHMe | O |
| 14-30 | 4-Cl | 2 | NMe₂ | O |
| 14-31 | 4-Cl | 2 | Pip | O |
| 14-32 | 4-Cl | 2 | Mor | O |
| 14-33 | 4-Cl | 2 | NHMe | S |
| 14-34 | 4-Cl | 2 | NMe₂ | S |
| 14-35 | 4-Cl | 2 | Pip | S |
| 14-36 | 4-Cl | 2 | Mor | S |
| 14-37 | 5-Cl | 2 | NHMe | O |
| 14-38 | 5-Cl | 2 | NMe₂ | O |
| 14-39 | 5-Cl | 2 | Pip | O |
| 14-40 | 5-Cl | 2 | Mor | O |
| 14-41 | 7-Cl 5-Cl | 2 | NHMe | O |
| 14-42 | 7-Cl 5-Cl | 2 | NMe₂ | O |
| 14-43 | 7-Cl 5-Cl | 2 | Pip | O |
| 14-44 | 7-Br | 2 | Mor | O |
| 14-45 | 4-Br | 2 | NHMe | O |
| 14-46 | 4-Br | 2 | NMe₂ | O |
| 14-47 | 4-Br | 2 | Pip | O |

TABLE 14-continued (IIf) X—(CH2)n—R²b on pyridoisoxazole

| Compound No. | (R¹)ₘ | n | R²_b | X |
|---|---|---|---|---|
| 14-48 | 4-Br | 2 | Mor | O |
| 14-49 | 4-Br | 2 | NHMe | S |
| 14-50 | 4-Br | 2 | NMe₂ | S |
| 14-51 | 5-Br | 2 | NHMe | O |
| 14-52 | 5-Br | 2 | NMe₂ | O |
| 14-53 | 5-Br | 2 | Pip | O |
| 14-54 | 5-Br | 2 | Mor | O |
| 14-55 | 7-Br 5-Cl | 2 | Pip | O |
| 14-56 | 7-Me | 2 | NHMe | O |
| 14-57 | 7-Me | 2 | NMe₂ | O |
| 14-58 | 7-Me | 2 | Pip | O |
| 14-59 | 7-Me | 2 | Mor | O |
| 14-60 | 7-Me | 2 | NHMe | S |
| 14-61 | 7-Me | 2 | NMe₂ | S |
| 14-62 | 7-Me | 2 | Pip | S |
| 14-63 | 7-Me | 2 | Mor | S |
| 14-64 | 4-Me | 2 | NHMe | O |
| 14-65 | 4-Me | 2 | NMe₂ | O |
| 14-66 | 4-Me | 2 | Pip | O |
| 14-67 | 4-Me | 2 | Mor | O |
| 14-68 | 4-Me | 2 | NHMe | S |
| 14-69 | 4-Me | 2 | NMe₂ | S |
| 14-70 | 5-Me | 2 | NHMe | O |
| 14-71 | 5-Me | 2 | NMe₂ | O |
| 14-72 | 5-Me | 2 | Pip | O |
| 14-73 | 5-Me | 2 | Mor | O |
| 14-74 | 5-Me 7-Cl | 2 | Pip | O |
| 14-75 | 7-Et | 2 | Pip | O |
| 14-76 | 7-Et | 2 | Mor | O |
| 14-77 | 4-Et | 2 | Pip | O |
| 14-78 | 4-Et | 2 | Mor | O |
| 14-79 | 4-Et | 2 | Pip | S |
| 14-80 | 4-Et | 2 | Mor | S |
| 14-81 | 5-Et | 2 | Pip | O |
| 14-82 | 5-Et | 2 | Mor | O |
| 14-83 | 5-Et 7-Cl | 2 | Mor | O |
| 14-84 | 7-OMe | 2 | NHMe | O |
| 14-85 | 7-OMe | 2 | NMe₂ | O |
| 14-86 | 7-OMe | 2 | Pip | O |
| 14-87 | 7-OMe | 2 | Mor | O |
| 14-88 | 7-OMe | 2 | NHMe | S |
| 14-89 | 7-OMe | 2 | NMe₂ | S |
| 14-90 | 7-OMe | 2 | Pip | S |
| 14-91 | 7-OMe | 2 | Mor | S |
| 14-92 | 4-OMe | 2 | NHMe | O |
| 14-93 | 4-OMe | 2 | NMe₂ | O |
| 14-94 | 4-OMe | 2 | Pip | O |
| 14-95 | 4-OMe | 2 | Mor | O |
| 14-96 | 4-OMe | 2 | NHMe | S |
| 14-97 | 4-OMe | 2 | NMe₂ | S |
| 14-98 | 4-OMe | 2 | Pip | S |
| 14-99 | 4-OMe | 2 | Mor | S |
| 14-100 | 5-OMe | 2 | NHMe | O |
| 14-101 | 5-OMe | 2 | NMe₂ | O |
| 14-102 | 5-OMe | 2 | Pip | O |
| 14-103 | 5-OMe | 2 | Mor | O |
| 14-104 | 7-OEt | 2 | Pip | O |
| 14-105 | 7-OEt | 2 | Mor | O |
| 14-106 | 7-OEt | 2 | Pip | S |
| 14-107 | 7-OEt | 2 | Mor | S |
| 14-108 | 4-OEt | 2 | Pip | O |
| 14-109 | 4-OEt | 2 | Mor | O |
| 14-110 | 4-OEt | 2 | Pip | S |
| 14-111 | 4-OEt | 2 | Mor | S |
| 14-112 | 5-OEt | 2 | Pip | O |
| 14-113 | 5-OEt | 2 | Mor | O |
| 14-114 | 7-NO₂ | 2 | NHMe | O |
| 14-115 | 7-NO₂ | 2 | NMe₂ | O |
| 14-116 | 7-NO₂ | 2 | Pip | O |
| 14-117 | 7-NO₂ | 2 | Mor | O |
| 14-118 | 7-NO₂ | 2 | NHMe | S |
| 14-119 | 7-NO₂ | 2 | NMe₂ | S |
| 14-120 | 7-NO₂ | 2 | Pip | S |
| 14-121 | 7-NO₂ | 2 | Mor | S |
| 14-122 | 4-NO₂ | 2 | NHMe | O |
| 14-123 | 4-NO₂ | 2 | NMe₂ | O |
| 14-124 | 4-NO₂ | 2 | Pip | O |
| 14-125 | 4-NO₂ | 2 | Mor | O |
| 14-126 | 4-NO₂ | 2 | NHMe | S |
| 14-127 | 4-NO₂ | 2 | NMe₂ | S |
| 14-128 | 4-NO₂ | 2 | Pip | S |
| 14-129 | 4-NO₂ | 2 | Mor | S |
| 14-130 | 5-NO₂ | 2 | NHMe | O |
| 14-131 | 5-NO₂ | 2 | NMe₂ | O |
| 14-132 | 5-NO₂ | 2 | Pip | O |
| 14-133 | 5-NO₂ | 2 | Mor | O |
| 14-134 | 7-NO₂ 5-Cl | 2 | Pip | O |

TABLE 15

(IIg)

| Compound No. | (R¹)ₘ | n | R²_b | X |
|---|---|---|---|---|
| 15-1 | H | 2 | NHMe | O |
| 15-2 | H | 2 | NMe₂ | O |
| 15-3 | H | 2 | Pip | O |
| 15-4 | H | 2 | Mor | O |
| 15-5 | H | 2 | NHMe | S |
| 15-6 | H | 2 | NMe₂ | S |
| 15-7 | H | 2 | Pip | S |
| 15-8 | H | 2 | Mor | S |
| 15-9 | 5-F | 2 | NHMe | O |
| 15-10 | 5-F | 2 | NMe₂ | O |
| 15-11 | 5-F | 2 | Pip | O |
| 15-12 | 5-F | 2 | Mor | O |
| 15-13 | 6-F | 2 | NHMe | O |
| 15-14 | 6-F | 2 | NMe₂ | O |
| 15-15 | 6-F | 2 | Pip | O |
| 15-16 | 6-F | 2 | Mor | O |
| 15-17 | 6-F | 2 | NHMe | S |
| 15-18 | 6-F | 2 | NMe₂ | S |
| 15-19 | 6-F | 2 | Pip | S |
| 15-20 | 6-F | 2 | Mor | S |
| 15-21 | 5-Cl | 2 | NHMe | O |
| 15-22 | 5-Cl | 2 | NMe₂ | O |
| 15-23 | 5-Cl | 2 | Pip | O |
| 15-24 | 5-Cl | 2 | Mor | O |
| 15-25 | 6-Cl | 2 | NHMe | O |
| 15-26 | 6-Cl | 2 | NMe₂ | O |
| 15-27 | 6-Cl | 2 | Pip | O |
| 15-28 | 6-Cl | 2 | Mor | O |
| 15-29 | 6-Cl | 2 | NHMe | S |

TABLE 15-continued $$(R^1)_m \underset{6}{\overset{5}{\bigsqcup}} \underset{\text{(IIg)}}{\overset{X-(CH_2)_n-R^2_b}{\bigsqcup}}$$

| Compound No. | (R¹)ₘ | n | R²ᵦ | X |
|---|---|---|---|---|
| 15-30 | 6-Cl | 2 | NMe₂ | S |
| 15-31 | 6-Cl | 2 | Pip | S |
| 15-32 | 6-Cl | 2 | Mor | S |
| 15-33 | 5-Br | 2 | Mor | O |
| 15-34 | 6-Br | 2 | NHMe | O |
| 15-35 | 6-Br | 2 | NMe₂ | O |
| 15-36 | 6-Br | 2 | Pip | O |
| 15-37 | 6-Br | 2 | Mor | O |
| 15-38 | 5-Me | 2 | NHMe | O |
| 15-39 | 5-Me | 2 | NMe₂ | O |
| 15-40 | 5-Me | 2 | Pip | O |
| 15-41 | 5-Me | 2 | Mor | O |
| 15-42 | 6-Me | 2 | NHMe | O |
| 15-43 | 6-Me | 2 | NMe₂ | O |
| 15-44 | 6-Me | 2 | Pip | O |
| 15-45 | 6-Me | 2 | Mor | O |
| 15-46 | 6-Me | 2 | NHMe | S |
| 15-47 | 6-Me | 2 | NMe₂ | S |
| 15-48 | 6-Me | 2 | Pip | S |
| 15-49 | 6-Me | 2 | Mor | S |
| 15-50 | 5-Et | 2 | Pip | O |
| 15-51 | 5-Et | 2 | Mor | O |
| 15-52 | 6-Et | 2 | Pip | O |
| 15-53 | 6-Et | 2 | Mor | O |
| 15-54 | 5-MeO | 2 | NHMe | O |
| 15-55 | 5-MeO | 2 | NMe₂ | O |
| 15-56 | 5-MeO | 2 | Pip | O |
| 15-57 | 5-MeO | 2 | Mor | O |
| 15-58 | 6-MeO | 2 | NHMe | O |
| 15-59 | 6-MeO | 2 | NMe₂ | O |
| 15-60 | 6-MeO | 2 | Pip | O |
| 15-61 | 6-MeO | 2 | Mor | O |
| 15-62 | 6-MeO | 2 | NHMe | S |
| 15-63 | 6-MeO | 2 | NMe₂ | S |
| 15-64 | 6-MeO | 2 | Pip | S |
| 15-65 | 6-MeO | 2 | Mor | S |
| 15-66 | 5-EtO | 2 | Pip | O |
| 15-67 | 5-EtO | 2 | Mor | O |
| 15-68 | 6-EtO | 2 | Pip | O |
| 15-69 | 6-EtO | 2 | Mor | O |
| 15-70 | 5-NO₂ | 2 | NHMe | O |
| 15-71 | 5-NO₂ | 2 | NMe₂ | O |
| 15-72 | 5-NO₂ | 2 | Pip | O |
| 15-73 | 5-NO₂ | 2 | Mor | O |
| 15-74 | 6-NO₂ | 2 | NHMe | O |
| 15-75 | 6-NO₂ | 2 | NMe₂ | O |
| 15-76 | 6-NO₂ | 2 | Pip | O |
| 15-77 | 6-NO₂ | 2 | Mor | O |
| 15-78 | 6-NO₂ | 2 | NHMe | S |
| 15-79 | 6-NO₂ | 2 | NMe₂ | S |
| 15-80 | 6-NO₂ | 2 | Pip | S |
| 15-81 | 6-NO₂ | 2 | Mor | S |

TABLE 16

$$(R^1)_m \underset{5}{\overset{4}{\bigsqcup}} \underset{\text{(IIh)}}{\overset{X-(CH_2)_n-R^2_b}{\bigsqcup}}$$

| Compound No. | (R¹)ₘ | n | R²ᵦ | X |
|---|---|---|---|---|
| 16-1 | H | 2 | NHMe | O |
| 16-2 | H | 2 | NMe₂ | O |
| 16-3 | H | 2 | Pip | O |
| 16-4 | H | 2 | Mor | O |
| 16-5 | H | 2 | NHMe | S |
| 16-6 | H | 2 | NMe₂ | S |
| 16-7 | H | 2 | Pip | S |
| 16-8 | H | 2 | Mor | S |
| 16-9 | 4-F | 2 | Pip | O |
| 16-10 | 4-F | 2 | Mor | O |
| 16-11 | 4-F | 2 | Pip | S |
| 16-12 | 4-F | 2 | Mor | S |
| 16-13 | 5-F | 2 | NHMe | O |
| 16-14 | 5-F | 2 | NMe₂ | O |
| 16-15 | 5-F | 2 | Pip | O |
| 16-16 | 5-F | 2 | Mor | O |
| 16-17 | 4-Cl | 2 | NHMe | O |
| 16-18 | 4-Cl | 2 | NMe₂ | O |
| 16-19 | 4-Cl | 2 | Pip | O |
| 16-20 | 4-Cl | 2 | Mor | O |
| 16-21 | 4-Cl | 2 | NHMe | S |
| 16-22 | 4-Cl | 2 | NMe₂ | S |
| 16-23 | 4-Cl | 2 | Pip | S |
| 16-24 | 4-Cl | 2 | Mor | S |
| 16-25 | 5-Cl | 2 | NHMe | O |
| 16-26 | 5-Cl | 2 | NMe₂ | O |
| 16-27 | 5-Cl | 2 | Pip | O |
| 16-28 | 5-Cl | 2 | Mor | O |
| 16-29 | 4-Br | 2 | NHMe | O |
| 16-30 | 4-Br | 2 | NMe₂ | O |
| 16-31 | 4-Br | 2 | Pip | O |
| 16-32 | 5-Br | 2 | Mor | O |
| 16-33 | 4-Me | 2 | NHMe | O |
| 16-34 | 4-Me | 2 | NMe₂ | O |
| 16-35 | 4-Me | 2 | Pip | O |
| 16-36 | 4-Me | 2 | Mor | O |
| 16-37 | 4-Me | 2 | NHMe | S |
| 16-38 | 4-Me | 2 | NMe₂ | S |
| 16-39 | 4-Me | 2 | Pip | S |
| 16-40 | 4-Me | 2 | Mor | S |
| 16-41 | 5-Me | 2 | NHMe | O |
| 16-42 | 5-Me | 2 | NMe₂ | O |
| 16-43 | 5-Me | 2 | Pip | O |
| 16-44 | 5-Me | 2 | Mor | O |
| 16-45 | 4-Et | 2 | Pip | O |
| 16-46 | 4-Et | 2 | Mor | O |
| 16-47 | 5-Et | 2 | Pip | O |
| 16-48 | 5-Et | 2 | Mor | O |
| 16-49 | 4-MeO | 2 | NHMe | O |
| 16-50 | 4-MeO | 2 | NMe₂ | O |
| 16-51 | 4-MeO | 2 | Pip | O |
| 16-52 | 4-MeO | 2 | Mor | O |
| 16-53 | 4-MeO | 2 | NHMe | S |
| 16-54 | 4-MeO | 2 | NMe₂ | S |
| 16-55 | 4-MeO | 2 | Pip | S |
| 16-56 | 4-MeO | 2 | Mor | S |
| 16-57 | 5-MeO | 2 | NHMe | O |
| 16-58 | 5-MeO | 2 | NMe₂ | O |
| 16-59 | 5-MeO | 2 | Pip | O |
| 16-60 | 5-MeO | 2 | Mor | O |
| 16-61 | 4-EtO | 2 | Pip | O |
| 16-62 | 4-EtO | 2 | Mor | O |
| 16-63 | 5-EtO | 2 | Pip | O |
| 16-64 | 5-EtO | 2 | Mor | O |
| 16-65 | 4-NO₂ | 2 | NHMe | O |
| 16-66 | 4-NO₂ | 2 | NMe₂ | O |
| 16-67 | 4-NO₂ | 2 | Pip | O |

TABLE 16-continued

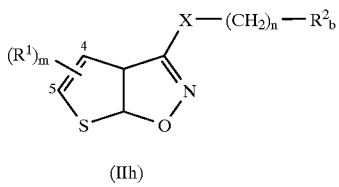

(IIh)

| Compound No. | $(R^1)_m$ | n | $R^2_b$ | X |
|---|---|---|---|---|
| 16-68 | 4-NO$_2$ | 2 | Mor | O |
| 16-69 | 4-NO$_2$ | 2 | NHMe | S |
| 16-70 | 4-NO$_2$ | 2 | NMe$_2$ | S |
| 16-71 | 4-NO$_2$ | 2 | Pip | S |
| 16-72 | 4-NO$_2$ | 2 | Mor | S |
| 16-73 | 5-NO$_2$ | 2 | NHMe | O |
| 16-74 | 5-NO$_2$ | 2 | NMe$_2$ | O |
| 16-75 | 5-NO$_2$ | 2 | Pip | O |
| 16-76 | 5-NO$_2$ | 2 | Mor | O |

The following compounds can be given as those suitable for isoxazole derivatives [Formulae (Ia), (Ib), (Ic), (Id) and (Ie)] having the general formula (I) of this invention: 1-3, 1-13, 1-15, 1-19, 1-22, 1-25, 1-28, 1-31, 1-38, 1-41, 1-44, 1-47, 1-48, 1-49, 1-50, 1-51, 1-53, 1-56, 1-59, 1-60, 1-62, 1-66, 1-68, 1-69, 1-72, 1-75, 1-76, 1-85, 1-96, 1-97, 1-98, 1-107, 1-119, 1-122, 1-125, 1-126, 1-128, 1-135, 1-142, 1-148, 1-151, 1-160, 1-168, 1-169, 1-170, 1-173, 1-176, 1-185, 1-186, 1-191, 1-193, 1-197, 1-198, 1-199, 1-200, 1-204, 1-207, 1-216, 1-217, 1-218, 1-219, 1-220, 1-221, 1-224, 1-231, 1-240, 1-241, 1-242, 1-243, 1-244, 1-247, 1-263, 1-264, 1-265, 1-266, 1-267, 1-268, 1-269, 1-272, 1-275, 1-277, 1-278, 1-281, 1-283, 1-284, 1-285, 1-286, 1-287, 1-291, 1-292, 1-293, 1-294, 1-310, 1-311, 1-312, 1-328, 1-346, 1-362, 1-363, 1-364, 1-365, 1-381, 1-384, 1400, 1401, 1402, 1-403, 1404, 1-405, 1-406, 1-414, 1-421, 1-422, 1-423, 1-429, 1-435, 1-438, 1-439, 1-440, 1-441, 1-442, 1-448, 1-457, 1-460, 1-461, 1-462, 1-463, 1-464, 1-465, 1-471, 1-473, 1-474, 1-480, 1-481, 1-482, 1-490, 1-497, 1-498, 1-499, 1-500, 1-501, 1-502, 1-518, 1-519, 1-520, 1-521, 1-528, 1-534, 1-537, 1-550, 1-553, 1-554, 1-555, 1-556, 1-572, 1-573, 1-574, 1-575, 1-576, 1-577, 1-578, 1-579, 1-580, 1-581, 1-582, 1-583, 1-586, 1-594, 1-596, 1-598, 1-618, 2-3, 2-53, 3-2, 3-3, 3-18, 3-19, 3-41, 3-83, 4-2, 4-3, 5-2, 5-3, 6-2 or 6-3.

More preferably, the compounds represented by No. 1-3, 1-13, 1-15, 1-22, 1-28, 1-31, 1-38, 144, 1-51, 1-53, 1-59, 1-60, 1-62, 1-68, 1-69, 1-75, 1-76, 1-85, 1-97, 1-98, 1-107, 1-119, 1-126, 1-128, 1-142, 1-148, 1-151, 1-160, 1-169, 1-170, 1-173, 1-176, 1-191, 1-193, 1-197, 1-200, 1-207, 1-224, 1-247, 1-269, 1-275, 1-277, 1-293, 1-294, 1-312, 1-328, 1-346, 1-365, 1-384, 1-405, 1-406, 1-414, 1-422, 1-441, 1-464, 1-473, 1-480, 1-481, 1-482, 1-490, 1-498, 1-502, 1-521, 1-537, 1-556, 1-572, 1-574, 1-580, 1-581, 1-583, 1-586, 1-594, 1-596, 1-598, 1-618, 2-3, 3-2, 3-18, 3-19, 3-83 or 4-2 are given.

The following compounds are particularly favorable:
Compound No. 1-3: 3-(2-Aminoethoxy)-1,2-benzisoxazole,
Compound No. 1-15: 3-(2-Aminoethoxy)-5-fluoro-1,2-benzisoxazole,
Compound No. 1-22: 3-(2-Aminoethoxy)-5-fluoro-4-methyl-1,2-benzisoxazole,
Compound No. 1-31: 3-(2-Aminoethylthio)-5-fluoro-1,2-benzisoxazole,
Compound No. 1-53: 3-(2-Aminoethoxy)-5-chloro-1,2-benzisoxazole,
Compound No. 1-59: 3-(2-Aminoethoxy)-5,7-dichloro-1,2-benzisoxazole,
Compound No. 1-62: 3-(2-Aminoethylthio)-5-chloro-7-methyl-1,2-benzisoxazole,
Compound No. 1-69: 3-(2-Aminoethylthio)-5-chloro-1,2-benzisoxazole,
Compound No. 1-85: 3-(2-Aminoethoxy)-6-chloro-1,2-benzisoxazole,
Compound No. 1-97: 3-(2-Aminoethoxy)-7-chloro-1,2-benzisoxazole,
Compound No. 1-119: 3-(2-Aminoethoxy)-5-bromo-1,2-benzisoxazole,
Compound No. 1-142: 3-(2-Aminoethoxy)-5-methyl-1,2-benzisoxazole,
Compound No. 1-151: 3-(2-Aminoethylthio)-5-methyl-1,2-benzisoxazole,
Compound No. 1-160: 3-(2-Aminoethoxy)-6-methyl-1,2-benzisoxazole,
Compound No. 1-169: 3-(2-Aminoethoxy)-7-methyl-1,2-benzisoxazole,
Compound No. 1-193: 3-(2-Aminoethoxy)-5-methoxy-1,2-benzisoxazole,
Compound No. 1-197: 3-(2-Aminoethylthio)-5-methoxy-1,2-benzisoxazole,
Compound No. 1-224: 3-(2-Aminoethoxy)-5-difluoromethoxy-1,2-benzisoxazole,
Compound No. 1-269: 3-(2-Aminoethoxy)-5-fluoro-4-methylthio-1,2-benzisoxazole,
Compound No. 1-422: 3-(2-Aminoethoxy)-5-methoxycarbonyl-1,2-benzisoxazole,
Compound No. 1-521: 3-(2-Aminoethoxy)-5-nitro-1,2-benzisoxazole,
Compound No. 1-537: 3-(2-Aminoethylthio)-5-nitro-1,2-benzisoxazole,
Compound No. 1-572: 3-(2-Aminoethoxy)-4-cyano-1,2-benzisoxazole, or
Compound No. 3-2: 3-(2-Aminoethoxy)pyrido[3,2-d]isoxazole.

The following compounds can be given as those suitable for isoxazole derivatives [Formulae (Ia), (Ib), (Ic), (Id), (Ie), (IIa), (IIb), (IIc), (IId) and (IIe)] having the general formula (II) and being active ingredients of monoamine oxidase inhibitors of this invention: 1-3, 1-13, 1-15, 1-19, 1-22, 1-25, 1-28, 1-31, 1-38, 1-41, 1-44, 1-47, 1-48, 1-49, 1-50, 1-51, 1-53, 1-56, 1-59, 1-60, 1-62, 1-66, 1-68, 1-69, 1-72, 1-75, 1-76, 1-85, 1-96, 1-97, 1-98, 1-107, 1-119, 1-122, 1-125, 1-126, 1-128, 1-135, 1-142, 1-148, 1-151, 1-160, 1-168, 1-169, 1-170, 1-173, 1-176, 1-185, 1-186, 1-191, 1-193, 1-197, 1-198, 1-199, 1-200, 1-204, 1-207, 1-216, 1-217, 1-218, 1-219, 1-220, 1-221, 1-224, 1-231, 1-240, 1-241, 1-242, 1-243, 1-244, 1-247, 1-263, 1-264, 1-265, 1-266, 1-267, 1-268, 1-269, 1-272, 1-275, 1-277, 1-278, 1-281, 1-283, 1-284, 1-285, 1-286, 1-287, 1-291, 1-292, 1-293, 1-294, 1-310, 1-311, 1-312, 1-328, 1-346, 1-362, 1-363, 1-364, 1-365, 1-381, 1-384, 1-400, 1-401, 1-402, 1-403, 1-404, 1-405, 1-406, 1-414, 1-421, 1-422, 1-423, 1-429, 1-435, 1-438, 1-439, 1-440, 1-441, 1-442, 1-448, 1-457, 1-460, 1-461, 1-462, 1-463, 1-464, 1-465, 1-471, 1-473, 1-474, 1-480, 1-481, 1-482, 1-490, 1-497, 1-498, 1-499, 1-500, 1-501, 1-502, 1-518, 1-519, 1-520, 1-521, 1-528, 1-534, 1-537, 1-550, 1-553, 1-554, 1-555, 1-556, 1-572, 1-573, 1-574, 1-575, 1-576, 1-577, 1-578, 1-579, 1-580, 1-581, 1-582, 1-583, 1-586, 1-594, 1-596, 1-598, 1-618, 2-3, 2-53, 3-2, 3-3, 3-18, 3-19, 4-2, 4-3, 5-2, 5-3, 6-2, 6-3, 9-1, 9-2, 9-5, 9-6, 10-1, 10-2, 10-5, 10-6, 11-1, 11-2, 11-5, 11-6, 12-1, 12-2, 12-5, 12-6, 13-1, 13-2, 13-5, 13-6, 14-1, 14-2, 14-5, 14-6, 15-1, 15-2, 15-5, 15-6, 16-1, 16-2, 16-5 or 16-6.

More preferably, the compounds of 1-3, 1-13, 1-15, 1-22, 1-28, 1-31, 1-38, 1-44, 1-51, 1-53, 1-59, 1-60, 1-62, 1-68, 1-69, 1-75, 1-76, 1-85, 1-97, 1-98, 1-107, 1-119, 1-126, 1-128, 1-142, 1-1-48, 1-151, 1-160, 1-169, 1-170, 1-173, 1-176, 1-191, 1-193, 1-197, 1-200, 1-207, 1-224, 1-247, 1-269, 1-275, 1-277, 1-293, 1-294, 1-312, 1-328, 1-346, 1-365, 1-384, 1-405, 1-406, 1414, 1-422, 1-441, 1-464, 1-473, 1-480, 1-481, 1-482, 1-490, 1-498, 1-502, 1-521, 1-537, 1-556, 1-572, 1-574, 1-580, 1-581, 1-583, 1-586, 1-594, 1-596, 1-598, 1-618, 2-3, 3-2, 3-18, 3-19, 3-41, 3-83 or 4-2 are given.

The following compounds are particularly favorable:
Compound No. 1-3: 3-(2-Aminoethoxy)-1,2-benzisoxazole,
Compound No. 1-15: 3-(2-Aminoethoxy)-5-fluoro-1,2-benzisoxazole,
Compound No. 1-22: 3-(2-Aminoethoxy)-5-fluoro-4-methyl-1,2-benzisoxazole,
Compound No. 1-31: 3-(2-Aminoethylthio)-5-fluoro-1,2-benzisoxazole,
Compound No. 1-53: 3-(2-Aminoethoxy)-5-chloro-1,2-benzisoxazole,
Compound No. 1-59: 3-(2-Aminoethoxy)-5,7-dichloro-1,2-benzisoxazole,
Compound No. 1-62: 3-(2-Aminoethylthio)-5-chloro-7-methyl-1,2-benzisoxazole,
Compound No. 1-69: 3-(2-Aminoethylthio)-5-chloro-1,2-benzisoxazole,
Compound No. 1-85: 3-(2-Aminoethoxy)-6-chloro-1,2-benzisoxazole,
Compound No. 1-97: 3-(2-Aminoethoxy)-7-chloro-1,2-benzisoxazole,
Compound No. 1-119: 3-(2-Aminoethoxy)-5-bromo-1,2-benzisoxazole,
Compound No. 1-142: 3-(2-Aminoethoxy)5-methyl-1,2-benzisoxazole,
Compound No. 1-151: 3-(2-Aminoethylthio)-5-methyl-1,2-benzisoxazole,
Compound No. 1-160: 3-(2-Aminoethoxy)-6-methyl-1,2-benzisoxazole,
Compound No. 1-169: 3-(2-Aminoethoxy)-7-methyl-1,2-benzisoxazole,
Compound No. 1-193: 3-(2-Aminoethoxy)-5-methoxy-1,2-benzisoxazole,
Compound No. 1-197: 3-(2-Aminoethylthio)-5-methoxy-1,2-benzisoxazole,
Compound No. 1-224: 3-(2-Aminoethoxy)-5-difluoromethoxy-1,2-benzisoxazole,
Compound No. 1-269: 3-(2-Aminoethoxy)-5-fluoro-4-methylthio-1,2-benzisoxazole,
Compound No. 1-422: 3-(2-Aminoethoxy)5-methoxycarbonyl-1,2-benzisoxazole,
Compound No. 1-521: 3-(2-Aminoethoxy)-5-nitro-1,2-benzisoxazole,
Compound No. 1-537: 3-(2-Aminoethylthio)-5-nitro-1,2-benzisoxazole,
Compound No. 1-572: 3-(2-Aminoethoxy)-4-cyano-1,2-benzisoxazole, or
Compound No. 3-2: 3-(2-Aminoethoxy)pyrido[3,2-d]isoxazole.

The synthetic methods for the compounds of this invention are shown below.

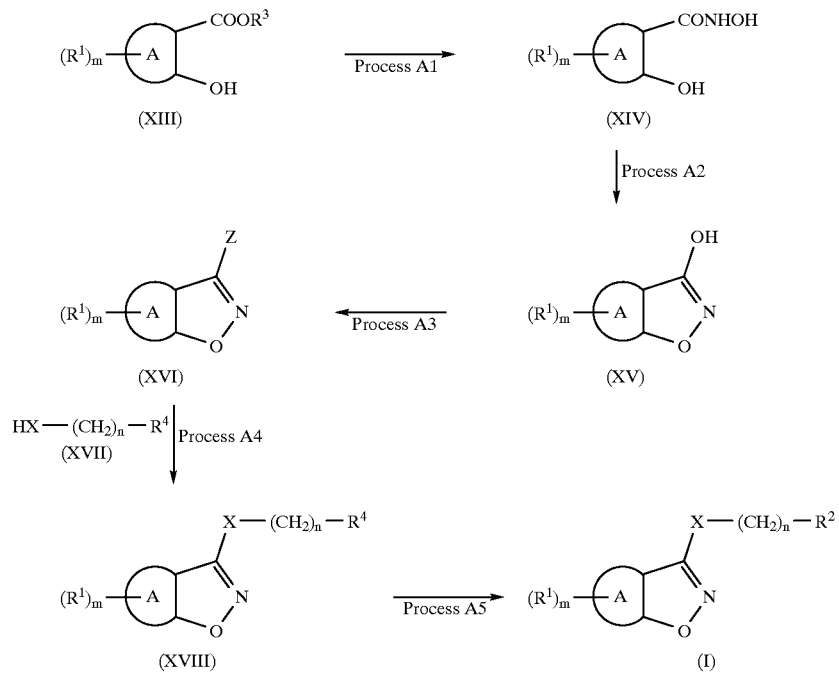

[Method A]

-continued
[Method B]
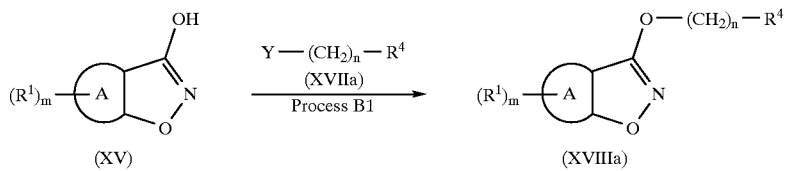
[Method C]
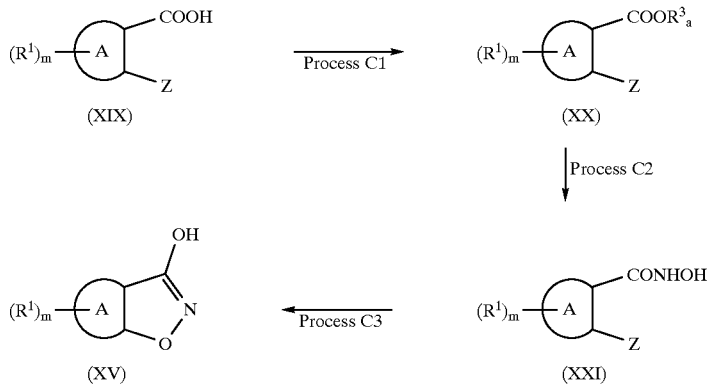
[Method D]
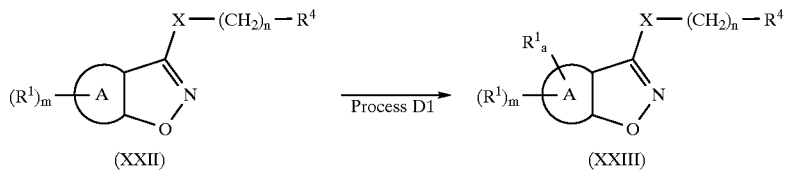
[Method E]
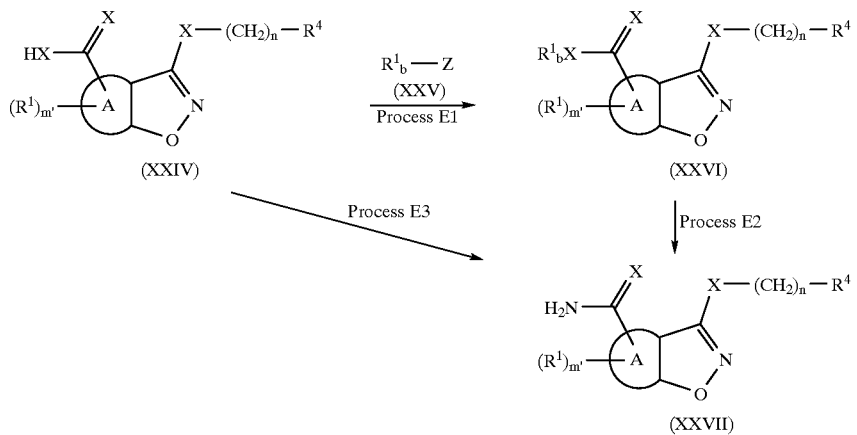
[Method F]
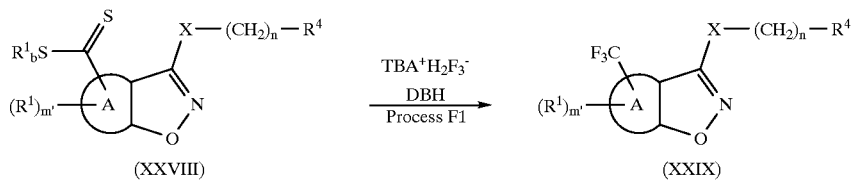

-continued

[Method G]

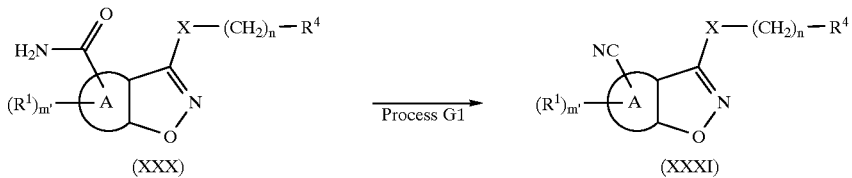

In the above formulae, $R^1$, $R^2$, m, n, Ring A and X are the same as those mentioned previously, while $R^1_a$ represents a $C_1$–$C_6$ alkyl, $C_1$–$C_6$ alkylthio, $C_1$–$C_6$ alkoxycarbonyl, carboxy, dithiocarboxy or ($C_1$–$C_6$ alkylthio)thiocarbonyl radical, $R^1_b$ represents a $C_1$–$C_6$ alkyl radical, $R^3$ represents an ester residue, $R^3_a$ represents a $C_1$–$C_4$ alkyl radical, $R^4$ represents a protected amino radical, Y represents a hydroxy or a leaving group, Z represents a halogen atom and m' represents an integer of 1 or 2.

The $C_1$–$C_6$ alkyl parts in the $C_1$–$C_6$ alkyl radical or $C_1$–$C_6$ alkylthio radical of $R^1$a are the same as those mentioned previously; $R^1$a may be, for example, methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, methylthio, ethylthio, propylthio, isopropylthio, butylthio, isobutylthio, s-butylthio, t-butylthio, pentylthio, isopentylthio, 2-methylbutylthio, neopentylthio, 1-ethylpropylthio, hexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio, 2-ethylbutylthio, methoxycarbonyl, ethoxycarbonyl, propoxycarbonyl, isopropoxycarbonyl, butoxycarbonyl, i-butoxycarbonyl, s-butoxycarbonyl, t-butoxycarbonyl, pentyloxycarbonyl, hexyloxycarbonyl, carboxy, dithiocarboxy or (methylthio) thiocarbonyl radical, preferably $C_1$–$C_4$ alkyl, $C_1$–$C_4$ alkylthio, $C_1$–$C_4$ alkoxycarbonyl, carboxy or dithiocarboxy radical and, more preferably, methyl, ethyl, methylthio, ethylthio or carboxy radical.

The $C_1$–$C_6$ alkyl radicals in $R^1$b are the same as those mentioned previously and it may be, for example, methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl,2,2-dimethylbutyl, 1,1-dimethylbutyl, 1,2-dimethylbutyl, 1,3-dimethylbutyl, 2,3-dimethylbutyl or 2-ethylbutyl radical, preferably $C_1$–$C_4$ alkyl radical and, more preferably, methyl or ethyl radical.

The ester residue in $R^3$ may be, for example, $C_1$–$C_6$ alkyl radical such as methyl, ethyl, propyl, isopropyl, butyl, isobutyl, s-butyl, t-butyl, pentyl or hexyl radical; or substituted $C_1$–$C_4$ alkyl radical (the substituting radical may be halogen atom, $C_1$–$C_4$ alkoxy radical, halogen- or $C_1$–$C_4$ alkoxy-substituted $C_1$–$C_4$ alkoxy radical, $C_6$–$C_{14}$ aryl radical, or $C_6$–$C_{14}$ aryl radical substituted by 1 to 3 radicals selected from the groups of $C_1$–$C_4$ alkyl radicals, $C_1$–$C_4$ alkoxy radical, nitro, halogen and cyano groups) such as 2-fluoroethyl, 2-chloroethyl, 2-bromoethyl, 2,2-dibromoethyl, 2,2,2-trichloroethyl, 3-fluoropropyl, 4-chlorobutyl, methoxymethyl, 1,1-dimethyl-1-methoxymethyl, ethoxymethyl, n-propoxymethyl, isopropoxymethyl, n-butoxymethyl, t-butoxymethyl, 1-ethoxyethyl, 1-methyl-1-methoxyethyl, 1-(isopropoxy)ethyl, 3-methoxypropyl-4-methoxybutyl, fluoromethoxymethyl, 2,2,2-trichloroethoxymethyl, bis(2-chloroethoxy)methyl, 3-fluoropropoxymethyl, 4-chlorobutoxyethyl, dibromomethoxyethyl, 2-chloroethoxypropyl, fluoromethoxybutyl, 2-methoxyethoxymethyl, ethoxymethoxyethyl, methoxyethoxypropyl, methoxyethoxybutyl, benzyl, phenethyl, 3-phenylpropyl, 4-phenylbutyl, α-naphthylmethyl, β-naphthylmethyl, diphenylmethyl, triphenylmethyl, α-naphthyldipheylmethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl or piperonyl radical, preferably $C_1$–$C_4$alkyl, 2-fluorothyl, 2-chloroethyl, 2-bromoethyl, 2,2,2-trichloroethyl, methoxymethyl, ethoxymethyl, fluoromethoxymethyl, 2,2,2-trichloroethoxymethyl, bis(2-chloroethoxy)methyl, benzyl, phenethyl, 4-methylbenzyl, 2,4,6-trimethylbenzyl, 4-methoxybenzyl, 4-nitrobenzyl, 4-chlorobenzyl or 4-cyanobenzyl radical and, more preferably, methyl, ethyl, 2,2,2-trichloroethyl, methoxymethyl, ethoxymethyl, fluoromethoxymethyl, 2,2,2-trichloroethoxymethyl, benzyl, phenethyl, 4-methylbenzyl, 4-methoxybenzyl, 4-nitrobenzyl, 4-chlorobenzyl or 4-cyanobenzyl radical, Methyl or ethyl radical is particularly favorable.

The $C_1$–$C_4$ alkyl radical in $R^3$a may be, for example, methyl, ethyl, propyl, isopropyl, butyl, isobutyl, s-butyl or t-butyl radical, preferably methyl or ethyl radical and, more preferably, methyl radical.

The protecting group of the protected amino radical in $R^4$ is not particularly restricted and may be any radical generally utilizable for amino radical protection and may be for example, $C_1$–$C_6$ alkanoyl radical such as formyl, acetyl, propionyl, butyryl, isobutyryl, pentanoyl, pivaloyl, valeryl, isovaleryl or hexanoyl radical; halogen- or $C_1$–$C_4$ alkoxy-substituted $C_1$–$C_4$ alkanoyl radical such as chloroacetyl, dichloroacetyl, trichloroacetyl, trifluoroacetyl, 3-fluoropropionyl, 4,4-dichlorobutyryl, methoxyacetyl, butoxyacetyl, ethoxypropionyl or propoxybutyryl radical; unsaturated $C_1$–$C_4$ alkanoyl radical such as acryloyl, propioloyl, methacryloyl, crotonoyl or isocrotonoyl radical; $C_6$–$C_{10}$ arylcarbonyl radical which may be substituted by halogen, $C_1$–$C_4$ alkyl, $C_1$–$C_4$ alkoxy, $C_1$–$C_4$ alkoxycarbonyl, $C_6$–$C_{10}$ aryl or nitro radical, such as for example, benzoyl, α-naphthoyl, β-naphthoyl, 2-fluorobenzoyl, 2-bromobenzoyl, 2,4-dichlorobenzoyl, 6-chloro-α-naphthoyl, 4-toluoyl, 4-propylbenzoyl, 4-t-butylbenzoyl, 2,4,6-trimethylbenzoyl, 6-ethyl-α-naphthoyl, 4-anisoyl, 4-propoxybenzoyl, 4-t-butoxybenzoyl, 6-ethoxy- α-naphthoyl, 2-ethoxycarbonylbenzoyl, 4-t-butoxycarbonylbenzoyl, 6-methoxycarbonyl-α-naphthoyl, 4-phenylbenzoyl, 4-phenyl-α-naphthoyl, 6-α-naphthylbenzoyl, 4-nitrobenzoyl, 2-nitrobenzoyl or 6-nitro-α-naphthoyl radical; $C_1$–$C_4$ alkoxycarbonyl radical which may be substituted by a halogen or a tri $C_1$–$C_4$ alkylsilyl such as methoxycarbonyl, ethoxycarbonyl, propoxycarbonyl, isopropoxycarbonyl, butoxycarbonyl, isobutoxycarbonyl, s-butoxycarbonyl, t-butoxycarbonyl, chloromethoxycarbonyl, 2,2,2-trichloroethoxycarbonyl, 2-fluoropopoxycarbonyl, 2-bromo-t-butoxycarbonyl, 2,2-dibormo-t-butoxycarbonyl, triethylsilylmethoxycarbonyl, 2-trimethylsilylethoxycarbonyl, 4-tripropylsilylbutoxycarbonyl or t-butyldimethylsilylpropoxycarbonyl radical; $C_2$–$C_5$ alkenyloxycarbonyl radical such as, for example, vinyloxycarbonyl, allyloxycarbonyl, 1,3-butadienyloxycarbonyl or 2-pentenyloxycarbonyl radical; aryldicarbonyl radical such as, for example, phthaloyl radical; aralkyl radical such as, for example, benzyl, phenethyl, 3-phenylpropyl, 4-phenylbutyl, α-naphthylmethyl, β-naphthylmethyl, diphenylmethyl, triphenylmethyl, α-naphthyldiphenylmethyl or 9-anthrylmethyl radical; or $C_7$–$C_{15}$ aralkyloxycarbonyl radical which may be substituted by a methoxy or nitro radical such as, for example, benzyloxycarbonyl, (1-phenyl)benzyloxycarbonyl, α-naphthylmethyloxycarbonyl, β-naphthylmethyloxycarbonyl, 9-anthrylmethyloxycarbonyl, p-methoxybenzyloxycarbonyl or p-nitrobenzyloxycarbonyl radical, preferably $C_1$–$C_4$ alkanoyl, trifluoroacetyl, methoxyacetyl, benzoyl, α-naphthoyl, β-naphthoyl, anisoyl, nitrobenzoyl, $C_1$–$C_4$ alkoxycarbonyl, methoxycarbonyl, ethoxycarbonyl, t-butoxycarbonyl, 2,2,2-trichloroethoxycarbonyl, triethylsilylmethoxycarbonyl, 2-trimethylsilylethoxycarbonyl, vinyloxycarbonyl, allyloxycarbonyl, phthaloyl, benzyl, benzyloxycarbonyl or nitrobenzyloxycarbonyl radical and, more preferably, formyl, acetyl, benzoyl, 4-anisoyl, 4-nitrobenzoyl, methoxycarbonyl, ethoxycarbonyl, butoxycarbonyl, t-butoxycarbonyl, phthaloyl, benzyl, benzyloxycarbonyl or p-nitrobenzyloxycarbonyl radical. t-Butoxycarbonyl radical is particularly favorable.

The leaving group in Y is not particularly restricted provided that it is usually eliminated as a nucleophilic residue and it may be, for example, a halogen atom such as fluorine, chlorine, bromine or iodine atom; $C_1$–$C_4$ alkane sulfonyloxy radical such as methane sulfonyloxy, ethane sulfonyloxy, propane sulfonyloxy or butane sulfonyloxy radical; halogeno $C_1$–$C_4$ alkane sulfonyloxy radical such as trifluoromethane sulfonyloxy, 2,2,2-trichloroethane sulfonyloxy, 3,3,3-tribromopropane sulfonyloxy or 4,4,4-trifluorobutane sulfonyloxy radical; or $C_6$–$C_{10}$ arylsulfonyloxy radical which may contain 1 to 3 $C_1$–$C_4$ alkyl radicals such as benzene sulfonyloxy, α-naphthylsulfonyloxy, β-naphthylsulfonyloxy, p-toluenesulfonyloxy, 4-t-butylbenzene sulfonyloxy, mesitylene sulfonyloxy or 6-ethyl-α-naphthylsulfonyloxy radical. It is preferably chlorine, bromine, iodine atom; methane sulfonyloxy, ethane sulfonyloxy, trifluoromethane sulfonyloxy, 2,2,2-trichloroethane sulfonyloxy radical; benzene sulfonyloxy, toluene sulfonyloxy or mesitylene sulfonyloxy radical and more preferably, chlorine bromine, iodine atom; methane sulfonyloxy, trifluoromethane sulfonyloxy, benzen sulfonyloxy, p-toluene sulfonyloxy or mesitylene sulfonyloxy radical.

The halogen atom in Z may be, for example, a fluorine, chlorine, bromine or iodine atom and, preferably, fluorine or chlorine atom.

The compounds (XIII) or (XIX) which are the starting materials of this invention are either a well known compound or that which can be synthesized according to a well known method [e.g., *Chem. Abstr.*, 49,11594(1955)., *Tetrahedron*, 38,1457(1982)., Japanese Patent Application No. Kokai Hei3-294267, *Synth. Commun.*, 9,731(1979)., *J. Org. Chem.*, 44,3292(1979). or *Chem. Ber.*, 100,954(1967).]

The compound having the general formula (XVII) may be a well known compound or can be synthesized by a well known method [e.g., *Synthesis*, 366(1990)., or *J. Med. Chem.*, 34,1258(1991).].

The compound having the general formula (XV) in which the ring A is a pyridyl ring may be a well known compound or can be synthesized according to a well known method [e.g., *J. Med. Chem.*, 32,2116(1989). or *J. Chem. Soc. (C)*, 172(1968).].

Method A is the method for synthesizing the compound (I).

In Process A1, a compound having the general formula (XIII) is treated with hydroxylamine in an inert solvent in the presence of a base to prepare a compound having the general formula (XIV).

The solvent used is not particularly restricted provided that it does not interfere with the reaction and can dissolve a certain amount of the starting material and it may be, for example, an aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlorobenzene; ether such as diethylether, diisopropylether, tetrahydrofuran, dioxane, dimethoxyethane or diethyleneglycol dimethylether; alcohol such as methanol, ethanol, propanol, isopropanol, butanol or isobutanol; amide such as formamide, dimethylformamide, dimethylacetamide or hexamethylphosphoramide; sulfoxide such as dimethylsulfoxide or sulfolan; water or an aqueous mixture of the above organic solvent. It is preferably selected from ethers, alcohols, amides, sulfoxides or an aqueous mixture of these organic solvents and it is more preferably an alcohol (particularly methanol or ethanol) or an aqueous alcohol (particularly aqueous methanol or aqueous ethanol).

The base used may be, for example, an alkali metal carbonate such as sodium carbonate, potassium carbonate or lithium carbonate, an alkali metal hydrogen carbonate such as sodium hydrogen carbonate, potassium hydrogen carbonate or lithium hydrogen carbonate; an alkali metal hydride such as sodium hydride, potassium hydride or lithium hydride; an alkali metal hydroxide such as sodium hydroxide, potassium hydroxide or lithium hydroxide; alkali metal alkoxide such as sodium methoxide, sodium ethoxide, potassium t-butoxide or lithium methoxide; alkali metal mercaptan such as sodium methylmercaptan or sodium ethylmercaptan; organic amine such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4,3,0]non-5-ene, 1,4-diazabicyclo[2,2,2]octane (DABCO) or 1,8-diazabicyclo[5,4,0]undec-7-ene (DBU); alkyl lithium such as methyl lithium, ethyl lithium or butyl lithium; lithium alkylamide such as lithium diisopropylamide or lithium dicyclohexylamide. It is preferably alkali metal carbonate, alkali metal hydroxide or alkali metal alkoxide and, more preferably, alkali metal hydroxide (particularly sodium hydroxide or potassium hydroxide).

The reaction temperature may be altered depending on the starting material or reagents but it is usually in the range from −10 to 100° C. and preferably from 0 to 50° C.

The reaction time may be altered depending on the starting material, reagents or reaction temperature but it is usually between 10 minutes and 10 hours and preferably between 30 minutes and 5 hours.

After completion of the reaction, the target compound of this process is isolated from the reaction mixture according to a usual method. For example, the solvent is removed by evaporation After the completion of the reaction, water is added to the residue to make the aqueous layer acidic, and the precipitated compound is filtered. Or water is added to the reaction mixture and a hydrophobic solvent (e.g., benzene, ether, ethylacetate) is added to extract the target compound. The organic layer is washed with water, dried over anhydrous magnesium sulphate, and the solvent is evaporated to obtain the target compound. The target compound obtained may be purified, if necessary, by a usual method, e.g., recrystallization, reprecipitation, chromatography or by converting it to a salt by addition of an acid.

In Process A2, the compound having the general formula (XV) is synthesized from that having the general formula (XIV) according to the reaction mentioned in *Chem. Ber.*, 100,954(1967). by
(1) the reaction with thionyl chloride, phosgene or their equivalents (e.g., diphosgene) (preferably thionyl chloride) in an inert solvent, and then
(2) the reaction with a base in an inert solvent.

The solvents used in the processes (1) and (2) are not particularly restricted provided that they do not interfere with the reactions and dissolve a certain amount of the starting materials. They may be, for example, aliphatic hydrocarbons such as hexane, heptane, ligroin or petroleum ether; aromatic hydrocarbons such as benzene, toluene or xylene; halogenated hydrocarbons such as methylenechloride, chloroform, carbontetrachloride, dichloroethane, chlorobenzene or dichlororbenzene; ethers such as diethylether, diisopropylether, tetrahydrofuran, dioxane, dimethoxyethane or diethyleneglycol dimethylether; or sulfoxides such as dimethylsulfoxide or sulforan. They are preferably halogenated hydrocarbons (particularly methylenechloride, chloroform, carbontetrachloride or dichloroethane) or ethers (particularly diethylether, diisopropylether, tetrahydrofuran or dioxane) and, more preferably, ethers (particularly diethylether, diisopropylether, tetrahydrofuran or dioxane).

The base used in the process (2) may be, for example, alkali metal carbonate such as sodium carbonate, potassium carbonate or lithium carbonate; alkali metal hydrogen carbonate such as sodium hydrogen carbonate, potassium hydrogen carbonate or lithium hydrogen carbonate; alkali metal hydride such.as lithium hydride, sodium hydride or potassium hydride; alkali metal hydroxide such as sodium hydroxide, potassium hydroxide or lithium hydroxide; alkali metal alkoxide such as sodium methoxide, sodium ethoxide, potassium t-butoxide or lithium methoxide; alkali metal mercaptan such as sodium methylmercaptan or sodium ethylmercaptan; organic amine such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4,3,0]non-5-ene, 1,4-diazabicyclo[2,2,2]octane (DABCO) or 1,8-diazabicyclo[5,4,0]undec-7-ene (DBU); alkyl lithium such as methyl lithium or butyl lithium: or lithium alkylamide such as lithium diisopropylamide or lithium dicyclohexylamide. It is preferably an organic amine and, more preferably, triethylamine, tributylamine, diisopropylethylamine, pyridine, 1,5-diazabicyclo[4,3,0]non-5-ene, 1,4-diazabicyclo[2,2,2]octane (DABCO) or 1,8-diazabicyclo[5,4,0]undec-7-ene (DBU). Triethylamine is particularly favorable.

The reaction temperatures in the steps (1) and (2) are altered depending on the starting materials or reagents but they are usually between −10 and 100° C., and preferably, between 0 and 50° C.

The reaction times in the steps (1) and (2) change depending on the starting materials, reagents or reaction temperatures but they are usually between 10 minutes and 10 hours, and preferably, between 15 minutes and 5 hours.

After the completion of the reaction, the target compound of this process is isolated from the reaction mixture according to a usual method. For example, the target compound is isolated by removing the solvent by evaporation, adding water to the reaction mixture, making the aqueous layer acidic to filter the precipitated product or by adding a hydrophobic solvent (e.g., benzene, ether, ethyl acetate), washing the extract with water, drying it over anhydrous magnesium sulphate and removing the solvent by evaporation. The target compound obtained may be, if necessary, purified by recrystallization, reprecipitation or chromatography.

In Process A3, the compound (XVI) is synthesized by the reaction between the compound (XV) and a halogenating agent in an inert solvent or without a solvent in the presence or absence of a base (preferably in the presence of a base).

The halogenating agent may be, for example, phosphorus oxychloride, phosphorus oxybromide, phosphorus oxyiodide or phosphorus pentachloride, and preferably, phosphorus oxychloride, phosphorus pentachloride or their mixtures.

The solvent used is not particularly restricted provided that it does not interfere with the reaction and dissolved a certain amount of the starting material and it may be, for example, aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlororbenzene; ether such as diethylether, diisopropylether, tetrahydrofuran, dioxane, dimethoxyethane or diethyleneglycol dimethylether; or sulfoxide such as dimethylsulfoxide or sulforan, preferably a halogenated hydrocarbon (particularly methylenechloride) or ether (particularly tetrahydrofuran or dioxane).

The base used may be, for example, alkali metal carbonate such as sodium carbonate, potassium carbonate or lithium carbonate; alkali metal hydrogen carbonate such as sodium hydrogen carbonate, potassium hydrogen carbonate or lithium hydrogen carbonate; alkali metal hydride such as lithium hydride, sodium hydride or potassium hydride; alkali metal hydroxide such as sodium hydroxide, potassium hydroxide or lithium hydroxide; or organic amine such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4,3,0]non-5-ene, 1,4-diazabicyclo[2,2,2] octane (DABCO) or 1,8-diazabicyclo[5,4,0]undec-7-ene (DBU), preferably an alkali metal carbonate or an organic amine, and more preferably, organic amine (particularly triethylamine or pyridine).

The reaction temperature is altered depending on the starting material or reagents but it is usually between 0 and 150° C. and, preferably between 10 and 100° C.

The reaction time changes depending on the starting material, reagents or reaction temperature but it is usually between 30 minutes and 10 hours and, preferably, between 1 and 5 hours.

After the completion of the reaction, the target compound of this process is isolated from the reaction mixture according to a usual method. For example, the target compound is isolated by removing the solvent by evaporation, adding water to the reaction mixture followed by addition of a hydrophobic solvent (e.g., benzene, ether, ethyl acetate) to extract the compound, washing the organic layer with water, drying it over anhydrous magnesium sulphate and removing the solvent by evaporation. The target compound obtained may be, if necessary, purified by recrystallization, reprecipitation or chromatography.

In Process A4, the compound (XVIII) is synthesized by the reaction between the compound (XVI) and the compound having the general formula (XVII) in an inert solvent in the presence of a base.

The solvent used is not particularly restricted provided that it does not interfere with the reaction and dissolved a certain amount of the starting material and it may be, for example, aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlororbenzene; ether such as diethylether, diisopropylether, tetrahydrofuran, dioxane, dimethoxyethane or diethyleneglycol dimethylether; or amide such as formamide, dimethylformamide, dimethylacetamide or hexamethylphosphoramide; or sulfoxide such as dimethylsulfoxide or sulforan. It is preferably an ether, amide or sulfoxide and, more preferably, an ether (particularly diethylether, tetrahydrofuran or dioxane) or amide (particularly dimethylformamide).

The base used may be, for example, alkali metal carbonate such as sodium carbonate, potassium carbonate or lithium carbonate; alkali metal hydrogen carbonate such as sodium hydrogen carbonate, potassium hydrogen carbonate or lithium hydrogen carbonate; alkali metal hydride such as lithium hydride, sodium hydride or potassium hydride; alkali metal hydroxide such as sodium hydroxide, potassium hydroxide or lithium hydroxide; or organic amine such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4,3,0]non-5-ene, 1,4-diazabicyclo[2,2,2]octane (DABCO) or 1,8-diazabicyclo[5,4,0]undec-7-ene (DBU); alkyl lithium such as methyl lithium, ethyl lithium or butyl lithium; lithium alkylamide such as lithium diisopropylamide or lithium dicyclohexylamide, preferably an alkali metal carbonate, alkali metal hydride or an organic amine, and more preferably, alkali metal carbonate (particularly sodium carbonate or potassium carbonate) or alkali metal hydride (particularly sodium hydride).

A crown ether such as dibenzo-18-crown-6 may be added to enhance the reaction.

The reaction temperature is altered depending on the starting material or reagents but it is usually between $-10$ and $150°$ C. and, preferably, between 0 and $80°$ C.

The reaction time changes depending on the starting material, reagents or reaction temperature but it is usually between 30 minutes and 30 hours and, preferably, between 1 and 10 hours.

After the completion of the reaction, the target compound of this process is isolated from the reaction mixture according to a usual method. For example, the target compound is isolated by neutralizing the reaction mixture appropriately, filtering any insoluble material if present, removing the solvent by evaporation, adding water to the reaction mixture followed by addition of a hydrophobic solvent (e.g., benzene, ether, ethyl acetate) to extract the compound, washing the organic layer with water, drying it over anhydrous magnesium sulphate and removing the solvent by evaporation. The target compound obtained may be, if necessary, purified by recrystallization, reprecipitation or chromatography.

In Process A5, the amino-protecting group is removed to yield the compound (I).

Removal of the amino-protecting group changes depending on the type of protecting group but it is carried out as follows using a well known method in the general organic synthetic chemistry.

If the amino-protecting group is any of $C_1$–$C_6$ alkanoyl radicals (preferably formyl or acetyl radical); $C_6$–$C_{10}$ arylcarbonyl radicals (preferably benzoyl radical); $C_1$–$C_4$ alkoxycarbonyl radicals which may be substituted by halogen or tri $C_1$–$C_4$ alkylsilyl (preferably methoxycarbonyl, ethoxycarbonyl, t-butoxycarbonyl, 2-trimethylsilylethoxycarbonyl, 2-bromo-t-butoxycarbonyl, or 2,2-dibromo-t-butoxycarbonyl radical); $C_2$–$C_5$ alkenyloxycarbonyl radicals which may be substituted by methoxy or nitro (preferably vinyloxycarbonyl radical); or $C_7$–$C_{15}$ aralkyloxy-carbonyl radicals which may be substituted by methoxy or nitro (preferably benzyloxycarbonyl, (1-phenyl) benzyloxycarbonyl, 9-anthrylmethyloxycarbonyl, p-methoxybenzyloxycarbonyl or p-nitrobenzyloxycarbonyl radical), it can be eliminated by the acid treatment in an inert solvent or an aqueous solvent. The target product may be obtained as a salt in this case.

The acid used may be, for example, hydrochloric acid, sulphuric acid, phosphoric acid, hydrobromic acid or trifluoroacetic acid and it is preferably any of hydrochloric acid, sulphuric acid, hydrobromic acid or trifluoroacetic acid.

The solvent used is not particularly restricted provided that it does not interfere with the reaction and dissolved a certain amount of the starting material and it may be, for example, aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlororbenzene; ether such as diethylether, diisopropylether, tetrahydrofuran, dioxane, dimethoxyethane or diethyleneglycol dimethylether; or ester such as methyl acetate or ethyl acetate; alcohol such as methanol, ethanol, propanol, isopropanol or butanol; amide such as formamide, dimethylformamide, dimethylacetamide or hexamethylphosphoramide; sulfoxide such as dimethylsulfoxide or sulforan; aliphatic acid such as formic acid or acetic acid; or water or an aqueous mixture of the above solvents, preferably a halogenated hydrocarbon, ether, alcohol, aliphatic acid; water or an aqueous mixture of the above solvent and, more preferably, haogenated hydrocarbon (particularly methlene chloride), ether (particularly tetrahydrofuran or dioxane), aliphatic acid (particularly acetic acid), water or an aqueous mixture of the above solvent.

The reaction temperature is altered depending on the starting material, solvent or the acid used but it is usually between $-10$ and $150°$ C. and, preferably, between 0 and $60°$ C.

The reaction time changes depending on the starting material, solvent or the acid used but it is usually between 5 minutes and 20 hours and, preferably, between 10 minutes and 5 hours.

After the completion of the reaction, the target compound of this process is isolated from the reaction mixture according to a usual method. For example, the target compound is isolated by filtering the target product precipitated in the reaction mixture, or neutralizing the reaction mixture appropriately, removing the solvent by evaporation, adding water to the reaction mixture followed by addition of a hydrophobic solvent (e.g., benzene, ether, ethyl acetate) to extract the compound, washing the organic layer with water, drying it over anhydrous magnesium sulphate and removing the solvent by evaporation. The target compound obtained may be, if necessary, purified by recrystallization, reprecipitation or chromatography.

If the amino-protecting group is any of alkanoyl, arylcarbonyl, alkoxycarbonyl, alkenyloxycarbonyl, aryldicarbonyl, aralkyl, or aralkyloxycarbonyl radicals, it can be eliminated by a base treatment in an inert solvent or an aqueous solvent.

The base used may be, for example, alkali metal carbonate such as sodium carbonate, potassium carbonate or lithium carbonate; alkali metal hydrogen carbonate such as sodium hydrogen carbonate, potassium hydrogen carbonate or lithium hydrogen carbonate; alkali metal hydride such as lithium hydride, sodium hydride or potassium hydride; alkali metal hydroxide such as sodium hydroxide, potassium hydroxide or lithium hydroxide; alkali metal alkoxide such as sodium methoxide, sodium ethoxide, potassium t-butoxide, or lithium methoxide; alkali metal mercaptan such as sodium methylmercaptan or sodium ethylmercaptan, preferably alkali metal carbonate (particularly sodium carbonate or potassium carbonate), alkali metal hydroxide (particularly sodium hydoroxide or potassium hydroxide), alkali metal alkoxide (particularly sodium methoxide, sodium ethoxide or potassium t-butoxide) or organic amine (particularly hydrazine or methylamine).

The solvent used is not particularly restricted provided that it does not interfere with the reaction and dissolved a certain amount of the starting material and it may be, for example, aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlororbenzene; ether such as diethylether, diisopropylether, tetrahydrofuran, dioxane, dimethoxyethane or diethyleneglycol dimethylether; alcohol such as methanol, ethanol, propanol, isopropanol or butanol; amide such as dimethylacetamide or hexamethylphosphoramide; sulfoxide such as dimethylsulfoxide or sulforan; or an aqueous mixture of the above solvents, preferably a halogenated hydrocarbon, ether, alcohol or an aqueous mixture of the above solvents, and more preferably, ether (particularly tetrahydrofuran or dioxane), alcohol (particularly methanol or ethanol) or an aqueous mixture of the above solvents.

The reaction temperature is altered depending on the starting material, solvent or the base used but it is usually between −10 and 150° C. and, preferably, between 0 and 50° C.

The reaction time changes depending on the starting material, solvent or the base used but it is usually between 30 minutes and 20 hours and, preferably, between 1 and 5 hours.

After the completion of the reaction, the target compound of this process is isolated from the reaction mixture according to a usual method. For example, the target compound is available by filtering the product precipitated in the reaction mixture or by removing the solvent by evaporation, adding water to make the aqueous layer alkaline to filter off the precipitated product, or adding hydrophobic solvent (e.g., benzene, ether, ethyl acetate) to extract the compound, washing the organic layer containing the target product with water, drying it over anhydrous magnesium sulphate and removing the solvent by evaporation. The target compound obtained may be, if necessary, purified by recrystallization, reprecipitation or chromatography.

If the amino-protecting group is a tertiary-butoxycarbonyl radical, it can also be eliminated by treating with a silyl compound or Lewis acid in an inert solvent.

The silyl compound used may be, for example, trimethylsilylchloride, trimethylsilyliodide or trimethylsilyltrifluoromethanesulfonate and the Lewis acid used may be aluminium chloride.

The solvent used is not particularly restricted provided that it does not interfere with the reaction and dissolved a certain amount of the starting material and it may be, for example, halogenated hydrocarbon such as methylenechloride, chloroform or carbontetrachloride; ether such as diethylether, tetrahydrofuran or dioxane; or nitrile such as acetonitrile, preferably a halogenated hydrocarbon (particularly methylene chloride or chloroform) or nitrile (particularly acetonitrile).

The reaction temperature is altered depending on the starting material, reagent or solvent but it is usually between −20 and 100° C. and, preferably, between 0 and 50° C.

The reaction time changes depending on the starting material, reagent, solvent or the reaction temperature but it is usually between 10 minutes and 10 hours and, preferably, between 30 minutes and 3 hours.

After the completion of the reaction, the target compound of this process is isolated from the reaction mixture according to a usual method. For example, the target compound is isolated by removing the solvent by evaporation, adding water to the reaction mixture to make the aqueous layer alkaline and filtering the precipitated product or by adding a hydrophobic solvent (e.g., benzene, ether, ethyl acetate) to extract the compound, washing the organic layer containing the target product with water, drying it over anhydrous magnesium sulphate and removing the solvent by evaporation. The target compound obtained may be, if necessary, purified by recrystallization, reprecipitation or chromatography.

In case that the amino-protecting group is an allyloxycarbonyl radical, it can be eliminated using similar reaction conditions including solvent, reaction temperature and time as those of the elimination of aralkyl radical by the catalytic hydrogenation, with palladium and triphenylphosphine or nickel tetracarbonyl.

In case that the amino-protecting group is an aralkyl or $C_7$–$C_{11}$ aralkyloxycarbonyl radical, it can be removed easily by contacting with a reductant in an inert solvent (preferably catalytic hydrogenation in the presence of a catalyst) or by using an oxidant.

The solvent used in the catalytic hydrogenation to remove the protecting group is not particularly restricted provided that it does not participate in the reaction and it may be, for example, aliphatic hydrocarbon such as hexane or cyclohexane; aromatic hydrocarbon such as toluene, benzene or xylene; ether such as diethylether, tetrahydrofuran or dioxane; ester such as ethyl acetate or propyl acetate; alcohol such as methanol, ethanol or isopropanol; aliphatic acid such as formic acid and acetic acid; or an aqueous mixture of these organic solvents. It is preferably an aliphatic hydrocarbon, aromatic hydrocarbon, ether, ester, alcohol, aliphatic acid or an aqueous mixture of these solvents and, more preferably, alcohol (particularly methanol or ethanol), aliphatic acid (particularly formic acid or acetic acid) or an aqueous mixture of these solvents.

The catalyst used is not particularly restricted provided that it is used in a general catalytic hydrogenation and it may be, for example, palladium-carbon, Raney nickel, rhodiumaluminium oxide or palladium-barium sulphate. It is preferably palladium-carbon or Raney nickel.

The hydrogen pressure is not particularly restricted but it is usually between 1 and 10 atmospheric pressures and, preferably, it is 1 atmospheric pressure.

The reaction temperature is altered depending on the starting material, solvent or the catalyst used but it is usually between 0 and 100° C. and, preferably, between 10 and 50° C.

The reaction time changes depending on the starting material, solvent, the catalyst used or the reaction temperature but it is usually between 15 minutes and 10 hours and, preferably, between 30 minutes and 3 hours.

After the completion of the reaction, the target compound of this process is isolated from the reaction mixture according to a usual method. For example, the target compound is isolated by removing the solvent by evaporation after filtering the catalyst, adding water, making the aqueous layer alkaline and filtering the precipitated product, or by adding a hydrophobic solvent (e.g., benzene, ether, ethyl acetate) to extract the compound, washing the organic layer containing the target product with water, drying it over anhydrous magnesium sulphate and removing the solvent by evaporation. The target compound obtained may be, if necessary, purified by recrystallization, reprecipitation or chromatography.

The solvent used in the oxidation to remove the protecting group is not particularly restricted provided that it does not participate in the reaction and it may be, for example, a ketone such as acetone; halogenated hydrocarbon such as methylenechloride, chloroform or carbontetrachloride; nitrile such as acetonitrile; ether such as diethylether, tetrahydrofuran or dioxane; amide such as dimethylformamide, dimethylacetamide or hexamethylphosphoramide; sulfoxide such as dimethylsulfoxide; or an aqueous mixture of these organic solvents. It is preferably any of ketones, halogenated hydrocarbons, nitrites, ethers, amides, sulfoxides or an aqueous mixture of these solvents and, more preferably, ketones (particularly acetone), halogenated hydrocarbons (particularly methylenechloride), nitrites (particularly acetonitrile), amides (particularly hexamethylphosphoramide), sulfoxides (particularly dimethylsulfoxide) or an aqueous mixture of these solvents.

The oxidant used may be, for example, potassium persulphate, sodium persulphate, ceric ammonium nitrate (CAN) or 2,3-dichloro- 5,6-dicyano-p-benzoquinone (DDQ) and, preferably, ceric ammonium nitrate (CAN) or 2,3-dichloro-5,6-dicyano-p-benzoquinone (DDQ).

The reaction temperature is altered depending on the starting material, solvent or the oxidant used but it is usually between 0 and 150° C. and, preferably, between 10 and 50° C.

The reaction time changes depending on the compound, solvent or the oxidant used but it is usually between 15 minutes and 24 hours and, preferably, between 30 minutes and 5 hours.

After the completion of the reaction, the target compound of this process is isolated from the reaction mixture according to a usual method. For example, the target compound is isolated by removing the solvent by evaporation after filtering the oxidant, adding water making the aqueous layer alkaline and filtering the precipitated product, or by adding a hydrophobic solvent (e.g., benzene, ether, ethyl acetate) to extract the compound, washing the organic layer containing the target product with water, drying it over anhydrous magnesium sulphate and removing the solvent by evaporation. The target compound obtained may be, if necessary, purified by recrystallization, reprecipitation or chromatography.

Method B is the method for synthesizing the compound (XVIIIa) in which X is an oxygen in the intermediate compound (XVIII) of Method A.

In Process B1, the compound (XVIIIa) is prepared by the reaction of the compound (XV) with that having the general formula (XVIIa).

If Y is a hydroxyl radical, the reaction is carried out by dehydration-condensation between the compound (XV) and the corresponding compound (XVIIa) in an inert solvent in the presence of a phosphine-compound and azo-compound as conducted based on Mitsunobu reaction reported in *Bull.Chem.Soc.Jap.*, 40,2380(1967).

The solvent used is not particularly restricted provided that it does not interfere with the reaction and dissolves a certain amount of the starting material. It may be, for example, aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlorobenzene; or ether such as diethylether, diisopropylether, tetrahydrofuran, dioxane, dimethoxyethane or diethyleneglycol dimethylether. It is preferably aliphatic hydrocarbon, aromatic hydrocarbone or ether and, more preferably, ether (particularly diethylether or tetrahydrofuran).

The phosphine-compound used may be, for example, tri $C_1$–$C_6$ alkylphosphine such as trimethylphosphine, triethylphosphine, tripropylphosphine, tributylphosphine, tripentylphosphine or trihexylphosphine; tri $C_6$–$C_{10}$ arylphosphine such as triphenylphosphine, triindenylphosphine or trinaphthylphosphine; or tri $C_6$–$C_{10}$ arylphosphine which may have $C_1$–$C_4$ alkyl radical as a substitution radical such as tolyldiphenylphosphine, tritolylphosphine, trimesitylphosphine, tributylphenylphosphine or tri-6-ethyl-2-naphthylphosphine. It is preferably tri $C_1$–$C_6$ alkylphosphine (particularly trimethylphosphine, triethylphosphine, tripropylphosphine or tributylphosphine) or tri $C_6$–$C_{10}$ arylphosphine (particularly triphenylphosphine, triindenylphosphine or trinaphthylphosphine) and, more preferably, tri $C_6$–$C_{10}$ arylphosphine (particularly triphenylphosphine).

The azo-compound used may be, for example, a di $C_1$–$C_4$ alkyl-azodicarboxylate such as dimethyl azodicarboxylate, diethyl azodicarboxylate, dipropyl azodicarboxylate or dibutyl azodicarboxylate and it is preferably dimethyl azodicarboxylate or diethyl azodicarboxylate.

The reaction temperature is altered depending on the starting material or reagents but it is usually between −10 and 100° C. and, preferably, between 0 and 50° C.

The reaction time changes depending on the starting material, reagents or reaction temperature but it is usually between 15 minutes and 48 hours and, preferably, between 30 minutes and 24 hours.

After the completion of the reaction, the target compound of this process is isolated from the reaction mixture according to a usual method. For example, the target compound is available by filtering insoluble materials if any and removing the solvent by evaporation, or by adding water to the residue after removing the solvent, adding a hydrophobic solvent (e.g., benzene, ether, ethyl acetate) to extract the compound, washing with water, drying over anhydrous magnesium sulphate and removing the solvent by evaporation. The target compound obtained may be, if necessary, purified by recrystallization, reprecipitation or chromatography.

If Y is a leaving group, the compound (XVIIIa) is prepared by the reaction of compound (XV) with the corresponding compound (XVIIa) in an inert solvent in the presence of a base.

The solvent used is not particularly restricted provided that it does not interfere with the reaction and dissolves a certain amount of the starting material. It may be, for example, aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlorobenzene; or ether such as diethylether, diisopropylether, tetrahydrofuran, dioxane, dimethoxyethane or diethyleneglycol dimethylether, amide such as formamide, dimethylformamide, dimethylacetamide or hexamethylphosphoramide; or sulfoxide such as dimethylsulfoxide or sulforan. It is preferably an amide or a sulfoxide and, more preferably, an amide (particularly dimethylformamide, dimethylacetamide or hexamethylphosphoramide).

The base used may be, for example, alkali metal carbonate such as sodium carbonate, potassium carbonate or lithium carbonate; alkali metal hydrogen carbonate such as sodium hydrogen carbonate, potassium hydrogen carbonate or lithium hydrogen carbonate; alkali metal hydride such as lithium hydride, sodium hydride or potassium hydride; alkali metal hydroxide such as sodium hydroxide, potassium hydroxide or lithium hydroxide; alkali metal alkoxide such as sodium methoxide, sodium ethoxide, potassium t-butoxide, or lithium methoxide; alkali metal mercaptan such as sodium methylmercaptan or sodium ethylmercaptan; organic amine such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4,3,0]non-5-ene, 1,4-diazabicyclo[2,2,2]octane (DABCO) or 1,8-diazabicyclo[5,4,0]undec-7-ene (DBU); alkyl lithium such as methyl lithium, ethyl lithium or butyl lithium; or lithium alkylamide such as lithium diisopropylamide or lithium dicyclohexylamide. It is preferably alkali metal carbonate, alkali metal hydride or alkali metal hydroxide and, more preferably, alkali metal hydride (particularly sodium hydride).

A crown ether such as dibenzo-18-crown-6 may be added to enhance the reaction.

The reaction temperature is altered depending on the starting material or reagents but it is usually between −10 and 100° C., and preferably between 0 and 50° C.

The reaction time changes depending on the starting material, reagents or reaction temperature but it is usually between 30 minutes and 20 hours, and preferably between 1 and 5 hours.

After the completion of the reaction, the target compound of this process is isolated from the reaction mixture according to a usual method. For example, the target compound is isolated by neutralizing the reaction mixture appropriately, filtering insoluble materials if any, removing the solvent by evaporation, adding water to the reaction mixture, adding a hydrophobic solvent (e.g., benzene, ether, ethyl acetate) to extract the compound, washing the organic layer containing the target compound with water, drying over anhydrous magnesium sulphate and removing the solvent by evaporation. The target compound obtained may be, if necessary, purified by recrystallization, reprecipitation or chromatography.

Method C is an alternative method for synthesizing the compound (XV) which is the intermediate in Method A or the starting material in Method B.

In Process C1, the compound having the general formula (XX) is prepared by the reaction of the compound having the general formula (XIX) with a diazo $C_1$–$C_4$ alkane.

Diazo $C_1$–$C_4$ alkane may be any of diazomethane, diazoethane, diazopropane or diazobutane and it is preferably diazomethane.

The solvent used is not particularly restricted provided that it does not interfere with the reaction and dissolves a certain amount of the starting material. It may be, for example, aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlorobenzene; or ether such as diethylether, diisopropylether, tetrahydrofuran, dioxane, dimethoxyethane or diethyleneglycol dimethylether; ester such as methyl acetate or ethyl acetate; or a mixture of the above mentioned solvents. It is preferably a halogenated hydrocarbon, ether, ester or a mixture of the above mentioned solvents and, more preferably, an ether (particularly diethylether), ester (particularly ethyl acetate) or a mixture of the above mentioned solvents.

The reaction temperature is altered depending on the starting material or reagents but it is usually between −10 and 100° C., and preferably between 10 and 50° C.

The reaction time changes depending on the starting material, reagents or reaction temperature but it is usually between 10 minutes and 10 hours, and preferably between 15 minutes and 3 hours.

After the completion of the reaction, the target compound of this process is isolated from the reaction mixture according to a usual method. For example, the target compound is isolated by removing the solvent by evaporation. The target compound obtained may be, if necessary, purified by recrystallization, reprecipitation or chromatography.

In Process C2, the compound having the general formula (XXI) is prepared by the reaction of the compound (XX) with a hydroxylamine in an inert solvent in the presence of a base.

The solvent and the base are the same as those mentioned in Process A1.

The reaction temperature is altered depending on the starting material or reagents but it is usually between −10 and 100° C., and preferably between 10 and 50° C.

The reaction time changes depending on the starting material, reagents or reaction temperature but it is usually between 10 minutes and 10 hours, and preferably between 30 minutes and 5 hours.

After the completion of the reaction, the target compound of this process is isolated from the reaction mixture according to a usual method. For example, the target compound is isolated by removing the solvent by evaporation, adding water to the residue, making the aqueous layer acidic and filtering the precipitated product or by adding water to the reaction mixture, making the aqueous layer acidic, adding a hydrophobic solvent (e.g., benzene, ether or ethyl acetate) to extract the target compound, washing the extracted organic layer with water, drying over anhydrous magnesium sulphate and removing the solvent by evaporation. The target compound obtained may be, if necessary, purified by recrystallization, reprecipitation or chromatography.

In Process C3, the compound (XV) is prepared by the reaction of the compound (XXI) with a base in an inert solvent.

The solvent used is not particularly restricted provided that it does not interfere with the reaction and dissolves a certain amount of the starting material. It may be, for example, aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlorobenzene; or ether such as diethylether, diisopropylether, tetrahydrofuran, dioxane, dimethoxyethane or diethyleneglycol dimethylether; amide such as formamide, dimethylformamide, dimethylacetamide or hexamethylphosphoramide; sulfoxide such as dimethylsulfoxide or sulforan; or water. It is preferably an amide, a sulfoxide or water and, more preferably water.

The base used may be, for example, alkali metal carbonate such as sodium carbonate, potassium carbonate or lithium carbonate; alkali metal hydrogen carbonate such as sodium hydrogen carbonate, potassium hydrogen carbonate or lithium hydrogen carbonate; alkali metal hydride such as lithium hydride, sodium hydride or potassium hydride; alkali metal hydroxide such as sodium hydroxide, potassium hydroxide or lithium hydroxide; organic amine such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4,3,0]non-5-ene, 1,4-diazabicyclo[2,2,2] octane (DABCO) or 1,8-diazabicyclo[5,4,0]undec-7-ene (DBU); alkyl lithium such as methyl lithium, ethyl lithium or butyl lithium; or lithium alkylamide such as lithium diisopropylamide or lithium dicyclohexylamide. It is preferably alkali metal carbonate, alkali metal hydrogen carbonate or alkali metal hydroxide and, more preferably, alkali metal hydroxide (particularly sodium hydroxide or potassium hydroxide).

The reaction temperature is altered depending on the starting material or reagents but it is usually between 0 and 150° C., and preferably between 10 and 100° C.

The reaction time changes depending on the starting material, reagents or reaction temperature but it is usually between 10 minutes and 10 hours, and preferably between 15 minutes and 5 hours.

After the completion of the reaction, the target compound of this process is isolated from the reaction mixture according to a usual method. For example, the target compound is isolated by making the reaction mixture acidic and filtering the precipitated product or making the reaction mixture acidic, adding a hydrophobic solvent (e.g., benzene, ether, ethyl acetate) to extract the compound, washing the organic layer containing the target compound with water, drying over anhydrous magnesium sulphate and removing the solvent by evaporation. The target compound obtained may be, if necessary, purified by recrystallization, reprecipitation or chromatography.

Method D is the method for synthesizing the compound (XXIII) in which the substituting radical on the ring A of the intermediate compound (XVIII) in Method A contains $R^1a$.

In Process D1, the compound (XXIII) is synthesized by the reaction of the compound (XXII) with halogeno $C_1$–$C_6$alkane, carbon dioxide, carbon disulphide, di$C_1$–$C_6$alkyldisulphide, di$C_1$–$C_6$alkylcarbonate, S-(trifluoromethyl)dibenzothiophenium trifluoromethane sulphonate or S-(trifluoromethyl)-3,7-dinitrodibenzothiophenium trifluoromethane sulphonate (preferably halogeno $C_1$–$C_6$ alkyl or carbon dioxide) in an inert solvent in the presence of a base.

Halogeno $C_1$–$C_6$alkane may be, for example, methyl chloride, methyl bromide, methyl iodide, ethyl chloride, ethyl iodide, propyl bromide, butyl iodide, pentyl iodide or hexyl iodide. It is preferably methyl bromide or methyl iodide, and more preferably methyl iodide.

Di $C_1$–$C_6$alkyl disulphide may be, for example, dimethyl disulphide, diethyl disulphide, dipropyl disulphide, dibutyl disulphide, dipentyl disulphide or dihexyl disulphide, and it is preferably dimethyl disulphide or diethyl disulphide.

Di $C_1$–$C_6$alkylcarbonate may be, for example, dimethylcarbonate, diethylcarbonate, dipropylcarbonate, diisopropylcarbonate, dibutylcarbonate, di-s-butylcarbonate, di-t-butylcarbonate, dipentylcarbonate or dihexylcarbonate, and it is preferably dimethyl carbonate or diethyl carbonate.

The solvent used is not particularly restricted provided that it does not interfere with the reaction and dissolves a certain amount of the starting material. It may be, for example, aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlorobenzene; ether such as diethylether, diisopropylether, tetrahydrofuran, dioxane, dimethoxyethane or diethyleneglycol dimethylether; diamine such as N,N,N',N'-tetramethylethylenediamine; amide such as formamide, dimethylformamide, dimethylacetamide, hexamethylphosphoramide or hexamethylphosphoramide; or sulfoxide such as dimethylsulfoxide or sulforan. It is preferably an ether, an amide or a sulfoxide, and more preferably an ether (particularly tetrahydrofuran).

The base used may be, for example, alkali metal hydride as lithium hydride, sodium hydride or potassium hydride; alkyl lithium such as methyl lithium, ethyl lithium, butyl lithium or s-butyl lithium; or lithium alkylamide such as lithium diisopropylamide, lithium dicyclohexylamide, lithium bis(trimethylsilyl)amide, potassium bis (trimethylsilyl)amide or sodium bis(trimethylsilyl)amide. It is preferably alkali lithium (particularly butyl lithium) or lithium alkylamide (particularly lithium diisopropylamide).

The reaction temperature is altered depending on the starting material or reagents but it is usually between –100 and 30° C., and preferably between –70 and 0° C.

The reaction time changes depending on the starting material, reagents or reaction temperature but it is usually between 5 minutes and 10 hours, and preferably between 10 minutes and 5 hours.

After the completion of the reaction, the target compound of this process is isolated from the reaction mixture according to a usual method. For example, the target compound is isolated by removing the solvent by evaporation, or by removing the solvent by evaporation, adding water to the residue, adding a hydrophobic solvent (e.g., benzene, ether, ethyl acetate) to extract the compound, washing the extracting organic layer with water, drying over anhydrous magnesium sulphate and removing the solvent by evaporation. The target compound obtained may be, if necessary, purified by recrystallization, reprecipitation or chromatography.

Meanwhile, the target compound of this process is used in the next process without isolation or purification after completion of the reaction.

Method E is the method for synthesizing the compound (XXVII) in which the substituent on the ring A of the intermediate compound (XVIII) in Method A contains a carbamoyl radical and the compound (XXVIII) which is the starting material for Method F.

In Process E1, the compound (XXVI) is prepared by reaction of the compound (XXIV) with the compound having the general formula (XXV) in an inert solvent in the presence of a base. If X in the compound (XXVI) is a sulphur atom, it is the starting material (XXVIII) for Method F.

The solvent used is not particularly restricted provided that it does not interfere with the reaction and dissolves a certain amount of the starting material. It may be, for example, aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlorobenzene; ether such as diethylether, diisopropylether, tetrahydrofuran, dioxane, dimethoxyethane or diethyleneglycol dimethylether; diamine such as N,N,N',N'-tetramethylethylenediamine; amide such as formamide, dimethylformamide, dimethylacetamide, hexamethylphosphoramide or hexamethylphosphoramide; or sulfoxide such as dimethylsulfoxide or sulforan. It is preferably an amide or a sulfoxide, and more preferably an amide (particularly dimethylformamide).

The base used may be, for example, alkali metal carbonate such as sodium carbonate, potassium carbonate or lithium carbonate; alkali metal hydrogen carbonate such as sodium hydrogen carbonate, potassium hydrogen carbonate or lithium hydrogen carbonate; alkali metal hydride as lithium hydride, sodium hydride or potassium hydride; alkali metal hydroxide such as sodium hydroxide, potassium hydroxide or lithium hydroxide; organic amine such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4,3,0]non-5-ene, 1,4-diazabicyclo[2,2,2] octane (DABCO) or 1,8-diazabicyclo[5,4,0]undec-7-ene (DBU); alkyl lithium such as methyl lithium, ethyl lithium or butyl lithium; or lithium alkylamide such as lithium diisopropylamide or lithium dicyclohexylamide. It is preferably an alkali metal carbonate, alkali metal hydrogen carbonate or alkali metal hydroxide, and more preferably an alkali metal carbonate (particularly sodium carbonate, potassium carbonate or lithium carbonate).

The reaction temperature is altered depending on the starting material or reagents but it is usually between −10 and 100° C., and preferably between 0 and 50° C.

The reaction time changes depending on the starting material, reagents or reaction temperature but it is usually between 30 minutes and 30 hours, and preferably between 1 and 20 hours.

After the completion of the reaction, the target compound of this process is isolated from the reaction mixture according to a usual method. For example, the target compound is isolated by removing the solvent by evaporation, or by removing the solvent by evaporation, adding water to the residue, adding a hydrophobic solvent (e.g., benzene, ether, ethyl acetate) to extract the compound, washing the extracting organic layer with water, drying over anhydrous magnesium sulphate and removing the solvent by evaporation. The target compound obtained may be, if necessary, purified by recrystallization, reprecipitation or chromatography.

In Process E2, the compound (XXVII) is prepared by the reaction of the compound (XXVI) with ammonia gas or a concentrated ammonia solution in an inert solvent. If X in the compound (XXVII) is a sulphur atom, then, the substituent on the ring A in the compound (XVIII) contains a carbamoyl radical.

The solvent used is not particularly restricted provided that it does not interfere with the reaction and dissolves a certain amount of the starting material. It may be, for example, aliphatic hydrocarbon such as hexane, heptane, ligroin or petroleum ether; aromatic hydrocarbon such as benzene, toluene or xylene; halogenated hydrocarbon such as methylenechloride, chloroform, carbontetrachloride, dichloroethane, chlorobenzene or dichlorobenzene; or ether such as diethylether, diisopropylether, tetrahydrofuran, dioxane, dimethoxyethane or diethyleneglycol dimethylether; alcohol such as methanol, ethanol, propanol, isopropanol, butanol or isobutanol; diamine such as N,N,N', N'-tetramethylethylenediamine; amide such as formamide, dimethylformamide, dimethylacetamide or hexamethylphosphoramide; or sulfoxide such as dimethylsulfoxide or sulforan. It is preferably an ether or an alcohol, and more preferably an alcohol (particularly methanol or ethanol).

The reaction temperature is altered depending on the starting material or reagents but it is usually between −10 and 100° C., and preferably between 0 and 50° C.

The reaction time changes depending on the starting material, reagents or reaction temperature but it is usually between 1 and 30 hours, and preferably between 3 and 20 hours.

After the completion of the reaction, the target compound of this process is isolated from the reaction mixture according to a usual method. For example, the target compound is isolated by removing the solvent by evaporation, or by removing the solvent by evaporation, adding water to the residue, adding a hydrophobic solvent (e.g., benzene, ether, ethyl acetate) to extract the compound, washing the extracting organic layer with water, drying over anhydrous magnesium sulphate and removing the solvent by evaporation. The target compound obtained may be, if necessary, purified by recrystallization, reprecipitation or chromatography.

In Process E3, the compound (XXVII) is prepared alternatively by condensation of the compound (XXIV) with ammonia in an inert solvent and it is carried out as conducted under the usual method for peptide synthesis, e.g., azide method, active ester method, mixed acid anhydride method or condensation (preferably mixed acid anhydride method).

In the azide-method in the above mentioned methods, the compound (XXIV) is treated with a hydrazine in an inert solvent (e.g., amide such as formamide, dimethylformamide, dimethylacetamide or hexamethylphosphoramide, preferably dimethylformamide) at the temperature between −10 and 100° C. (preferably between 0 and 50° C.). The amino acid hydrazide thus synthesized is converted to an azide by the reaction with a nitrite compound, then reacted with ammonia.

The nitrite compound used may be, for example, an alkali metal nitrite such as sodium nitrite or alkyl nitrite such as isoamyl nitrite.

The reaction takes place preferably in an inert solvent, which may be an amide such as fornamide, dimethylformamide, dimethylacetamide or hexamethylphosphoramide; sulfoxide such as dimethylsulfoxide or sulforan; or pyrrolidone such as N-methylpyrrolidon, it is preferably an amide (particularly dimethylformamide).

Moreover, the 2 processes (azide formation reaction and reaction with ammonia) in this method may be done by one pot reaction.

The reaction temperature is altered depending on the starting material or reagents but azide formation reaction takes place usually between −70 and 50° C. (preferably between −50 and 0° C.) and the reaction with ammonia takes place between −70 and 50° C. (preferably between −10 and 10° C.).

The reaction time changes depending on the starting material, reagents or reaction temperature but the azide formation reaction takes usually between 5 minutes and 3 hours (preferably between 10 minutes and 1 hour) and the reaction with ammonia takes between 5 hours and (preferably between 10 hours and 5 days).

After the completion of the reaction, the target compound of this process is isolated from the reaction mixture according to a usual method. For example, the target compound is isolated by removing the solvent by evaporation, or by removing the solvent by evaporation, adding water to the residue, adding a hydrophobic solvent (e.g., benzene, ether, ethyl acetate) to extract the compound, washing the extracting organic layer with water, drying over anhydrous magnesium sulphate and removing the solvent by evaporation. The target compound obtained may be, if necessary, purified by recrystallization, reprecipitation or chromatography.

The active ester method is performed by treating the compound (XXIV) with an ester forming reagent in an inert solvent and by treating the active ester thus synthesized with ammonia in an inert solvent.

The solvent used in both reactions are not particularly restricted provided that it does not interfere with the reaction and dissolves a certain amount of the starting material. They may be, for example, halogenated hydrocarbon such as methylenechloride, chloroform, carbontetrachloride, dichloroethane, chlorobenzene or dichlorobenzene; ether such as diethylether, diisopropylether, tetrahydrofuran, dioxane, dimethoxyethane or diethyleneglycol dimethylether; amide such as formamide, dimethylformamide, dimethylacetamide or hexamethylphosphoramide; or a nitrile such as acetonitrile. It is preferably an ether (particularly tetrahydrofuran) or an amide (particularly dimethylformamide).

The active ester forming reagents agent used may be, for example, N-hydroxy compound such as N-hydroxysuccinimide, 1-hydroxybenzotriazole or N-hydroxy-5-norbornene-2,3-dicarboximide or disulphide such as dipyridyldisulphide. The active esterification takes place preferably in the presence of a condensing agent such as dicyclohexylcarbodiimide, carbonyldiimidazole or triphenylphosphine.

The reaction temperature is altered depending on the starting material or reagents but the active esterification takes place usually between −70 and 150° C. (preferably between −10 and 100° C.) and the reaction with ammonia takes place between −20 and 100° C. (preferably between 0 and 50° C.).

The reaction time changes depending on the starting material, reagents or reaction temperature but both reactions take usually between 30 minutes and 80 hours (preferably, between 1 and 48 hours).

After the completion of the reaction, the target compound of this process is isolated from the reaction mixture according to a usual method. For example, the target compound is isolated by removing the solvent by evaporation, or by removing the solvent by evaporation, adding water to the residue, adding a hydrophobic solvent (e.g., benzene, ether, ethyl acetate) to extract the compound, washing the extracting organic layer with water, drying over anhydrous magnesium sulphate and removing the solvent by evaporation. The target compound obtained may be, if necessary, purified by recrystallization, reprecipitation or chromatography.

The mixed acid anhydride method is performed by treating the compound (XXIV) with a mixed acid anhydride forming reagent in an inert solvent in the presence of a base and traeting the produced mixed anhydride with ammonia in an inert solvent.

The solvent used in the reaction synthesizing the mixed acid anhydride is not particularly restricted provided that it does not interfere with the reaction and dissolves a certain amount of the starting material. It may be, for example, halogenated hydrocarbon such as methylenechloride, chloroform, carbontetrachloride, dichloroethane, chlorobenzene or dichlorobenzene; ether such as diethylether, diisopropylether, tetrahydrofuran, dioxane, dimethoxyethane or diethyleneglycol dimethylether; or amide such as formamide, dimethylformamide, dimethylacetamide or hexamethylphosphoramide, and it is preferably an ether (particularly tetrahydrofuran).

The mixed acid anhydride forming reagent may be, for example, $C_1$–$C_4$alkylhalogenocarbonate such as a ethylchlorocarbonate or isobutylchlorocarbonate; $C_1$–$C_5$alkanoylhalide such as pivaloylchloride; or $C_1$–$C_4$alkylcyanophosphate or $C_6$–$C_{14}$arylcyanophosphate such as diethylcyanophosphate or diphenylcyanophosphate. It is preferably $C_1$–$C_4$ alkylhalogenocarbonate (particularly isobutylchlorocarbonate).

The base used may be, for example, alkali metal carbonate such as sodium carbonate, potassium carbonate or lithium carbonate; or organic amine such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4,3,0]non-5-ene, 1,4-diazabicyclo[2,2,2]octane (DABCO) or 1,8-diazabicyclo[5,4,0]undec-7-ene (DBU) and it is preferably an organic amine (particularly triethylamine).

The reaction temperature in the reaction producing a mixed acid anhydride is altered depending on the starting material or reagents but it is usually between −50 and 100° C. (preferably, between −10 and 50° C.).

The reaction time in the reaction producing a mixed acid anhydride is altered depending on the starting material, reagents or reaction temperature but it is usually between 5 minutes and 20 hours (preferably between 10 minutes and 10 hours).

The solvent used in the reaction of the mixed acid anhydride with ammonia is not particularly restricted provided that it does not interfere with the reaction and dissolves a certain amount of the starting material. It may be, for example, ether such as diethylether, diisopropylether, tetrahydrofuran, dioxane, dimethoxyethane or diethyleneglycol dimethylether; or amide such as formamide, dimethylformamide, dimethylacetamide or hexamethylphosphoramide, and it is preferably an ether (particularly tetrahydrofuran).

The reaction temperature in the reaction of the mixed acid anhydride with ammonia is altered depending on the starting material or reagents but it is usually between −30 and 100° C. (preferably between 0 and 80° C.).

The reaction time in the reaction of the mixed acid anhydride with ammonia is altered depending on the starting material, reagents or reaction temperature but it is usually between 5 minutes and 24 hours (preferably between 10 minutes and 5 hours).

After the completion of the reaction, the target compound of this process is isolated from the reaction mixture according to a usual method. For example, the target compound is isolated by removing the solvent by evaporation, or by removing the solvent by evaporation, adding water to the residue, adding a hydrophobic solvent (e.g., benzene, ether, ethyl acetate) to extract the compound, washing the extracting organic layer with water, drying over anhydrous magnesium sulphate and removing the solvent by evaporation. The target compound obtained may be, if necessary, purified by recrystallization, reprecipitation or chromatography.

The condensation is performed by treating the compound (XXIV) directly with ammonia in an inert solvent in the presence of a condensation agent.

The condensing agent used may be, for example, dicyclohexylcarbodiimide, carbonyldiimidazole or 1-methyl-2-chloropyridinium iodide-triethylamine and it is preferably dicyclohexylcarbodiimide.

This reaction can be performed under a similar condition as that for the reaction to synthesize an active ester mentioned previously.

After the completion of the reaction, the target compound of this process is isolated from the reaction mixture according to a usual method. For example, the target compound is isolated by removing the solvent by evaporation, or by removing the solvent by evaporation, adding water to the residue, adding a hydrophobic solvent (e.g., benzene, ether, ethyl acetate) to extract the compound, washing the extracting organic layer with water, drying over anhydrous magnesium sulphate and removing the solvent by evaporation. The target compound obtained may be, if necessary, purified by recrystallization, reprecipitation or chromatography.

Method F is an alternative method for synthesizing the compound (XXIX), which contains a trifluoromethyl radical as the substituent on the ring A of the intermediate compound (XVIII) in Method A.

In Process F1, the compound (XXIX) is synthesized by the reaction of the compound (XXVIII) with tetrabutylammonium dihydrogen trifluoride ($TBA^+H_2F_3^-$) and 1,3-dibromo-5,5-dimethylhydantoin (DBH) in an inert solvent according to the method reported in Chemistry Letters, 827(1992).

The solvent used is not particularly restricted provided that it does not interfere with the reaction and dissolve a certain amount of the starting materials. It may be, for example, halogenated hydrocarbon such as methylene chloride, chloroform, carbon tetrachloride, dichloroethane, chlorobenzene or dichlorobenzene; or ether such as diethylether, diisopropylether, tetrahydrofuran, dioxane, dimethoxyethane or diethyleneglycol dimethylether, and it is preferably a halogenated hydrocarbon (particularly methylene chloride).

The reaction temperature is altered depending on the starting materials or reagents but it is usually between −30 and 100° C., and preferably between 0 and 50° C.

The reaction time is altered depending on the starting material, reagents or reaction temperature but it is usually between 10 minutes and 5 hours, and preferably between 30 minutes and 3 hours.

After the completion of the reaction, the target compound of this process is isolated from the reaction mixture according to a usual method. For example, the target compound is isolated by removing the solvent by evaporation, adding water to the reaction mixture, adding a hydrophobic solvent (e.g., benzene, ether, ethyl acetate) to extract the compound, washing the extract with water, drying it over anhydrous magnesium sulphate and removing the solvent by evaporation. The target compound obtained may be, if necessary, purified by recrystallization, reprecipitation or chromatography.

Method G is an alternative method for synthesizing the compound (XXXI), which contains a cyano radical as the substituent on the ring A of the intermediate compound (XVIII) in Method A.

In Process G1, the compound (XXXI) is prepared by the reaction of the compund (XXX) with a dehydrating agent in an inert solvent.

The solvent used is not particularly restricted provided that it does not interfere with the reaction and dissolve a certain amount of the starting materials. It may be, for example, aliphatic hydrocarbon such as hexane, heptane, ligroin or petroleum ether; aromatic hydrocarbon such as benzene, toluene or xylene; halogenated hydrocarbon such as methylene chloride, chloroform, carbon tetrachloride, dichloroethane, chlorobenzene or dichlorobenzene; ether such as diethylether, diisopropylether, tetrahydrofuran, dioxane, dimethoxyethane or diethyleneglycol dimethylether; ester such as methyl acetate or ethyl acetate; ketone such as acetone; amide such as formamide, dimethylformamide, dimethylacetamide, hexamethylphosphoramideor hexamethylphosphorous triamide; or sulfoxide such as dimethylsulfoxide or sulforan. It is preferably an ether, amide or sulfoxide, and more preferably an amide (particularly dimethylformamide).

The dehydrating agent used may be, for example, phosphorus oxychloride, trifluoroacetic anhydride, methanesulfonyl chloride, p-toluenesulfonyl chloride or phosphorus pentoxide, and it is preferably phosphorus oxychloride.

The reaction temperature is altered depending on the starting materials or reagents but it is usually between −30 and 100° C., and preferably between −10 and 30° C.

The reaction time changes depending on the starting material, reagents or reaction temperature but it is usually between 5 minutes and 10 hours, and preferably between 10 minutes and 3 hours.

After the completion of the reaction, the title compound of this process is isolated from the reaction mixture according to a usual method. For example, the target compound is isolated by removing the solvent by evaporation, adding water to the reaction mixture, adding a hydrophobic solvent (e.g., benzene, ether, ethyl acetate) to extract the compound, washing the extract with water, drying it over anhydrous magnesium sulphate and removing the solvent by evaporation. The target compound obtained may be, if necessary, purified by recrystallization, reprecipitation or chromatography.

The compound (II) which is an active component of monoamine oxidase inhibitors is well known, or synthesized by the reaction between the compound (XVI) and the compound having the general formula,

$$HX\!-\!(CH_2)_n\!-\!R^4_a \qquad\qquad (XVIIb)$$

(wherein X is the same as that described previously and $R^4_a$ is the same as $R^{2a}$ except that its amino radical and monoC$_1$–C$_4$alkylamino radical are protected), similarly as in Process A4 and eliminating, if desired, protecting group of amino or alkylamino group as in Process A5.

Further, the compound having oxygen atom at X of the compound (II) is synthesized by the reaction of the compound (XVI) with the compound having the general formula,

$$Y\!-\!(CH_2)_n\!-\!R^4_a \qquad\qquad (XVIIc)$$

(wherein $R^4_a$ and Y are the same as described above), similarly as in Process B1 and eliminating, if desired, protecting group of amino or alkylamino group as in Process A5.

The isoxazole derivatives (I) and (II) of this invention are useful as a therapeutic agent or a prophylactic agent for Parkinson's disease, depression and Alzheimer's disease (particularly for Parkinson's disease) since they have excellent type-B and type-A monoamine oxidase inhibitory effects (inhibition of type-B monoamine oxidase is particularly potent) and, moreover, they show weak toxicity.

BEST MODE FOR CARRYING OUT THE INVENTION

The invention is described in detail in the following parts with examples, preparation and test method, but the invention is not restricted in the range of these examples.

EXAMPLE 1

3-(2-Aminoethoxy)-5-chloro-1,2-benzisoxazole hydrochloride (a) Ethyl 5-chlorosalicylate.

To a suspension of 5-chlorosalicylic acid (500 g) in ethanol (2 L) was added concentrated sulphuric acid (40 ml) with stirring at room temperature. After the reaction mixture was refluxed for 12 hours, the solvent was evaporated under reduced pressure and the residue was dissolved in ethyl acetate. The organic layer was washed with 10% NaCl solution and 4% sodium hydrogen carbonate solution, and then evaporated under reduced pressure, dried over anhydrous magnesium sulphate. After filtration, the solvent was evaporated under reduced pressure to give the title compound (514 g, 88%) as a pale-yellow oil.

IR spectrum (KBr)$\nu_{max}$cm$^{-1}$: 1680, 1475; NMR spectrum (DMSO-d$_6$)δppm: 1.42(3H, t,J=7.3 Hz), 4.43(2H,q,J=7.3 Hz), 6.93(1H,d,J=7.3 Hz), 7.35(1H,dd,J=7.3 Hz,J=2.5 Hz), 7.82(1H,d,J=2.5 Hz), 11.80(1H,s).

(b) 5-Chlorosalicylcarbohydroxamic acid.

Hydroxylamine hydrochloride (197 g) was dissolved in water (400 ml) and cooled to 5° C. A methanolic solution (1.5 L) of potassium hydroxide (545 g) was added and, while stirring further at the same temperature, a methanolic solution (400 ml) of ethyl 5-chlorosalicylate ester (500 g) was dropped. After stirring for 30 minutes at a temperature between 5 and 10° C., stirring was continued for 3 hours at the room temperature. The solvent was evaporated under reduced pressure and the residue was dissolved in ice water (6 L). The solution was adjusted to pH 2 using concentrated hydrochloric acid and the title compound (438 g, 93%) was obtained as colorless crystals by filtering the precipitated crystals and washing with water.

Melting point: 216–220° C.; IR spectrum (KBr)$\nu_{max}$cm$^{-1}$: 3127, 1618, 1577, 1523, 1492, 1413; NMR spectrum (DMSO-d$_6$)δppm: 6.96(1H,d,J=7.3 Hz), 7.43(1H,dd,J=7.3 Hz,J=2.5 Hz), 9.31–9.52 (1H,brs), 10.88–11.03(1H,brs), 11.66–11.87(1H,brs).

(c) 5-Chloro-3-hydroxy-1,2-benzisoxazole.

To a solution of 5-chlorosalicylcarbohydroxamic acid (216 g) in tetrahydrofuran (600 ml) was added thionyl chloride (100 ml) dropwise with stirring at 10°20° C. After being stirred for 2 hours at the same temperature, the reaction mixture was evaporated under reduced pressure and the residue was dissolved in dioxane (600 ml) and cooled to 0–5° C. Triethylamine (383 ml) was added to the reaction mixture and stirred at room temperature for 1 hour. The solvent was evaporated under reduced pressure and ice water (3 L) was added to the residue. The mixture was adjusted to pH 2 with concentrated hydrochloric acid and the crystals precipitated were filtered and washed with water. The title compound (172 g, 88%) was obtained as colorless needle crystals by recrystallization from ethyl acetate.

Melting point: 219–222° C.; IR spectrum(KBr)$\nu_{max}$cm$^{-1}$: 3400–2000, 1613, 1560, 1516; NMR spectrum(DMSO-d$_6$) δppm: 7.43–7.72(2H,m), 7.82(1H,d,J=2.5 Hz), 10.78–11.02 (1H,brs).

(d) 2-(N-t-Butoxycarbonylamino)ethanol.

To a solution of 2-aminoethanol (6.1 g) in tetrahydrofuran and water (1:1, 100 ml) was added di-t-butyldicarbonate (21.8 g) with stirring under ice cooling. The reaction mixture was stirred at the same temperature for 1 hour then at room temperature for 5 hours. Ethyl acetate (200 ml) was added to the reaction mixture, washed with water and the organic layer was dried over anhydrous magnesium sulphate. After filtration, the solvent was evaporated under reduced pressure to give the title compound (15.3 g) as a colorless oil.

Rf: (cyclohexane:ethyl acetate=1:1): 0.35; NMR spectrum(CDCl$_3$)δppm: 1.45(9H,s), 2.35–2.50(1H,brs), 3.29(2H,q,J=5.3 Hz), 3.71 (2H,q,J=5.3 Hz), 4.85–5.05(1H, brs).

(e) 3-(2-(N-t-Butoxycarbonylamino)ethoxy)-5-chloro-1,2-benzisoxazole.

To a solution of triphenylphosphine (0.87 g) in tetrahydrofuran (10 ml), was added diethyl azodicarboxylate (0.57 g) dropwise with stirring under ice cooling. The reaction mixture was stirred at the same temperature for 10 minutes. Then, 2-(N-t-butoxycarbonylamino)ethanol (0.48 g) and 5-chloro-3-hydroxy-1,2-benzisoxazole (0.51 g) were added to the reaction mixture successively and stirred under ice cooling for 10 minutes and at room temperature for 24 hours. The solvent was evaporated under reduced pressure and the residue was purified by silica gel column chromatography with cyclohexane/ethyl acetate (4/1) as an eluent. The title compound (0.70 g) was obtained as colorless crystals by crystallization from isopropylether.

Melting point: 106–107° C.; IR spectrum (KBr)$\nu_{max}$cm$^{-1}$: 3376, 1706, 1611, 1541, 1525; NMR spectrum(CDCl$_3$) δppm: 1.46(9H,s), 3.64(2H,q,J=5.1 Hz), 4.50(2H,t,J=5.1 Hz), 4.95(1H,brs), 7.37(1H,d,J=8.8 Hz), 7.49(1H,dd,J=8.8 Hz,J=2.0 Hz), 7.63(1H,d,J=2.0 Hz).

(f) 3-(2-Aminoethoxy)-5-chloro-1,2-benzisoxazole hydrochloride.

To 3-(2-(N-t-butoxycarbonylamino)-ethoxy)-5-chloro-1,2-benzisoxazole (0.50 g) was added a solution of 4N-hydrochloric acid/1,4-dioxane (4.0 ml) and stirred at room temperature for 15 minutes. After filtering the precipitated crystals and washing with 1,4-dioxane, the title compound (0.38 g) was obtained as colorless crystals.

Melting point: 217–221° C. (decomposed); IR spectrum (KBr)$\nu_{max}$cm$^{-1}$: 3300–2400, 1612, 1534, 1519; NMR spectrum(DMSO-d$_6$)δppm: 3.33(2H,t,J=5.1 Hz), 4.61(2H,t, J=5.1 Hz), 7.73(2H,d,J=1.4 Hz), 7.88(1H,d,J=1.4 Hz), 8.28 (3H,brs).

EXAMPLE 2

3-(2-Aminoethoxy)-1,2-benzisoxazole hydrochloride (a) 3-(2-(N-t-Butoxycarbonylamino)ethoxy)-1,2-benzisoxazole.

The title compound was obtained in 68% yield from 3-hydroxy-1,2-benzisoxazole and 2-(N-t-butoxycarbonylamino)ethanol by similar reactions and treatments as in example 1(e).

Melting point: 106–107° C.; IR spectrum(KBr)$\nu_{max}$cm$^{-1}$: 3326, 1716, 1707, 1615, 1536; NMR spectrum(CDCl$_3$) δppm: 1.46(9H,s), 3.65(2H,q,J=5.1 Hz), 4.51(2H,t,J=5.1 Hz), 4.90–5.05(1H,brs), 7.26–7.66(4H,m).

(b) 3-(2-Aminoethoxy)-1,2-benzisoxazole hydrochloride.

The title compound was obtained in 98% yield from 3-(2-(N-t-butoxycarbonylamino)ethoxy-1,2-benzisoxazole by similar reactions and treatments as in example 1(f).

Melting point: 194–197° C. (decomposed); IR spectrum (KBr)$\nu_{max}$cm$^{-1}$: 3300–2400, 1614, 1541, 1521; NMR spectrum(D$_2$O)δppm: 3.60(2H,t,J=5.1 Hz), 4.94(2H,t,J=5.1 Hz), 7.41–7.80(4H,m).

EXAMPLE 3

3-(3-Aminopropoxy)-1,2-benzisoxazole hydrochloride (a) 3-(N-t-Butoxycarbonylamino)propanol.

The title compound was obtained (1.65 g) from 3-aminopropanol (0.75 g) and di-t-butyldicarbonate (2.18 g) by similar reactions and treatments as in example 1(d).

Rf (cyclohexane: ethyl acetate=1:1): 0.35; NMR spectrum (CDCl$_3$)δppm: 1.49(9H,s), 1.70(2H,q,J=5.9 Hz), 2.85–2.95 (1H,brs), 3.33(2H,q,J=5.9 Hz), 3.70(2H,q,J=5.9 Hz), 4.65–4.90(1H,brs).

(b) 3-(3-(N-t-Butoxycarbonylamino)propoxy)-1,2-benzisoxazole.

The title compound was obtained in 75% yield from 3-hydroxy-1,2-benzoisoxazle and 3-(N-t-butoxycarbonylamino)propanol by similar reactions and treatments as in example 1(e).

Melting point: 59–60° C.; IR spectrum(KBr)ν$_{max}$cm$^{-1}$: 3383, 1690, 1613, 1539, 1521; NMR spectrum(CDCl$_3$) δppm: 1.44(9H,s), 2.05–2.13(2H,m), 3.36(2H,q,J=6.3 Hz), 4.52(2H,t,J=5.9 Hz), 4.70–4.85(1H, brs), 7.25–7.65(4H,m).

(c) 3-(3-Aminopropoxy)-1,2-benzisoxazole hydrochloride.

The title compound was obtained in 96% yield from 3-(3-(N-t-butoxycarbonylamino)propoxy)-1,2-benzisoxazole by similar reactions and treatments as in example 1(f).

Melting point: 146–147° C. (decomposed); IR spectrum (KBr)ν$_{max}$cm$^{-1}$: 3300–2400, 1615, 1541, 1536; NMR spectrum(D$_2$O)δppm: 2.29–2.36(2H,m), 3.31(2H,t,J=7.3 Hz), 4.59(2H,t,J=5.9 Hz), 7.40–7.78(4H,m).

EXAMPLE 4

3-(4-Aminobutoxy)-1,2-benzisoxazole hydrochloride (a) 4-(N-t-Butoxycarbonylamino)butanol.

The title compound was obtained (1.80 g) from 4-aminobutanol (0.89 g) and di-t-butyldicarbonate (2.18 g) by similar reactions and treatments as in example 1(d).

Rf (cyclohexane: ethyl acetate=1:1): 0.35; NMR spectrum (CDCl$_3$)δppm: 1.44(9H,s), 1.55–1.65(4H,m), 3.16(2H,q,J=5.9 Hz), 3.67(2H,q,J=5.9 Hz), 4.55–4.75(1H,brs).

(b) 3-(4-(N-t-Butoxycarbonylamino)butoxy)-1,2-benzisoxazole.

The title compound was obtained in 71% yield from 3-hydroxy-1,2-benzisoxazole and 4-(N-t-butoxycarbonylamino)butanol by similar reactions and treatments as in example 1(e). IR spectrum(KBr)ν$_{max}$cm$^{-1}$: 3321, 1701, 1615, 1539, 1509; NMR spectrum(CDCl$_3$) δppm: 1.14(9H,s), 1.62–1.74(2H,m), 1.91–1.97(2H,m), 3.15–3.27(2H,brs), 4.46(2H,t,J=6.5 Hz), 4.55–4.70(1H,brs), 7.24–7.66(4H,m).

(c) 3-(4-Aminobutoxy)-1,2-benzisoxazole hydrochloride.

The title compound was obtained in 97% yield from 3-(4-(N-t-butoxycarbonylamino)butoxy)-1,2-benzisoxazole by similar reactions and treatments as in example 1(f).

Melting point: 138–139° C. (decomposed); IR spectrum (KBr)ν$_{max}$cm$^{-1}$: 3300–2400, 1613, 1541; NMR spectrum (D$_2$O)δppm: 1.88–1.97(2H,m), 1.99–2.06(2H,m), 3.14(2H, t,J=7.6 Hz), 4.50(2H,t,J=6.1 Hz), 7.39–7.78(4H,m).

EXAMPLE 5

3-(2-Aminoethoxy)-5-fluoro-1,2-benzisoxazole hydrochloride (a) 3-(2-(N-t-Butoxycarbonylamino)ethoxy)-5-fluoro-1,2-benzisoxazole.

The title compound was obtained in 60% yield from 5-fluoro-3-hydroxy-1,2-benzisoxazole and 2-(N-t-butoxycarbonylamino)ethanol by similar reactions and treatments as in example 1(e). IR spectrum(KBr)ν$_{max}$cm$^{-1}$: 3338, 1707, 1623, 1543, 1534, 1504; NMR spectrum (CDCl$_3$)δppm: 1.46(9H,s), 3.64(2H,q,J=5.1 Hz), 4.50(2H, J=5.1 Hz), 4.88–5.03(1H,brs), 7.22–7.42(3H,m).

(b) 3-(2-Aminoethoxy)-5-fluoro-1,2-benzisoxazole hydrochloride.

The title compound was obtained in 98% yield from 3-(2-(N-t-butoxycarbonylamino)ethoxy)-5-fluoro-1,2-benzisoxazole by similar reactions and treatments as in example 1(f).

Melting point: 209–211° C. (decomposed); IR spectrum (KBr)ν$_{max}$cm$^{-1}$: 3300–2400, 1621, 1606, 1538, 1505; NMR spectrum(D$_2$O)δppm: 3.59(2H,t,J=5.1 Hz), 4.73(2H,t,J=5.1 Hz), 7.42–7.58(3H,m).

EXAMPLE 6

3-(2-Aminoethoxy)-5-methoxy-1,2-benzisoxazole hydrochloride (a) 3-(2-(N-t-Butoxycarbonylamino)ethoxy)-5-methoxy-1,2-benzisoxazole.

The title compound was obtained in 74% yield from 3-hydroxy-5-methoxy-1,2-benzisoxazole and 2-(N-t-butoxycarbonylamino)ethanol by similar reactions and treatments as in example 1(e). IR spectrum(KBr)ν$_{max}$cm$^{-1}$: 3255, 1698, 1615, 1540, 1508; NMR spectrum(CDCl$_3$) δppm: 1.46(9H,s), 3.65(2H,q,J=5.1 Hz), 3.86(3H,s), 4.50 (2H,t,J=5.1 Hz), 4.90–5.05(1H,brs), 6.98(1H,d,J=2.6 Hz), 7.15(1H,dd,J=9.2 Hz,J=2.6 Hz), 7.33(1H,d,J=9.2 Hz).

(b) 3-(2-Aminoethoxy)-5-methoxy-1,2-benzisoxazole hydrochloride.

The title compound was obtained in 96% yield from 3-(2-(N-t-butoxycarbonylamino)ethoxy)-5-methoxy-1,2-benzisoxazole by similar reactions and treatments as in example 1(f).

Melting point: 210–212° C. (decomposed); IR spectrum (KBr)ν$_{max}$cm$^{-1}$: 3300–2400, 1606, 1538, 1521, 1505; NMR spectrum(D$_2$O)δppm: 3.59(2H,t,J=5.1 Hz), 3.90(3H,s), 4.71 (2H,t,J=5.1 Hz), 7.22(1H,d,J=2.6 Hz), 7.32(1H,dd,J=9.2 Hz,J=2.6 Hz), 7.48(1H,d,J=9.2 Hz).

EXAMPLE 7

3-(2-Aminoethoxy)-5-methyl-1,2-benzisoxazole hydrochloride (a) Ethyl 5-methylsalicylate.

The title compound was obtained in 84% yield from 5-methylsalicylic acid by similar reactions and treatments as in example 1(a).

(b) 5-Methylsalicylcarbohydroxamic acid.

The title compound was obtained in 94% yield from ethyl 5-methylsalicylate and hydroxylamine hydrochloride by similar reactions and treatments as in example 1(b).

Melting point: 172–175° C. (decomposed); NMR spectrum(DMSO-d$_6$)δppm: 2.22(3H,s), 6.78(1H,d,J=8.6 Hz), 7.17(1H,d,J=8.6 Hz), 7.50(1H,s), 9.25(1H,s), 11.33 (1H,s), 11.95(1H,s).

(c) 3-Hydroxy-5-methyl-1,2-benzisoxazole.

The title compound was obtained in 94% yield from 5-methylsalicylcarbohydroxamic acid by similar reactions and treatments as in example 1(c).

Melting point: 95–97° C.; NMR spectrum(CDCl$_3$)δppm: 2.45(3H,s), 7.13–7.43(3H,m), 9.02–9.15(1H,brs).

(d) 3-(2-(N-t-Butoxycarbonylamino)ethoxy)-5-methyl-1,2-benzisoxazole.

The title compound was obtained in 69% yield from 3-hydroxy-5-methyl-1,2-benzisoxazole and 2-(N-t-butoxycarbonylamino)ethanol by similar reactions and treatments as in example 1(e). IR spectrum(KBr)ν$_{max}$cm$^{-1}$: 3367, 1717, 1614, 1538–1522; NMR spectrum(CDCl$_3$) δppm: 1.46(9H,s), 2.45(3H,s), 3.64(2H,q,J=5.1 Hz), 4.50 (2H,t,J=5.1 Hz), 4.90–5.05(1H,brs), 7.31–7.52(3H,m).

(e) 3-(2-Aminoethoxy)-5-methyl-1,2-benzisoxazole hydrochloride.

The title compound was obtained in 97% yield from 3-(2-(N-t-butoxycarbonylamino)ethoxy)-5-methyl-1,2-benzisoxazole by similar reactions and treatments as in example 1(f).

Melting point: 218–220° C. (decomposed); IR spectrum (KBr)$v_{max}$cm$^{-1}$: 3300–2400, 1625, 1612, 1536, 1502; NMR spectrum(DMSO-d$_6$)δppm: 2.43(3H,s), 3.26–3.41(2H,m), 4.60(2H,t,J=5.1 Hz), 7.48–7.55(3H,m), 8.32(3H,brs).

EXAMPLE 8

3-(2-Aminoethoxy)-5-nitro-1,2-benzisoxazole hydrochloride (a) 3-(2-(N-t-Butoxycarbonylamino)ethoxy)-5-nitro-1,2-benzisoxazole.

The title compound was obtained in 74% yield from 3-hydroxy-5-nitro-1,2-benzisoxazole and 2-(N-t-butoxycarbonylamino)ethanol by similar reactions (continuing the reaction for a further three hours), and treatments as in example 1(e).

Melting point: 136–137° C.; IR spectrum(KBr)$v_{max}$cm$^{-1}$: 3346, 1688, 1624, 1555, 1531; NMR spectrum(CDCl$_3$) δppm: 1.46(9H,s), 3.67(2H,q,J=5.1 Hz), 4.55(2H,t,J=5.1 Hz), 4.87–5.05(1H,brs), 7.56(1H,d,J=9.2 Hz), 8.46(1H,dd, J=9.2 Hz,J=2.2 Hz), 8.62(1H,d,J=2.2 Hz).

(b) 3-(2-Aminoethoxy)-5-nitro-1,2-benzisoxazole hydrochloride.

The title compound was obtained in 99% yield from 3-(2-(N-t-butoxycarbonylamino)ethoxy)-5-nitro-1,2-benzisoxazole by similar reactions and treatments as in example 1(f).

Melting point: 228–231° C. (decomposed); IR spectrum (KBr)$v_{max}$cm$^{-1}$: 3300–2400, 1620, 1543, 1519; NMR spectrum(DMSO-d$_6$)δppm: 3.36(2H,t,J=5.1 Hz), 4.66(2H,t, J=5.1 Hz), 7.93(2H,d,J=9.2 Hz), 8.34(3H,brs), 8.54(1H,dd, J=9.2 Hz,J=2.2 Hz), 8.74(1H,d,J=2.2 Hz).

EXAMPLE 9

3-(2-Aminoethoxy)-7-chloro-1,2-benzisoxazole hydrochloride (a) 3-(2-(N-t-Butoxycarbonylamino)ethoxy)-7-chloro-1,2-benzisoxazole.

The title compound was obtained in 62% yield from 3-hydroxy-7-chloro-1,2-benzisoxazole and 2-(N-t-butoxycarbonylamino)ethanol by similar reactions and treatments as in example 1(e).

Melting point 64–65° C. IR spectrum(KBr)$v_{max}$cm$^{-1}$: 3355, 1714, 1690, 1615, 1556, 1538; NMR spectrum (CDCl$_3$)δppm: 1.46(9H,s), 3.65(2H,q,J=5.1 Hz), 4.53(2H,t, J=5.1 Hz), 4.87–5.03(1H,brs), 7.23(1H,dd,J=8.0 Hz,J=8.0 Hz), 7.52–7.58(2H,m).

(b) 3-(2-Aminoethoxy)-7-chloro-1,2-benzisoxazole hydrochloride.

The title compound was obtained in 98% yield from 3-(2-(N-t-butoxycarbonylamino)ethoxy)-7-chloro-1,2-benzoisoxazle by similar reactions and treatments as in example 1(f).

Melting point: 198–200° C. (decomposed); IR spectrum (KBr)$v_{max}$cm$^{-1}$: 3300–2400, 1616, 1599, 1541, 1516; NMR spectrum(DMSO-d$_6$)δppm: 3.35(2H,t,J=5.1 Hz), 4.65(2H,t, J=5.1 Hz), 7.44(1H,dd,J=8.0 Hz,J=8.0 Hz), 7.79(1H,d,J=8.0 Hz), 7.83(1H,d,J=8.0 Hz), 8.34(3H,brs).

EXAMPLE 10

3-(2-Aminoethoxy)pyrido[3,2-d]isoxazole hydrochloride and 3-(2-Aminoethoxy)pyrido[3,2-d]isoxazole dihydrochloride (a) Methyl 2-chloronicotinate.

To a suspension of 2-chloronicotinic acid (15.75 g) in ethyl acetate (200 ml) was added excess diazomethane (ether solution) with stirring at room temperature. The reaction mixture was stirred at the same temperature for 30 minutes. The solvent was evaporated under reduced pressure and the residue was dissolved in ethyl acetate with addition of charcoal. The title compound (15.5 g) was obtained by filtering the mixture and then evaporating under reduced pressure.

(b) 2-Chloropyridine-3-carbohydroxamic acid.

To a solution of hydroxylamine hydrochloride (6.75 g) in water (25 ml) was added sodium hydroxide solution (7.65 g sodium hydroxide in 50 ml water) with stirring under ice cooling. To this stirring solution was added methyl 2-chloronicotinate (1 5.5 g) in methanol. After being stirred at room temperature for 2.5 hours, pH was adjusted to 3.5 with 6N-hydrochloric acid under ice cooling. After 1 hour, the title compound (11.0 g) was obtained by filtering the precipitated crystals and washing with water and, then, a methanol-ether mixture (1:1).

Melting point: 179° C.; IR spectrum(Nujol)$v_{max}$cm$^{-1}$: 3154, 1645, 1580; NMR spectrum(DMSO-d$_6$)δppm: 7.34 (1H,dd,J=7.5 Hz,J=5.0 Hz), 7.80(1H,dd,J=7.5 Hz,2.0 Hz), 8.42(1H,dd,J=5.0 Hz,J=2.0 Hz), 9.30(1H,s), 11.00 Hz(1H, s).

(c) 3-Hydroxypyrido[3,2-d]isoxazole.

To 10% aqueous sodium hydroxide solution (26 ml) was added 2-chloropyridine-3-carbohydroxamic acid (2.60 g) and refluxed for 30 minutes. After pH was adjusted to 2.0 with 6N-hydrochloric acid under ice cooling, the reaction mixture was left to stand for 30 minutes at the same temperature. The title compound (1.68 g) was obtained by filtering the precipitated crystals and washing with water and then with a methanol-ether mixture (1:1).

Melting point: 258° C.; IR spectrum(Nujol)$v_{max}$cm$^{-1}$: 2750–2050, 1620, 1600; NMR spectrum(DMSO-d$_6$)δppm: 7.40(1H,dd,J=8.0 Hz,J=5.0 Hz), 8.40–8.70(2H,m).

(d) 3-(2-(N-t-Butoxycarbonylamino)ethoxy)pyrido[3,2-d] isoxazole.

The title compound was obtained in 61% yield from 3-hydroxypyrido[3,2-d]isoxazole and 2-(N-t-butoxycarbonylamino)ethanol by similar reactions and treatments as in example 1(e).

Melting point: 127–128° C.; IR spectrum(KBr)$v_{max}$cm$^{-1}$: 3335, 1716, 1707, 1615, 1605, 1537; NMR spectrum (CDCl$_3$)δppm: 1.46(9H,s), 3.65(2H,q,J=5.1 Hz), 4.54(2H,t, J=5.1 Hz), 4.85–5.05(1H,brs), 7.31(1H,dd,J=7.9 Hz,J=4.6 Hz), 8.06(1H,dd,J=7.9 Hz,J=1.5 Hz), 8.61(1H,dd,J=4.6 Hz,J=1.5 Hz).

(e) 3-(2-Aminoethoxy)pyrido[3,2-d]isoxazole dihydrochloride.

The title compound was obtained in 99% yield from 3-(2-(N-t-butoxycarbonylamino)ethoxy)pyrido[3,2-d] isoxazole by similar reactions and treatments as in example 1(f).

Melting point: 204–210° C. (decomposed); IR spectrum (KBr)$v_{max}$cm$^{-1}$: 3300–2400, 1606, 1538, 1508; NMR spectrum(DMSO-d$_6$)δppm: 3.35(2H,td,J=5.1 Hz,J=5.1 Hz), 4.65(2H,t,J=5.1 Hz), 7.54(1H,dd,J=7.9 Hz,J=4.6 Hz), 8.34 (1H,dd,J=7.9 Hz,J=1.5 Hz), 8.34(3H,brs), 8.70(1H,dd,J=4.6 Hz,J=1.5 Hz).

(f) 3-(2-Aminoethoxy)pyrido[3,2-d]isoxazole hydrochloride.

To a solution of 3-(2-aminoethoxy)pyrido[3,2-d] isoxazole dihydrochloride in water (10 ml) was added aqueous 1N sodium hydroxide solution (16 ml) with stirring under ice cooling, and the mixture was then stirred at the same temperature for 5 minutes. The reaction mixture was evaporated under reduced pressure and the title compound (3.2 g, 94%) was obtained as colorless crystals by recrystallizing from methanol-water mixture (1:1).

Melting point: 210–213° C. (decomposed); IR spectrum (KBr)$v_{max}$cm$^{-1}$: 3012, 3003, 2968, 2899, 2845, 2803, 2752, 1636, 1615, 1606, 1538, 1509; NMR spectrum(DMSO-d$_6$) δppm: 3.35(2H,t,J=5.1 Hz), 4.65(2H,t,J=5.1 Hz), 7.54 (1H, dd,J=7.9 Hz,J=4.6 Hz), 8.34 (1H, dd, J=7.9 Hz, J=1.5 Hz), 8.36(3H,brs), 8.70(1H,dd,J=4.6 Hz,J=1.5 Hz).

EXAMPLE 11

3-(2-Aminoethoxy)-6-chloro-1,2-benzisoxazole hydrochloride (a) 3-(2-(N-t-Butoxycarbonylamino)ethoxy)-6-chloro-1,2-benzisoxazole.

The title compound was obtained in 66% yield from 3-hydroxy-6-chloro-1,2-benzisoxazole and 2-(N-t-butoxycarbonylamino)ethanol by similar reactions and treatments as in example 1(e).

Melting point: 95–96° C.; IR spectrum(KBr)$v_{max}$cm$^{-1}$: 3398, 1698, 1614, 1541, 1519; NMR spectrum(CDCl$_3$) δppm: 1.46(9H,s), 3.64(2H,q,J=5.1 Hz), 4.50(2H,t,J=5.1 Hz), 4.88–5.02(1H,brs), 7.27(1H,dd,J=8.4 Hz,J=1.5 Hz), 7.47(1H,d,J=1.5 Hz), 7.55(1H,d,J=8.4 Hz).

(b) 3-(2-Aminoethoxy)-6-chloro-1,2-benzisoxazole hydrochloride.

The title compound was obtained in 97% yield from 3-(2-(N-t-butoxycarbonylamino)ethoxy)-6-chloro-1,2-benzisoxazole by similar reactions and treatments as in example 1(f).

Melting point: 198–202° C. (decomposed); IR spectrum (KBr)$v_{max}$cm$^{-1}$: 3300–2400, 1612, 1537; NMR spectrum (DMSO-d$_6$)δppm: 3.34(2H,t,J=5.1 Hz), 4.62(2H,t,J=5.1 Hz), 7.48(1H,dd,J=8.4 Hz,J=1.5 Hz), 7.81(1H,d,J=8.4 Hz), 7.92(1H,d,J=1.5 Hz), 8.36(3H,brs).

EXAMPLE 12

3-(2-Aminoethoxy)-5,7-dichloro-1,2-benzisoxazole hydrochloride (a) 3-(2-(N-t-Butoxycarbonylamino)ethoxy)-5,7-dichloro-1,2-benzisoxazole.

The title compound was obtained in 68% yield from 3-hydroxy-5,7-dichloro-1,2-benzisoxazole and 2-(N-t-butoxycarbonylamino)ethanol by similar reactions and treatments as in example 1(e).

Melting point: 94–95° C.; IR spectrum(KBr)$v_{max}$cm$^{-1}$: 3359, 1678, 1542, 1524; NMR spectrum(CDCl$_3$)δppm: 1.46 (9H,s), 3.64(2H,q,J=5.1 Hz), 4.51(2H,t,J=5.1 Hz), 4.85–5.00(1H,brs), 7.54(2H,d,J=1.0 Hz).

(b) 3-(2-Aminoethoxy)-5,7-dichloro-1,2-benzisoxazole hydrochloride.

The title compound was obtained in 92% yield from 3-(2-(N-t-butoxycarbonylamino)ethoxy)-5,7-dichloro-1,2-benzisoxazole by similar reactions and treatments as in example 1(f).

Melting point: 198–203° C. (decomposed); IR spectrum (KBr)$v_{max}$cm$^{-1}$: 3300–2400, 1600, 1541, 1514; NMR spectrum(DMSO-d$_6$)δppm: 3.34(2H,t,J=5.1 Hz), 4.63(2H,t, J=5.1 Hz), 7.91(1H,d,J=2.0 Hz), 8.03(1H,d,J=2.0 Hz), 8.31 (3H,brs).

EXAMPLE 13

3-(2-Aminoethoxy)-7-methyl-1,2-benzisoxazole hydrochloride (a) 3-(2-(N-t-Butoxycarbonylamino)ethoxy)-7-methyl-1,2-benzisoxazole.

The title compound was obtained in 66% yield from 3-hydroxy-7-methyl-1,2-benzisoxazole and 2-(N-t-butoxycarbonylamino)ethanol by similar reactions and treatments as in example 1(e).

Melting point: 54–55° C.; IR spectrum(KBr)$v_{max}$cm$^{-1}$: 3332, 1713, 1699, 1615, 1539, 1506; NMR spectrum (CDCl$_3$)δppm: 1.46(9H,s), 2.51(3H,s), 3.65(2H,q,J=5.1 Hz), 4.51(2H,t,J=5.1 Hz), 4.90–5.06(1H,brs), 7.15–7.47(3H, m).

(b) 3-(2-Aminoethoxy)-7-methyl-1,2-benzisoxazole hydrochloride.

The title compound was obtained in 96% yield from 3-(2-(N-t-butoxycarbonylamino)ethoxy)-7-methyl-1,2-benzisoxazole by similar reactions and treatments as in example 1(f).

Melting point: 195–197° C. (decomposed); IR spectrum (KBr)$v_{max}$cm$^{-1}$: 3300–2400, 1614, 1545, 1520, 1505; NMR spectrum(DMSO-d$_6$)δppm: 2.47(3H,s), 3.34(2H,t,J=5.1 Hz), 4.62(2H,t,J=5.1 Hz), 7.28–7.61(3H,m).

EXAMPLE 14

3-(2-Aminoethoxy)-6-methyl-1,2-benzisoxazole hydrochloride (a) 3-(2-(N-t-Butoxycarbonylamino)ethoxy-6-methyl-1,2-benzisoxazole.

The title compound was obtained in 64% yield from 3-hydroxy-6-methyl-1,2-benzisoxazole and 2-(N-t-butoxycarbonylamino)ethanol by similar reactions and treatments as in example 1(e).

Melting point: 128–129° C.; IR spectrum(KBr)$v_{max}$cm$^{-1}$: 3331, 1718, 1708, 1629, 1613, 1534; NMR spectrum (CDCl$_3$)δppm: 1.46(9H,s), 2.50(3H,s), 3.65(2H,q,J=5.1 Hz), 4.49(2H,t,J=5.1 Hz), 4.90–5.05(1H,brs), 7.10(1H,d,J= 8.0 Hz), 7.23(1H,s), 7.50(1H,d,J=8.0 Hz).

(b) 3-(2-Aminoethoxy)-6-methyl-1,2-benzisoxazole hydrochloride.

The title compound was obtained in 92% yield from 3-(2-(N-t-butoxycarbonylamino)ethoxy)-6-methyl-1,2-benzisoxazole by similar reactions and treatments as in example 1(f).

Melting point: 207–212° C. (decomposed); IR spectrum (KBr)$v_{max}$cm$^{-1}$: 3300–2400, 1618, 1600, 1533; NMR spectrum(DMSO-d$_6$)δppm: 2.48(3H,s), 3.33(2H,t,J=5.1 Hz), 4.59(2H,t,J=5.1 Hz), 7.23(1H,d,J=8.0 Hz), 7.46(1H,s), 7.65(1H,d,J=8.0 Hz), 8.33(3H,brs).

EXAMPLE 15

3-(2-Aminoethoxy)-5-bromo-1,2-benzisoxazole hydrochloride (a) 3-(2-(N-t-Butoxycarbonylamino)ethoxy)-5-bromo-1,2-benzisoxazole.

The title compound was obtained in 67% yield from 3-hydroxy-5-bromo-1,2-benzisoxazole and 2-(N-t-butoxycarbonylamino)ethanol by similar reactions and treatments as in example 1(e).

Melting point: 123–124° C.; IR spectrum(KBr)$v_{max}$cm$^-$: 3313, 1699, 1683, 1611, 1545; NMR spectrum(CDCl$_3$) δppm: 1.46(9H,s), 3.64(2H,q,J=5.1 Hz), 4.50(2H,t,J=5.1 Hz), 4.85–5.00(1H,brs), 7.33(1H,d,J=8.9 Hz), 7.62(1H,dd, J=8.9 Hz,J=1.9 Hz), 7.80(1H,d,J=1.9 Hz).

(b) 3-(2-Aminoethoxy)-5-bromo-1,2-benzisoxazole hydrochloride.

The title compound was obtained in 95% yield from 3-(2-(N-t-butoxycarbonylamino)ethoxy)-5-bromo-1,2-benzisoxazole by similar reactions and treatments as in example 1(f).

Melting point: 220–224° C. (decomposed); IR spectrum (KBr)$v_{max}$cm$^{-1}$: 3300–2400, 1611, 1535, 1516; NMR spectrum(DMSO-d$_6$)δppm: 3.38(2H,t,J=5.1 Hz), 4.61(2H,t, J=5.1 Hz), 7.67(1H,d,J=8.9 Hz), 7.83(1H,dd,J=8.9 Hz,J=1.9 Hz), 8.02(1H,d,J=1.9 Hz), 8.25(3H,brs).

EXAMPLE 16

3,5-Dichloro-1,2-benzisoxazole

To a suspension of 5-chloro-3-hydroxy-1,2-benzisoxazole (100 g) in phosphorus oxychloride (80 ml) was added pyridine (48 ml) dropwise over 1 hours with stirring at room temperature, and the mixture was then refluxed for 5 hours. The reaction mixture was added to ice water (500 ml) and extracted with ethyl acetate and the combined extracts were dried over anhydrous magnesium sulphate. The solvent was evaporated under reduced pressure and the title compound (102 g, 92%) was obtained by recrystallizng the residue from petroleum ether as a colorless needle.

Melting point: 43–44° C.; IR spectrum(KBr)$v_{max}$cm$^{-1}$: 1468, 1419, 1285; NMR spectrum(CDCl$_3$)δppm: 7.59(2H, d,J=1.5 Hz), 7.70(1H,brs).

EXAMPLE 17

3-(2-Aminoethoxy)-5-fluoro-4-methyl-1,2-benzisoxazole hydrochloride (a) 3-(2-(N-t-Butoxycarbonylamino)ethoxy)-5-fluoro-1,2-benzisoxazole.

To a solution of triphenylphosphine (0.87 g) in tetrahydrofuran (20 ml) was added diethyl azodicarboxylate (0.57 g) at 5° C. and the mixture was stirred at the same temperature for 15 minutes. Then 5-fluoro-3-hydroxy-1,2-benzisoxazole (0.46 g) was added and the mixture was stirred at the same temperature for 15 minutes followed by addition of N-t-butoxycarbonyl ethanolamine (0.48 g) and stirring at room temperature for 24 hours. The solvent was evaporated under reduced pressure and the residue was purified by silica gel column chromatography with cyclohexane/ethyl acetate (9/1) as an eluent, to give the title compound (0.53 g, 60%) as a colorless powder.

Melting point: 104–105° C.; IR spectrum(KBr)$v_{max}$cm$^{-1}$: 3338, 1707, 1623, 1543, 1534, 1504; NMR spectrum (CDCl$_3$)δppm: 1.46(9H,s), 3.64(2H,q,J=5.1 Hz), 4.50(2H,t, J=5.1 Hz), 4.95(1H,brs), 7.22–7.42(3H,m).

(b) 3-(2-(N-t-Butoxycarbonylamino)ethoxy-5-fluoro-4-methyl-1,2-benzisoxazole.

To a solution of 3-(2-(N-t-butoxycarbonylaminoethoxy)-5-fluoro-1,2-benzisoxazole (0.27 g) in tetrahydrofuran (10 ml) was added lithium diisopropylamide (1.1 ml, 1.5M cyclohexane solution) dropwise with stirring at −70° C. under nitrogen atmosphere, and the mixture was then stirred at the same temperature for 15 minutes, before methyl iodide (0.13 g) was added. After being stirred at −70° C. for 15-minute, the temperature was allowed to rise to 0° C. The reaction mixture was poured into ice water (40 ml), extracted twice with ethyl acetate (40 ml each) and the combined extracts were dried over anhydrous magnesium sulphate and filtered. The solvent was evaporated under reduced pressure and the residue was purified by silica gel column chromatography with cyclohexane/ethyl acetate (9/1) as an eluent, to give title compound (0.22 g, 94% yield) as a colorless powder.

Melting point: 124–127° C.; IR spectrum(KBr)$v_{max}$cm$^{-1}$: 3353, 1688, 1539, 1505 NMR spectrum(CDCl$_3$)δppm: 1.45 (9H,s), 2.50(3H,d,J=2.0 Hz), 3.65(2H,q,J=5.1 Hz), 4.49(2H, t,J=5.1 Hz), 4.88(1H,brs), 7.15–7.30(2H,m)

(c) 3-(2-Aminoethoxy)-5-fluoro-4-methyl-1,2-benzisoxazole hydrochloride.

3-(2-(N-t-butoxycarbonylamino)ethoxy)-5-fluoro-4-methyl-1,2-benzisoxazole (0.15 g) was dissolved in 4N hydrochloric acid/dioxane solution (1.4 ml) and stirred for 15 minutes. The reaction mixture was evaporated under reduced pressure and the precipitated crystals were filtered. The title compound (0.13 g, 98% yield) was obtained as a colorless powder by washing the crystals with ethyl acetate (3 ml).

Melting point: 213–215° C. (decomposed); IR spectrum (KBr)$v_{max}$cm$^{-1}$: 3300–2400, 1630, 1583, 1537, 1505; NMR spectrum(DMSO-d$_6$)δppm: 2.51(3H,d,J=2.0 Hz), 3.34(2H, q,J=5.1 Hz), 4.62(2H,t,J=5.1 Hz), 7.45–7.55(2H,m), 8.33 (3H,brs).

EXAMPLE 18

3-(2-Aminoethoxy)-4-carbamoyl-5-fluoro-1,2-benzisoxazole hydrochloride (a) 3-(2-(N-t-Butoxycarbonylamino)ethoxy)-4-carboxy-5-fluoro-1,2-benzisoxazole.

To a solution of 3-(2-(N-t-butoxycarbonylmino)ethoxy)-5-fluoro-1,2-benzisoxazole (0.30 g) in tetrahydrofuran (20 ml) was added lithium diisopropylamide (1.4 ml, 1.5M cyclohexane solution) dropwise at −70° C. under nitrogen atmosphere, and the reaction mixture was stirred at the same temperature for 15 minutes. Gaseous carbon dioxide was introduced for 10 minutes and the temperature was allowed to rise to 0° C. The reaction mixture was poured into ice water (40 ml) and washed with diethylether (40 ml each) twice. The aqueous layer was separated, and after the pH was adjusted to 4 with potassium dihydrogen phosphate, it was then extracted with ethyl acetate (each with 40 ml) twice. The combined extracts were dried over anhydrous magnesium sulphate, filtered and the solvent was evaporated under reduced pressure to give the title compound (0.31 g, 90% yield) as a colorless oil.

IR spectrum(KBr)$v_{max}$cm$^{-1}$: 3474, 3358, 3326, 3194, 1683, 1673, 1611, 1538, 1505; NMR spectrum(CDCl$_3$) δppm: 1.38(9H,s), 3.62(2H,q,J=5.1 Hz), 4.52(2H,t,J=5.1 Hz), 5.27(1H,brs), 6.04(1H,brs), 6.40(1H,brs), 7.34(1H,t,J= 9.1 Hz), 7.48(1H,dd,J=9.1 Hz, J=3.6 Hz).

(b) 3-(2-(N-t-Butoxycarbonylamino)ethoxy)-4-carbamoyl-5-fluoro-1,2-benzisoxazole.

To a solution of 3-(2-(N-t-butoxycarbonylamino)ethoxy)-4-carboxy-5-fluoro-1,2-benzisoxazole (0.31 g) in tetrahydrofuran (20 ml) was added isobutyl chlorocarbonate (0.14 g) and triethylamine (0.11 g) with stirring at 5° C., and the mixture was then stirred for 15 minutes. Ammonia-saturated tetrahydrofuran solution (saturated at room temperature, 5 ml) was added to the reaction mixture and stirred for 15 minutes. The reaction mixture was poured into ice water (40 ml), extracted with diethylether (twice each with 40 ml) and the combined extracts were dried over anhydrous magnesium sulphate and filtered. The solvent was evaporated under reduced pressure and the residue was purified by silica gel column chromatography with cyclohexane/ethyl acetate (4/1) as an eluent, to give title compound (0.24 g, 78% yield) as a colorless powder.

Melting point: 63–65° C.; IR spectrum(KBr)$v_{max}$cm$^{-1}$: 3473, 3359, 3327, 3195, 1683, 1673, 1612, 1538, 1503; NMR spectrum(CDCl$_3$)δppm: 1.38(9H,s), 3.62(2H,q,J=5.1 Hz), 4.52(2H,t,J=5.1 Hz), 5.27(1H,brs), 6.04(1H,brs), 6.40 (1H,brs), 7.34(1H,t,J=9.5 Hz), 7.48(1H,dd,J=9.5 Hz,J=3.6 Hz).

(c) 3-(2-Aminoethoxy)-4-carbamoyl-5-fluoro-1,2-benzisoxazole hydrochloride.

The title coumpound (20 mg, 99%) was obtained as a colorless powder from 3-(2-(N-t-butoxycarbonylamino)ethoxy)-4-carbamoyl-5-fluoro-1,2-benzisoxazole (25 mg) and 4N hydrochloric acid/dioxane solution (0.2 ml) by similar reactions and treatments as in example 17(c).

Melting point: 201–205° C. (decomposed); IR spectrum (KBr)$\nu_{max}$cm$^{-1}$: 3382, 3400–2400, 1656, 1605, 1590, 1543; NMR spectrum(DMSO-d$_6$)δppm: 3.30(2H,t,J=5.1 Hz), 4.62 (2H,t,J=5.1 Hz), 7.63(1H,t,J=9.5 Hz), 7.77(1H,dd,J=9.5 Hz,J=3.6 Hz), 7.86(1H,brs), 8.19(4H,brs).

EXAMPLE 19

3-(2-Aminoethoxy)-4-cyano-5-fluoro-1,2-benzisoxazole hydrochloride (a) 3-(2-(N-t-Butoxycarbonylamino)ethoxy)-4-cyano-5-fluoro-1,2-benzisoxazole.

To a solution of 3-(2-(N-t-butoxycarbonylamino)ethoxy)-4-carbamoyl-5-fluoro-1,2-benzisoxazole (0.25 g) in dimethylformamide (2.0 ml) was added phosphorus oxychloride (0.12 g) with stirring at 5° C., and the mixture was then stirred at the same temperature for 15 minutes. The reaction mixture was poured into ice water (20 ml), extracted with ethyl acetate (twice each with 20 ml) and the combined extracts were dried over anhydrous magnesium sulphate and filtered. The solvent was evaporated under reduced pressure and the residue was purified by silica gel column chromatography with cyclohexane/ethyl acetate (4/1) as an eluent, to give the title compound (0.20 g, 87% yield) as a colorless powder.

Melting point: 116–117° C.; IR spectrum(KBr)$\nu_{max}$cm$^{-1}$: 3368, 2240, 1702, 1532, 1507; NMR spectrum(CDCl$_3$) δppm: 1.45(9H,s), 3.67(2H,q,J=5.1 Hz), 4.54(2H,t,J=5.1 Hz), 5.05(1H,brs), 7.43(1H,t,J=9.5 Hz), 7.68(1H,dd,J=9.5 Hz,J=3.6 Hz).

(b) 3-(2-Aminoethoxy)-4-cyano-5-fluoro-1,2-benzisoxazole hydrochloride.

The title compound (0.12 g, 96% yield) was obtained as a colorless powder from 3-(2-(N-t-butoxycarbonylamino)ethoxy)-4-cyano-5-fluoro-1,2-benzisoxazole (0.17 g) and 4N-hydrochloric acid/dioxane solution (1.3 ml) by similar reactions and treatments as in example 17(c).

Melting point: 190–193° C. (decomposed); IR spectrum (KBr)$\nu_{max}$cm$^{-1}$: 3300–2400, 2240, 1607, 1541, 1505; NMR spectrum(DMSO-d$_6$)δppm: 3.34(2H,t,J=5.2 Hz), 4.72(2H,t, J=5.2 Hz), 7.91(1H,t,J=9.5 Hz), 8.19(1H,dd,J=9.5 Hz,J=3.7 Hz), 8.30(3H,brs).

EXAMPLE 20

3-(2-Aminoethoxy)-5-fluoro-4-methoxycarbonyl-1,2-benzisoxazole hydrochloride (a) 3-(2-(N-t-Butoxycarbonylamino)ethoxy)-5-fluoro-4-methoxycarbonyl-1,2-benzisoxazole.

To a solution of 3-(2-(N-t-butoxycarbonylamino)ethoxy)-4-carboxy-5-fluoro-1,2-benzisoxazole (0.31 g) in diethylether (20 ml) was added diazomethane/diethylether solution at 5° C. until the reaction mixture became yellow, and the mixture was then stirred for 15 minutes. The reaction mixture was evaporated under reduced pressure to give the title compound (0.32 g, 100% yield) as an oil.

IR spectrum(KBr)$\nu_{max}$cm$^{-1}$: 3457, 1733, 1713, 1541, 1504; NMR spectrum(CDCl$_3$)δppm: 1.46(9H,s), 3.62(2H,q, J=5.1 Hz), 4.01(3H,s), 4.49(2H,t,J=5.1 Hz), 5.08(1H,brs), 7.35(1H,t,J=9.5 Hz), 7.52(1H,dd,J=9.5 Hz,J=3.6 Hz).

(b) 3-(2-Aminoethoxy)-5-fluoro-4-methoxycarbonyl-1,2-benzisoxazle hydrochloride.

The title compound (0.15 g, 97% yield) was obtained as a colorless powder from 3-(2-(N-t-butoxycarbonylamino) ethoxy)-5-fluoro-4-methoxycarbonyl-1,2-benzisoxazole (0.18 g) and 4N-hydrochloric acid/dioxane solution (1.3 ml) by similar reactions and treatments as in example 17(c).

Melting point: 168–170° C. (decomposed); IR spectrum (KBr)$\nu_{max}$cm$^{-1}$: 3300–2400, 1729, 1584, 1539, 1501; NMR spectrum(DMSO-d$_6$)δppm: 3.31(2H,t,J=5.1 Hz), 3.96(3H, s), 4.62(2H,t,J=5.1 Hz), 7.73(2H,t,J=9.5 Hz), 7.96(2H,dd,J= 9.5 Hz,J=3.6 Hz), 8.23(3H,brs).

EXAMPLE 21

3-(2-Aminoethoxy)-5-fluoro-4-methylthio-1,2-benzisoxazole hydrochloride (a) 3-(2-(N-t-Butoxycarbonylamino)ethoxy)-5-fluoro-4-methylthio-1,2-benzisoxazole.

To a solution of 3-(2-(N-t-butoxycarbonylamino)ethoxy)-5-fluoro-1,2-benzisoxazole (0.30 g) in tetrahydrofuran (20 ml) was added lithium diisopropylamide (1.50 ml, 1.5M hexane solution) dropwise with stirring at −70° C. under nitrogen atmosphere, then after being stirred at the same temperature for 15 minutes dimethyldisulphide (0.21 g) was added. The reaction mixture was stirred for 15 minutes at −70° C. and then the temperature was raised to 0° C. The reaction mixture was poured into ice water (40 ml), extracted with ethyl acetate (twice each with 40 ml) and the combined extracts were dried over anhydrous magnesium sulphate. After filtration, the solvent was evaporated under reduced pressure and the residue was purified by silica gel column chromatography with cyclohexane/ethyl acetate (9/1) as an eluent, to give the title compound (0.32 g, 94% yield) as a colorless powder.

Melting point: 91–92° C.; IR spectrum(KBr)$\nu_{max}$cm$^{-1}$: 3355, 1694, 1618, 1540; NMR spectrum(CDCl$_3$)δppm: 1.45 (9H,s), 2.60(3H,d,J=2.1 Hz), 3.67(2H,q,J=5.1 Hz), 4.50(2H, t,J=5.1 Hz), 5.04(1H,brs), 7.20–7.30(2H,m).

(b) 3-(2-Aminoethoxy)-5-fluoro-4-methylthio-1,2-benzisoxazole hydrochloride.

The title compound (0.15 g, 99% yield) was obtained as a colorless powder from 3-(2-(N-t-butoxycarbonylamino) ethoxy)-5-fluoro-4-methylthio-1,2-benzisoxazole (0.18 g) and 4N hydrochloric acid/dioxane solution (1.3 ml) by similar reactions and treatments as in example 17(c).

Melting point: 183–185° C. (decomposed); IR spectrum (KBr)$\nu_{max}$cm$^{-1}$: 3400–2400, 1617, 1592, 1535; NMR spectrum(DMSO-d$_6$)δppm: 2.57(3H,d,J=1.4 Hz), 3.35(3H, t,J=5.1 Hz), 4.64(2H,t,J=5.1 Hz), 7.59(1H,t,J=9.5 Hz), 7.63 (1H,dd,J=9.5 Hz, J=3.6 Hz), 8.24(3H,brs).

EXAMPLE 22

3-(2-Aminoethoxy)-4-methoxycarbonyl-1,2-benzisoxazole hydrochloride, and 3-(2-Aminoethoxy)-7-methoxycarbonyl-1,2-benzisoxazle hydrochloride (a) 3-(2-(N-t-Butoxycarbonylamino)ethoxy)-1,2-benzisoxazole.

To a solution of triphenylphosphine (0.95 g) in tetrahydrofuran (20 ml) was added diethyl azodicarboxylate (0.63 g) with stirring at 5° C., then stirred at the same temperature for 15 minutes. To a reaction mixture, 3-hydroxy-1,2-benzisoxazole (0.45 g) was added and stirred for 15 minutes, then N-t-butoxycarbonyl ethanolamine (0.53 g) was added and the mixture stirred at room temperature for 24 hour. The solvent was evaporated under reduced pressure and residue was purified by silica gel column chromatography with cyclohexane/ethyl acetate (9/1) as an eluent, to give the title compound (0.63 g, 68%).

Melting point: 106–107° C.; IR spectrum(KBr)$\nu_{max}$cm$^{-1}$: 3326, 1716, 1707, 1615, 1536; NMR spectrum(CDCl$_3$)

δppm: 1.46(9H,s), 3.65(2H,q,J=5.1 Hz), 4.51(2H,t,J=5.1 Hz), 4.90–5.05(1H,brs), 7.26–7.66(4H,m).

(b) 3-(2-(N-t-Butoxycarbonylamino)ethoxy)-4-methoxycarbonyl-1,2-benzisoxazole, and 3-(2-(N-t-Butoxycarbonylamino)ethoxy)-7-methoxycarbonyl-1,2-benzisoxazole.

To a solution of 3-(2-(N-t-butoxycarbonylamino)ethoxy)-1,2-benzisoxazole (0.28 g) in tetrahydrofuran (30 ml) was added butyl lithium (1.40 ml, 1.6M hexane solution) dropwise with stirring at −70° C. under nitrogen atmosphere, and the mixture then stirred at the same temperature for 15 minutes. Gaseous carbon dioxide was introduced to the reaction mixture for 10 minutes and the temperature was raised to 0° C. The reaction mixture was poured into ice water (40 ml) and washed with diethylether (twice each with 40 ml). The aqueous layer was separated, after pH was adjusted to 4 with potassium dihydrogen phosphate, and extracted with ethyl acetate (twice each with 40 ml). The combined extracts was dried over anhydrous magnesium sulphate and filtered. The solvent was evaporated under reduced pressure and 3-(2-(N-t-butoxycarbonylamino)ethoxy)-4-carboxy-1,2-benzisoxazole and 3-(2-(N-t-butoxycarbonylamino)ethoxy)-7-carboxy-1,2-benzisoxazole were obtained as a colorless oily mixture (0.31 g, 92%).

Then, the obtained mixture was dissolved in diethylether (15 ml) and, after cooling to 5° C., diazomethane/diethylether solution was added dropwise until the reaction mixture became yellow, and the mixture then stirred at the same temperature for 15 minutes. The solvent was evaporated under reduced pressure and the residue was purified by silica gel column chromatography with cyclohexane/ethyl acetate (4/1) as an eluent, to give the title compounds, 3-(2-(N-t-butoxycarbonylamino)ethoxy)-4-methoxycarbonyl-1,2-benzisoxazole (0.15 g, 45%) and 3-(2-(N-t-butoxycarbonylamino)ethoxy)-7-methoxycarbonyl-1,2-benzisoxazole (0.08 g, 24%), as colorless powders respectively.

Data for 3-(2-(N-t-butoxycarbonylamino)ethoxy)-4-methoxycarbonyl-1,2-benzisoxazole.

Melting point: 95–96° C.; IR spectrum(KBr)$\nu_{max}$cm$^{-1}$: 3397, 1705, 1601, 1533, 1524, 1503; NMR spectrum (CDCl$_3$)δppm: 1.46(9H,s), 3.66(2H,q,J=5.1 Hz), 3.99(3H,s), 4.51(2H,t,J=5.1 Hz), 5.29(1H,brs), 7.55–7.65(2H,m), 7.85(1H,d,J=7.5 Hz).

Data for 3-(2-(N-t-butoxycarbonylamino)ethoxy)-7-methoxycarbonyl-1,2-benzisoxazole.

Melting point: 90–91° C.; IR spectrum(KBr)$\nu_{max}$cm$^{-1}$: 3387, 1718, 1693, 1620, 1610, 1552, 1525; NMR spectrum (CDCl$_3$)δppm: 1.46(9H,s), 3.66(2H,q,J=5.1 Hz), 4.03(3H,s), 4.54(2H,t,J=5.1 Hz), 4.96(1H,brs), 7.37(1H,t,J=8.1 Hz), 7.85(1H,d,J=8.1 Hz), 8.23(3H,d,J=8.0 Hz).

(c) 3-(2-Aminoethoxy)-4-methoxycarbonyl-1,2-benzisoxazole hydrochloride.

The title compound (0.08 g, 100%) was obtained as a colorless powder from 3-(2-(N-t-butoxycarbonylamino)ethoxy)-4-methoxycarbonyl-1,2-benzisoxazole (0.10 g) and 4N hydrochloric acid/dioxane solution (1.0 ml) by similar reactions and treatments as in example 17(c).

Melting point: 169–172° C. (decomposed); IR spectrum (KBr)$\nu_{max}$cm$^{-1}$: 3300–2400, 1718, 1601, 1525, 1499; NMR spectrum(DMSO-d$_6$)δppm: 3.34(2H,t,J=5.1 Hz), 3.93(3H,s), 4.62(2H,t,J=5.1 Hz), 7.75–7.85(2H,m), 7.95(1H,d,J=8.1 Hz), 8.23(3H,brs).

(d) 3-(2-Aminoethoxy)-7-methoxycarbonyl-1,2-benzisoxazole hydrochloride.

The title compound (0.06 g, 100%) was obtained as a colorless powder from 3-(2-(N-t-butoxycarbonylamino)ethoxy)-7-methoxycarbonyl-1,2-benzisoxazole (0.08 g) and 4N-hydrochloric acid/dioxane solution (1.0 ml) by similar reactions and treatments as in example 17(c).

Melting point: 211–213° C. (decomposed); IR spectrum (KBr)$\nu_{max}$cm$^{-1}$: 3300–2400, 1730, 1719, 1618, 1608, 1550, 1502; NMR spectrum(DMSO-d$_6$)δppm: 3.36(2H,t,J=5.1 Hz), 3.95(3H,s), 4.65(2H,t,J=5.1 Hz), 7.56(1H,t,J=8.0 Hz), 8.10(1H,d,J=8.1 Hz), 8.23(1H,d,J=8.1 Hz), 8.30(3H,brs).

EXAMPLE 23

3-(2-Aminoethoxy)-4-carbamoyl-1,2-benzisoxazole hydrochloride, and 3-(2-Aminoethoxy)-7-carbamoyl-1,2-benzisoxazole hydrochloride (a) 3-(2-(N-t-Butoxycarbonylamino)ethoxy)-4-carbamoyl-1,2-benzisoxazole, and 3-(2-(N-t-Butoxycarbonylamino)ethoxy)-7-carbamoyl-1,2-benzisoxazole.

To a solution of 3-(2-(N-t-butoxycarbonylamino)ethoxy)-1,2-benzisoxazole (0.55 g) in tetrahydrofuran (30 ml) was added butyl lithium (3.0 ml, 1.6M hexane solution) dropwise with stirring at −70° C. under nitrogen atmosphere, and the mixture was then stirred at the same temperature for 15 minutes. Gaseous carbon dioxide was introduced to the reaction mixture over 10 minutes and the temperature was raised to 0° C. The reaction mixture was poured into ice water (40 ml) and washed with diethylether (twice each with 40 ml). The aqueous layer was separated, after pH was adjusted to 4 with potassium dihydrogen phosphate, then extracted with ethyl acetate (twice each with 40 ml). The combined extracts were dried over anhydous magnesium sulphate, filtered and the solvent was evaporated under reduced pressure, to give 3-(2-(N-t-butoxycarbonylamino)ethoxy)-4-carboxy-1,2-benzisoxazole and 3-( 2-(N-t-butoxycarbonylamino)ethoxy)-7-carboxyl-1,2-benzisoxazole as a colorless oily mixture (0.48 g).

Then, the obtained mixture was dissolved in tetrahydrofuran (30 ml) and, to this solution was added isobutyl chlorocarbonate (0.23 g) and triethylamine (0.18 g) with stirring at 5° C., and the mixture was then stirred for 15 minutes followed by addition of ammonia-saturated tetrahydrofuran solution (saturated at room temperature, 5 ml) and stirring for 15 minute. The reaction mixture was poured into ice water (40 ml), extracted with ethyl acetate (twice each with 40 ml) and the combined extracts were dried over anhydrous magnesium sulphate and filtered. The solvent was evaporated under reduced pressure and the residue was purified by silica gel column chromatography with cyclohexane/ethyl acetate (4/1) as an eluent, to give 3-(2-(N-t-butoxycarbonylamino)ethoxy)-4-carbamoyl-1,2-benzisoxazole (0.30 g, 47%) and 3-(2-(N-t-butoxycarbonylamino)ethoxy)-7-carbamoyl-1,2-benzisoxazole (0.17 g, 26%) as colorless powders respectively.

Data for 3-(2-(N-t-butoxycarbonylamino)ethoxy)-4-carbamoyl-1,2-benzisoxazole.

Melting point: 119–120° C.; IR spectrum(KBr)$\nu_{max}$cm$^{-1}$: 3488, 3443, 3358, 3196, 1688, 1663, 1610, 1592, 1533; NMR spectrum(CDCl$_3$)δppm: 1.42(9H,s), 3.70(2H,q,J=5.1 Hz), 4.62(2H,t,J=5.1 Hz), 4.93(1H,brs), 5.91(1H,brs), 7.60–7.70(2H,m), 7.79(1H,brs), 8.14(1H,d,J=7.0 Hz).

Data for 3-(2-(N-t-butoxycarbonylamino)ethoxy)-7-carbamoyl-1,2-benzisoxazole.

Melting point: 151–153° C.; IR spectrum(KBr)$\nu_{max}$cm$^{-1}$: 3463, 3396, 3353, 3304, 3232, 3182, 1716, 1680, 1618, 1544; NMR spectrum(CDCl$_3$)δppm: 1.46(9H,s), 3.67(2H,q, J=5.1 Hz), 4.54(2H,t,J=5.1 Hz), 4.97(1H,brs), 5.95(1H,brs), 7.14(1H,brs), 7.44(1H,t,J=7.0 Hz), 7.83(1H,d,J=7.0 Hz), 8.35(1H,d,J=7.0 Hz).

(b) 3-(2-Aminoethoxy)-4-carbamoyl-1,2-benzisoxazole hydrochloride.

The title compound (0.08 g, 100%) was obtained as a colorless powder from 3-(2-(N-t-butoxycarbonylamino)ethoxy)-4-carbamoyl-1,2-benzisoxazole (0.10 g) and 4N-hydrochloric acid/dioxane solution (1.0 ml) by similar reactions and treatments as in example 17(c).

Meltling point: 210–213° C. (decomposed); IR spectrum (KBr)$v_{max}$cm$^{-1}$: 3383, 3300–2400, 1656, 1605, 1590, 1543; NMR spectrum(DMSO-d$_6$)δppm: 3.57(2H,t,J=5.1 Hz), 4.64 (2H,t,J=5.1 Hz), 7.58(1H,d,J=7.0 Hz), 7.71(1H,brs), 7.73 (1H,dd,J=9.0 Hz,J=7.0 Hz), 7.79(1H,d,J=9.0 Hz), 7.99(1H, brs), 8.21(3H,brs).

(c) 3-(2-Aminoethoxy)-7-carbamoyl-1,2-benzisoxazole hydrochloride.

The title compound (0.04 g, 100%) was obtained as a colorless powder from 3-(2-(N-t-butoxycarbonylamino)ethoxy)-7-carbamoyl-1,2-benzisoxazole (0.05 g) and 4N-hydrochloric acid/dioxane solution (1.0 ml) by similar reactions and treatments as in example 17(c).

Meltling point: 227–230° C. (decomposed); IR spectrum (KBr)$v_{max}$cm$^{-1}$: 3461, 3180, 3300–2400, 1675, 1618, 1596, 1547; NMR spectrum(DMSO-d$_6$)δppm: 3.34(2H,t,J=5.1 Hz), 4.65(2H,t,J=5.1 Hz), 7.50(1H,t,J=7.0 Hz), 7.77(1H, brs), 7.83(1H,brs), 7.95(1H,d,J=7.0 Hz), 8.05(1H, d,J=7.0 Hz), 8.31(3H,brs).

EXAMPLE 24

3-(2-Aminoethoxy)-4-cyano-1,2-benzisoxazole hydrochloride (a) 3-(2-(N-t-Butoxycarbonylamino)ethoxy)-4-cyano-1,2-benzisoxazole.

To a solution of 3-(2-(N-t-butoxycarbonylamino)ethoxy)-4-carbamoyl-1,2-benzisoxazole (0.15 g) in diethylformamide (1.5 ml) was added phosphorus oxychloride (0.09 g) with stirring at 5° C., and the mixture was then stirred at the same temperature for 15 minutes. The reaction mixture was poured into ice water (20 ml), extracted with ethyl acetate (twice each with 20 ml) and the combined extracts were dried over anhydrous magnesium sulphate. After filtration, the solvent was evaporated under reduced pressure and the residue was purified by silica gel column chromatography with cyclohexane/ethyl acetate (4/1) as an eluent, to give the title compound (0.13 g, 93%) as a colorless powder.

Melting point: 116–117° C.; IR spectrum(KBr)$v_{max}$cm$^{-1}$: 3370, 2232, 1701, 1601, 1530; NMR spectrum(CDCl$_3$) δppm: 1.45(9H,s), 3.69(2H,q,J=5.1 Hz), 4.55(2H,t,J=5.1 Hz), 5.08(1H,brs), 7.60–7.75(3H,m).

(b) 3-(2-Aminoethoxy)-4-cyano-1,2-benzisoxazole hydrochloride.

The title compound (0.08 g, 100%) was obtained as a colorless powder from 3-(2-(N-t-butoxycarbonylamino)ethoxy)-4-cyano-1,2-benzisoxazole (0.10 g) and 4N-hydrochloric acid/dioxane solution (1.0 ml) by similar reactions and treatments as in example 17(c).

Meltling point: 210–213° C. (decomposed); IR spectrum (KBr)$v_{max}$cm$^{-1}$: 3400–2400, 2234, 1601, 1538; NMR spectrum(DMSO-d$_6$)δppm: 3.35(2H,t,J=5.1 Hz), 4.72(2H,t, J=5.1 Hz), 7.87(1H,t,J=8.1 Hz), 7.98(1H,d,J=8.1 Hz), 8.09 (1H,d,J=8.1 Hz), 8.26(3H,brs).

EXAMPLE 25

3-(2-Aminoethoxy)-7-cyano-1,2-benzisoxazole hydrochloride (a) 3-(2-(N-t-Butoxycarbonylamino)ethoxy)-7-cyano-1,2-benzisoxazole.

To a solution of 3-(2-(N-t-butoxycarbonylamino)ethoxy)-7-carbamoyl-1,2-benzisoxazole (0.10 g) in dimethylformamide (1.0 ml) was added phosphorus oxychloride (0.06 g) with stirring at 5° C., and the mixture was then stirred at the same temperature for 15 minutes. The reaction mixture was poured into ice water (20 ml), extracted with ethyl acetate (twice each with 20 ml) and the combined extracts were dried over anhydrous magnesium sulphate. After filtration, the solvent was evaporated under reduced pressure and the residue was purified by silica gel column chromatography with cyclohexane/ethyl acetate (4/1) as an eluent, to give the title compound (0.09 g, 90%) as a colorless powder.

Melting point: 91–92° C.; IR spectrum(KBr)$v_{max}$cm$^{-1}$: 3437, 3349, 3316, 2238, 1719, 1701, 1688, 1621, 1607, 1546, 1528; NMR spectrum(CDCl$_3$)δppm: 1.45(9H,s), 3.66 (2H,q,J=5.1 Hz), 4.54(2H,t,J=5.1 Hz), 4.92(1H,brs), 7.40 (1H,t,J=8.0 Hz), 7.86(1H,d,J=8.0 Hz), 7.90(1H,d,J=8.0 Hz).

(b) 3-(2-Aminoethoxy)-7-cyano-1,2-benzisoxazole hydrochloride.

The title compound (0.05 g, 100%) was obtained as a colorless powder from 3-(2-(N-t-butoxycarbonylamino)ethoxy)-7-cyano-1,2-benzisoxazole (0.07 g) and 4N-hydrochloric acid/dioxane solution (1.0 ml) by similar reactions and treatments as in example 17(c).

Meltling point: 205–208° C. (decomposed); IR spectrum (KBr)$v_{max}$cm$^{-1}$: 3241, 3400–2400, 2239, 1623, 1607, 1547; NMR spectrum(DMSO-d$_6$)δppm: 3.36(2H,t,J=5.1 Hz), 4.67 (2H,t,J=5.1 Hz), 7.61(1H,t,J=8.1 Hz), 8.18(1H,d,J=8.1 Hz), 8.26(1H,d,J=8.1 Hz), 8.34(3H,brs).

EXAMPLE 26

3-(2-Aminoethylthio)-5-fluoro-1,2-benzisoxazole hydrochloride (a) 3-Chloro-5-fluoro-1,2-benzisoxazole.

To a solution of 5-fluoro-3-hydroxyisoxazole (1.0 g) in pyridine (0.53 ml) was added phosphorus oxychloride (0.89 ml) and the mixture was refluxed for 8 hours. The reaction mixture was poured into ice water, extracted with ethyl acetate and the combined extracts were washed with saturated salt water and dried over anhydrous magnesium sulphate. After filtration, the solvent was evaporated under reduced pressure and the residue was purified by silica gel column chromatography, to give the title compound (0.85 g, 77%) as a colorless oil.

(b) 3-(2-(N-t-Butoxycarbonylamino)ethylthio)-5-fluoro-1,2-benzisoxazole.

To a solution of 3-chloro-5-fluoro-1,2-benzisoxazole (0.83 g) in dimethylformamide (8 ml) was added 2-t-butoxycarbonylaminoethanethiol (0.86 g) and potassium carbonate (0.67 g) with stirring under nitrogen atmosphere, and the mixture was then stirred at 80° C. for 3 hours. The reaction mixture was poured into ice water, extracted with ethyl acetate and the combined extracts were washed with brine and dried over anhydrous magnesium sulphate. After filtration, the solvent was evaporated under reduced pressure and the residue was purified by silica gel column chromatography, to give the title compound (1.21 g, 80%) as a colorless powder.

NMR spectrum(CDCl$_3$)δppm: 1.44(9H,s), 3.41(2H,t,J= 6.2 Hz), 3.58(2H,td,J=6.2 Hz,J=6.2 Hz), 4.98(1H,brs), 7.21–7.51(3H,m).

(c) 3-(2-Aminoethylthio)-5-fluoro-1,2-benzisoxazole hydrochloride.

To a solution of 3-(2-(N-t-butoxycarbonylamino)ethylthio)-5-fluoro-1,2-benzisoxazole (0.20 g) in dioxane (2 ml) was added 4N-hydrochloric acid/dioxane solution (0.8 ml) with stirring at 5° C., and the mixture was then stirred at room temperature for 30 minutes. After completion of the reaction, the solvent was evaporated under reduced pressure and the residue was recrystallized from ethanol and ethyl acetate, to give the title compound (0.14 g) as a colorless needle.

Melting point: 202–206° C. (decomposed); IR spectrum (KBr)$\nu_{max}$cm$^{-1}$: 2992, 2955, 2915, 1594, 1511, 1493; NMR spectrum(DMSO-d$_6$)δppm: 3.25(2H,t,J=7.1 Hz), 3.53(2H,t, J=7.1 Hz), 7.60–7.86(3H,m), 8.22(3H,brs).

EXAMPLE 27

3-(2-Aminoethylthio)-7-chloro-1,2-benzisoxazole hydrochloride (a) 3,7-Dichloro-1,2-benzisoxazole.

The title compound (0.73 g, 78%) was obtained from 7-chloro-3-hydroxy-1,2-benzisoxazole (0.85 g) by similar reactions and treatments as in example 26(a).

(b) 3-(2-(N-t-Butoxycarbonylamino)ethylthio)-7-chloro-1, 2-benzisoxazole.

The title compound (0.22 g, 63%) was obtained from 3,7-dichloro-1,2-benzisoxazole (0.20 g) by similar reactions and treatments as in Application example 26(b).

NMR spectrum(CDCl$_3$)δppm: 1.43(9H,s), 3.42(2H,t,J= 6.2 Hz), 3.60(2H,td,J=6.2 Hz,J=6.2 Hz), 5.01(1H,brs), 7.24 (1H,t,J=9.1 Hz), 7.48(1H,d,J=9.1 Hz), 7.56(1H,d,J=9.1 Hz).

(c) 3-(2-Aminoethylthio)-7-chloro-1,2-benzisoxazole hydrochloride.

The title compound (0.12 g, quant) was obtained from 3-(2-(N-t-butoxycarbonylamino)ethylthio)-7-chloro-1,2-benzisoxazole (0.15 g) by similar reactions and treatments as in example 26(c).

Melting point: 196–201° C. (decomposed); IR spectrum (KBr)$\nu_{max}$cm$^{-1}$: 2971, 2909, 1592, 1502, 1492; NMR spectrum (DMSO-d$_6$)δppm: 3.26(2H,t,J=7.1 Hz), 3.56(2H,t,J= 7.1 Hz), 7.45(1H,t,J=7.9 Hz), 7.79(1H,d,J=7.9 Hz), 7.86 (1H,d,J=7.9 Hz), 8.20(3H,brs).

EXAMPLE 28

3-(2-Aminoethylthio)-7-methyl-1,2-benzisoxazole hydrochloride (a) 3-Chloro-7-methyl-1,2-benzisoxazole.

The title compound (0.30 g, 77%) was obtained from 3-hydroxy-7-methyl-1,2-benzisoxazole (0.35 g) by similar reactions and treatments as in example 26(a).

(b) 3-(2-(N-t-Butoxycarbonylamino)ethylthio)-7-methyl-1, 2-benzisoxazole.

The title compound (0.24 g, 55%) was obtained from 3-chloro-7-methyl-1,2-benzisoxazole (0.24 g) by similar reactions and treatments as in example 26(b).

NMR spectrum(CDCl$_3$)δppm: 1.43(9H,s), 2.52(3H,s), 3.42(2H,t,J=6.2 Hz), 3.58(2H,td,J=6.2 Hz,J=6.2 Hz), 5.12 (1H,brs), 7.18(1H,t,J=9.1 Hz), 7.33(1H,d,J=9.1 Hz), 7.40 (1H,d,J=9.1 Hz).

(c) 3-(2-Aminoethylthio)-7-methyl-1,2-benzisoxazole hydrochloride.

The title compound (0.08 g, quant) was obtained from 3-(2-(N-t-butoxycarbonylamino)ethylthio)-7-methyl-1,2-benzisoxazole (0.10 g) by similar reactions and treatments as in example 26(c).

Melting point: 198–203° C. (decomposed); IR spectrum (KBr)$\nu_{max}$cm$^{-1}$: 2985, 2913, 1598, 1501; NMR spectrum (DMSO-d$_6$)δppm: 2.51(3H,s), 3.24(2H,t,J=7.1 Hz), 3.54 (2H,t,J=7.1 Hz), 7.33(1H,t,J=7.4 Hz), 7.52(1H,d,J=7.4 Hz), 7.58(1H,d,J=7.4 Hz), 8.22(3H,brs).

EXAMPLE 29

3-(2-Aminoethylthio)-5,7-dichloro-1,2-benzisoxazole hydrochloride (a) 3,5,7-Trichloro-1,2-benzisoxazole.

The title compound (1.81 g, 83%) was obtained from 5,7-dichloro-3-hydroxy-1,2-benzisoxazole (2.00 g) by similar reactions and treatments as in example 26(a).

(b) 3-(2-(N-t-Butoxycarbonylamino)ethylthio)-5,7-dichloro-1,2-benzisoxazole.

The title compound (0.25 g, 68%) was obtained from 3,5,7-trichloro-1,2-benzisoxazole (0.23 g) by similar reactions and treatments as in example 26(b).

NMR spectrum(CDCl$_3$)δppm: 1.43(9H,s), 3.42(2H,t,J= 6.2 Hz), 3.58(2H,td,J=6.2 Hz,J=6.2 Hz), 5.03(1H,brs), 7.48 (1H,s), 7.56(1H,s).

(c) 3-(2-Aminoethylthio)-5,7-dichloro-1,2-benzisoxazole hydrochloride.

The title compound (0.18 g, quant) was obtained from 3-(2-(N-t-butoxycarbonylamino)ethylthio)-5,7-dichloro-1, 2-benzisoxazole (0.22 g) by similar reactions and treatments as in example 26(c).

Melting point: 199–202° C. (decomposed); IR spectrum (KBr)$\nu_{max}$cm$^{-1}$: 3003, 2970, 2915, 1590, 1480; NMR spectrum(DMSO-d$_6$)δppm: 3.25(1H,t,J=6.9 Hz), 3.54(2H,t, J=6.9 Hz), 8.00(1H,s), 8.06(1H,s), 8.18(3H,brs).

EXAMPLE 30

3-(2-Aminoethylthio)-7-nitro-1,2-benzisoxazole hydrochloride (a) 3-Chloro-7-nitro-1,2-benzisoxazole.

The title compound (0.93 g, 80%) was obtained from 3-hydroxy-7-nitro-1,2-benzisoxazole (1.05 g) by similar reactions and treatments as in example 26(a).

(b) 3-(2-(N-t-Butoxycarbonylamino)ethylthio)-7-nitro-1,2-benzisoxazole.

The title compound (0.20 g, 51%) was obtained from 3-chloro-7-nitro-1,2-benzisoxazole (0.23 g) by similar reactions and treatments as in example 26(b).

NMR spectrum(CDCl$_3$)δppm: 1.43(9H,s), 3.48(2H,t,J= 6.2 Hz), 3.62(2H,td,J=6.2 Hz,J=6.2 Hz), 4.98(1H,brs), 7.50 (1H,t,J=9.1 Hz), 7.94(1H,d,J=9.1 Hz), 8.44(1H,d,J=9.1 Hz).

(c) 3-(2-Aminoethylthio)-7-nitro-1,2-benzisoxazole hydrochloride.

The title compound (0.14 g, quant) was obtained from 3-(2-(N-t-butoxycarbonylamino)ethylthio)-7-nitro-1,2-benzisoxazole (0.18 g) by similar reactions and treatments as in example 26(c).

Melting point: 193–196° C. (decomposed); IR spectrum (KBr)$\nu_{max}$cm$^{-1}$: 2990, 2924, 2882, 1620, 1589, 1532, 1512; NMR spectrum(DMSO-d$_6$)δppm: 3.28(2H,t,J=7.1 Hz), 3.61 (2H,t,J=7.1 Hz), 7.69(1H,t,J=7.9 Hz), 8.24(3H,brs), 8.29 (1H,d,J=7.9 Hz), 8.57(1H,d,J=7.9 Hz).

EXAMPLE 31

3-(2-Aminoethylthio)-7-methoxy-1,2-benzisoxazole hydrochloride (a) 3-Chloro-7-methoxy-1,2-benzisoxazole.

The title compound (0.61 g, 69%) was obtained from 3-hydroxy-7-methoxy-1,2-benzisoxazole (0.80 g) by similar reactions and treatments as in example 26(a).

(b) 3-(2-(N-t-Butoxycarbonylamino)ethylthio)-7-methoxy-1,2-benzisoxazole.

The title compound (0.25 g, 54%) was obtained from 3-chloro-7-methoxy-1,2-benzisoxazole (0.26 g) by similar reactions and treatments as in example 26(b).

NMR spectrum(CDCl$_3$)δppm: 1.44(9H,s), 3.42(2H,t,J= 6.2 Hz), 3.58(2H,td,J=6.2 Hz,J=6.2 Hz), 4.04(3H,s), 5.02 (1H,brs), 6.98(1H,d,J=9.1 Hz), 7.15(1H,d,J=9.1 Hz), 7.23 (1H,t,J=9.1 Hz).

(c) 3-(2-Aminoethylthio)-7-methoxy-1,2-benzisoxazole hydrochloride.

The title compound (90 mg, quant) was obtained from 3-(2-(N-t-butoxycarbonylamino)ethylthio-7-methoxy-1,2-benzisoxazole (120 mg) by similar reactions and treatments as in example 26(c).

Melting point: 232–237° C. (decomposed); IR spectrum (KBr)$v_{max}$cm$^{-1}$: 3019, 2969, 2907, 1619, 1600, 1512; NMR spectrum(DMSO-d$_6$)δppm: 3.25(2H,t,J=7.1 Hz), 3.54(2H,t, J=7.1 Hz), 3.98(3H,s), 7.27–7.40(3H,m), 8.21(3H,brs).

EXAMPLE 32

3-(2-Aminoethylthio)-7-amino-1,2-benzisoxazole dihydrochloride (a) 3-(2-(N-t-Butoxycarbonylamino)ethylthio)-7-amino-1,2-benzisoxazole.

To a solution of 3-(2-(N-t-butoxycarbonylamino) ethylthio)-7-nitro-1,2-benzisoxazole (250 mg) in 90% aqueous acetic acid (2 ml) was added zinc powder (250 mg) with stirring under ice cooling, and the mixture was then stirred at room temperature for 30 minutes. After the completion of the reaction, the reaction mixture was filtered with Celite and the filtrate was concentrated under reduced pressure. Water was added to the residue, then extracted with ethyl acetate. The combined extracts were washed with brine and dried over anhydrous magnesium sulphate. After filtration, the solvent was evaporated under reduced pressure and the residue was purified by silical gel column chromatography with ethyl acetate as an eluent, to give the title compound (230 mg, quant).

NMR spectrum(CDCl$_3$)δppm: 1.43(9H,s), 3.41(2H,t,J=6.2 Hz), 3.59(2H,td,J=6.2 Hz,J=6.2 Hz), 4.08(2H,brs), 5.02 (1H,brs), 6.82(1H,d,J=8.7 Hz), 6.96(1H,d,J=8.7 Hz), 7.12 (1H,t,J=8.7 Hz).

(b) 3-(2-Aminoethylthio)-7-amino-1,2-benzisoxazole dihydrochloride.

The title compound (120 mg, quant.) was obtained from 3-(2-(N-t-butoxycarbonylamino)ethylthio)-7-amino-1,2-benzisoxazole (140 mg) by similar reactions and treatments as in example 26(c).

Melting point: 157–160° C. (decomposed); IR spectrum (KBr)$v_{max}$cm$^{-1}$: 3035, 2969, 2884, 2807, 2581, 1631, 1614, 1570, 1521, 1504; NMR spectrum(DMSO-d$_6$)δppm: 3.24 (2H,t,J=7.0 Hz), 3.52(2H,t,J=7.0 Hz), 4.05–5.35(2H,brs), 6.88(2H,d,J=7.9 Hz), 7.12(1H,t,J=7.9 Hz), 8.23(3H,brs).

EXAMPLE 33

3-(2-Aminoethylthio)-5-methoxy-1,2-benzisoxazole hydrochloride (a) 3-Chloro-5-methoxy-1,2-benzisoxazole.

The title compound (730 mg, 71%) was obtained from 3-hydroxy-5-methoxy-1,2-benzisoxazole (920 mg) by similar reactions and treatments as in example 26(a).

(b) 3-(2-(N-t-Butoxycarbonylamino)ethylthio)-5-methoxy-1,2-benzisoxazole.

The title compound (280 mg, 61%) was obtained from 3-chloro-5-methoxy-1,2-benzisoxazole (260 mg) by similar reactions and treatments as in example 26(b).

NMR spectrum(CDCl$_3$)δppm: 1.43(9H,s), 3.40(2H,t,J=6.2 Hz), 3.58(2H,td,J=6.2 Hz,J=6.2 Hz), 3.86(3H,s), 5.02 (1H,brs), 6.91(1H,s), 7.18(1H,d,J=9.1 Hz), 7.43(1H,d,J=9.1 Hz).

(c) 3-(2-Aminoethylthio)-5-methoxy-1,2-benzisoxazole hydrochloride.

The title compound (190 mg, quant.) was obtained from 3-(2-(N-t-butoxycarbonylamino)ethylthio)-5-methoxy-1,2-benzisoxazole (240 mg) by similar reactions and treatments as in example 26(c).

Melting point: 213–217° C. (decomposed); IR spectrum (KBr)$v_{max}$cm$^{-1}$: 2997, 2947, 2883, 1592, 1514, 1495; NMR spectrum(DMSO-d$_6$)δppm: 3.23(2H,t,J=7.1 Hz), 3.52(2H,t, J=7.1 Hz), 3.84(3H,s), 7.16(1H,s), 7.32(1H,d,J=9.1 Hz), 7.69(1H,d,J=9.1 Hz), 8.17(3H,brs).

EXAMPLE 34

3-(2-Aminoethylthio)-5-methyl-1,2-benzisoxazole hydrochloride (a) 3-Chloro-5-methyl-1,2-benzisoxazole.

The title compound (0.81 g, 71%) was obtained from 3-hydroxy-5-methyl-1,2-benzisoxazole (1.02 g) by similar reactions and treatments as in example 26(a).

(b) 3-(2-(N-t-Butoxycarbonylamino)ethylthio)-5-methyl-1,2-benzisoxazole.

The title compound (90 mg, 56%) was obtained from 3-chloro-5-methyl-1,2-benzisoxazole (90 mg) by similar reactions and treatments as in example 26(b).

NMR spectrum(CDCl$_3$)δppm: 1.44(9H,s), 2.46(3H,s), 3.40(2H,t,J=6.2 Hz), 3.58(2H,td,J=6.2 Hz,J=6.2 Hz), 5.02 (1H,brs), 7.38(2H,d,J=9.1 Hz), 7.42(1H,s).

(c) 3-(2-Aminoethylthio)-5-methyl-1,2-benzisoxazole hydrochloride.

The title compound (60 mg, quant.) was obtained from 3-(2-(N-t-butoxycarbonylamino)ethylthio)-5-methyl-1,2-benzisoxazole (80 mg) by similar reactions and treatments as in example 26(c).

Melting point: 132–135° C.(decomposed); IR spectrum (KBr)$v_{max}$cm$^{-1}$: 2996, 2919, 1600, 1592, 1497; NMR spectrum(DMSO-d$_6$)δppm: 2.44(3H,s), 3.24(2H,t,J=7.1 Hz), 3.53(2H,t,J=7.1 Hz), 7.54(1H,d,J=8.5 Hz), 7.55(1H,s), 7.65(1H,d,J=8.5 Hz), 8.21(3H,brs).

EXAMPLE 35

3-(2-Aminoethylthio)-5-nitro-1,2-benzisoxazole hydrochloride (a) 3-Chloro-5-nitro-1,2-benzisoxazole.

The title compound (0.63 g, 56%) was obtained from 3-hydroxy-5-nitro-1,2-benzisoxazole (1.02 g) by similar reactions and treatments as in example 26(a).

(b) 3-(2-(N-t-Butoxycarbonylamino)ethylthio)-5-nitro-1,2-benzisoxazole.

The title compound (560 mg, 58%) was obtained from 3-chloro-5-nitro-1,2-benzisoxazole (560 mg) by similar reactions and treatments as in example 26(b).

NMR spectrum(CDCl$_3$)δppm: 1.44(9H,s), 3.47(2H,t,J=6.2 Hz), 3.62(2H,td,J=6.2 Hz,J=6.2 Hz), 4.96(1H,brs), 7.64 (1H,d,J=9.1 Hz), 8.48(1H,d,J=9.1 Hz), 8.56(1H,s).

(c) 3-(2-Aminoethylthio)-5-nitro-1,2-benzisoxazole hydrochloride.

The title compound (200 mg, quant) was obtained from 3-(2-(N-t-butoxycarbonylamino)ethylthio-5-nitro-1,2-benzisoxazole (250 mg) by similar reactions and treatments as in example 26(c).

Melting point: 183–186° C. (decomposed); IR spectrum (KBr)$v_{max}$cm$^{-1}$: 3013, 2971, 2892, 1619, 1594, 1530; NMR spectrum(DMSO-d$_6$)δppm: 3.26(2H,t,J=7.1 Hz), 3.59(2H,t, J=7.1 Hz), 8.03(1H,d,J=9.1 Hz), 8.24(3H,brs), 8.56(1H,d,J= 9.1 Hz), 8.72(1H,s).

EXAMPLE 36

3-(2-Aminoethylthio)-5-amino-1,2-benzisoxazole dihydrochloride (a) 3-(2-(N-t-Butoxycarbonylamino)ethylthio-5-amino-1,2-benzisoxazole.

The title compound (140 mg, quant.) was obtained from 3-(2-(N-t-butoxycarbonylamino)ethylthio-5-nitro-1,2-benzisoxazole (150 mg) by similar reactions and treatments as in example 32(a).

NMR spectrum(CDCl$_3$)δppm: 1.43(9H,s), 3.37(2H,t,J=6.2 Hz), 3.57(2H,td,J=6.2 Hz,J=6.2 Hz), 3.91(2H,brs), 5.03 (1H,brs), 6.77(1H,s), 6.94(1H,d,J=8.7 Hz), 7.33(1H,d,J=8.7 Hz).

(b) 3-(2-Aminoethylthio)-5-amino-1,2-benzisoxazole dihydrochloride.

The title compound (200 mg, quant) was obtained from 3-(2-(N-t-butoxycarbonylamino)ethylthio)-5-amino-1,2-benzisoxazole (200 mg) by similar reactions and treatments as in example 26(c).

Melting point: 201–205° C. (decomposed); IR spectrum (KBr)ν$_{max}$cm$^{-1}$: 3045, 3021, 2964, 2885, 1628, 1582, 1494; NMR spectrum(DMSO-d$_6$)δppm: 3.26(2H,t,J=7.0 Hz), 3.354.85(2H,brs), 3.55(2H,t,J=7.0 Hz), 7.54(1H,d,J=6.5 Hz), 7.56(1H,s), 7.80(1H,d,J=6.5 Hz), 8.24(3H,brs).

EXAMPLE 37

3-(2-Aminoethoxy)-1,2-naphtho[2,3-e]isoxazole hydrochloride (a) 3-Hydroxy-1,2-naphto[2,3-e]isoxazole.

The title compound (3.1 g, 31%) was obtained from 3-hydroxy-2-naphthoic acid (10.0 g) by similar reactions and treatments as in examples 1(a), 1(b) and 1(c).

IR spectrum(KBr)ν$_{max}$cm$^{-1}$: 3044, 3001, 2940, 2869, 2824, 2746, 2696, 2661, 2623, 1770, 1645, 1618, 1598, 1573, 1521; NMR spectrum(DMSO-d$_6$)δppm: 7.45–7.65 (2H,m), 8.01(1H,s), 8.04(1H,d,J=8.4 Hz), 8.15(1H,d,J=8.4 Hz), 8.43(1H,s), 12.67(1H,brs).

(b) 3-(2-(N-t-Butoxycarbonylamino)ethoxy)-1,2-naptho[2,3-e]isoxazole.

The title compound (0.59 g, 72%) was obtained from 3-hydroxy-1,2-naphtho[2,3-e]isoxazole (0.46 g) and 2-(N-t-butoxycarbonylamino)ethanol by similar reactions and treatments as in example 1(e).

Melting point: 148–149° C.; IR spectrum(KBr)ν$_{max}$cm$^{-1}$: 3314, 1707, 1643, 1545, 1535; NMR spectrum(CDCl$_3$) δppm: 1.47(9H,s), 3.70(2H,q,J=5.1 Hz), 4.59(2H,t,J=5.1 Hz), 5.01(1H,brs), 7.33–7.60(2H,m), 7.81(1H,s), 7.94(1H, d,J=8.4 Hz), 8.00(1H,d,J=8.4 Hz), 8.22(1H,s).

(c) 3-(2-Aminoethoxy)-1,2-naphtho[2.3-e]isoxazole hydrochloride.

The title compound (0.40 g, 99%) was obtained from 3-(2-(N-t-butoxy carbonylamino)ethoxy)-1,2-naphtho[2,3-e]isoxazole (0.50 g) by similar reactions and treatments as in example 1(f).

Melting point: 207–213° C. (decomposed); IR spectrum (KBr)ν$_{max}$cm$^{-1}$: 3300–2400, 1641, 1615, 1545, 1516, 1505; NMR spectrum(DMSO-d$_6$)δppm: 3.39(2H,q,J=5.1 Hz), 4.71(2H,t,J=5.1 Hz), 7.50–7.70(2H,m), 8.09(1H,d,J=8.4 Hz), 8.13(1H,s), 8.18(1H,d,J=8.4 Hz), 8.36(3H,brs), 8.47 (1H,s).

EXAMPLE 38

3-(2-Aminoethylthio)-5-chloro-1,2-benzisoxazole hydrochloride (a) 3-(2-(N-t-Butoxycarbonylamino)ethylthio)-5-chloro-1,2-benzisoxazole.

The title compound (0.63 g, 62%) was obtained from 3,5-dichloro-1,2-benzisoxazole (0.53 g) by similar reactions and treatments as in example 26(b).

Melting point: 95–96° C.; IR spectrum(KBr)ν$_{max}$cm$^{-1}$: 3283, 1687, 1523; NMR spectrum(CDCl$_3$)δppm: 1.44(9H, s), 3.42(2H,t,J=6.3 Hz), 3.58(2H,q,J=6.3 Hz), 4.98(1H,brs), 7.47(1H,d,J=8.8 Hz), 7.52(1H,dd,J=8.8 Hz,J=1.5 Hz), 7.57 (1H,d,J=1.5 Hz).

(b) 3-(2-Aminoethylthio)-5-chloro-1,2-benzisoxazole hydrochloride.

The title compound (0.41 g, 97%) was obtained from 3-(2-(N-t-butoxycarbonylamino)ethylthio)-5-chloro-1,2-benzisoxazole (0.52 g) by similar reactions and treatments as in example 22(c).

Melting point: 201–206° C. (decomposed); IR spectrum (KBr)ν$_{max}$cm$^{-1}$: 3300–2400, 1588, 1524; NMR spectrum (DMSO-d$_6$)δppm: 3.24(2H,q,J=7.0 Hz), 3.55(2H,t,J=7.0 Hz), 7.75(1H,dd,J=8.9 Hz,J=2.0 Hz), 7.83(1H,d,J=8.9 Hz), 7.95(1H,d,J=2.0 Hz), 8.23(3H,brs).

EXAMPLE 39

3-(2-Aminoethylthio)-5-fluoro-4-methyl-1,2-benzisoxazole hydrochloride (a) 3-(2-(N-t-Butoxycarbonylamino)ethylthio)-5-fluoro-4-methyl-1,2-benzisoxazole.

The title compound (0.10 g, 91%) was obtained from 3-(2-(N-t-butoxycarbonylamino)ethylthio)-5-fluoro-1,2-benzisoxazole (0.11 g) by similar reactions and treatments as in example 17(b).

NMR spectrum(CDCl$_3$)δppm: 1.44(9H,s), 2.55(3H,s), 3.42(2H,t,J=6.1 Hz), 3.58(2H,td,J=6.1 Hz,J=6.1 Hz), 5.02 (1H,brs), 7.19–7.34(2H,m).

(b) 3-(2-Aminoethylthio)-5-fluoro-4-methyl-1,2-benzisoxazole hydrochloride.

The title compound (0.07 g, quant.) was obtained from 3-(2-(N-t-butoxycarbonylamino)ethylthio)-5-fluoro-4-methyl-1,2-benzisoxazole (0.09 g) by similar reactions and treatments as in example 1(f).

Melting point: 209–212° C. (decomposed); IR spectrum (KBr)ν$_{max}$cm$^{-1}$: 3103, 2963, 2901, 1499; NMR spectrum (DMSO-d$_6$)δppm: 2.53(3H,s), 3.26(2H,t,J=6.9 Hz), 3.55 (2H,t,J=6.9 Hz), 7.53–7.65(2H,m), 8.20(3H,brs).

EXAMPLE 40

3-(2-Aminoethylthio)-5-fluoro-4-cyano-1,2-benzisoxazole hydrochloride (a) 3-(2-(N-t-Butoxycarbonylamino)ethylthio-5-fluoro-4-carbamoyl-1,2-benzisoxazole.

3-(2-(N-t-butoxycarbonylamino)ethylthio-5-fluoro-4-carboxy-1,2-benzisoxazole (0.25 g, 74%) was obtained from 3-(2-(N-t-butoxycarbonylamino)ethylthio)-5-fluoro-1,2-benzisoxazole (0.30 g) by similar reactions and treatments as in example 18(a). Then, the title compound (0.16 g, 70%) was obtained from 3-(2-(N-t-butoxycarbonylamino) ethylthio-5-fluoro-4-carboxy-1,2-benzisoxazole (0.23 g) by similar reactions and treatments as in example 18(b).

NMR spectrum(CDCl$_3$)δppm: 1.43(9H,s), 3.35(2H,t,J=6.1 Hz), 3.58(2H,td,J=6.1 Hz,J=6.1 Hz), 5.03(1H,brs), 6.02 (1H,brs), 6.29(1H,brs), 7.37(1H,t,J=8.9 Hz), 7.62(1H,dd,J=3.8 Hz,J=8.9 Hz).

(b) 3-(2-(N-t-Butoxycarbonylamino)ethylthio-5-fluoro-4-cyano-1,2-benzisoxazole.

The title compound (0.12 g, 92%) was obtained from 3-(2-(N-t-butoxycarbonylamino)ethylthio-5-fluoro-4-carbamoyl-1,2-benzisoxazole (0.14 g) by similar reactions and treatments as in example 19(a).

NMR spectrum(CDCl$_3$)δppm: 1.45(9H,s), 3.46(2H,t,J=6.0 Hz), 3.60(2H,td,J=6.0 Hz,J=6.0 Hz), 4.97(1H,brs), 7.45 (1H,t,J=8.9 Hz), 7.77(1H,dd,J=3.9 Hz,J=8.9 Hz).

(c) 3-(2-Aminoethylthio)-5-fluoro-4-cyano-1,2-benzisoxazole hydrochloride.

The title compound (0.09 g, quant.) was obtained from 3-(2-(N-t-butoxycarbonylamino)ethylthio-5-fluoro-4-cyano-1,2-benzisoxazole (0.11 g) by similar reactions and treatments as in example 1(f).

Melting point: 215–219° C. (decomposed); IR spectrum (KBr)$\nu_{max}$cm$^{-1}$: 3436, 3090, 3005, 1494; NMR spectrum (DMSO-d$_6$)δppm: 3.27(2H,t,J=6.9 Hz), 3.59(2H,t,J=6.9 Hz), 7.94(1H,t,J=9.4 Hz), 8.19(3H,brs), 8.30(H,dd,J=3.9 Hz,J=9.4 Hz).

EXAMPLE 41

3-(2-Aminoethoxy)-7-methoxy-1,2-benzisoxazole hydrochloride (a) 3-(2-(N-t-Butoxycarbonylamino)ethoxy)-7-methoxy-1,2-benzisoxazole.

The title compound (0.39 g, 63%) was obtained from 3-hydroxy-7-methoxy-1,2-benzisoxazole (0.33 g) by similar reactions and treatments as in example 1(e).

Melting point: 98–99° C.; IR spectrum(KBr)$\nu_{max}$cm$^{-1}$: 3348, 1708, 1683, 1624, 1615, 1542, 1533, 1509; NMR spectrum(CDCl$_3$)δppm: 1.46(9H,s), 3.64(2H,q,J=5.1 Hz), 4.03(3H,s), 4.51(2H,t,J=5.1 Hz), 4.97(1H,brs), 6.95–7.00 (1H,m), 7.15–7.20(2H,m).

(b) 3-(2-Aminoethoxy)-7-methoxy-1,2-benzisoxazole hydrochloride.

The title compound (0.23 g, 96%) was obtained from 3-(2-(N-t-butoxycarbonylamino)ethoxy)-7-methoxy-1,2-benzisoxazole (0.30 g) by similar reactions and treatments as in example 1(f).

Melting point: 208–213° C. (decomposed); IR spectrum (KBr)$\nu_{max}$cm$^{-1}$: 3022, 2983, 2909, 2840, 1627, 1614, 1546, 1509; NMR spectrum(DMSO-d$_6$)δppm: 3.30(2H,t,J=5.1 Hz), 3.97(3H,s), 4.61(2H,t,J=5.1 Hz), 7.20–7.25(1H,m), 7.30–7.35(2H,m), 8.29(3H,brs).

EXAMPLE 42

3-(2-Aminoethoxy)-5-methoxycarbonyl-1,2-benzisoxazole hydrochloride (a) 5-Bromo-3-(2-(N-t-Butoxycarbonylamino)ethoxy)-1,2-benzisoxazole.

The title compound (4.80 g, 67%) was obtained from 5-bromo-3-hydroxy-1,2-benzisoxazole (4.30 g) and 2-(N-t-butoxycarbonylamino)ethanol by similar reactions and treatments as in Example 1(e).

Melting point: 123–124° C.; IR spectrum(KBr)$\nu_{max}$cm$^{-1}$: 3313, 1699, 1683, 1611, 1545; NMR spectrum (CDCl$_3$) δppm: 1.46(9H,s), 3.64(2H,q,J=5.1 Hz), 4.50(2H,t,J=5.1 Hz), 4.92(1H,brs), 7.33(1H,d,J=8.9 Hz), 7.62(1H,dd,J=8.9 Hz,J=1.9 Hz), 7.80(1H, d, J=1.9 Hz).

(b) 3-(2-(N-t-Butoxycarbonylamino)ethoxy)-5-methoxycarbonyl-1,2-benzisoxazole.

The title compound (0.27 g, 29%) was obtained from 5-bromo-3-(2-(N-t-butoxycarbonylamino)ethoxy)-1,2-benzisoxazole (1.00 g) by similar reactions and treatments as in Example 22(b).

Melting point: 154–155° C.; IR spectrum(KBr)$\nu_{max}$cm$^{-1}$: 3326, 1720, 1702, 1687, 1629, 1611, 15477; NMR spectrum (CDCl$_3$)δppm: 1.46(9H,s), 3.66(2H,q,J=5.1 Hz), 3.96(3H, s), 4.53(2H,t,J=5.1 Hz), 4.97(1H,brs), 7.47(1H,d,J=8.8 Hz), 8.24(1H,dd,J=8.8 Hz,J=1.6 Hz), 8.41(1H,d,J=1.6 Hz).

(c) 3-(2-Aminoethoxy)-5-methoxycarbonyl-1,2-benzisoxazole hydrochloride.

The title compound (0.16 g, 98%) was obtained from 3-(2-(N-t-butoxycarbonylamino)ethoxy)-5-methoxycarbonyl-1,2-benzisoxazole (0.20 g) by similar reactions and treatments as in Example 22(c).

Melting point: 211–213° C.; IR spectrum(KBr)$\nu_{max}$cm$^{-1}$: 3300–2400, 1718, 1625, 1610, 1544; NMR spectrum (DMSO-d$_6$)δppm: 3.37(2H,q,J=5.1 Hz), 3.91(3H,s), 4.63 (2H,t,J=5.1 Hz), 7.80(1H,d,J=8.8 Hz), 8.26(1H,dd,J=8.8 Hz,J=1.6 Hz), 8.44(1H,d,J=1.6 Hz).

EXAMPLE 43

3-(2-Aminoethoxy)-5-methylamino-1,2-benzisoxazole dihydrochloride and 3-(2-Aminoethoxy)-5-dimethylamino-1,2-benzisoxazole dihydrochloride (a) 3-(2-(N-t-Butoxycarbonylamino)ethoxy)-5-methylamino-1,2-benzisoxazole and 3-(2-(N-t-Butoxycarbonylamino)ethoxy)-5-dimethylamino-1,2-benzisoxazole.

To a solution of 5-amino-3-(2-(N-t-butoxycarbonylamino)ethoxy)-1,2-benzisoxazole (0.88 g) in tetrahydrofuran (10 ml) was added sodium borohydride (0.66 g) with stirring at 5° C. 37% aqueous formaldehyde solution (0.99 g) and 3M sulphuric acid (1.0 ml) in tetrahydrofuran (10 ml) were dropped and stirred for 15 minutes at 5° C. After being stirred at room temperature for 1.5-hour, the reaction mixture was cooled to 5° C. and 37% aqueous formaldehyde solution (3.0 g) and sodium borohydride (0.66 g) were added and stirred at the same temperature for 30 minutes. The reaction mixture was poured into ice water (100 ml) and extracted with ethyl acetate (twice each with 50 ml). The organic layer was dried over anhydrous magnesium sulphate and filtered. The solvent was evaporated under reduced pressure and the residue was purified by silica gel column chromatography with cyclohexane/ethyl acetate (4/1) as an eluent, to give 3-(2-(N-t-butoxycarbonylamino) ethoxy)-5-methylamino-1,2-benzisoxazole (0.49 g, 53%) and 3-(2-(N-t-butoxycarbonylamino)ethoxy)-5-dimethylamino-1,2-benzisoxazole (0.14 g, 15%).

Data for 3-(2-(N-t-butoxycarbonylamino)ethoxy)-5-methylamino-1,2-benzisoxazole.

Melting point: 122–123° C.; IR spectrum(KBr)$\nu_{max}$cm$^{-1}$: 3392,3317, 1695, 1673, 1636, 1611, 1548, 1538, 1523; NMR spectrum(CDCl$_3$)δppm: 1.46(9H,s), 2.88(3H,s), 3.64 (2H,q,J=5.1 Hz), 3.79(1H,brs), 4.49(2H,t,J=5.1 Hz), 4.99 (1H,brs), 6.64(1H,d,J=2.3 Hz), 6.87(1H,dd,J=8.9 Hz,J=2.3 Hz), 7.23(1H,d,J=8.9 Hz).

Data for 3-(2-(N-t-butoxycarbonylamino)ethoxy)-5-dimethylamino-1,2-benzisoxazole.

IR spectrum(KBr)$\nu_{max}$cm$^{-1}$: 3387, 2979, 2934, 1703, 1547, 1526, 1507; NMR spectrum(CDCl$_3$)δppm: 1.46(9H, s), 2.97(6H,s), 3.65(2H,m), 4.49(2H,t,J=5.1 Hz), 4.99(1H, brs), 6.78(1H,d,J=2.4 Hz), 7.10(1H,dd,J=9.2 Hz,J=2.4 Hz), 7.30(1H,d,J=9.2 Hz).

(b) 3-(2-Aminoethoxy)-5-methylamino-1,2-benzisoxazole dihydrochloride.

The title compound (0.27 g, 99%) was obtained from 3-(2-(N-t-butoxycarbonylamino)ethoxy)-5-methylamino-1,2-benzisoxazole (0.30 g) by similar reactions and treatments as in Example 1(f).

Melting point: 240–250° C.(decomposed); IR spectrum (KBr)$\nu_{max}$cm$^{-1}$: 3030, 2961, 2889, 2841, 2756, 2720, 2683, 2646, 2609, 2579, 2535, 2506, 2479, 2421, 2379, 1623, 1604, 1567, 1544, 1528; NMR spectrum(DMSO-d$_6$)δppm: 2.84(3H,s), 3.34(2H,q,J=5.1 Hz), 4.61(2H,t,J=5.1 Hz), 7.43 (1H,brs), 7.49(1H,d,J=8.9 Hz), 7.64(1H,d,J=8.9 Hz), 8.34 (3H,brs).

(c) 3-(2-Aminoethoxy)-5-dimethylamino-1,2-benzisoxazole dihydrochloride.

The title compound was obtained from 3-(2-(N-t-butoxycarbonylamino) ethoxy)-5-dimethylamino-1,2-benzisoxazole by similar reactions and treatments as in Example 1(f).

Melting point: 150–160° C. (decomposed); IR spectrum (KBr)$\nu_{max}$cm$^{-1}$: 3500–3200, 3100–2800, 2700–2400, 1626, 1551, 1467, 1434; NMR spectrum(DMSO-d$_6$)δppm: 3.06 (6H,s), 3.34(2H,dd,J=10.6 Hz,J=5.5 Hz), 4.62(2H,t,J=5.5 Hz), 7.8–7.5(3H,m), 8.37(2H,brs).

EXAMPLE 44

3-(2-Aminoethoxy)-5-difluoromethoxy-1,2-benzisoxazole hydrochloride (a) 5-Hydroxy-3-(2-(N-t-butoxycarbonylamino)ethoxyl)-1,2-benzisoxazole.

The title compound (0.60 g, 62%) was obtained from 3,5-dihydroxy-1,2-benzisoxazole (0.50 g) by similar reactions and treatments as in Example 1(e).

Melting point: 152–153° C.; IR spectrum(KBr)$\nu_{max}$cm$^{-1}$: 3286, 1672, 1543, 1529; NMR spectrum(CDCl$_3$)δppm: 1.38 (9H,s), 3.40(2H,q,J=5.1 Hz), 4.34(2H,t,J=5.1 Hz), 6.88(1H, d,J=2.5 Hz), 7.08(1H,dd,J=8.9 Hz,J=2.5 Hz), 7.42(1H,d,J=8.9 Hz), 9.68(1H,s).

(b) 3-(2-(N-t-Butoxycarbonylamino)ethoxy)-5-difluoromethoxy-1,2-benzisoxazole.

To a solution of 5-hydroxy-3-(2-(N-t-butoxycarbonylamino)ethoxy)-1,2-benzisoxazole (100 mg) in dimethylformamide (4 ml) was added sodium methoxide (90 mg) and the mixture was stirred at room temperature for 10 minutes, then followed by introduction of chlorodifluoromethane gas for 20 minutes. The reaction mixture was poured into ice water (30 ml), extracted with ethyl acetate (twice each with 30 ml) and the combined extracts were dried over anhydrous magnesium sulphate and filtered. The solvent was evaporated under reduced pressure and the residue was purified by silica gel column chromatography with cyclohexane/ethyl acetate (9/1) as an eluent, to give the title compound (19 mg, 16%) as a colorless powder.

Melting point: 155–156° C.; IR spectrum(KBr)$\nu_{max}$cm$^{-1}$: 3322, 1699, 1683, 1541; NMR spectrum(CDCl$_3$)δppm: 1.46 (9H,s), 3.65(2H,q,J=5.1 Hz), 4.51(2H,t,J=5.1 Hz), 4.94(1H, brs), 6.52(1H,t,J=73.4 Hz), 7.30–7.50(3H,m).

(c) 3-(2-Aminoethoxy)-5-difluoromethoxy-1,2-benzisoxazole hydrochloride.

The title compound (20 mg, 95%) was obtained from 3-(2-(N-t-butoxycarbonylamino)ethoxy)-5-difluoromethoxy-1,2-benzisoxazole (25 mg) by similar reactions and treatments as in Example 1(f).

Melting point: 162–164° C. (decomposed); IR spectrum (KBr)$\nu_{max}$cm$^{-1}$: 3300–2400, 1618, 1599, 1544, 1497; NMR spectrum(DMSO-d$_6$)δppm: 3.34(2H,q,J=5.1 Hz), 4.63(2H, t,J=5.1 Hz), 4.62(1H,brs), 7.27(1H,d,J=73.6 Hz), 7.54(1H, dd,J=9.0 Hz,J=2.3 Hz), 7.58(1H,d,J=2.3 Hz), 7.75(1H,d,J=9.0 Hz), 8.29(3H,brs).

EXAMPLE 45

3-(2-Aminoethoxy)-7-amino-1,2-benzisoxazole dihydrochloride (a) 3-(2-(N-t-Butoxycarbonylamino)ethoxy)-7-nitro-1,2-benzisoxazole.

The title compound (2.20 g, 68%) was obtained from 3-hydroxy-7-nitro-1,2-benzisoxazole (1.80 g) by similar reactions and treatments as in Example 1(e).

Melting point: 116–117° C.; IR spectrum (KBr)$\nu_{max}$cm$^{-1}$: 3359, 3307, 1718, 1700, 1691, 1628, 1604, 1553; NMR spectrum (CDCl$_3$)δppm: 1.46(9H,s), 3.67(2H,q,J=5.1 Hz), 4.57(2H,t,J=5.1 Hz), 4.93(1H,brs), 7.46(1H,t,J=8.1 Hz), 7.99(1H,d,J=8.1 Hz), 8.41(1H,d,J=8.1 Hz).

(b) 3-(2-(N-t-Butoxycarbonylamino)ethoxy)-7-amino-1,2-benzisoxazole.

The title compound (1.26 g, 93%) was obtained from 3-(2-(N-t-butoxycarbonylamino)ethoxy)-7-nitro-1,2-benzisoxazole (1.50 g) by similar reactions and treatments as in Example 32(a).

Melting point: 107–108° C.; IR spectrum(KBr)$\nu_{max}$cm$^{-1}$: 3438, 3349, 1700, 1640, 1604; NMR spectrum(CDCl$_3$) δppm: 1.46(9H,s), 3.64(2H,q,J=5.1 Hz), 4.03(2H,s), 4.50 (2H,t,J=5.1 Hz), 4.98(1H,brs), 6.79(1H,d,J=7.9 Hz), 7.00 (1H,d,J=7.9 Hz), 7.07(1H,t,J=7.9 Hz).

(c) 3-(2-Aminoethoxy)-7-amino-1,2-benzisoxazole dihydrochloride.

The title compound (0.23 g, 98%) was obtained from 3-(2-(N-t-butoxycarbonylamino)ethoxy)-7-amino-1,2-benzisoxazole (0.26 g) by similar reactions and treatments as in Example 1(f).

Melting point: 185–195° C. (decomposed); IR spectrum (KBr)$\nu_{max}$cm$^{-1}$: 3300–2400, 3026, 2870, 2583, 1640, 1611, 1582, 1553, 1525, 1509; NMR spectrum(DMSO-d$_6$)δppm: 3.33(2H,q,J=5.1 Hz), 4.59(2H,t,J=5.1 Hz), 6.88(1H,d,J=7.9 Hz), 6.97(1H,d,J=7.9 Hz), 7.10(1H,t,J=7.9 Hz), 8.33(3H, brs).

EXAMPLE 46

3-(2-Aminoethoxy)-7-carboxy-1,2-benzisoxazole hydrochloride

The title compound (0.036 g, 14%) was obtained from 3-(2-(N-t-butoxycarbonylamino)ethoxy)-1,2-benzisoxazole (0.28 g) by similar reactions and treatments as in Example 18(a) then, by similar reactions and treatments as in Example 1(e).

Melting point: 123–126° C. (decomposed); IR spectrum (KBr)$\nu_{max}$cm$^{-1}$: 3140, 3081, 3024, 2960, 2896, 1714, 1620, 1615, 1553, 1548, 1495; NMR spectrum(DMSO-d$_6$)δppm: 3.36(2H,t,J=5.1 Hz), 4.65(2H,t,J=5.1 Hz), 7.53(1H,t,J=7.1 Hz), 8.05(1H,d,J=7.1 Hz), 8.18(1H,d,J=7.1 Hz), 8.32(3H, brs).

EXAMPLE 47

3-(2-Aminoethoxy)-5-hydroxy-1,2-benzisoxazole hydrochloride

The title compound (0.16 g, 97%) was obtained from 3-(2-(N-t-butoxycarbonylamino)ethoxy)-5-hydroxy-1,2-benzisoxazole (0.20 g) by similar reactions and treatments as in Example 1(f).

Melting point: 205–209° C. (decomposed); IR spectrum (KBr)$\nu_{max}$cm$^{-1}$: 3467, 3388, 3112, 3024, 2932, 1617, 1541, 1528, 1503; NMR spectrum(DMSO-d$_6$)δppm: 3.32(2H,t,J=5.1 Hz), 4.57(2H,t,J=5.1 Hz), 7.01(1H,d,J=2.5 Hz), 7.13 (1H,dd,J=9.0 Hz,J=2.5 Hz), 7.45(1H,d,J=9.0 Hz), 8.26(3H, brs), 9.84(1H,s).

EXAMPLE 48

3-(2-Aminoethoxy)-5-acetoxy-1,2-benzisoxazole hydrochloride (a) 5-Acetoxy-3-(2-(N-t-butoxycarbonylamino)ethoxy)-1,2-benzisoxazole.

To a solution of 3-(2-(N-t-butoxycarbonylamino)ethoxy)-5-hydroxy-1,2-benzisoxazole (100 mg) in tetrahydrofuran (5 ml) was added triethylamine (44 mg) and acetyl chloride (34 mg) with stirring at 5° C., and the mixture was then stirred at the same temperature for 15 minutes. The reaction mixture was poured into ice water (40 ml), extracted with ethyl acetate (twice each with 40 ml) and the combined extracts were dried over anhydrous magnesium sulphate and filtered. The solvent was evaporated under reduced pressure and the residue was purified by silica gel column chromatography with cyclohexane/ethyl acetate (9/1) as an eluent, to give the title compound (101 mg, 88%) as a colorless powder.

Melting point: 108–110° C. (decomposed); IR spectrum (KBr)$\nu_{max}$cm$^{-1}$: 3346, 1767, 1705, 1626, 1618, 1541, 1529; NMR spectrum(CDCl$_3$)δppm: 1.46(9H,s), 2.34(3H,s), 3.63 (2H,q,J=5.1 Hz), 4.50(2H,t,J=5.1 Hz), 4.94(1H,brs), 7.25 (1H,dd,J=9.0 Hz,J=2.2 Hz), 7.39(1H,d,J=2.2 Hz), 7.43(1H, d,J=9.0 Hz).

(b) 3-(2-Aminoethoxy)-5-acetoxy-1,2-benzisoxazole hydrochloride.

The title compound (59 mg, 98%) was obtained from 5-acetoxy-3-(2-(N-t-butoxycarbonylamino)ethoxy)-1,2-benzisoxazole (80 mg) by similar reactions and treatments as in Example 1(f).

Melting point: 168–170° C. (decomposed); IR spectrum (KBr)$\nu_{max}$cm$^{-1}$: 3064, 3002, 2962, 2891, 2741, 1748, 1726, 1618, 1592, 1545, 1510; NMR spectrum(DMSO-d$_6$)δppm: 2.31(3H,s), 3.31(2H,q,J=5.1 Hz), 4.62(2H,t,J=5.1 Hz), 7.46 (1H,dd,J=9.0 Hz,J=2.2 Hz), 7.55(1H,d,J=2.2 Hz), 7.71(1H, d,J=9.0 Hz), 8.27(3H,brs).

EXAMPLE 49

3-(2-Aminoethoxy)-7-methylamino-1,2-benzisoxazole dihydrochloride (a) 3-(2-(N-t-Butoxycarbonylamino)ethoxy)-7-methylamino-1,2-benzisoxazole.

The title compound (0.12 g, 13%) was obtained from 7-amino-3-(2-(N-t-butoxycarbonylamino)ethoxy)-1,2-benzisoxazole (0.88 g) by similar reactions and treatments as in Example 43(a).

Melting point: 162–164° C.; IR spectrum(KBr)$\nu_{max}$cm$^{-1}$: 3346, 3312, 1709, 1639, 1626, 1550, 1514; NMR spectrum (CDCl$_3$)δppm: 1.46(9H,s), 2.99(3H,d,J=5.0 Hz), 3.63(2H,q, J=5.1 Hz), 3.63(1H,q,J=5.0 Hz), 4.49(2H,t,J=5.1 Hz), 4.98 (1H,brs), 6.64(1H,d,J=7.8 Hz), 6.92(1H,d,J=7.8 Hz), 7.15 (1H,t,J=7.8 Hz).

(b) 3-(2-Aminoethoxy)-7-methylamino-1,2-benzisoxazole dihydrochloride.

The title compound (72 mg, 99%) was obtained from 3-(2-(N-t-butoxycarbonylamino)ethoxy)-7-methylamino-1, 2-benzisoxazole (80 mg) by similar reactions and treatments as in Example 1(f).

Melting pointb: 171–181° C. (decomposed); IR spectrum (KBr)$\nu_{max}$cm$^{-1}$: 3026, 2965, 2912, 2866, 2786, 2730, 2638, 2600, 1573, 1546, 1504; NMR spectrum(DMSO-d$_6$)δppm: 2.82(3H,s), 3.33(2H,q,J=5.1 Hz), 4.59(2H,t,J=5.1 Hz), 6.65 (1H,d,J=7.9 Hz), 6.89(1H,d,J=7.9 Hz), 7.16(1H,t,J=7.9 Hz), 8.34(3H,brs).

EXAMPLE 50

5-Amino-3-(2-aminoethoxy)-1,2-benzisoxazole dihydrochloride (a) 3-(2-(N-t-Butoxycarbonylamino)ethoxy)-5-nitro-1,2-benzisoxazole.

The title compound (3.60 g, 74%) was obtained from 3-hydroxy-5-nitro-1,2-benzisoxazole (2.70 g) by similar reactions and treatments as in Example 1(e).

Melting point: 136–137° C.; IR spectrum(KBr)$\nu_{max}$cm$^{-1}$: 3346, 1688, 1624, 1555, 1531; NMR spectrum(CDCl$_3$) δppm: 1.46(9H,s), 3.67(2H,q,J=5.1 Hz), 4.55(2H,t,J=5.1 Hz), 4.95(1H,brs), 7.56(1H,d,J=9.2 Hz), 8.46(1H,dd,J=9.2 Hz,J=2.2 Hz), 8.62(1H,d,J=2.2 Hz).

(b) 5-Amino-3-(2-(N-t-butoxycarbonylamino)ethoxy)-1,2-benzisoxazole.

The title compound (1.65 g, 91%) was obtained from 3-(2-(N-t-butoxycarbonylamino)ethoxy)-5-nitro-1,2-benzisoxazole (2.00 g) by similar reactions and treatments as in Example 32(a).

Melting point: 134–135° C.; IR spectrum(KBr)$\nu_{max}$cm$^{-1}$: 3470, 3442, 3384, 3360, 3325, 3276, 1699, 1639; NMR spectrum(CDCl$_3$)δppm: 1.46(9H,s), 3.63(2H,q,J=5.1 Hz), 3.70(2H,s), 4.47(2H,t,J=5.1 Hz), 4.95(1H,brs), 6.83(1H,d, J=2.7 Hz), 6.92(1H,dd,J=8.9 Hz,J=2.7 Hz), 7.23(1H,d,J=8.9 Hz).

(c) 5-Amino-3-(2-aminoethoxy)-1,2-benzisoxazole dihydrochloride.

The title compound (0.21 g, 99%) was obtained from 5-amino-3-(2-(N-t-butoxycarbonylamino)ethoxy)-1,2-benzisoxazole (0.24 g) by similar reactions and treatments as in Example 1(f).

Melting point: 182–202° C. (decomposed); IR spectrum (KBr)$\nu_{max}$cm$^{-1}$: 3428, 3379, 2963, 2859, 2726, 2665, 2581, 1656, 1637, 1628, 1609, 1549, 1507; NMR spectrum (DMSO-d$_6$)δppm: 3.46(2H,q,J=5.1 Hz), 4.63(2H,t,J=5.1 Hz), 7.57(1H,dd,J=8.9 Hz,J=2.0 Hz), 7.67(1H,d,J=2.0 Hz), 7.93(1H,d,J=8.9 Hz), 8.35(3H,brs).

EXAMPLE 51

3-(2-Aminoethoxy)-4,7-dimethyl-1,2-benzisoxazole hydrochloride (a) 3-(2-(N-t-Butoxycarbonylamino)ethoxy)-4,7-dimethyl-1,2-benzisoxazole.

To a solution of 3-(2-(N-t-butoxycarbonylamino)ethoxy)-7-methyl-1,2-benzisoxazole (0.15 g) in tetrahydrofuran (5 ml) was added butyl lithium (0.7 ml, 1.6M hexane solution) dropwise with stirring at −70° C. under nitrogen atmosphere, the mixture was stirred at the same temperature for 10 minutes, and then the temperature was raised to 0° C. After cooling the reaction mixture to −70° C., methyl iodide (0.11 g) was added and the temperature was allowed to rise to 0° C. The reaction mixture was poured into ice water (40 ml), extracted with ethyl acetate (twice each with 40 ml) and the combined extracts were dried over anhydrous magnesium sulphate and filtered. The solvent was evaporated under reduced pressure and the residue was purified by silica gel column chromatography with cyclohexane/ethyl acetate (9/1) as an eluent, to give the title compound (0.12 g, 80%) as a colorless powder.

Melting point: 78–79° C.; IR spectrum(KBr)$\nu_{max}$cm$^{-1}$: 3352, 1694, 1604, 1543, 1517; NMR spectrum(CDCl$_3$) δppm: 1.45(9H,s), 2.44(3H,s), 2.56(3H,s), 4.26(2H,q,J=5.1 Hz), 4.49(2H,t,J=5.1 Hz), 4.90(1H,brs), 6.89(1H,d,J=7.3 Hz), 7.15(1H,d,J=7.3 Hz).

(b) 3-(2-Aminoethoxy)-4,7-dimethyl-1,2-benzisoxazole hydrochloride.

The title compound (0.08 g, quant.) was obtained from 3-(2-(N-t-butoxycarbonylamino)ethoxy)-4,7-dimethyl-1,2-benzisoxazole (0.10 g) by similar reactions and treatments as in Example 1(f).

Melting point: 222–225° C. (decomposed); IR spectrum (KBr)$\nu_{max}$cm$^{-1}$: 3300–2400, 1601, 1561, 1542, 1511; NMR spectrum(DMSO-d$_6$)δppm: 2.40(3H,s), 2.57(3H,s), 3.35 (2H,t,J=5.1 Hz), 4.60(2H,t,J=5.1 Hz), 7.01(1H,d,J=7.3 Hz), 7.31(1H,d,J=7.3 Hz), 8.31(3H,brs).

EXAMPLE 52

3-(2-Aminoethoxy)-4-methoxy-1,2-benzisoxazole hydrochloride (a) Methyl 2-fluoro-6-methoxybenzoate.

To a solution of 6-fluorosalicylic acid (5.00 g) in dimethylformamide (50 ml) was added anhydrous potassium carbonate (6.00 g) and methyl iodide (6.0 ml) with stirring at room temperature, then followed by vigorous stirring at room temperature for 12 hours. After the completion of the reaction, the reaction mixture was diluted by ether, washed with water and dried over anhydrous sodium sulphate. The solvent was evaporated under reduced pressure, to give the title compound (5.80 g, 98%) as an oil.

NMR spectrum($CDCl_3$)δppm: 3.86(3H,s), 3.93(3H,s), 6.70–6.80(2H,m), 7.28–7.37(1H,m).

(b) 2-Fluoro-6-methoxybenzhydroxamic acid.

The title compound (44%) was obtained from methyl 2-fluoro-6-methoxybenzoate and hydroxylamine hydrochloride by similar reactions and treatments as in Example 1(b).

NMR spectrum($CDCl_3$+MeOH-$d_4$)δppm: 3.92(3H,s), 6.75–6.86(2H,m), 7.35–7.45(1H,m).

(c) 3-Hydroxy-4-methoxy-1,2-benzisoxazole.

2-fluoro-6-methoxybenzhydroxamic acid (2.55 g) and potassium hydroxide (4.50 g) were dissolved in butanol (25 ml) and refluxed for 4 hours. After the completion of the reaction, the reaction mixture was adjusted to acidic, extracted with ethyl acetate and the extract was washed with water and dried over anhydrous sodium sulphate. The solvent was evaporated under reduced pressure and the residue was recrystallized from isopropylether, to give the title compound (2.05 g, 90%).

Melting point: 183–185° C.; NMR spectrum($CDCl_3$) δppm: 4.02(3H,s), 6.65(1H,d,J=8.2 Hz), 6.99(1H,d,J=8.2 Hz), 7.50(1H,t,J=8.2 Hz).

(d) 3-(2-(N-t-Butoxycarbonylamino)ethoxy)-4-methoxy-1,2-benzisoxazole.

The title compound (81%) was obtained from 3-hydroxy-4-methoxy-1,2-benzisoxazole by similar reactions and treatments as in Example 1(e).

NMR spectrum($CDCl_3$)δppm: 1.46(9H,s), 3.65(2H,m), 3.96(3H,s), 4.50(2H,t,J=5.1 Hz), 5.06(1H,brs), 6.61(1H,d, J=8.2 Hz), 7.02(1H,d,J=8.2 Hz), 7.43(1H,t,J=8.2 Hz).

(e) 3-(2-Aminoethoxy)-4-methoxy-1,2-benzisoxazole hydrochloride.

The title compound (82%) was obtained from 3-(2-(N-t-butoxycarbonylamino)ethoxy)-4-methoxy-1,2-benzisoxazole by similar reactions and treatments as in Example 1(f).

Melting point: 193–197° C.; IR spectrum(KBr)$v_{max}cm^{-1}$: 3435, 3220, 2960, 1630, 1615, 1535, 1505; NMR spectrum (DMSO-$d_6$)δppm: 3.34(2H,t,J=5.2 Hz), 3.92(3H,s), 4.60 (2H,t,J=5.2 Hz), 6.86(1H,d,J=8.4 Hz), 7.17(1H,d,J=8.4 Hz), 7.58(1H,t,J=8.4 Hz).

EXAMPLE 53

3-(2-Aminoethoxyl)-4-methoxy-7-methyl-1,2-benzisoxazole hydrochloride

The title compound was obtained from 3-(2-(N-t-butoxycarbonylamino) ethoxy)-4-methoxy-1,2-benzisoxazole by similar reactions and treatments as in Example 51(a) and then as in Example 1(f).

Melting point: 208–211° C.; IR spectrum(KBr)$v_{max}cm^{-1}$: 3160, 2840, 1640, 1620, 1540, 1520, 1510; NMR spectrum (DMSO-$d_6$)δppm: 2.35(3H,s), 3.33(2H,t,J=5.4 Hz), 3.89 (3H,s), 4.59(2H,t,J=5.4 Hz), 6.75(1H,d,J=8.1 Hz), 7.37 (1Hd,J=8.1 Hz), 8.30(3H,brs).

EXAMPLE 54

3-(2-Aminoethoxy)-4-fluoro-1,2-benzisoxazole hydrochloride (a) 2,6-Difluorobenzhydroxamic acid.

The title compound (65%) was obtained from methyl 2,6-difluorobenzoate and hydroxylamine hydrochloride by similar reactions and treatments as in Example 1(b). NMR spectrum(DMSO-$d_6$)δppm: 7.14–7.25(2H,m), 7.50–7.60 (1H,m), 9.40(1H,brs), 11.15(1H,brs).

(b) 3-Hydroxy-4-fluoro-1,2-benzisoxazole.

The title compound (36%) was obtained from 2,6-difluorobenzhydroxamic acid by similar reactions and treatments as in Example 52(c).

Melting point: 175–178° C.; NMR spectrum(DMSO-$d_6$) δppm: 7.09(1H,t,J=8.5 Hz), 7.40(1H,d,J=8.5 Hz), 7.57–7.65 (1H,m).

(c) 3-(2-(N-t-Butoxycarbonylamino)ethoxy)-4-fluoro-1,2-benzisoxazole.

The title compound (67%) was obtained from 3-hydroxy-4-fluoro-1,2-benzisoxazole by similar reactions and treatments as in Example 1(e).

NMR spectrum($CDCl_3$)δppm: 1.47(9H,s), 3.65(2H,m), 4.51(2H,t,J=5.1 Hz), 4.90–5.06(1H,brs), 6.91(1H,t,J=8.5 Hz), 7.23(1H,t,J=8.5 Hz), 7.44–7.52(1H,m).

(d) 3-(2-Aminoethoxy)-4-fluoro-1,2-benzisoxazole hydrochloride.

The title compound (75%) was obtained from 3-(2-(N-t-butoxycarbonylamino) ethoxy)-4-fluoro-1,2-benzisoxazole by similar reactions and treatments as in Example 1(f).

Melting point: 230–233° C. (decomposed); IR spectrum (KBr)$v_{max}cm^{-1}$: 3435, 2970, 1635, 1620, 1545, 1520, 1510; NMR spectrum(DMSO-$d_6$)δppm: 3.34(2H,t,J=5.2 Hz), 4.66 (2H,t,J=5.2 Hz), 7.21(1H,t,J=8.3 Hz), 7.53(1H,d,J=8.3 Hz), 7.68–7.74(1H,m), 8.35(3H,brs).

EXAMPLE 55

3-(2-Aminoethoxy)-4-fluoro-5-methyl-1,2-benzisoxazole hydrochloride, and 3-(2-Aminoethoxy)-4-fluoro-7-methyl-1,2-benzisoxazole hydrochloride 3-(2-aminoethoxy)-4-fluoro-5-methyl-1,2-benzisoxazole hydrochloride and 3-(2-aminoethoxy)-4-fluoro-7-methyl-1,2-benzisoxazole hydrochloride were obtained from 3-(2-(N-t-butoxycarbonylamino)ethoxy)-4-fluoro-1,2-benzisoxazole by similar reactions and treatments as in Example 51(a) and then as in Example 1(f).

(a) Data for 3-(2-aminoethoxy)-4-fluoro-5-methyl-1,2-benzisoxazole hydrochloride.

Melting point: 201–208° C.; IR spectrum(KBr)$v_{max}cm^{-1}$: 3430, 3305, 2840, 1645, 1615, 1540, 1515; NMR spectrum (DMSO-$d_6$)δppm: 2.32(3H,s), 3.34(2H,q,J=5.0 Hz), 4.64 (2H,t,J=5.0 Hz), 7.42(2H,d,J=8.4 Hz), 7.60(1H,t,J=8.4 Hz), 8.27(3H,brs).

(b) Data for 3-(2-Aminoethoxy)-4-fluoro-7-methyl-1,2-benzisoxazole hydrochloride.

Melting point: 196–202° C.; IR spectrum(KBr)$v_{max}cm^{-1}$: 2975, 1635, 1550, 1520; NMR spectrum(DMSO-$d_6$)δppm: 2.42(3H,s), 3.35(2H,t,J=5.2 Hz), 4.65(2H,t,J=5.2 Hz), 7.10 (1H,t,J=8.9 Hz), 7.47–7.51(1H,m), 8.32(3H,brs).

EXAMPLE 56

3-(2-Aminoethylthio)-5-chloro-7-methyl-1,2-benzisoxazole hydrochloride (a) 3-(2-(N-t-Butoxycarbonylamino)ethylthio)-5-chloro-7-methyl-1,2-benzisoxazole.

The title compound (0.13 g, 62%) was obtained from 3-(2-(N-t-butoxycarbonylamino)ethylthio)-5-chloro-1,2-benzisoxazole (0.20 g) by similar reactions and treatments as in Example 17(b).

NMR spectrum (CDCl$_3$)δppm: 1.44(9H,s), 2.51(3H,s) 3.40(2H,t,J=6.3 Hz), 3.58(2H,q,J=6.3 Hz), 5.07(1H,brs), 7.29(1H,s), 7.36(1H,s).
(b) 3-(2-Aminoethylthio)-5-chloro-7-methyl-1,2-benzisoxazole hydrochloride.

The title compound (0.10 g, quant.) was obtained from 3-(2-(N-t-butoxycarbonylamino)ethylthio)-5-chloro-7-methyl-1,2-benzisoxazole (0.12 g) by similar reactions and treatments as in Example 1(f).

Melting point: 205–208° C. (decomposed); IR spectrum (KBr)ν$_{max}$cm$^{-1}$: 2966, 2927, 2848, 2802, 1481; NMR spectrum(DMSO-d$_6$)δppm: 2.50(3H,s), 3.23(2H,t,J=6.9 Hz), 3.53(2H,t,J=6.9 Hz), 7.62(1H,s), 7.74(1H,s), 8.19(3H, brs).

EXAMPLE 57

3-(2-Aminoethylthio)-5-chloro-7-cyano-1,2-benzisoxazole hydrochloride (a) 3-(2-(N-t-Butoxycarbonylamino)ethylthio)-5-chloro-7-carboxy-1,2-benzisoxazole.

The title compound (0.42 g, 72%) was obtained from 3-(2-(N-t-butoxycarbonylamino)ethylthio)-5-chloro-1,2-benzisoxazole (0.51 g) by similar reactions and treatments as in Example 18(a).
(b) 3-(2-(N-t-Butoxycarbonylamino)ethylthio)-5-chloro-7-carbamoyl-1,2-benzisoxazole.

The title compound (0.17 g, 85%) was obtained from 3-(2-(N-t-butoxycarbonylamino)ethylthio)-5-chloro-7-carboxy-1,2-benzisoxazole (0.20 g) by similar reactions and treatments as in Example 18(b).

IR spectrum(KBr)ν$_{max}$cm$^{-1}$: 3471, 3354, 3143, 1693, 1678; NMR spectrum(CDCl$_3$)δppm: 1.45(9H,s), 3.45(2H,t, J=6.1 Hz), 3.59(2H,q,J=6.1 Hz), 4.96(1H,brs), 5.97(1H,brs), 7.12(1H,brs), 7.73(1H,s), 8.34(1H,s).
(c) 3-(2-(N-t-Butoxycarbonylamino)ethylthio)-5-chloro-7-cyano-1,2-benzisoxazole.

The title compound (0.13 g, 90%) was obtained from 3-(2-(N-t-butoxycarbonylamino)ethylthio)-5-chloro-7-carbamoyl-1,2-benzisoxazole (0.15 g) by similar reactions and treatments as in Example 19(a).

IR spectrum(KBr)ν$_{max}$cm$^{-1}$: 3366, 2240, 1685; NMR spectrum(CDCl$_3$)δppm: 1.45(9H,s), 3.46(2H,t,J=6.2 Hz), 3.60(2H,q,J=6.2 Hz), 4.96(1H,brs), 7.81(1H,s), 7.84(1H,s).
(d) 3-(2-Aminoethylthio)-5-chloro-7-cyano-1,2-benzisoxazole hydrochloride.

The title compound (0.10 g, quant.) was obtained from 3-(2-(N-t-butoxycarbonylamino) ethylthio)-5-chloro-7-cyano-1,2-benzisoxazole (0.12 g) by similar reactions and treatments as in Example 1(f).

Melting point: 178–181° C. (decomposed); IR spectrum (KBr)ν$_{max}$cm$^{-1}$: 3432, 3038, 2990, 2235, 1607, 1598, 1588; NMR spectrum(DMSO-d$_6$)δppm: 3.25(2H,t,J=7.0 Hz), 3.57 (2H,t,J=7.0 Hz), 8.23(3H,brs), 8.42(1H,s), 8.49(1H,s).

EXAMPLE 58

3-(2-Aminoethoxy)-5-chloropyrido[3,2-d]isoxazole hydrochloride
(a) Methyl 2,5-dichloronicotinate.

2,5-dichloronicotinic acid chloride (5.0 g) was dissolved in methanol (30 ml) with stirring under ice cooling and then stirred at room temperature for 30 minutes. The solvent was evaporated under reduced pressure and the residue was dissolved in ether and washed with saturated sodium hydrogen carbonate water solution and brine. The extract was dried over anhydrous magnesium sulphate and filtered. The solvent was evaporated under reduced pressure and the residue was purified by silica gel column chromatography with cyclohexane/ethyl acetate (30/1), to give the title compound (4.2 g, 86%).

NMR spectrum(CDCl$_3$)δppm: 3.98(3H,s), 8.16(1H,s), 8.48(1H,s).
(b) 2,5-Dichloropyridine-3-carbohydroxamic acid.

The title compound (3.3 g, 79%) was obtained from methyl 2,5-dichloronicotinate (4.2 g) by similar reactions and treatments as in Example 10(b).

IR spectrum (KBr)ν$_{max}$cm$^{-1}$: 3187, 3073, 3058, 2985, 2906, 2851, 1661, 1575, 1553; NMR spectrum (DMSO-d$_6$) δppm: 8.11(1H,s), 8.58(1H,s), 9.50(1H,s), 11.40(1H,s).
(c) 3-Hydroxy-5-chloropyrido[3,2-d]isoxazole.

The title compound (0.82 g, 66%) was obtained from 2,5-dichloropyridine-3-carbohydroxamic acid (1.5 g) by similar reactions and treatments as in Example 10(c).

IR spectrum (KBr)ν$_{max}$cm$^{-1}$: 3193, 3166, 3069, 3055, 3003, 2919, 2821, 2783, 2734, 2689, 2633, 2587, 2550, 1697, 1615, 1602, 1554, 1508; NMR spectrum (DMSO-d$_6$) δppm: 8.40(1H,s), 8.63(1H,s), 12.90(1H,brs).
(d) 3-(2-(N-t-Butoxycarbonylamino)ethoxy)-5-chloropyrido[3,2-d]isoxazole.

The title compound (0.27 g, 73%) was obtained from 3-hydroxy-5-chloropyrido[3,2-d]isoxazole (0.20 g) by similar reactions and treatments as in Example 1(e).

IR spectrum(KBr)ν$_{max}$cm$^{-1}$: 3360, 1709, 1701, 1599, 1537, 1525; NMR spectrum (CDCl$_3$)δppm: 1.46(9H,s), 3.64 (2H,q,J=5.2 Hz), 4.52(2H,t,J=5.2 Hz), 4.90(1H,brs), 8.03 (1H,s), 8.54(1H,s).
(e) 3-(2-Aminoethoxy)-5-chloropyrido[3,2-d]isoxazole hydrochloride.

The title compound (0.19 g, quant.) was obtained from 3-(2-(N-t-butoxycarbonylamino)ethoxy)-5-chloropyrido[3, 2-d]isoxazole (0.21 g) by similar reactions and treatments as in Example 1(f).

Melting point: 225–230° C. (decomposed); IR spectrum (Kbr)ν$_{max}$cm$^{-1}$: 3065, 3036, 2978, 2900, 1604, 1598, 1535; NMR spectrum (DMSO-d$_6$)δppm: 3.34(2H,t,J=5.0 Hz), 4.64(2H,t,J=5.0 Hz), 8.25(3H,brs), 8.50(1H,s), 8.76(1H,s).

EXAMPLE 59

3-(2-Aminoethylthio)-5-chloropyrido[3,2-d]isoxazole hydrochloride
(a) 3,5-Dichloropyrido[3,2-d]isoxazole.

The title compound (0.21 g, 73%) was obtained from 5-chloro-3-hydroxypyrido[3,2-d]isoxazole (0.27 g) by similar reactions and treatments as in Example 16.

NMR spectrum (CDCl$_3$)δppm: 8.08(1H,s), 8.64(1H,s).
(b) 3-(2-(N-t-Butoxycarbonylamino)ethylthio)-5-chloropyrido[3,2-d]isoxazole.

The title compound (0.12 g, 71%) was obtained from 3,5-dichloropyrido[3,2-d]isoxazole (0.10 g) by similar reactions and treatments as in Example 26(b).

IR spectrum (Kbr)ν$_{max}$cm$^{-1}$: 3369, 1688, 1530; NMR spectrum (CDCl$_3$)δppm: 1.46(9H,s), 3.44(2H,t,J=6.3 Hz), 3.59(2H,q,J=6.3 Hz), 4.97(1H,brs), 7.95(1H,s), 8.57(1H,s).
(c) 3-(2-Aminoethylthio)-5-chloropyrido[3,2-d]isoxazole hydrochloride.

The title compound (0.08 g, quant.) was obtained from 3-(2-(N-t-butoxycarbonylamino)ethylthio)-5-chloropyrido [3,2-d]isoxazole (0.10 g) by similar reactions and treatments as in Example 1(f).

Melting point: 194–198° C. (decomposed); IR spectrum (Kbr)ν$_{max}$cm$^{-1}$: 3040, 3001, 2909, 1586, 1515; NMR spectrum (DMSO-d$_6$)δppm: 3.24(2H,t,J=7.1 Hz), 3.55(2H,t,J= 7.1 Hz), 8.17(3H,brs), 8.69(1H,s), 8.79(1H,s).

EXAMPLE 60

3-(2-Aminoethoxy)-4-methoxycarbonyl-7-methyl-1,2-benzisoxazole hydrochloride
(a) 3-(2-(N-t-Butoxycarbonylamino)ethoxy)-4-methoxycarbonyl-7-methyl-1,2-benzisoxazole.

The title compound (91%) was obtained from 3-(2-(N-t-butoxycarbonylamino)ethoxy)-7-methyl-1,2-benzisoxazole by similar reactions and treatments as in Example 22(b).

Melting point: 62–64° C.; IR spectrum (Kbr)$v_{max}$cm$^{-1}$: 3380, 1715, 1703, 1621, 1591, 1534, 1513; NMR spectrum (CDCl$_3$)δppm: 1.46(9H,s), 2.56(3H,s), 3.66(2H,q), 3.97(3H, s), 4.51(2H,t,J=5.1 Hz), 5.33(1H,brs), 7.35(1H,d,J=7.6 Hz), 7.78(1H,d,J=7.6 Hz).

(b) 3-(2-Aminoethoxy)-4-methoxycarbonyl-7-methyl-1,2-benzisoxazole hydrochloride.

The title compound (97%) was obtained from 3-(2-(N-t-butoxycarbonylamino)ethoxy)-4-methoxycarbonyl-7-methyl-1,2-benzisoxazole by similar reactions and treatments as in Example 17(c).

Melting point: 200–202° C. (decomposed); IR spectrum (Kbr)$v_{max}$cm$^{-1}$: 3148, 3003, 2953, 1699, 1608, 1591, 1534, 1511; NMR spectrum (DMSO-d$_6$)δppm: 2.53(3H,s), 3.34 (2H,t,J=5.1 Hz), 3.91(3H,s), 4.61(2H,t,J=5.1 Hz), 7.59(1H, d,J=7.5 Hz), 7.76(1H,d,J=7.5 Hz), 8.19(3H,brs).

EXAMPLE 61

3-(2-Aminoethoxy)-4-carbamoyl-7-methyl-1,2-benzisoxazole hydrochloride (a) 3-(2-(N-t-Butoxycarbonylamino)ethoxy)-4-carbamoyl-7-methyl-1,2-benzisoxazole.

The title compound (83%) was obtained from 3-(2-(N-t-butoxycarbonylamino)ethoxy)-7-methyl-1,2-benzisoxazole by similar reactions and treatments as in Example 23(a).

Melting point: 140–141° C.; IR spectrum (Kbr)$v_{max}$cm$^{-1}$: 3451, 3351, 3199, 1705, 1675, 1618, 1585, 1539, 1525, 1509; NMR spectrum (CDCl$_3$)δppm: 1.43(9H,s), 2.56(3H, s), 3.70(2H,q,J=5.1 Hz), 4.61(2H,t,J=5.1 Hz), 4.94(1H,brs), 5.89(1H,brs), 7.41(1H,d,J=7.6 Hz), 7.80(1H,brs), 8.06(1H, d,J=7.6 Hz).

(b) 3-(2-Aminoethoxy)-4-carbamoyl-7-methyl-1,2-benzisoxazole hydrochloride.

The title compound (99%) was obtained from 3-(2-(N-t-butoxycarbonylamino)ethoxy)-4-carbamoyl-7-methyl-1,2-benzisoxazole by similar reactions and treatments as in Example 17(c).

Melting point: 202–205° C. (decomposed); IR spectrum (Kbr)$v_{max}$cm$^{-1}$: 3435, 3347, 3293, 3203, 2950, 1901, 1687, 1659, 1608, 1581, 1544, 1512; NMR spectrum (DMSO-d$_6$) δppm: 2.50(3H,s), 3.34(2H,t,J=5.1 Hz), 4.64(2H,t,J=5.1 Hz), 7.53(2H,s), 7.64(1H,brs), 7.92(1H,brs), 8.22(3H,brs).

EXAMPLE 62

3-(2-Aminoethoxy)-4-cyano-7-methl-1,2-benzisoxazole hydrochloride (a) 3-(2-(N-t-Butoxycarbonylamino)ethoxy)-4-cyano-7-methyl-1,2-benzisoxazole.

The title compound (95%) was obtained from 3-(2-(N-t-butoxycarbonylamino)ethoxy)-4-carbamoyl-7-methyl-1,2-benzisoxazole by similar reactions and treatments as in Example 24(a).

Melting point: 84–85° C.; IR spectrum (Kbr)$v_{max}$cm$^{-1}$: 3452, 3397, 2231, 1716, 1597, 1552, 1541, 1509; NMR spectrum (CDCl$_3$)δppm: 1.45(9H,s), 2.59(3H,s), 3.68(2H,q, J=5.1 Hz), 4.54(2H,t,J=5.1 Hz), 5.10(1H,brs), 7.40(1H,d,J= 7.4 Hz), 7.54(1H,d,J=7.4 Hz).

(b) 3-(2-Aminoethoxy)-4-cyano-7-methyl-1,2-benzisoxazole hydrochloride.

The title compound (96%) was obtained from 3-(2-(N-t-butoxycarbonylamino)ethoxy)-4-cyano-7-methyl-1,2-benzisoxazole by similar reactions and treatments as in Example 17(c).

Melting point: 208–211° C.; IR spectrum (KBr)$v_{max}$cm$^{-1}$: 3099, 3036, 2966, 2908, 2873, 2850, 2754, 2733, 2232, 1598, 1542, 1514; NMR spectrum (DMSO-d$_6$)δppm: 2.56 (3H,s), 3.39(2H,t,J=5.1 Hz), 4.71(2H,t,J=5.1 Hz), 7.68(1H, d,J=7.5 Hz), 7.87(1H,d,J=7.5 Hz), 8.26(3H,brs).

EXAMPLE 63

3-(2-Aminoethoxy)-7-methyl-4-methylthio-1,2-benzisoxazole hydrochloride (a) 3-(2-(N-t-Butoxycarbonylamino)ethoxy)-7-methyl-4-methylthio-1,2-benzisoxazole.

To a solution of 3-(2-(N-t-butoxycarbonylamino)ethoxy)-7-methyl-1,2-benzisoxazole (0.15 g) in tetrahydrofuran (20 ml) was added butyl lithium (0.75 ml, 1.6M hexane solution) dropwise with stirring at −70° C. under nitrogen atmosphere, and the mixture was stirred at the same temperature for 15 minutes, then followed by addition of dimethyldisulphide (0.11 g). The reaction mixture was poured into ice water (40 ml), extracted with ethyl acetate (twice each with 40 ml) and the combined extracts were dried over anhydrous magnesium sulphate and filtered. The solvent was evaporated under reduced pressure and the residue was purified by silica gel column chromatography with cyclohexane/ethyl acetate (9/1) as an eluent, to give the title compound (0.15 g, 88%) as a colorless powder.

Melting point: 85–86° C.; IR spectrum (KBr)$v_{max}$cm$^{-1}$: 3376, 1699, 1627, 1589, 1549, 1533; NMR spectrum (CDCl$_3$)δppm: 1.46(9H,s), 2.44(3H,s), 2.53(3H,s), 3.66(2H, q,J=5.1 Hz), 4.49(2H,t,J=5.1 Hz), 5.07(1H,brs), 6.86(1H,d, J=7.5 Hz), 7.22(1H,d,J=7.5 Hz).

(b) 3-(2-Aminoethoxy)-7-methyl-4-methylthio-1,2-benzisoxazole hydrochloride.

The title compound (94%) was obtained from 3-(2-(N-t-butoxycarbonylamino)ethoxy)-7-methyl-4-methylthio-1,2-benzisoxazole by similar reactions and treatments as in Example 17(c).

Melting point: 216–218° C. (decomposed); IR spectrum (KBr)$v_{max}$cm$^{-1}$: 2940, 2917, 2883, 1629, 1593, 1541, 1508; NMR spectrum (DMSO-d$_6$)δppm: 2.39(3H,s), 2.53(3H,s), 3.34(2H,t,J=5.1 Hz), 4.61 (2H,t,J=5 .1 Hz), 7.03(1H,d,J=7.5 Hz), 7.41(1H,d,J=7.5 Hz), 8.26(3H,brs).

EXAMPLE 64

3-(2-Arninoethoxy)-7-chloro-4-methyl-1,2-benzisoxazole hydrochloride (a) 3-(2-(N-t-Butoxycarbonylamino)ethoxy)-7-chloro-4-methyl-1,2-benzisoxazole.

The title compound was obtained in 93% yield from 3-(2-(N-t-butoxycarbonylamino)ethoxy)-7-chloro-1,2-benzisoxazole by similar reactions and treatments as in Example 51(a).

IR spectrum (KBr)$v_{max}$cm$^{-1}$: 3355, 1691, 1605, 1551, 1536; NMR spectrum (CDCl$_3$)δppm: 1.45(9H,s), 2.57(3H, s), 3.65(2H,q,J=5.1 Hz), 4.50(2H,t,J=5.1 Hz), 4.87(1H,brs), 6.94(1H,d,J=7.8 HZ), 7.37(1H,d,J=7.8 Hz).

(b) 3-(2-Aminoethoxy)-7-chloro-4-methyl-1,2-benzisoxazole hydrochloride.

The title compound was obtained in 98% yield from 3-(2-(N-t-butoxycarbonylamino)ethoxy)-7-chloro-4-methyl-1,2-benzisoxazole by similar reactions and treatments as in Example 17(c).

Melting point: 215–218° C. (decomposed); IR spectrum (KBr)$v_{max}$cm$^{-1}$: 3194, 2967, 2892, 1606, 1540; NMR spectrum (DMSO-d$_6$)δppm: 2.60(3H,s), 3.35(2H,t,J=5.1 Hz), 4.63 (2H,t,J=5.1 Hz), 7.17(1H,d,J=7.7 Hz), 7.66(1H,d,J=7.7 Hz), 8.24(3H,brs).

EXAMPLE 65

3-(2-Aminoethoxy)-5,7-dichloro-4-methyl-1,2-benzisoxazole hydrochloride (a) 3-(2-(N-t-Butoxycarbonylamino)ethoxy)-5,7-dichloro-4-methyl-1,2-benzisoxazole.

The title compound was obtained in 95% yield from 3-(2-(N-t-butoxycarbonylamino)ethoxy)-5,7-chloro-1,2-benzisoxazole by similar reactions and treatments as in Example 51(a).

Melting point: 109–111° C.; IR spectrum (KBr)$\nu_{max}$cm$^{-1}$: 3354, 1697, 1616, 1552, 1528; NMR spectrum (CDCl$_3$) δppm: 1.46(9H,s), 2.59(3H,s), 3.63(2H,q,J=5.1 Hz), 4.50 (2H,t,J=5.1 Hz), 4.93(1H,brs), 7.58(1H,s).

(b) 3-(2-Aminoethoxy)-5,7-dichloro-4-methyl-1,2-benzisoxazole hydrochloride.

The title compound was obtained in 99% yield from 3-(2-(N-t-butoxycarbonylamino)ethoxy)-5,7-dichloro-4-methyl-1,2-benzisoxazole by similar reactions and treatments as in Example 17(c).

Melting point: 222–225° C. (decomposed); IR spectrum (KBr)$\nu_{max}$cm$^{-1}$: 3062, 2970, 2897, 2770, 1618, 1596, 1542, 1521; NMR spectrum (DMSO-d$_6$)δppm: 2.56(3H,s), 3.38 (2H,t,J=5.1 Hz), 4.62(2H,t,J=5.1 Hz), 7.90(1H,s), 8.28(3H, brs).

EXAMPLE 66

3-(2-Aminoethoxy)-7-carbamoyl-5-chloro-1,2-benzisoxazole hydrochloride (a) 3-(2-(N-t-Butoxycarbonylamino)ethoxy)-7-carbamoyl-5-chloro-1,2-benzisoxazole.

The title compound was obtained in 88% yield from 3-(2-(N-t-butoxycarbonylamino)ethoxy)-5-chloro-1,2-benzisoxazole by similar reactions and treatments as in Example 18(a) and subsequently Example 18(b), IR spectrum (KBr)$\nu_{max}$cm$^{31\ 1}$: 3428, 3375, 3297, 3187, 1691, 1658, 1620, 1560, 1531; NMR spectrum (CDCl$_3$) δppm: 1.46(9H,s), 3.66(2H,q,J=5.1 Hz), 4.53(2H,t,J=5 .1 Hz), 4.94(1H,brs), 5.99(1H,brs), 7.08(1H,brs), 7.80(1H,d,J= 2.1 Hz), 8.31(1H,d,J=2.1 Hz).

(b) 3-(2-(Aminoethoxy)-7-carbamoyl-5-chloro-1,2-benzisoxazole hydrochloride.

The title compound was obtained in 98% yield from 3-(2-(N-t-butoxycarbonylamino)ethoxy)-7-carbamoyl-5-chloro-1,2-benzisoxazole by similar reactions and treatments as in Example 17(c).

Melting point: 232–237° C. (decomposed); IR spectrum (KBr)$\nu_{max}$cm$^{-1}$: 3450, 3339, 3290, 3238, 3164, 3082, 3047, 3011, 2952, 2878, 2847, 2818, 2766, 2688, 1672, 1626, 1608, 1594, 1547, 1520; NMR spectrum (DMSO-d$_6$)δppm: 3.47(2H,t,J=5.1 Hz), 4.63(2H,t,J=5.1 Hz), 7.94(1H,brs), 7.97(1H,brs), 8.03(1H,d,J=2.2 Hz), 8.05(1H,d,J=2.2 Hz), 8.33(3H,brs).

EXAMPLE 67

3-(2-Aminoethoxy)-5-chloro-7-cyano-1,2-benzisoxazole hydrochloride (a) 3-(2-(N-t-Butoxycarbonylamino)ethoxy)-5-chloro-7-cyano-1,2-benzisoxazole.

The title compound was obtained in 92% yield from 3-(2-(N-t-butoxycarbonylamino)ethoxy)-5-chloro-7-carbamoyl-1,2-benzisoxazole by similar reactions and treatments as in Example 24(a).

Melting point: 141–143° C.; IR spectrum (KBr)$\nu_{max}$cm$^{-1}$: 3364, 2244, 1684, 1609, 1547, 1527; NMR spectrum (CDCl$_3$)δppm: 1.45(9H,s), 3.62(2H,q,J=5.1 Hz), 4.53(2H,t, J=5.1 Hz), 4.90(1H,brs), 7.81(1H,d,J=2.2 Hz), 7.88(1H,d,J= 2.2 Hz).

(b) 3-(2-(Aminoethoxy)-5-chloro-7-cyano-1,2-benzisoxazole hydrochloride.

The title compound was obtained in 94% yield from 3-(2-(N-t-butoxycarbonylamino)ethoxy)-5-chloro-7-cyano-1,2-benzisoxazole by similar reactions and treatments as in Example 17(c).

Melting point: 211–214° C. (decomposed); IR spectrum (KBr)$\nu_{max}$cm$^{-1}$: 3070, 3047, 2943, 2878, 2810, 2769, 2739, 2685, 2637, 2243, 1611, 1586, 1548, 1507; NMR spectrum (DMSO-d$_6$)δppm: 3.34(2H,t,J=5.1 Hz), 4.65(2H,t,J=5.1 Hz), 8.32(1H,d,J=2.2 Hz), 8.39(3H,brs), 8.48(1H,d,J=2.2 Hz).

EXAMPLE 68

3-(2-Aminoethoxy)pyrido[2,3-d]isoxazole hydrochloride (a) 3-(2-(N-t-Butoxycarbonylamino)ethoxy)pyridor[2,3-d]isoxazole.

The title compound was obtained in 63% yield from 3-hydroxypyrido[2,3-d]isoxazole by similar reactions and treatments as in Example 1(e).

Melting point: 94–95° C.; IR spectrum (KBr)$\nu_{max}$cm$^{-1}$: 3374, 3247, 1754, 1698, 1678, 1587, 1529; NMR spectrum (CDCl$_3$)δppm: 1.44(9H,s), 3.68(2H,q,J=5.1 Hz), 4.59(2H,t, J=5.1 Hz), 5.12(1H,brs), 7.50(1H,dd,J=8.6 Hz,J=4.4 Hz), 7.81(1H,dd,J=8.6 Hz,J=1.4 Hz), 8.68(1H,dd,J=4.4 Hz,J=1.4 Hz).

(b) 3-(2-Aminoethoxy)pyrido[2,3-d]isoxazole hydrochloride.

The title compound was obtained in 89% yield from 3-(2-(N-t-butoxycarbonylamino)ethoxy)pyrido[2,3-d]isoxazole by similar reactions and treatments as in Example 1(f).

Melting point: 217–222° C. (decomposed); IR spectrum (KBr)$\nu_{max}$cm$^{-1}$: 3070, 3020, 2980, 2911, 2870, 2783, 2700, 2658, 2601, 1631, 1586, 1541; NMR spectrum (DMSO-d$_6$) δppm: 3.35(2H,t,J=5.1 Hz), 4.72(2H,t,J=5.1 Hz), 7.73(1H, dd,J=8.6 Hz,J=4.4 Hz), 8.21(1H,d,J=8.6 Hz), 8.32(3H,brs), 8.73(1H,d,J=4.4 Hz).

EXAMPLE 69

3-(2-Aminoethoxy)-4-trifluoromethylpyrido[3,2-d]isoxazole hydrochloride (a) 4-Trifluoromethylnicotinic acid N-oxide.

4-Trifluoromethylnicotinic acid (5.00 g) was dissolved in a solution of acetic acid (20 ml) and 31% hydrogen peroxide solution (5 ml), and stirred at 100° C. for 10 hours. The solvent was evaporated under reduced pressure, to give the title compound (5.40 g, quant.) as a solid.

Melting point: 210–215° C. (decomposed); NMR spectrum (CDCl$_3$)δppm: 7.61(1H,d,J=6.9 Hz), 8.32(1H,d,J=6.9 Hz), 8.56(1H,s).

(b) 2-Chloro-4-trifluoromethylnicotinic acid methyl ester.

Phosphorus oxychloride (4.0 ml) and phosphorus pentachloride (4.0 g) were added to 4-trifluoromethylnicotinic acid N-oxide (2.00 g), and the mixture was stirred at 100° C. for 4 hours. Phosphorus oxychloride was evaporated under reduced pressure. Methanol (30 ml) was added to the residue under ice cooling, then stirred at room temperature for 30 minues. After aqueous sodium hydrogencarbonate was added to the reaction mixture, the pH was adjusted to alkaline, the mixture was then extracted with ether, and washed with water, and the extract was dried over anhydrous sodium sulfate. After filtration, the solvent was evaporated under reduced pressure, then the residue was purified by silica gel column chromatography with hexane/ethyl acetate (9/1) as an eluent, to give the title compound (310 mg, 14%) as an oil.

NMR spectrum (CDCl$_3$)δppm: 4.01(3H,s), 7.54(1H,d,J=5.3 Hz), 8.65(1H,d,J=5.3 Hz).

(c) 3-Hydroxy-4-trifluoromethylpyrido[3,2-d]isoxazole.

A water solution (5 ml) of hydroxylamine hydrochloride (450 mg) and sodium hydroxide (520 mg) was added to 2-chloro-4-trifluoromethylnicotinic acid methyl ester (300 mg) at room temperature, and the mixture was then stirred for 5 days at room temperature. After dilute aqueous hydrochloric acid was added to the reaction mixture, the pH was adjusted to acidic, and the mixture was then extracted with ethyl acetate. The combined extracts were dried over anhydrous sodium sulfate. The solvent was evaporated under reduced pressure, and the residue was recrystallized from ethyl acetate to give the title compound (180 mg, 67%) as a solid.

Melting point 196–202° C.; NMR spectrum (DMSO-d$_6$) δppm: 7.81(1H,d,J=4.9 Hz), 8.88(1H,d,J=4.9 Hz), 13.30 (1H,brs).

(d) 3-(2-(N-t-Butoxycarbonylamino)ethoxy)-4-trifluoromethylpyrido[3,2-d]isoxazole.

The title compound was obtained as a solid in 75% yield from 3-hydroxy-4-trifluoromethylpyrido[3,2-d]isoxazole and 2-(N-t-butoxycarbonylamino)ethanol by similar reactions and treatments as in Example 1(e).

NMR spectrum (CDCl$_3$)δppm: 1.45(9H,s), 3.65(2H,q,J=5.2 Hz), 4.55(2H,t,J=5.2 Hz), 4.90(1H,brs), 7.56(1H,d,J=4.9 Hz), 8.77(1H,d,J=4.9 Hz).

(e) 3-(2-Aminoethoxy)-4-trifluoromethylpyrido[3,2-d]isoxazole hydrochloride.

The title compound was obtained in 96% yield from 3-(2-(N-t-butoxycarbonylamino)ethoxy)-4-trifluoromethylpyrido[3,2-d]isoxazole by smilar reactions and treatments as in Example 1(f).

Melting point: 203–207° C.; IR spectrum (KBr)ν$_{max}$cm$^{-1}$: 3100, 2970, 1600, 1540; NMR spectrum (DMSO-d$_6$)δppm: 3.34(2H,t,J=5.5 Hz), 4.71(2H,t,J=5.5 Hz), 7.94(1H,d,J=4.8 Hz), 8.26(3H,brs), 8.97(1H,d,J=4.8 Hz).

EXAMPLE 70

3-(2-Aminoethoxy)-7-trifluoromethyl-1,2-benzisoxazole hydrochloride (a) 2-Fluoro-3-trifluoromethylbenzoic acid methyl ester.

The title compound was obtained as an oil from 2-fluoro-3-trifluoromethylbenzoic acid by similar reactions and treatments as in Example 52(a).

NMR spectrum (CDCl$_3$)δppm: 3.96(3H,s), 7.31(1H,t,J=5.0 Hz), 7.79(1H,t,J=5.0 Hz), 8.18(1H,t,J=5.0 Hz).

(b) 2-Fluoro-3-trifluoromethylbenzhydroxamic acid.

The title compound was obtained from 2-fluoro-3-trifluoromethylbenzoic acid methyl ester by similar reactions and treatments as in Example 52(b).

NMR spectrum (DMSO-d$_6$)δppm: 7.46(1H,t,J=5.0 Hz), 7.82(2H,m).

(c) 3-Hydroxy-7-trifluromethyl-1,2-benzisoxazole.

The title compound was obtained as a solid from 2-fluoro-3-trifluoromethylbenzohydroxamic acid by similar reactions and treatments as in Example 52(c).

Melting point: 204–207° C.; NMR spectrum (DMSO-d$_6$) δppm: 7.54(1H,t,J=7.6 Hz), 7.98(1H,d,J=7.6 Hz), 8.09(1H, d,J=7.6 Hz), 12.80(1H,brs).

(d) 3-(2-(N-t-Butoxycarbonylamino)ethoxy)-7-trifluoromethyl-1,2-benzisoxazole.

The title compound was obtained as a solid in 65% yield from 3-hydroxy-7-trifluromethyl-1,2-benzisoxazole and 2-(N-t-butoxycarbonylamino)ethanol by similar reactions and treatments as in Example 1(e).

NMR spectrum (CDCl$_3$)δppm: 1.45(9H,s), 3.65(2H,q,J=5.2 Hz), 4.54(2H,t,J=5.2 Hz), 4.52(1H,brs), 7.39(1H,t,J=7.6 Hz), 7.79(1H,d,J=7.6 Hz), 7.85(1H,d,J=7.6 Hz).

(e) 3-(2-Aminoethoxy)-7-trifluoromethyl-1,2-benzisoxazole hydrochloride.

The title compound was obtained in 77% yield from 3-(2-(N-t-butoxycarbonylamino)ethoxy)-7-trifluoromethyl-1,2-benzisoxazole by similar reactions and treatments as in Example 1(f).

Melting point: 190–194° C.; IR spectrum (KBr)ν$_{max}$cm$^{-1}$: 2970, 2905, 1615, 1555, 1510; NMR spectrum (DMSO-d$_6$) δppm: 3.37(2H,t,J=5.1 Hz), 4.68(2H,t,J=5.1 Hz), 7.62(1H, t,J=7.6 Hz), 8.09(1H,d,J=7.6 Hz), 8.16(1H,d,J=7.6 Hz), 8.44 (3H,brs).

EXAMPLE 71

3-(2-Aminoethoxy)-4-chloro-1,2-benzisoxazole hydrochloride (a) 3-(2-(N-t-Butoxycarbonylamino)ethoxy)-4-chloro-1,2-benzisoxazole.

The title compound was obtained in 63% yield from 3-hydroxy-4-chloro-1,2-benzisoxazole and 2-(N-t-butoxycarbonylamino)ethanol by similar reactions and treatments as in Example 1(e).

Melting point: 110–111° C.; IR spectrum (KBr)ν$_{max}$cm$^{-1}$: 3357, 1691, 1607, 1537; NMR spectrum (CDCl$_3$)δppm: 1.46(9H,s), 3.66(2H,q,J=5.1 Hz), 4.51(2H,t,J=5.1 Hz), 4.99 (1H,brs), 7.23(1H,d,J=7.6 Hz), 7.34(1H,d,J=8.4 Hz), 7.44 (1H,dd,J=8.4 Hz,J=7.6 Hz).

(b) 3-(2-Aminoethoxy)-4-chloro-1,2-benzisoxazole hydrochloride.

The title compound was obtained in 99% yield from 3-(2-(N-t-butoxycarbonylamino)ethoxy)-4-chloro-1,2-benzisoxazole by similar reactions and treatments as in Example 17(c).

Melting point: 221–226° C. (decomposed); IR spectrum (KBr)ν$_{max}$cm$^{-1}$: 3440, 3070, 3006, 2969, 2898, 1610, 1538, 1515; NMR spectrum (DMSO-d$_6$)δppm: 3.35(2H,t,J=5.4 Hz), 4.65(2H,t,J=5.4 Hz), 7.42–7.49(1H,m), 7.62–7.71(2H, m), 8.23(3H,brs).

EXAMPLE 72

3-(2-Aminoethoxy)-6-methylpyrido[3,2-d]isoxazole hydrochloride (a) 2-Chloro-6-methylnicotinic acid ethyl ester.

The title compound was obtained as an oil from 2-chloro-6-methylnicotinic acid by similar reactions and treatments as in Example 1(a).

NMR spectrum (CDCl$_3$)δppm: 1.41(3H,t,J=7.2 Hz), 2.59 (3H,s), 4.41(2H,q,J=7.2 Hz), 7.16(1H,d,J=7.2 Hz), 8.08(1H, d,J=7.2 Hz).

(b) 2-Chloro-6-methylpyridine-3-carbohydroxamic acid.

The title compound was obtained as a powder from 2-chloro-6-methylnicotinic acid ethyl ester by similar reactions and treatments as in Example 10(b).

NMR spectrum (DMSO-d$_6$)δppm: 2.51(3H,s), 7.33(1H, d,J=7.8 Hz), 7.75(1H,d,J=7.8 Hz).

(c) 3-Hydroxy-6-methylpyrido[3,2-d]isoxazole.

The title compound was obtained as a powder from 2-chloro-6-methylpyridine-3-carbohydroxamic acid by similar reactions and treatments as in Example 10(c).

IR spectrum (KBr)ν$_{max}$cm$^{-1}$: 2985, 2907, 2739, 2559, 1663, 1610, 1595, 1561, 1541; NMR spectrum (DMSO-d$_6$) δppm: 2.60(3H,s), 7.30(1H,d,J=8.0 Hz), 8.14(1H,d,J=8.0 Hz).

(d) 3-(2-(N-t-Butoxycarbonylamino)ethoxy)-6-methylpyrido[3,2-d]isoxazole.

The title compound was obtained in 71% yield from 3-hydroxy-6-methylpyrido[3,2-d]isoxazole and 2-(N-t- butoxycarbonylamino)ethanol by similar reactions and treatments as in Example 1(e).

Melting point: 151–152° C.; IR spectrum (KBr)$v_{max}$cm$^{-1}$: 3332, 1718, 1708, 1614, 1609, 1534; NMR spectrum (CDCl$_3$)δppm: 1.45(9H,s), 2.69(3H,s), 3.64(2H,q,J=5.1 Hz), 4.51(2H,t,J=5.1 Hz), 4.94(1H,brs), 7.15(1H,d,J=8.0 Hz), 7.90(1H,d,J=8.0 Hz).

(e) 3-(2-Aminoethoxy)-6-methylpyrido[3,2-d]isoxazole hydrochloride.

The title compound was obtained in 97% yield from 3-(2-(N-t-butoxycarbonylamino)ethoxy)-6-methylpyrido[3,2-d]isoxazole by similar reactions and treatments as in Example 1(f).

Melting point: 209–213° C. (decomposed); IR spectrum (KBr)$v_{max}$cm$^{-1}$: 3426, 3063, 3000, 2938, 1669, 1609, 1565, 1536, 1506; NMR spectrum (DMSO-d$_6$)δppm: 2.63(3H,s), 3.30–3.40(2H,m), 4.62(2H,t,J=5.1 Hz), 7.40(1H,d,J=8.0 Hz), 8.18(1H,d,J=8.0 Hz), 8.29(3H,brs).

EXAMPLE 73

3-(2-Aminoethoxy)-5-chloro-4-methyl-1,2-benzisoxazole hydrochloride, and 3-(2-Aminoethoxy)-5-chloro-7-methyl-1,2-benzisoxazole hydrochloride (a) 3-(2-(N-t-Butoxycarbonylamino)ethoxy)-5-chloro-4-methyl-1,2-benzisoxazole, and 3-(2-(N-t-Butoxycarbonylamino)ethoxy)-5-chloro-7-methyl-1,2-benzisoxazole.

3-(2-(N-t-butoxycarbonylamino)ethoxy)-5-chloro-4-methyl-1,2-benzisoxazole was obtained in 40% yield and 3-(2-(N-t-butoxycarbonylamino)ethoxy)-5-chloro-7-methyl-1,2-benzisoxazole was obtained in 37% yield from 3-(2-(N-t-butoxycarbonylamino)ethoxy)-5-chloro-1,2-benzisoxazole by similar reactions and treatments as in Example 17(b).

Data for 3-(2-(N-t-butoxycarbonylamino)ethoxy)-5-chloro-4-methyl-1,2-benzisoxazole.

Melting point: 140–141° C.; IR spectrum (KBr)$v_{max}$cm$^{-1}$: 3351, 1688, 1615, 1601, 1537; NMR spectrum (CDCl$_3$) δppm: 1.46(9H,s), 2.62(3H,s), 3.66(2H,q,J=5.1 Hz), 4.50 (2H,t,J=5.1 Hz), 4.88(1H,brs), 7.19(1H,d,J=8.8 Hz), 8.83 (1H,d,J=8.8 Hz).

Data for 3-(2-(N-t-butoxycarbonylamino)ethoxy)-5-chloro-7-methyl-1,2-benzisoxazole.

Melting point: 94–95° C.; IR spectrum(KBr)$v_{max}$cm$^{-1}$: 3333, 1686, 1611, 1539; NMR spectrum (CDCl$_3$)δppm: 1.46(9H,s), 2.48(3H,s), 3.63(2H,q,J=5.1 Hz), 4.49(2H,t,J= 5.1 Hz), 4.94(1H,brs), 7.29(1H,d,J=1.8 Hz), 7.44(1H,d,J= 1.8 Hz).

(b) 3-(2-Aminoethoxy)-5-chloro-4-methyl-1,2-benzisoxazole hydrochloride.

The title compound was obtained in 99% yield from 3-(2-(N-t-butoxycarbonylamino)ethoxy)-5-chloro-4-methyl-1,2-benzisoxazole by similar reactions and treatments as in Example 17(c).

Melting point: 223–226° C. (decomposed); IR spectrum (KBr)$v_{max}$cm$^{-1}$: 3451, 3009, 2970, 1645, 1618, 1605, 1536; NMR spectrum (DMSO-d$_6$)δppm: 2.62(3H,s), 3.34(2H,t,J= 5.1 Hz), 4.63(2H,t,J=5.1 Hz), 7.52(1H,d,J=8.9 Hz), 7.68 (1H,d,J=8.9 Hz), 8.28(3H,brs).

(c) 3-(2-Aminoethoxy)-5-chloro-7-methyl-1,2-benzisoxazole hydrochloride.

The title compound was obtained in 98% yield from 3-(2-(N-t-butoxycarbonylamino)ethoxy)-5-chloro-7-methyl-1,2-benzisoxazole by similar reactions and treatments as in Example 17(c).

Melting point: 208–211° C. (decomposed); IR spectrum (KBr)$v_{max}$cm$^{-1}$: 3428, 3056, 2966, 2894, 2770, 1608, 1541, 1517; NMR spectrum (DMSO-d$_6$)δppm: 2.46(3H,s), 3.34 (2H,t,J=5.1 Hz), 4.60(2H,t,J=5.1 Hz), 7.59(1H,d,J=1.8 Hz), 7.69(1H,d,J=1.8 Hz), 8.32(3H,brs).

EXAMPLE 74

3-(2-Aminoethoxy)-5-bromo-4-methyl-1,2-benzisoxazole hydrochloride, and 3-(2-Aminoethoxy)-5-bromo-7-methyl-1,2-benzisoxazole hydrochloride (a) 3-(2-(N-t-Butoxycarbonylamino)ethoxy)-5-bromo-4-methyl-1,2-benzisoxazole, and 3-(2-N-t-Butoxycarbonylamino)ethoxy)-5-bromo-7-methyl-1,2-benzisoxazole.

3-(2-(N-t-butoxycarbonylamino )ethoxy)-5-bromo-4-methyl-1,2-benzisoxazole was obtained in 7% yield and 3-(2-(N-t-butoxycarbonylamino)ethoxy)-5-chloro-7-methyl-1,2-benzisoxazole was obtained in 68% yield from 3-(2-(N-t-butoxycarbonylamino)ethoxy)-5-bromo-1,2-benzisoxazole by similar reactions and treatments as in Example 17(b).

Data for 3-(2-(N-t-butoxycarbonylamino)ethoxy)-5-bromo-4-methyl-1,2-benzisoxazole.

Melting point: 140–141° C.; IR spectrum(KBr)$v_{max}$cm$^{-1}$: 3350, 1688, 1618, 1595, 1538; NMR spectrum (CDCl$_3$) δppm: 1.46(9H,s), 2.64(3H,s), 3.66(2H,q,J=5.1 Hz), 4.50 (2H,t,J=5.1 Hz), 4.88(1H,brs), 7.14(1H,d,J=8.8 Hz), 7.63 (1H,d,J=8.8 Hz).

Data for 3-(2-(N-t-butoxycarbonylamino)ethoxy)-5-bromo-7-methyl-1,2-benzisoxazole.

Melting point: 79–80° C.; IR spectrum(KBr)$v_{max}$cm$^{-1}$: 3350, 1692, 1612, 1535; NMR spectrum (CDCl$_3$)δppm: 1.46(9H,s), 2.48(3H,s), 3.65(2H,q,J=5.1 Hz), 4.49(2H,t,J= 5.1 Hz), 4.95(1H,brs), 7.29(1H,d,J=1.8 Hz), 7.44(1H,d,J= 1.8 Hz).

(b) 3-(2-Aminoethoxy)-5-bromo-4-methyl-1,2-benzisoxazole hydrochloride.

The title compound was obtained in 96% yield from 3-(2-(N-t-butoxycarbonylamino)ethoxy)-5-bromo-4-methyl-1,2-benzisoxazole by similar reactions and treatments as in Example 17(c).

Melting point: 208–212° C. (decomposed); IR spectrum (KBr)$v_{max}$cm$^{-1}$: 3436, 3000, 1615, 1599, 1535; NMR spectrum (DMSO-d$_6$)δppm: 2.64(3H,s), 3.34(2H,t,J=5.1 Hz), 4.63(2H,t,J=5.1 Hz), 7.46(1H,d,J=8.9 Hz), 7.82(1H,d,J=8.9 Hz), 8.24(3H,brs).

(c) 3-(2-Aminoethoxy)-5-bromo-7-methyl-1,2-benzisoxazole hydrochloride.

The title compound was obtained in 98% yield from 3-(2-(N-t-butoxycarbonylamino)ethoxy)-5-bromo-7-methyl-1,2-benzisoxazole by similar reactions and treatments as in Example 17(c).

Melting point 212–215° C. (decomposed); IR spectrum (KBr)$v_{max}$cm$^{-1}$: 3339, 3054, 2968, 2925, 2892, 1606, 1546, 1516; NMR spectrum (DMSO-d$_6$)δppm: 2.46(3H,s), 3.33 (2H,t,J=5.1 Hz), 4.60(2H,t,J=5.1 Hz), 7.70(1H,d,J=1.8 Hz), 7.82(1H,d,J=1.8 Hz), 8.28(3H,brs).

EXAMPLE 75

3-(2-Aminoethoxy)-4,5-dimethyl-1,2-benzisoxazole hydrochloride (a) 3-(2-(N-t-Butoxycarbonylamino)ethoxy)-4,5-dimethyl-1,2-benzisoxazole.

The title compound was obtained in 73% yield from 3-(2-(N-t-butoxycarbonylamino)ethoxy)-5-methyl-1,2-benzisoxazole by similar reactions and treatments as in Example 51(a).

Melting point: 125–126° C.; IR spectrum (KBr)$v_{max}$cm$^{-1}$: 3352, 1694, 1678, 1620, 1609, 1539; NMR spectrum (CDCl$_3$)δppm: 1.46(9H,s), 2.33(3H,s), 2.51(3H,s), 3.65(2H, q,J=5.1 Hz), 4.49(2H,t,J=5.1 Hz), 4.90(1H,brs), 7.13(1H,d, J=8.5 Hz), 7.29(1H,d,J=8.5 Hz).

(b) 3-(2-Aminoethoxy)-4,5-dimethyl-1,2-benzisoxazole hydrochloride.

The title compound was obtained in 96% yield from 3-(2-(N-t-butoxycarbonylamino)ethoxy)-4,6-dimethyl-1,2-benzisoxazole by similar reactions and treatments as in Example 17(c).

Melting point: 180–183° C. (decomposed); IR spectrum (KBr)$v_{max}$cm$^{-1}$: 3434, 2971, 2924, 2751, 1643, 1612, 1538; NMR spectrum (DMSO-d$_6$)δppm: 2.32(3H,s), 2.51(3H,s), 3.34(2H,t,J=5.1 Hz), 4.61(2H,t,J=5.1 Hz), 7.31(1H,d,J=8.5 Hz), 7.43(1H,d,J=8.5 Hz), 8.28(3H,brs).

EXAMPLE 76

3-(2-Aminoethoxy)-4-methyl-5-methoxy-1,2-benzisoxazole hydrochloride (a) 3-(2-(N-t-Butoxycarbonylamino)ethoxy)-4-methyl-5-methoxy-1,2-benzisoxazole.

The title compound was obtained in 88% yield from 3-(2-(N-t-butoxycarbonylamino)ethoxy)-5-methoxy-1,2-benzisoxazole by similar reactions and treatments as in Example 51(a).

Melting point: 137–138° C. IR spectrum (KBr)$v_{max}$cm$^{-1}$: 3361, 1689, 1618, 1538; NMR spectrum (CDCl$_3$)δppm: 1.45(9H,s), 2.46(3H,s), 3.65(2H,q,J=5.1 Hz), 3.87(3H,s), 4.48(2H,t,J=5.1 Hz), 4.90(1H,brs), 7.12(1H,d,J=8.9 Hz), 7.18(1H,d,J=8.9 Hz).

(b) 3-(2-Aminoethoxy)-4-methyl-5-methoxy-1,2-benzisoxazole hydrochloride.

The title compound was obtained in 99% yield from 3-(2-(N-t-butoxycarbonylamino)ethoxy)-4-methyl-5-methoxy-1,2-benzisoxazole by similar reactions and treatments as in Example 17(c).

Melting point: 173–176° C. (decomposed); IR spectrum (KBr)$v_{max}$cm$^{-1}$: 3423, 3008, 2971, 2920, 2842, 1617, 1601, 1536, 1500; NMR spectrum (DMSO-d$_6$)δppm: 2.44(3H,s), 3.35(2H,t,J=5.1 Hz), 3.84(3H,s), 4.60(2H,t,J=5.1 Hz), 7.35 (1H,d,J=9.0 Hz), 7.40(1H,d,J=9.0 Hz), 8.32(3H,brs).

EXAMPLE 77

3-(2-Aminoethoxy)-5-carbamoyl-1,2-benzisoxazole hydrochloride (a) 3-(2-(N-t-Butoxycarbonylamino)ethoxy)-5-carbamoyl-1,2-benzisoxazole.

The title compound was obtained in 12% yield from 3-(2-(N-t-butoxycarbonylamino)ethoxy)-5-bromo-1,2-benzisoxazole by similar reactions and treatments as in Example 23(a).

Melting point: 178–180° C.; IR spectrum (KBr)$v_{max}$cm$^{-1}$: 3348, 3197, 1717, 1672, 1624, 1599, 1543; NMR spectrum (CDCl$_3$)δppm: 1.46(9H,s), 3.65(2H,q,J=5.1 Hz), 4.53(2H,t, J=5.1 Hz), 5.00(1H,brs), 5.50–6.50(2H,brs), 7.49(1H,d,J= 8.8 Hz), 8.04(1H,d,J=8.8 Hz), 8.16(1H,s).

(b) 3-(2-Aminoethoxy)-5-carbamoyl-1,2-benzisoxazole hydrochloride.

The title compound was obtained in 96% yield from 3-(2-(N-t-butoxycarbonylamino)ethoxy)-5-carbamoyl-1,2-benzisoxazole by similar reactions and treatments as in Example 17(c).

Melting point: 218–222° C. (decomposed); IR spectrum (KBr)$v_{max}$cm$^{-1}$: 3429, 3353, 3317, 3195, 2977, 2901, 1671, 1622, 1596, 1546, 1501; NMR spectrum (DMSO-d$_6$)δppm: 3.33(2H,t,J=5.1 Hz), 4.64(2H,t,J=5.1 Hz), 7.51(1H,s), 7.72 (1H,d,J=8.8 Hz), 8.18(1H,s), 8.21(1H,d,J=8.8 Hz), 8.31(3H, brs), 8.40(1H,s).

EXAMPLE 78

3-(2-Aminoethoxy)-5-cyano-1,2-benzisoxazole hydrochloride (a) 3-(2-(N-t-Butoxycarbonylamino)ethoxy)-5-cyano-1,2-benzisoxazole.

The title compound was obtained in 92% yield from 3-(2-(N-t-butoxycarbonylamino)ethoxy)-5-carbamoyl-1,2-benzisoxazole by similar reactions and treatments as in Example 24(a).

Melting point: 138–140° C.; IR spectrum (KBr)$v_{max}$cm$^{-1}$: 3349, 2233, 1717, 1708, 1623, 1605, 1540, 1527; NMR spectrum (CDCl$_3$)δppm: 1.46(9H,s), 3.65(2H,q,J=5.1 Hz), 4.53(2H,t,J=5.1 Hz), 4.93(1H,brs), 7.56(1H,d,J=8.8 Hz), 7.79(1H,d,J=8.8 Hz), 8.04(1H,s).

(b) 3-(2-Aminoethoxy)-5-cyano-1,2-benzisoxazole hydrochloride.

The title compound was obtained in 96% yield from 3-(2-(N-t-butoxycarbonylamino)ethoxy)-5-cyano-1,2-benzisoxazole by similar reactions and treatments as in Example 17(c).

Melting point: 212–216° C. (decomposed); IR spectrum (KBr)$v_{max}$cm$^{-1}$: 3171, 3096, 3058, 3029, 2953, 2239, 1624, 1601, 1544, 1518; NMR spectrum (DMSO-d$_6$)δppm: 3.34 (2H,t,J=5.1 Hz), 4.65(2H,t,J=5.1 Hz), 7.91(1H,d,J=8.8 Hz), 8.12(1H,d,J=8.8 Hz), 8.35(3H,brs), 8.43(1H,s).

Test Method 1

Monoamine Oxidase-inhibitory Activity

Measurement was conducted based on the method described in *Biochem.Pharmacol.*, 12,1439(1963) and *J.Neurochem.*, 35,109(1980). 210 μl of phosphate buffer (pH 7.4) and 30 μl of the compound to be tested (which was dissolved in 10% DMSO-water solution) were added to 30 μl of the crude mitochondria sample of a mouse brain (30 μg protein), and the mixture was preincubated for 20 minutes at 38° C. Thereafter, $^{14}$C-2-Phenylethylamine (PEA, final concentration: 20 μM) was added for the measurement of B-type monoamine oxidase-inhibiting activity, and $^{14}$C-5-Hydroxytryptamine (5-HT, final concentration: 100 μM) was added for the measurement of A-type monoamine oxidase-inhibiting activity, and the mixtures were respectively reacted for 20 minutes at 38° C. After the completion of this time the reaction was suspended by adding 2N-HCl (200 μl), the $^{14}$C-labelled metabolite produced by the enzyme reaction was extracted by a solvent (ethyl acetate: toluene=1:1), and the $^{14}$C radioactive activity was measured by a liquid scintillation counter to determine the concentration (IC$_{50}$) of a compound which reduced the $^{14}$C radioactive activity of the control by 50%. The results are shown in Table 17.

TABLE 17

| | Monoamine oxidase-inhibitory activity |
|---|---|
| Example No. | B-type Monoamine oxidase-inhibitory activity (IC$_{50}$) |
| 1*) | 0.37 nM |
| 2 | 1.85 nM |
| 5*) | 1.35 nM |
| 6*) | 5.60 nM |
| 7*) | 0.56 nM |

TABLE 17-continued

Monoamine oxidase-inhibitory activity

| Example No. | B-type Monoamine oxidase-inhibitory activity (IC$_{50}$) |
|---|---|
| 8*) | 0.56 nM |
| 9 | 20.0 nM |
| 10(e) | 10.2 nM |
| 10(f) | 13.5 nM |
| 11 | 2.8 nM |
| 12 | 26.5 nM |
| 13 | 27.5 nM |
| 14 | 21.5 nM |
| 15*) | 0.32 nM |
| 17 | 4.2 nM |
| 21 | 4.7 nM |
| 24 | 6.8 nM |
| 26 | 2.7 nM |
| 33 | 4.5 nM |
| 34 | 2.2 nM |
| 35 | 9.0 nM |
| 38 | 2.95 nM |
| 42 | 18.0 nM |
| 44 | 6.0 nM |
| 56 | 6.6 nM |
| Compound A**) | 2.35 μM |
| Compound B***) | 4.70 μM |

Note:
*)They showed B-type monoamine oxidase-inhibitory activity 4500–55000 times as potent as A-type monoamine oxidase-inhibitory activity.
**)3-(2-N-Methylamino)ethoxy-1,2-benzisoxazole.
***)3-(2-N,N'-Dimethylamino)ethoxy-1,2-benzisoxazole.

PREPARATION EXAMPLE 1

Hard capsule agent

A unit capsule was prepared by filling 100 mg of the compound of Example 1 in a powdery form, 150 mg of lactose, 50 mg of cellulose and 6 mg of magnesium stearate into respective standard hard gelatin capsules. The prepared unit capsule was washed and dried to give a hard capsule agent.

INDUSTRIAL APPLICABILITY

The isoxazole derivatives (I) and (II) of the present invention have excellent B-type monoamine oxidase-inhibiting action and A-type monoamine oxidase-inhibiting action (especially having strong inhibiting action against B-type monoamine oxidase) and also have low toxicity, thereby they are useful as a therapeutic agent or a preventive agent against neuropathies such as Parkinson's disease, and depression (especially Parkinson's disease); and a therapeutic agent for Alzheimer's disease.

When the compounds (I) and (II) of the present invention or pharmaceutically acceptable salt are used as the therapeutic agent or the preventive agent of the above-mentioned nervous disease, said compounds may be administered orally in a form of tablet, capsule, granule, powder, syrup and the like, or non-orally by injection or suppository by itself or mixed with proper pharmaceutically acceptable excipients, diluents and the like.

These agents are prepared in a usual method by using additives, such as excipients (for example, sugar derivatives such as lactose, sucrose, glucose, mannitol and sorbitol; starch derivatives such as corn starch, potato starch, α-starch, dextrin and carboxymethyl starch; cellulose derivatives such as crystalline cellulose, low-substituted hydroxypropylcellulose, hydroxypropylmethylcellulose, carmellose, carmellose calcium and internally cros carmellose sodium; acacia; dextran; pullulan; silicate derivatives such as light anhydrous silicic acid, synthetic aluminum silicate and magnesium aluminometasilicate; phosphate salts such as calcium phosphate; carbonate salts such as calcium carbonate; sulfate salts such as calcium sulfate and the like), binders (for example, the afore-mentioned excipients; gelatin; polyvinylpyrrolidone; macrogol and the like), decay agents (for example, afore-mentioned excipients; croscarmellose sodium, sodium carboxymethyl starch, starch which is chemically modified like crospovidone, cellulose derivatives and the like), lubricants (for example, talc; stearic acid; metal stearate such as calcium stearate and magnesium stearate; colloidal silica; lacs such as bee gum and spermaceti; boric acid; glycol; carboxylic acids such as fumaric acid and adipic acid; sodium carboxylate such as sodium benzoate; sulfates such as sodium sulfate; leucine; lauryl sulfates such as sodium lauryl sulfate, magnesium lauryl sulfate; silicic acids such as silicic acid anhydride and silicic acid hydrate; starch derivatives in the afore-mentioned excipients), fungicides (for example, parahydroxybenzoate such as methylparaban and propylparaban; alcohols such as chlorobutanol, benzyl alcohol and phenylethyl alcohol; benzalkonium chloride; phenols such as phenol and cresol; thimerosal; acetic acid anhydride; sorbic acid and the like), taste or odor-masking agents (for example, generally used sweeteners, acidulants, flavors and the like), diluent, and solvents for injection (for example, water, ethanol, glycerol and the like). The dose used differs depending on the symptom, age and the like, but it is preferred that it is administered to an adult 1 mg at the minimum (preferably, 10 mg) and 2000 mg at the maximum (preferably, 400 mg) once a day, in the case of oral administration, and 0.1 mg at the minimum (preferably, 1 mg) and 500 mg at the maximum (preferably, 300 mg) once a day, in the case of intravenous administration, and it is administered one to six times a day according to the symptom.

We claim:

1. A compound of formula (I)

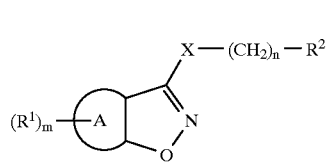

(I)

wherein:

R$^1$ represents a hydrogen atom; a halogen atom; an alkyl group having from 1 to 6 carbon atoms; an alkyl group having from 1 to 4 carbon atoms and substituted by a halogen atom or an alkoxy group having from 1 to 4 carbon atoms; an alkoxy group having from 1 to 6 carbon atoms; a halogeno alkoxy group having from 1 to 6 carbon atoms; a hydroxyl group; an alkylthio group having from 1 to 6 carbon atoms; an amino group; a monoalkylamino group in which said alkyl moiety has from 1 to 6 carbon atoms; a dialkylamino group in which each alkyl moiety independently has from 1 to 6 carbon atoms; an alkanoyl group having from 1 to 6 carbon atoms; an alkanoylamino group having from 1 to 6 carbon atoms; an alkanoyloxy group having from 1 to 6 carbon atoms; an alkoxycarbonyl group having from 1 to 6 carbon atoms; a carboxy group; an (alkylthio)thiocarbonyl group in which said alkylthio moiety has from 1 to 6 carbon atoms; a carbamoyl group; a monoalkylcarbamoyl group in which said alkyl moiety has from 1 to 6 carbon atoms; a dialkyl-carbamoyl group in which each alkyl moiety independently has from 1 to 6 carbon atoms; a nitro group; or a cyano group;

$R^2$ represents an amino group;

m represents 1;

n represents an integer of from 1 to 6;

ring A represents a phenyl ring fused with the isoxazole ring or a naphthyl ring fused with the isoxazole ring; and X represents an oxygen atom or a sulfur atom;

or a pharmaceutically acceptable salt thereof.

2. The compound of claim 1, wherein $R^1$ represents a hydrogen atom, a halogen atom, an alkyl group having from 1 to 4 carbon atoms, a fluoromethyl group, a difluoromethyl group, a trifluoromethyl group, a 2-fluoroethyl group, a 2-chloroethyl group, a 2,2,2-trifluoroethyl group, a methoxymethyl group, a methoxyethyl group, an alkoxy group having from 1 to 4 carbon atoms, a fluoromethoxy group, a chloromethoxy group, a difluoromethoxy group, a dichloromethoxy group, a trifluoromethoxy group, a trichloromethoxy group, a 1-fluoroethoxy group, a 2-fluoroethoxy group, a 2-chloroethoxy group, a 2,2,2-trifluoroethoxy group, a hydroxyl group, an alkylthio group having from 1 to 4 carbon atoms, an amino group, a monoalkylamino group in which said alkyl moiety has from 1 to 4 carbon atoms, a dialkylamino group in which each alkyl moiety independently has from 1 to 4 carbon atoms, a formyl group, an acetyl group, a formylamino group, an acetylamino group, an alkanoyloxy group having from 1 to 4 carbon atoms, an alkoxycarbonyl group having from 1 to 4 carbon atoms, a carboxy group, a (methylthio)thiocarbonyl group, an (ethylthio)thiocarbonyl group, a carbamoyl group, a methylcarbamoyl group, an ethylcarbamoyl group, a dimethylcarbamoyl group, a diethylcarbamoyl group, a nitro group or a cyano group, or a pharmaceutically acceptable salt thereof.

3. The compound of claim 1, wherein $R^1$ represents a hydrogen atom, a halogen atom, an alkyl group having from 1 to 4 carbon atoms, a fluoromethyl group, a difluoromethyl group, a trifluoromethyl group, a 2-fluoroethyl group, a 2,2,2-trifluoroethyl group, a methoxymethyl group, a methoxyethyl group, an alkoxy group having from 1 to 4 carbon atoms, a difluoromethoxy group, a hydroxyl group, an alkylthio group having from 1 to 4 carbon atoms, an amino group, a methylamino group, an ethylamino group, a dimethylamino group, a diethylamino group, a formyl group, an acetyl group, a formylamino group, an acetylamino group, an alkoxycarbonyl group having from 1 to 4 carbon atoms, a carboxy group, a carbamoyl group, a methylcarbamoyl group, an ethylcarbamoyl group, a dimethylcarbamoyl group, a diethylcarbamoyl group, a nitro group or a cyano group, or a pharmaceutically acceptable salt thereof.

4. The compound of claim 1, wherein $R^1$ represents a hydrogen atom, a fluorine atom, a chlorine atom, a bromine atom, a methyl group, an ethyl group, a trifluoromethyl group, a methoxy group, an ethoxy group, a difluoromethoxy group, a hydroxyl group, a methylthio group, an ethylthio group, an amino group, a methylamino group, an ethylamino group, a dimethylamino group, a formyloxy group, an acetyloxy group, a methoxycarbonyl group, an ethoxycarbonyl group, a carboxy group, a carbamoyl group, a nitro group or a cyano group, or a pharmaceutically acceptable salt thereof.

5. The compound of claim 1, wherein $R^1$ represents a hydrogen atom, a fluorine atom, a chlorine atom, a bromine atom, a methyl group, a methoxy group, a methylthio group, a difluoromethoxy group, a methoxycarbonyl group, a nitro group or a cyano group, or a pharmaceutically acceptable salt thereof.

6. The compound of claim 1, wherein n is 2 to 4, or a pharmaceutically acceptable salt thereof.

7. The compound of claim 1, wherein n is 2, or a pharmaceutically acceptable salt thereof.

8. The compound of claim 1, wherein ring A is a naphtyl ring, or a pharmaceutically acceptable salt thereof.

9. The compound of claim 1, wherein ring A is a phenyl ring, or a pharmaceutically acceptable salt thereof.

10. The compound of claim 1, wherein X is an oxygen atom, or a pharmaceutically acceptable salt thereof.

11. The compound of claim 1, wherein X is sulfur.

12. The compound of claim 1, selected from the group consisting of 3-(2-aminoethoxy)-1,2-benzisoxazole, 3-(2-aminoethoxy)-5-fluoro-1,2-benzisoxazole, 3-(2-aminoethylthio)-5-fluoro-1,2-benzisoxazole, 3-(2-aminoethoxy)-5-chloro-1,2-benzisoxazole, 3-(2-aminoethylthio)-5-chloro-1,2-benzisoxazole, 3-(2-aminoethoxy)-6-chloro-1,2-benzisoxazole, 3-(2-aminoethoxy)-7-chloro-1,2-benzisoxazole, 3-(2-aminoethoxy)-5-bromo-1,2-benzisoxazole, 3-(2-aminoethoxy)-5-methyl-1,2-benzisoxazole, 3-(2-aminoethoxy)-5-methyl-1,2-benzisoxazole, 3-(2-aminoethoxy)-6-methoxy-1,2-benzisoxazole, 3-(2-aminoethoxy)-7-methyl-1,2-benzisoxazole, 3-(2-aminoethoxy)-5-methoxy-1,2-benzisoxazole, 3-(2-aminoethylthio)-5-methoxy-1,2-benzisoxazole, 3-(2-aminoethoxy)-5-difluoromethoxy-1,2-benzisoxazole, 3-(2-aminoethoxy)-5-methoxycarbonyl-1,2-benzisoxazole, 3-(2-aminoethoxy)-5-nitro-1,2-benzisoxazole, 3-(2-aminoethylthio)-5-nitro-1,2-benzisoxazole, 3-(2-aminoethoxy)-4-cyano-1,2-benzisoxazole, and pharmaceutically acceptable salts thereof.

13. The compound of claim 1, wherein the compound is selected from the group consisting of 3-(2-aminoethoxy)-4-carbamoyl-1,2-benzisoxazole hydrochloride, 3-(2-aminoethylthio)-5-amino-1,2-benzisoxazole dihydrochloride, 3-(2-aminoethoxy)-1,2-naphtho[2,3-e]isoxazole hydrochloride, 3-(2-aminoethoxy)-5-methylamino-1,2-benzisoxazole dihydrochloride, 3-(2-aminoethoxy)-5-dimethylamino-1,2-benzisoxazole dihydrochloride, 3-(2-aminoethoxy)-7-carboxy-1,2-benzisoxazole hydrochloride, 3-(2-aminoethoxy)-5-hydroxy-1,2-benzisoxazole hydrochloride, 3-(2-aminoethoxy)-5-acetoxy-1,2-benzisoxazole hydrochloride and pharmaceutically acceptable salts thereof.

14. A pharmaceutical composition having monoamine oxidase inhibitory activity comprising an effective pharmaceutical amount of an isoxazole compound of formula (II) as defined below or a pharmaceutically acceptable salt thereof in admixture with a pharmaceutically acceptable diluent or carrier

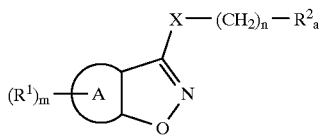

wherein:
- R¹ represents a hydrogen atom; a halogen atom; an alkyl group having from 1 to 6 carbon atoms; an alkyl group having from 1 to 4 carbon atoms and substituted by a halogen atom or an alkoxy group having from 1 to 4 carbon atoms; an alkoxy group having from 1 to 6 carbon atoms; a halogeno alkoxy group having from 1 to 6 carbon atoms; a hydroxyl group; an alkylthio group having from 1 to 6 carbon atoms; an amino group; a monoalkylamino group in which said alkyl moiety has from 1 to 6 carbon atoms; a dialkylamino group in which each alkyl moiety independently has from 1 to 6 carbon atoms; an alkanoyl group having from 1 to 6 carbon atoms; an alkanoylamino group having from 1 to 6 carbon atoms; an alkanoyloxy group having from 1 to 6 carbon atoms; an alkoxycarbonyl group having from 1 to 6 carbon atoms; a carboxy group; an (alkylthio)thiocarbonyl group in which said alkylthio moiety has from 1 to 6 carbon atoms; a carbamoyl group; a monoalkylcarbamoyl group in which said alkyl moiety has from 1 to 6 carbon atoms; a dialkylcarbamoyl group in which each alkyl moiety independently has from 1 to 6 carbon atoms; a nitro group; or a cyano group;
- R², represents an amino group;
- m represents 1;
- n represents an integer of from 1 to 6;
- ring A represents a phenyl ring fused with the isoxazole ring or a naphthyl ring fused with the isoxazole ring; and
- X represents oxygen atom or sulfur atom.

15. The pharmaceutical composition of claim 14, wherein R¹ represents a hydrogen atom, a halogen atom, an alkyl group having from 1 to 4 carbon atoms, a fluoromethyl group, a difluoromethyl group, a trifluoromethyl group, a 2-fluoroethyl group, a 2-chloroethyl group, a 2,2,2-trifluoroethyl group, a methoxymethyl group, a methoxyethyl group, an alkoxy group having from 1 to 4 carbon atoms, a fluoromethoxy group, a chloromethoxy group, a difluoromethoxy group, a dichloromethoxy group, a trifluoromethoxy group, a trichloromethoxy group, a 1-fluoroethoxy group, a 2-fluoroethoxy group, a 2-chloroethoxy group, a 2,2,2-trifluoroethoxy group, a hydroxyl group, an alkylthio group having from 1 to 4 carbon atoms, an amino group, a monoalkylamino group in which said alkyl moiety has from 1 to 4 carbon atoms, a dialkylamino group in which each alkyl moiety independently has from 1 to 4 carbon atoms, a formyl group, an acetyl group, a formylamino group, an acetylamino group, an alkanoyloxy group having from 1 to 4 carbon atoms, an alkoxycarbonyl group having from 1 to 4 carbon atoms, a carboxy group, a (methylthio)thiocarbonyl group, an (ethylthio)thiocarbonyl group, a carbamoyl group, a methylcarbamoyl group, an ethylcarbamoyl group, a dimethylcarbamoyl group, a diethylcarbamoyl group, a nitro group or a cyano group.

16. The pharmaceutical composition of claim 14, wherein R¹ represents a hydrogen atom, a halogen atom, an alkyl group having from 1 to 4 carbon atoms, a fluoromethyl group, a difluoromethyl group, a trifluoromethyl group, a 2-fluoroethyl group, a 2,2,2-trifluoroethyl group, a methoxymethyl group, a methoxyethyl group, an alkoxy group having from 1 to 4 carbon atoms, a difluoromethoxy group, a hydroxyl group, an alkylthio group having from 1 to 4 carbon atoms, an amino group, a methylamino group, an ethylamino group, a dimethylamino group, a diethylamino group, a formyl group, an acetyl group, a formylamino group, an acetylamino group, an alkoxycarbonyl group having from 1 to 4 carbon atoms, a carboxy group, a carbamoyl group, a methylcarbamoyl group, an ethylcarbamoyl group, a dimethylcarbamoyl group, a diethylcarbamoyl group, a nitro group or a cyano group.

17. The pharmaceutical composition of claim 14, wherein R¹ represents a hydrogen atom, a fluorine atom, a chlorine atom, a bromine atom, a methyl group, an ethyl group, a trifluoromethyl group, a methoxy group, an ethoxy group, a difluoromethoxy group, a hydroxyl group, a methylthio group, an ethylthio group, an amino group, a methylamino group, an ethylamino group, a dimethylamino group, a formyloxy group, an acetyloxy group, a methoxycarbonyl group, an ethoxycarbonyl group, a carboxy group, a carbamoyl group, a nitro group or a cyano group.

18. The pharmaceutical composition of claim 14, wherein R¹ represents a hydrogen atom, a fluorine atom, a chlorine atom, a bromine atom, a methyl group, a methoxy group, a methylthio group, a difluoromethoxy group, a methoxycarbonyl group, a nitro group or a cyano group.

19. The pharmaceutical composition of claim 14, wherein n is 2 to 4.

20. The pharmaceutical composition of claim 14, wherein n is 2.

21. The pharmaceutical composition of claim 15, wherein ring A is a naphthyl ring.

22. The pharmaceutical composition of claim 14, wherein ring A is a phenyl ring.

23. The pharmaceutical composition of claim 14, wherein X is an oxygen atom.

24. The pharmaceutical composition of claim 14, wherein said isoxazole derivative of formula (II) is selected from the group consisting of:
- 3-(2-aminoethoxy)-1,2-benzisoxazole,
- 3-(2-aminoethoxy)-5-fluoro-1,2-benzisoxazole,
- 3-(2-aminoethylthio)-5-fluoro-1,2-benzisoxazole,
- 3-(2-aminoethoxy)-5-chloro-1,2-benzisoxazole,
- 3-(2-aminoethylthio)-5-chloro-1,2-benzisoxazole,
- 3-(2-aminoethoxy)-6-chloro-1,2-benzisoxazole,
- 3-(2-aminoethoxy)-7-chloro-1,2-benzisoxazole,
- 3-(2-aminoethoxy)-5-bromo-1,2-benzisoxazole,
- 3-(2-aminoethoxy)-5-methyl-1,2-benzisoxazole,
- 3-(2-aminoethylthio)-5-methyl-1,2-benzisoxazole,
- 3-(2-aminoethoxy)-6-methyl-1,2-benzisoxazole,
- 3-(2-aminoethoxy)-7-methyl-1,2-benzisoxazole,
- 3-(2-aminoethoxy)-5-methoxy-1,2-benzisoxazole,
- 3-(2-aminoethylthio)-5-methoxy-1,2-benzisoxazole,
- 3-(2-aminoethoxy)-5-difluoromethoxy-1,2-benzisoxazole,
- 3-(2-aminoethoxy)-5-methoxycarbonyl-1,2-benzisoxazole,
- 3-(2-aminoethoxy)-5-nitro-1,2-benzisoxazole,
- 3-(2-aminoethylthio)-5-nitro-1,2-benzisoxazole, 3-(2-aminoethoxy)-4-cyano-1 2-benzisoxazole, or a pharmaceutically acceptable salt thereof.

25. A pharmaceutical composition having monoamine oxidase inhibitory activity comprising a monoamine oxidase inhibitory activity effective amount of an isoxazole compound selected from the group consisting of 3-(2-aminoethoxy)-4-cyano-5-fluoro-1,2-benzisoxazole; 3-(2-aminoethylthio)-5-fluoro-4-methyl-1,2-benzisoxazole; and pharmaceutically acceptable salts thereof, in admixture with a pharmaceutically acceptable diluent or carrier.

26. A compound which is 3-(2-aminoethoxy)-4-cyano-5-fluoro-1,2-benzisoxazole or a pharmaceutically acceptable salt thereof.

27. A compound which is 3-(2-aminoethylthio)-5-fluoro-4-methyl-1,2-benzisoxazole or a pharmaceutically acceptable salt thereof.

28. A compound of the formula

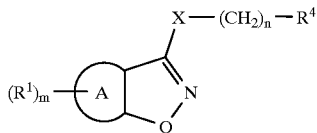

wherein:
R¹ represents a hydrogen atom; a halogen atom; an unsubstituted alkyl group having from 1 to 6 carbon atoms; an alkyl group having from 1 to 4 carbon atoms and substituted by a halogen atom or an alkoxy group having from 1 to 4 carbon atoms; an alkoxy group having from 1 to 6 carbon atoms; a halogeno alkoxy group having from 1 to 6 carbon atoms; a hydroxyl group; an alkylthio group having from 1 to 6 carbon atoms; an amino group; a monoalkylamino group in which the alkyl moiety thereof has from 1 to 6 carbon atoms; a dialkylamino group in which each alkyl moiety thereof independently has from 1 to 6 carbon atoms; an alkanoyl group having from 1 to 6 carbon atoms; an alkanoylamino group having from 1 to 6 carbon atoms; an alkanolyloxy group having from 1 to 6 carbon atoms; an alkoxycarbonyl group having from 1 to 6 carbon atoms; a carboxy group; an (alkylthio) thiocarbonyl group in which the alkylthio thereof moiety has from 1 to 6 carbon atoms; a carbamoyl group; a monoalkylcarbamoyl group in which the alkyl moiety thereof has from 1 to 6 carbon atoms; a dialkylcarbamoyl group in which each alkyl moiety thereof independently has from 1 to 6 carbon atoms; a nitro group; or a cyano group;

R⁴ represents an amino group substituted by a protecting group selected from the group consisting of $C_1$–$C_6$ alkanoyl; halogen $C_1$–$C_4$ alkoxy-substituted $C_1$–$C_4$ alkanoyl; unsaturated $C_1$–$C_4$ alkanoyl; unsubstituted $C_6$–$C_{10}$ arylcarbonyl; $C_6$–$C_{10}$ arylcarbonyl substituted by a substituent selected from the group consisting of $C_1$–$C_4$ alkyl, $C_1$–$C_4$ alkoxy, $C_1$–$C_4$ alkoxy carbonyl, $C_6$–$C_{10}$ aryl and nitro; unsubstituted $C_1$–$C_4$ alkoxycarbonyl; $C_1$–$C_4$ alkoxycarbonyl substituted by a halogen; $C_2$–$C_5$-alkenyloxycarbonyl; aryldicarbonyl and $C_7$–$C_{15}$ aralkyloxycarbonyl;

m represents 1;

n represents an integer of from 1 to 6;

ring A represents a phenyl ring fused with the isoxazole ring or a naphthyl ring fused with the isoxazole ring; and X represents an oxygen atom or a sulfur atom;

or a pharmaceutically acceptable salt thereof.

29. The compound of claim 28, wherein R⁴ is an amino protected by a protecting group selected from the group consisting of formyl, acetyl, propionyl, butyryl, isobutyryl, pentanoyl, pivaloyl, valeryl, isovaleryl, hexanoyl, chloroacetyl, dichloroacetyl, butoxyacetyl, ethoxypropionyl, propoxybutyrl, acryloyl, propiolyl, methacryloyl, crotonoyl, isocrotonoyl, benzoyl, α-naphthoyl, β-naphthoyl, 2-fluorobenzoyl, 2-bromobenzoyl, 2,4-dichlorobenzoyl, 6-chloro-α-naphthoyl, 4-toluoyl, 4-propylbenzoyl, 4-t-butylbenzoyl,2, 4,6-trimethylbenzoyl, 6-ethyl-α-naphthoyl, 4-anisoyl, 4-propoxybenzoyl, 4-t-butoxybenzoyl, 6-ethoxy-α-naphthoyl, 2-ethoxycarbonylbenzoyl, 4-t-butoxycarbonylbenzoyl, 6-methoxycarbonyl-α-naphthoyl, 4-phenylbenzoyl, 4-phenyl-α-naphthoyl, 6-α-naphthylbenzoyl, 4-nitrobenzoyl, 2-nitrobenzoy, 6-nitro-α-naphthoyl, methoxycarbonyl, ethoxycarbonyl, propoxycarbonyl, isopropoxycarbonyl, butoxycarbonyl, isobutoxycarbonyl, s-butoxycarbonyl, t-butoxycarbonyl, chloromethoxycarbonyl, 2,2,2-trichloroethoxycarbonyl, 2-fluoropopoxycarbonyl, 2-bromo-t-butoxycarbonyl, 2,2-dibormo-t-butoxycarbonyl, t-butyldimethylsilylpropoxycarbonyl, vinyloxycarbonyl, allyloxycarbonyl, 1,3-butadienyloxycarbonyl , 2-pentenyloxycarbonyl phthaloyl, benzyl, phenethyl, 3-phenylpropyl, 4-phenylbutyl, α-naphthylmethyl, β-naphthylmethyl, diphenylmethyl, triphenylmethyl, α-naphthyldiphenylmethyl , 9-anthrylmethyl, benzyloxycarbonyl, (1-phenyl)benzyloxycarbonyl, α-naphthylmethyloxycarbonyl, β-naphthylmethyloxycarbonyl, 9-anthrylmethyloxycarbonyl, p-methoxybenzyloxycarbonyl and p-nitrobenzyloxycarbonyl.

30. The compound of claim 28, wherein R⁴ is an amino group protected by a protecting group selected from the group consisting of $C_1$–$C_4$ alkanoyl, trifluoroacetyl, methoxyacetyl, benzoyl, α-naphthoyl, β-naphthoyl, anisoyl, nitrobenzoyl, $C_1$–$C_4$ alkoxycarbonyl, methoxycarbonyl, ethoxycarbonyl, t-butoxycarbonyl, 2,2,2-trichloroethoxycarbonyl, vinyloxycarbonyl, allyloxycarbonyl, phthaloyl, benzyl, benzyloxycarbonyl or nitrobenzyloxycarbonyl.

31. The compound of claim 28, wherein R⁴ is an amino group protected by t-butoxycarbonyl, acetyl or methoxycarbonyl.

32. The compound of claim 28, wherein R¹ represents a hydrogen atom, a halogen atom, an alkyl group having from 1 to 4 carbon atoms, a fluoromethyl group, a difluoromethyl group, a trifluoromethyl group, a 2-fluoroethyl group, a 2-chloroethyl group, a 2,2,2-trifluoroethyl group, a methoxymethyl group, a methoxyethyl group, an alkoxy group having from 1 to 4 carbon atoms, a fluoromethoxy group, a chloromethoxy group, a difluoromethoxy group, a dichloromethoxy group, a trifluoromethoxy group, a trichloromethoxy group, a 1-fluoroethoxy group, a 2-fluoroethoxy group, a 2-chloroethoxy group, a 2,2,2-tifluoroethoxy group, a hydroxyl group, an alkylthio group having from 1 to 4 carbon atoms, an amino group, a moncalkylamino group in which said alkyl moiety has from 1 to 4 carbon atoms, a dialkylamido group in which each alkyl moiety independently has from 1 to 4 carbon atoms, a formyl group, an acetyl group, a formylamino group, an acetylamino group, an alkanoyloxy group having from 1 to 4 carbon atoms, an alkoxycarbonyl group having from 1 to 4 carbon atoms, a carboxy group, a (methylthio)thiocarbonyl group, an (ethylthio)thiocarbonyl group, a carbamoyl group, a methylcarbamoyl group, an ethyylcarbamoyl group, a dimethylcarbamoyl group, a diethylcarbamoyl group , nitro group or a cyano group; and rin A is a phenyl ring or a naphthyl ring.

* * * * *

UNITED STATES PATENT AND TRADEMARK OFFICE
CERTIFICATE OF CORRECTION

PATENT NO.    : 5,965,591
DATED         : October 12, 1999
INVENTOR(S)   : Kojima et al.

It is certified that error appears in the above-identified patent and that said Letters Patent is hereby corrected as shown below:

<u>Column 1,</u>
Line 65, replace "THE INVENTION" with -- SUMMARY OF THE INVENTION --.
Line 66, delete "Summary of the Invention" and insert -- The inventors --.

<u>Column 120,</u>
Line 36, delete "claim 15" and insert -- claim 14 --.

Signed and Sealed this

Thirteenth Day of August, 2002

*Attest:*

*Attesting Officer*

JAMES E. ROGAN
*Director of the United States Patent and Trademark Office*